United States Patent
Hoang-Lindsay et al.

(10) Patent No.: US 11,642,440 B2
(45) Date of Patent: **\*May 9, 2023**

(54) COMPOSITIONS COMPRISING SILK FIBROIN PARTICLES AND USES THEREOF

(71) Applicant: Sofregen Medical, Inc., Framingham, MA (US)

(72) Inventors: Anh Hoang-Lindsay, Boston, MA (US); Christopher P. Gulka, Melrose, MA (US); Jodie E. M. Giordano, Bedford, MA (US); Joseph E. Brown, Melrose, MA (US); Thomas L. Carroll, Melrose, MA (US)

(73) Assignee: Sofregen Medical, Inc., Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/200,764

(22) Filed: Mar. 12, 2021

(65) Prior Publication Data

US 2021/0220516 A1 Jul. 22, 2021

Related U.S. Application Data

(63) Continuation of application No. 15/799,455, filed on Oct. 31, 2017.

(60) Provisional application No. 62/571,670, filed on Oct. 12, 2017, provisional application No. 62/488,402, filed on Apr. 21, 2017, provisional application No. 62/482,949, filed on Apr. 7, 2017, provisional application No. 62/415,107, filed on Oct. 31, 2016.

(51) Int. Cl.
| | | |
|---|---|---|
| *A61L 27/22* | (2006.01) | |
| *A61L 27/56* | (2006.01) | |
| *C08L 5/08* | (2006.01) | |
| *C08K 5/00* | (2006.01) | |
| *C08L 89/00* | (2006.01) | |
| *A61L 27/50* | (2006.01) | |
| *C08K 5/053* | (2006.01) | |
| *A61L 27/26* | (2006.01) | |

(52) U.S. Cl.
CPC ............. *A61L 27/227* (2013.01); *A61L 27/26* (2013.01); *A61L 27/502* (2013.01); *A61L 27/56* (2013.01); *C08K 5/0016* (2013.01); *C08K 5/053* (2013.01); *C08L 5/08* (2013.01); *C08L 89/00* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | |
|---|---|---|
| 5,034,135 A | 7/1991 | Fischel |
| 5,234,608 A | 8/1993 | Duff |
| 5,245,012 A | 9/1993 | Lombari et al. |
| 5,591,828 A | 1/1997 | Bosslet et al. |
| 6,287,340 B1 | 9/2001 | Altman et al. |
| 6,673,285 B2 | 1/2004 | Ma |
| 7,635,755 B2 | 12/2009 | Kaplan et al. |
| 7,662,409 B2 | 2/2010 | Masters |
| 7,842,780 B2 | 11/2010 | Kaplan et al. |
| 8,128,984 B2 | 3/2012 | Knight et al. |
| 8,178,656 B2 | 5/2012 | Kaplan et al. |
| 8,187,616 B2 | 5/2012 | Wang et al. |
| 9,187,538 B2 | 11/2015 | Altman et al. |
| 9,334,262 B2 * | 5/2016 | Van Epps ............... A61P 1/04 |
| 10,857,262 B2 | 12/2020 | Brown et al. |
| 2002/0143291 A1 | 10/2002 | Slater |
| 2003/0014010 A1 | 1/2003 | Carpenter et al. |
| 2005/0276791 A1 | 12/2005 | Hansford et al. |
| 2006/0063715 A1 | 3/2006 | Whitlow et al. |
| 2006/0273279 A1 | 12/2006 | Kaplan et al. |
| 2007/0187862 A1 | 8/2007 | Kaplan et al. |
| 2007/0212730 A1 | 9/2007 | Vepari et al. |
| 2008/0038236 A1 | 2/2008 | Gimble et al. |
| 2008/0085272 A1 | 4/2008 | Kaplan et al. |
| 2008/0213564 A1 | 9/2008 | Ma et al. |
| 2008/0280360 A1 | 11/2008 | Kaplan et al. |
| 2008/0293919 A1 | 11/2008 | Kaplan et al. |
| 2008/0317816 A1 | 12/2008 | Ma et al. |
| 2009/0004737 A1 | 1/2009 | Borenstein et al. |
| 2009/0202614 A1 | 8/2009 | Kaplan et al. |
| 2009/0214649 A1 | 8/2009 | Gazit et al. |
| 2009/0232963 A1 | 9/2009 | Kaplan et al. |
| 2009/0234026 A1 | 9/2009 | Kaplan et al. |

(Continued)

FOREIGN PATENT DOCUMENTS

| | | |
|---|---|---|
| CN | 102847197 A | 1/2013 |
| CN | 104480714 A | 4/2015 |

(Continued)

OTHER PUBLICATIONS

Dion et al. "Functional assessment of the e vivo vocal folds through biomechanical testing: a review" Apr. 2016.*

(Continued)

*Primary Examiner* — Danah Al-Awadi
(74) *Attorney, Agent, or Firm* — Wolf, Greenfield & Sacks, P.C.

(57) ABSTRACT

Various aspects described herein relate to compositions comprising silk fibroin particles and methods of using the same, as well as devices and methods of delivering such compositions. The compositions described herein are suitable for injection into a site of defect in a soft tissue to provide bulking and/or augmentation effect to the soft tissue.

7 Claims, 54 Drawing Sheets

(56) References Cited

U.S. PATENT DOCUMENTS

| | | | |
|---|---|---|---|
| 2010/0028451 A1 | 2/2010 | Kaplan et al. | |
| 2010/0046902 A1 | 2/2010 | Kaplan et al. | |
| 2010/0063404 A1 | 3/2010 | Kaplan et al. | |
| 2010/0068740 A1 | 3/2010 | Kaplan et al. | |
| 2010/0070068 A1 | 3/2010 | Kaplan et al. | |
| 2010/0120116 A1 | 5/2010 | Kaplan et al. | |
| 2010/0143487 A1 | 6/2010 | Masters | |
| 2010/0178304 A1 | 7/2010 | Wang et al. | |
| 2010/0191328 A1 | 7/2010 | Kaplan et al. | |
| 2010/0196447 A1 | 8/2010 | Kaplan et al. | |
| 2010/0279112 A1 | 11/2010 | Kaplan et al. | |
| 2010/0317587 A1 | 12/2010 | Chung et al. | |
| 2011/0008406 A1 | 1/2011 | Altman et al. | |
| 2011/0008444 A1* | 1/2011 | Bergman | C08F 8/14 424/488 |
| 2011/0020409 A1 | 1/2011 | Altman et al. | |
| 2011/0046686 A1 | 2/2011 | Kaplan et al. | |
| 2011/0076384 A1 | 3/2011 | Cannizzaro et al. | |
| 2011/0111031 A1* | 5/2011 | Jiang | A61K 9/0024 514/327 |
| 2011/0135697 A1 | 6/2011 | Omenetto et al. | |
| 2011/0189292 A1 | 8/2011 | Lebreton et al. | |
| 2011/0223153 A1 | 9/2011 | Lu et al. | |
| 2012/0052124 A1 | 3/2012 | Kaplan et al. | |
| 2012/0070427 A1 | 3/2012 | Kaplan et al. | |
| 2012/0076771 A1 | 3/2012 | Vepari et al. | |
| 2012/0121820 A1 | 5/2012 | Kaplan et al. | |
| 2012/0129255 A1 | 5/2012 | Kaplan et al. | |
| 2012/0171770 A1 | 7/2012 | Numata et al. | |
| 2012/0172317 A1 | 7/2012 | Altman et al. | |
| 2012/0187591 A1 | 7/2012 | Wang et al. | |
| 2012/0223293 A1 | 9/2012 | Borenstein et al. | |
| 2013/0158131 A1 | 6/2013 | Kaplan et al. | |
| 2013/0177608 A1 | 7/2013 | Kaplan et al. | |
| 2014/0135733 A1 | 5/2014 | Hauschild et al. | |
| 2014/0287043 A1 | 9/2014 | Kaplan et al. | |
| 2014/0308362 A1* | 10/2014 | Bellas | A61P 15/08 424/499 |
| 2014/0314817 A1 | 10/2014 | Leisk et al. | |
| 2014/0315828 A1 | 10/2014 | Pavlovic et al. | |
| 2014/0370094 A1 | 12/2014 | Wray et al. | |
| 2015/0010630 A1 | 1/2015 | Llamas et al. | |
| 2015/0056294 A1 | 2/2015 | Kaplan et al. | |
| 2015/0057685 A1* | 2/2015 | Serban | D04B 21/16 606/151 |
| 2015/0086605 A1 | 3/2015 | Mauney et al. | |
| 2015/0164117 A1 | 6/2015 | Kaplan et al. | |
| 2015/0174256 A1* | 6/2015 | Kaplan | A43B 1/06 424/443 |
| 2015/0183841 A1 | 7/2015 | Lo et al. | |
| 2015/0238617 A1 | 8/2015 | Kaplan et al. | |
| 2016/0038637 A1 | 2/2016 | Lu et al. | |
| 2016/0046679 A1 | 2/2016 | Kluge et al. | |
| 2018/0050109 A1 | 2/2018 | Kaplan et al. | |
| 2018/0272030 A1 | 9/2018 | Brown et al. | |
| 2018/0272033 A1 | 9/2018 | Hoang et al. | |
| 2018/0303742 A1 | 10/2018 | Pavlovic et al. | |
| 2021/0106721 A1 | 4/2021 | Brown et al. | |
| 2021/0106722 A1 | 4/2021 | Brown et al. | |
| 2021/0220517 A1 | 7/2021 | Hoang-Lindsay et al. | |

FOREIGN PATENT DOCUMENTS

| | | |
|---|---|---|
| JP | 2001-057851 A | 3/2001 |
| JP | 2002-369878 A2 | 12/2002 |
| WO | WO 97/08315 | 3/1997 |
| WO | WO 01/87267 A1 | 11/2001 |
| WO | WO 2004/001103 A2 | 12/2003 |
| WO | WO 2013/071123 A1 | 5/2013 |
| WO | WO 2014/125505 A1 | 8/2014 |
| WO | WO 2016/145281 A1 | 9/2016 |

OTHER PUBLICATIONS

Brown et al."Complex Shear Modulus (G*) Polymer Properties" 1989.*
Dion et al."Functional assessment of the ex vivo vocal folds through biomechanical testing:a review" Apr. 2016.*
Fuentes et al."The effect of hyaluronic acid on silk fibroin confirmation" 2008.*
International Search Report and Written Opinion for PCT/US2017/059363 dated Feb. 19, 2018.
International Search Report and Written Opinion for PCT/US2017/059322 dated Feb. 20, 2018.
[No Author Listed], Saving Voices with Silk: a new FDA-approved silk-based product may offer hope for long-term voice restoration. Harvard Otolaryngology. 2019 Fall;16(2):4-7.
Acharya et al., Performance evaluation of a silk protein-based matrix for the enzymatic conversion of tyrosine to L-DOPA. Biotechnol J. Feb. 2008;3(2):226-33.
Altman et al., Silk-based biomaterials. Biomaterials. Feb. 2003;24(3):401-16.
Batzer et al., Enhanced evolutionary PCR using oligonucleotides with inosine at the 3'-terminus. Nucleic Acids Res. Sep. 25, 1991;19(18):5081.
Bayraktar et al,. Silk fibroin as a novel coating material for controlled release of theophylline. Eur J Pharm Biopharm. Aug. 2005;60(3):373-81.
Borzacchiello et al., Rheological Characterization of Vocal Folds after Injection Augmentation in a Preliminary Animal Study. Journal of Bioactive and Compatible Polymers. 2004;19(4):331-41. Epub Jul. 1, 2004.
Carroll et al., A Novel Silk Based Vocal Fold Augmentation Material. The 2017 Fall Voice Conference. The Ritz-Carlton, Washington, DC. PowerPoint Presentation. Oct. 13, 2017:18 slides.
Caton et atl., Viscoelasticity of hyaluronan and nonhyaluronan based vocal fold injectables: implications for mucosal versus muscle use. Laryngoscope. Mar. 2007;117(3):516-21.
Chothia et al., Canonical structures for the hypervariable regions of immunoglobulins. J Mol Biol. Aug. 20, 1987;196(4):901-17.
Demura et al., Immobilization of glucose oxidase with Bombyx mori silk fibroin by only stretching treatment and its application to glucose sensor. Biotechnol Bioeng. Jan. 25, 1989;33(5):598-603.
Fattahi et al., 3D Near-Field Electrospinning of Biomaterial Microfibers with Potential for Blended Microfiber-Cell-Loaded Gel Composite Structures. Adv. Healthcare Mater. Oct. 2017;6(19):17 pages.
Guziewica et al., Lyophized silk fibroin hydrogels for the sustained local delivery of therapeutic monoclonal antibodies. Biomaterials. 2011;32:2642-50. Epub Jan. 8, 2011.
Hofmann et al., Silk fibroin as an organic polymer for controlled drug delivery. J Control Release. Mar. 10, 2006;111(1-2):219-27.
Holliger et al., "Diabodies": small bivalent and bispecific antibody fragments. Proc Natl Acad Sci U S A. Jul. 15, 1993;90(14):6444-8.
Jin et al., Water-Stable Silk Films with Reduced β-Sheet Content. Advanced Functional Materials. Aug. 2005;15(8):1241-7.
Kluge et al., Optimizing Molecular Weight of Lyophilized Silk as a Shelf-Stable Source Material. ACS Biomaterials Science & Engineering. Mar. 2016;2:595-605.
Kundu et al., Silk fibroin biomaterials for tissue regenerations. Advanced Drug Delivery Reviews. 2013;65:457-70. Epub Nov. 5, 2012.
Li et al., Silk-based stabilization of biomacromolecules. Journal of Controlled Release. 2015:15 pages.
Lu et al., Stabilization of enzymes in silk films. Biomacromolecules. May 11, 2009;10(5):1032-42. doi: 10.1021/bm800956n.
Lucas et al., The silk fibroins. Adv Protein Chem. 1958;13:107-242.
Minoura et al., Attachment and growth of cultured fibroblast cells on silk protein matrices. J Biomed Mater Res. Oct. 1995;29(10):1215-21.
Miri, Mechanical characterization of vocal fold tissue: a review study. J Voice. Nov. 2014;28(6):657-67. doi: 10.1016/j.jvoice.2014.03.001. Epub Jul. 5, 2014. Review.
Miyairi et al., Properties of β-Glucosidase Immobilized in Sericin Membrane. Journal of Fermentation Technology. 1978;56(4):303-8.

(56) References Cited

OTHER PUBLICATIONS

Murphy et al., Modification of silk fibroin using diazonium coupling chemistry and the effects on hMSC proliferation and differentiation. Biomaterials. Jul. 2008;29(19):2829-38. doi: 10.1016/j.biomaterials.2008.03.039.

Ohtsuka et al., An alternative approach to deoxyoligonucleotides as hybridization probes by insertion of deoxyinosine at ambiguous codon positions. J Biol Chem. Mar. 10, 1985;260(5):2605-8.

Park et al., The effect of heat on skin permeability. Int J Pharm. Jul. 9, 2008;359(1-2):94-103. doi: 10.1016/j.ijpharm.2008.03.032.

Perry et al., Nano- and Micropatterning of Optically Transparent, Mechanically Robust, Biocompatible Silk Fibroin Films. Advanced Materials. 2008;20:3070-2.

Pluckthun, Antibodies from *Escherichia coli*. The Pharmacology of Monoclonal Antibodies. Eds. Rosenburg and Moore. Springer-Verlag: New York. Chapter 11. 1994;113:269-315.

Rajkhowa et al. Ultra-fine silk powder preparation through rotary and ball milling. Powder Technology. Jun. 2008;185(1):87-95.

Rnjak-Kovacina et al., Lyophilized Silk Sponges: a versatile Biomaterial Platform for Soft Tissue Engineering. ACS Biomaterials Science & Engineering. 2015;1:260-70.

Rnjak-Kovacina et al., The Effect of Sterilization on Silk Fibroin Biomaterial Properties. Macromolecular Bioscience. 2015:14 pages. Epub Mar. 11, 2015.

Rockwood et al., Materials fabrication from Bombyx mori silk fabroin. Nature Protocols. 2011;6(10):1612-31.

Rossolini et al., Use of deoxyinosine-containing primers vs degenerate primers for polymerase chain reaction based on ambiguous sequence information. Mol Cell Probes. Apr. 1994;8(2):91-8.

Santin et al., In vitro evaluation of the inflammatory potential of the silk fibroin. J Biomed Mater Res. Sep. 5, 1999;46(3):382-9.

Sofia et al., Functionalized silk-based biomaterials for bone formation. J Biomed Mater Res. Jan. 2001;54(1):139-48.

Wang et al., In vivo degradation of three-dimensional silk fibroin scaffolds. Biomaterials. Aug.-Sep. 2008;29(24-25):3415-28. doi: 10.1016/j.biomaterials.2008.05.002.

Wang et al., Silk nanospheres and microspheres from silk/pva blend films for drug delivery. Biomaterials. Feb. 2010;31(6):1025-35. doi: 10.1016/j.biomaterials.2009.11.002.

Wenk et al., Silk fibroin spheres as a platform for controlled drug delivery. J Control Release. Nov. 24, 2008;132(1):26-34. doi: 10.1016/j.jconrel.2008.08.005.

Wray et al., Effect of processing on silk-based biomaterials: reproducibility and biocompatibility. J Biomed Mater Res B Appl Biomater. Oct. 2011;99(1):89-101. doi: 10.1002/jbm.b.31875. Epub Jun. 21, 2011.

Yucel et al., Vortex-induced injectable silk fibroin hydrogels. Biophys J. Oct. 7, 2009;97(7):2044-50. doi: 10.1016/j.bpj.2009.07.028.

Zapata et al., Engineering linear F(ab')2 fragments for efficient production in *Escherichia coli* and enhanced antiproliferative activity. Protein Eng. Oct. 1995;8(10):1057-62.

U.S. Appl. No. 15/799,455, filed Oct. 31, 2017, Hoang-Lindsay et al..

U.S. Appl. No. 17/081,684, filed Oct. 27, 2020, Brown et al..

U.S. Appl. No. 17/081,737, filed Oct. 27, 2020, Brown et al..

PCT/US2017/059363, International Search Report and Written Opinion, dated Feb. 19, 2018.

PCT/US2017/059322, International Search Report and Written Opinion, dated Feb. 20, 2018.

Fuentes et al., The effect of hyaluronic acid on silk fibroin conformation. Biomaterials. Feb. 2008;29(6):633-42. doi: 10.1016/j.biomaterials.2007.10.024. Epub Nov. 8, 2007.

Jeon et al., Mechanical properties and degradation behaviors of hyaluronic acid hydrogels cross-linked at various cross-linking densities. Carbohydr Polym. Oct. 1, 2007;70(3):251-7.

[No Author Listed], Steam Sterilization. Guideline for Disinfection and Sterilization in Healthcare Facilities. CDC. 2008. [last reviewed Sep. 18, 2016].

Correia et al., Development of silk-based scaffolds for tissue engineering of bone from human adipose-derived stem cells. Acta Biomater. Jul. 2012;8(7):2483-92. doi: 10.1016/j.actbio.2012.03.019. Epub Mar. 13, 2012.

Guan et al., Glass transitions in native silk fibres studied by dynamic mechanical thermal analysis. Soft Matter. Jul. 6, 2016;12(27):5926-36. doi: 10.1039/c6sm00019c.

Jiang et al., Tunable High-Molecular-Weight Silk Fibroin Polypeptide Materials: Fabrication and Self-Assembly Mechanism. ACS Appl Bio Mater. May 18, 2020;3(5):3248-3259. doi: 10.1021/acsabm.0c00231. Epub Apr. 28, 2020.

Lau et al., Dry Surface Treatments of Silk Biomaterials and Their Utility in Biomedical Applications. ACS Biomater Sci Eng. Oct. 12, 2020;6(10):5431-5452. doi: 10.1021/acsbiomaterials.0c00888. Epub Sep. 9, 2020. Just Accepted manuscript.

Meirovitch et al., Spider Silk-CBD-Cellulose Nanocrystal Composites: Mechanism of Assembly. Int J Mol Sci. Sep. 18, 2016;17(9):1573. doi: 10.3390/ijms17091573.

Tamada, New process to form a silk fibroin porous 3-D structure. Biomacromolecules. Nov.-Dec. 2005;6(6):3100-6. doi: 10.1021/bm050431f.

Wu et al., Impact of Sterilization Methods on the Stability of Silk Fibroin Solution. Adv Mater Res. Aug. 16, 2011;311-3:1755-9.

Yazawa et al., Influence of Water Content on the β-Sheet Formation, Thermal Stability, Water Removal, and Mechanical Properties of Silk Materials. Biomacromolecules. Mar. 14, 2016;17(3):1057-66. doi: 10.1021/acs.biomac.5b01685. Epub Feb. 12, 2016.

Yucel et al., Silk-based biomaterials for sustained drug delivery. J Control Release. Sep. 28, 2014;190:381-97. doi: 10.1016/j.jconrel.2014.05.059. Epub Jun. 5, 2014.

Zeng et al., Controlling silk fibroin microspheres via molecular weight distribution. Mater Sci Eng C Mater Biol Appl. May 2015;50:226-33. doi: 10.1016/j.msec.2015.02.005. Epub Feb. 7, 2015.

\* cited by examiner

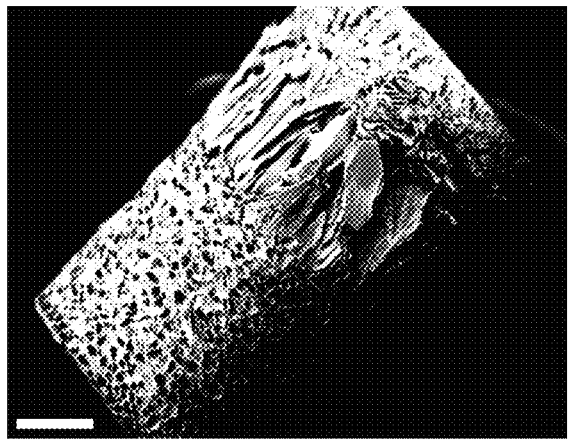 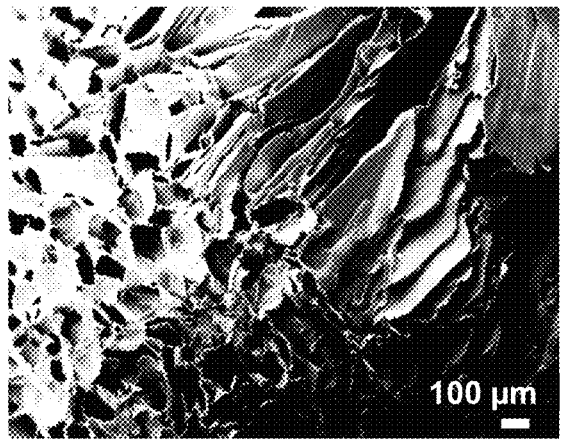
FIG. 4A  FIG. 4B
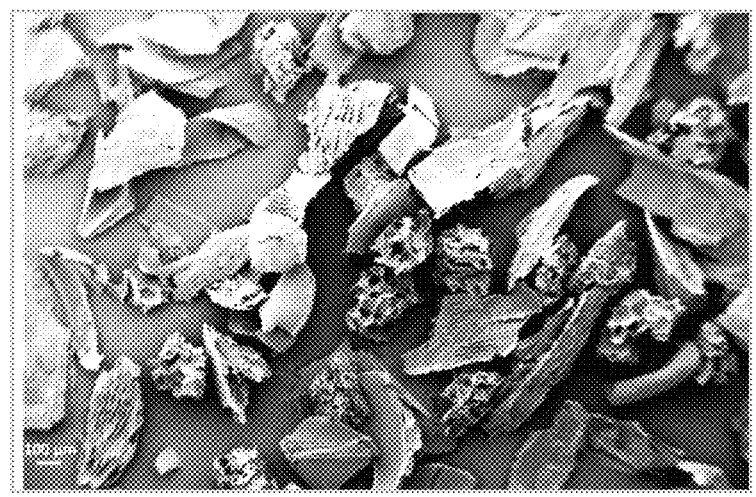
FIG. 4C

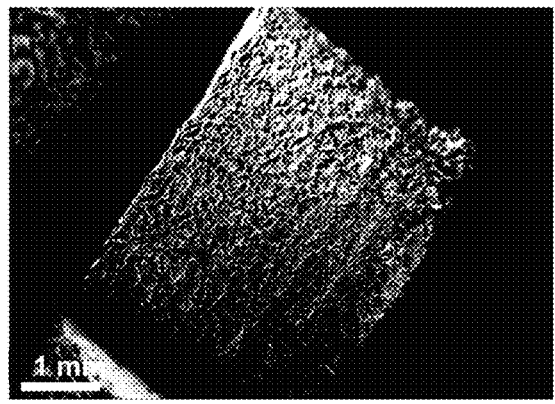 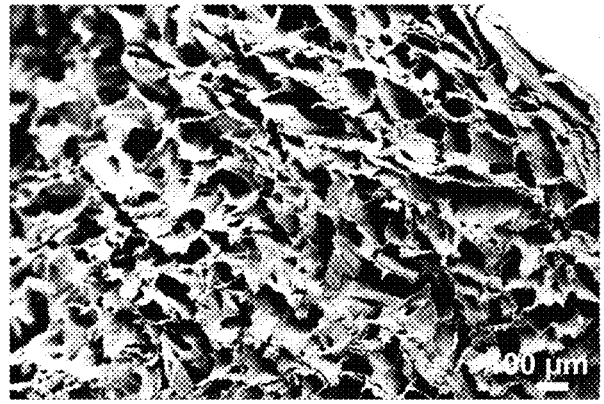
FIG. 5A　　　　　　　　　　　　FIG. 5B
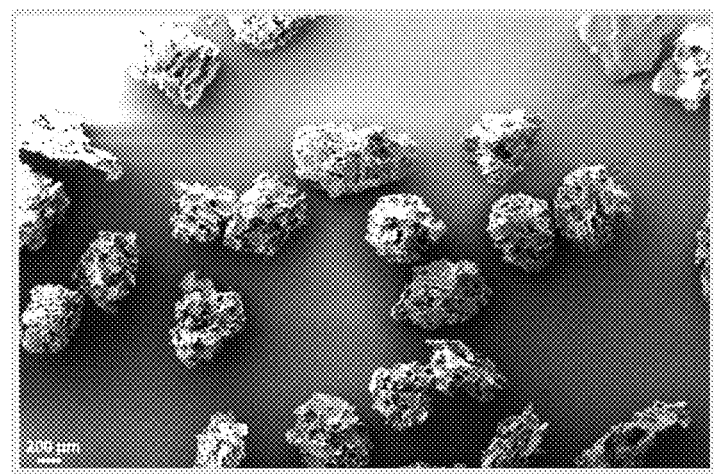
FIG. 5C

Representative macroscopic observation

FIG. 13A  FIG. 13B

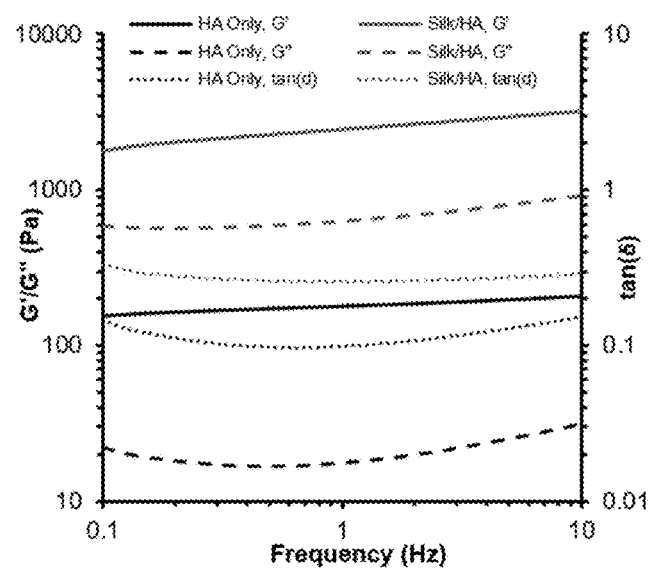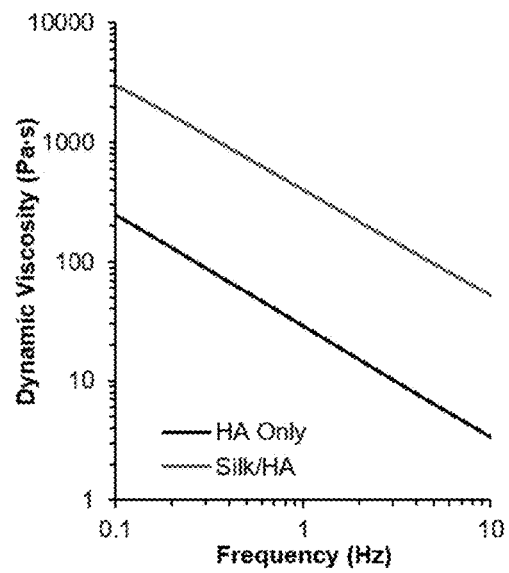
FIG. 20A  FIG. 20B
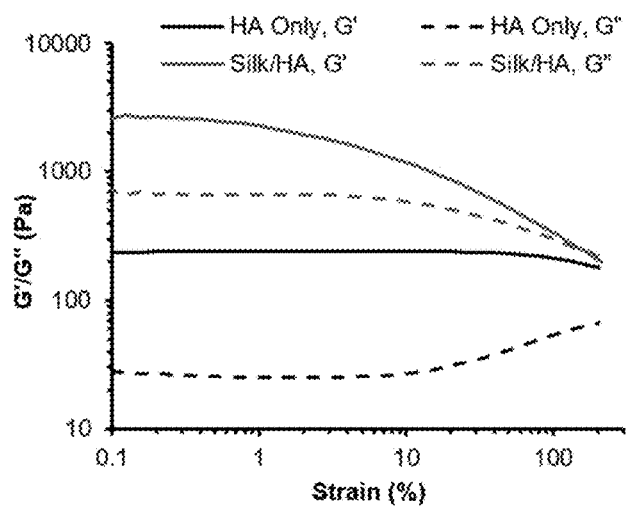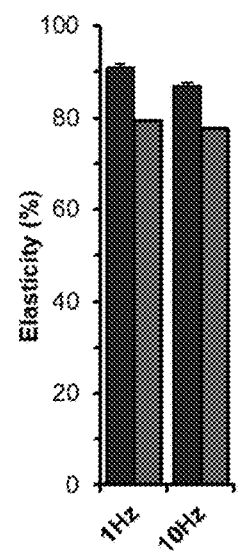
FIG. 20C  FIG. 20D

COMPOSITIONS COMPRISING SILK FIBROIN PARTICLES AND USES THEREOF

CROSS-REFERENCE TO RELATED APPLICATIONS

This application is a continuation of U.S. application Ser. No. 15/799,455, filed Oct. 31, 2017, which claims the benefit under 35 U.S.C. § 119(e) of U.S. provisional application No. 62/415,107 filed Oct. 31, 2016; U.S. provisional application No. 62/482,949 filed Apr. 7, 2017; U.S. provisional application No. 62/488,402 filed Apr. 21, 2017; and U.S. provisional application No. 62/571,670 filed Oct. 12, 2017, the contents of each of which are incorporated herein by reference in their entirety.

TECHNICAL FIELD

Various aspects described herein relate to compositions comprising silk fibroin particles for biomedical applications, e.g., in soft tissue augmentation, repair, and/or tissue regeneration.

BACKGROUND

Biomaterials or synthetic ceramic or polymeric materials have been used as bulking agents for soft tissue augmentation. For example, synthetic ceramic materials such as calcium hydroxylapatite (CaHA) suspended in carboxymethylcellulose have been used as laryngeal implants for correction of vocal fold paralysis or other causes of vocal fold insufficiency. Biomaterials such as collagen or hyaluronic acid have been used as injectable dermal fillers to provide temporary augmentation in a facial tissue or other soft tissue. While these biomaterials provide immediate bulking to the desired area, they degrade fast and thus require repeated treatment every few months. Synthetic polymeric materials (e.g., poly(lactic acid), poly(glycolic acid), and poly(methyl methacrylate)), silicone implants, and saline implants can provide a longer bulking effect, but they are less compatible with soft tissue and their use may cause certain complications including inflammation or scaring. Additionally, injection of these materials may provide a temporary protection from radiation damage by reducing collateral exposure. For example, an injection through the perineum into the anatomical space between the prostate gland and the rectum can provide temporary protection for men with prostate cancer who are undergoing radiotherapy from collateral damage to neighboring tissue, specifically to the rectal tissues.

Accordingly, there is a need to develop novel compositions that are injectable and are more effective for soft tissue augmentation, repair, and/or tissue regeneration. There is also a need for delivery devices to deliver such compositions.

SUMMARY

Embodiments of some aspects described herein are based on, at least in part, discovery of low extrusion force, injectable compositions (e.g., comprising highly-crosslinked hyaluronic acid), which, when administered alone, generally requires high extrusion force for administration by injection. These materials may provide immediate soft tissue bulking, while also acting to promote soft tissue regeneration over time. Thus, these new materials may be used to provide longer-lasting augmentation and/or correct aging or sagging of soft tissue by targeting and promoting tissue regeneration.

For example, while highly-crosslinked hyaluronic acid lasts longer in vivo than that of a low-crosslinked hyaluronic acid, the highly-crosslinked hyaluronic acid, when administered alone, typically exhibits a non-uniform extrusion profile in which the average extrusion force fluctuates during injection, which makes it an undesirable carrier as an injectable material. As described herein, it was discovered that when highly-crosslinked hyaluronic acid is mixed with biocompatible particles, e.g., silk fibroin particles, such a composition not only is more resistant to degradation in vivo than the highly-crosslinked hyaluronic acid alone, but also exhibits shear thinning behavior and can be extruded through a needle more smoothly than highly-crosslinked hyaluronic acid using a lower extrusion force. The hyaluronic acid component may promote immediate soft tissue augmentation, while the biocompatible particles, e.g., silk fibroin particles, may act to regenerate soft tissues, e.g., collagen, and provide a longer-lasting augmentation to the injected area.

Other aspects described herein relate to discovery of compositions comprising silk fibroin particles that (i) are compatible (e.g., biologically and/or mechanically) with soft tissue; (ii) are tunable to provide soft tissue augmentation for appropriate duration (e.g., to provide a long-lasting bulking effect to a soft tissue in need thereof); (iii) are consistently manufactured to a uniform composition and pore size; and (iv) are injectable. The inventors have also discovered compositions comprising silk fibroin particles and hyaluronic acid (e.g., highly crosslinked hyaluronic acid) that are suitable for use in vocal cord medialization or as soft tissue filler materials, e.g. as dermal fillers, as these compositions are biocompatible and extend treatment length (thus reducing the need for frequent re-injection).

The compositions of various aspects described herein can be used for any suitable biomedical applications such as soft tissue augmentation, tissue regeneration and/or ingrowth, cellular scaffolding, and/or wound sealing or clotting. In some embodiments, the compositions described herein can be also configured for drug delivery, e.g., incorporating an active agent into the compositions or silk fibroin particles or carrier as described herein. In some embodiments, the compositions are used as a dermal filler. In some embodiments, the compositions are used as an injectable implant for vocal fold augmentation. Other applications are also possible.

One aspect provided herein relates to an injectable composition comprising crosslinked hyaluronic acid carrier and biocompatible particles, wherein the crosslinked hyaluronic acid has a crosslink density of about 4 mol % to about 30 mol %, and wherein the composition is characterized in that a standard deviation of extrusion force of the composition through a 18-30 (e.g., 18, 19, 20, 21, 22, 23, 24, 25, 26, 27, 28, 29, or 30) gauge needle into air, as determined between about 50% extrusion volume and about 90% extrusion volume, is less than about 40% of an average extrusion force for the corresponding range of the extrusion volume.

Another aspect described herein relates to an injectable composition comprising crosslinked hyaluronic acid carrier and biocompatible particles, wherein the crosslinked hyaluronic acid has a crosslink density of about 4 mol % to about 30 mol %, and wherein the composition is characterized in that a stiffness of the composition under external strain is decreased by at least about 10% as measured between about 10% strain and about 90% strain. In some embodiments, the stiffness of the composition may be decreased by at least about 20%, at least about 30%, at least about 40%, or at least about 50% or more, as measured between about 10% strain and about 90% strain. In some embodiments, the stiffness of the composition is measured when the composition is fully saturated with water.

In some embodiments involving the compositions described above and herein, the biocompatible particles and the crosslinked hyaluronic acid are present in a volume ratio of about 5:95 to about 95:5.

The particles present in the compositions described above and herein may have an average particle size of about 50 μm to about 1000 μm. In some embodiments, the particles may have an average particle of about 60 μm to about 140 μm. In some embodiments, the particles may have an average particle of about 75 μm to about 125 μm. In some embodiments, the particles may have an average particle of about 325 μm to about 450 μm. In some embodiments, the particles may have an average particle of about 355 μm to about 425 μm. In some embodiments, smaller particles or larger particles may be used provided that the average force extruding about 1 mL of the composition through a 18-30 gauge needle into air remains less than 60N (including, e.g., less than 50 N, less than 40 N, or less than 30 N).

In some embodiments involving the compositions described above and herein, where the crosslinked hyaluronic acid and the particles are present in a volume ratio of between about 80% (v/v) particles to about 20% (v/v) HA and about 20% (v/v) particles to about 80% (v/v) HA, the average particle size is between about 200 μm to about 600 μm, and an average force of extruding about 1 mL of the composition through a 18-21 gauge (e.g., 18, 19, 20, 21) needle into air is about 40 N or lower. Alternatively, an average force of extruding about 1 mL of the composition through a needle with a larger gauge size (e.g., 22, 23, 24, 25, 26, 27, 28, 29, 30) is less than about 50 N. In some embodiments, the crosslinked hyaluronic acid and the particles are present in a volume ratio of between about 70:30 to about 30:70, the average particle size is less than about 200 μm, and an average force of extruding about 1 mL of the composition through a 21-30 (e.g., 21, 22, 23, 24, 25, 26, 27, 28, 29, or 30) gauge needle into air is about 40 N or lower. In some embodiments, the crosslinked hyaluronic acid and the particles are present in a volume ratio of about 60% (v/v) particles to about 40% (v/v) HA, the average particle size is between about 325 μm to about 450 μm, and an average force of extruding about 1 mL of the composition through a 21-30 (e.g., 21, 22, 23, 24, 25, 26, 27, 28, 29, or 30) gauge needle into air is about 40 N or lower.

The particles may comprise any biocompatible material that is suitable for soft tissue augmentation and/or drug delivery in vivo. For example, in some embodiments, the particles may comprise a polymer, a silk fibroin, a protein, a peptide, or combinations thereof. In some embodiments, the particles are silk fibroin particles.

The particles present in the composition described above and herein may be porous or non-porous. In some embodiments, the particles are porous. In these embodiments, the porous particles may have a porous structure characterized by interconnected pores having an average pore size of about 1 μm to about 100 μm, or about 20 μm to about 100 μm, or about 1 μm to about 10 μm. In some embodiments, the particles may have pores that are too small to be measured. In some embodiments, the porous particles may have an average porosity of at least about 90% or higher. The porosity of the particles can be carefully controlled during synthesis and/or preparation of the material.

In some embodiments involving the compositions described above and herein, the crosslinked hyaluronic acid can have a concentration of about 1% (w/v) to about 10% (w/v).

The compositions described herein can exist in different states, e.g., in hydrated state or dried state.

Another aspect described herein relates to a novel porous silk fibroin particle that exhibits little or minimal plastic deformation and its pores exhibit substantially rounded morphology. For example, the silk fibroin particle has an average particle size of about 50 μm to about 1000 μm and a porous structure characterized in that:

no more than about 10% of pores within the porous structure have an aspect ratio of about 4.0 or higher; and when a population of the silk fibroin particles is exposed to a compressive strain of at least about 20%, the silk fibroin particles recover at least about 90% of their original volume after release of the compression.

In some embodiments involving the silk fibroin particle described above and herein, the population of the silk fibroin particles may have an elastic modulus of at least about 5 kPa or higher (as measured at a 6-10% axial strain).

In some embodiments involving the silk fibroin particle described above and herein, at least about 40% (including, e.g., at least about 50%, at least about 60%, at least about 70%, or more) of the pores have an aspect ratio of about 1.0 to about 2.0.

In some embodiments involving the silk fibroin particle described above and herein, the pores of the silk fibroin particle have an average aspect ratio of about 1.5 to about 2.5.

In some embodiments involving the silk fibroin particle described above and herein, the pores of the silk fibroin particle have an average circularity of about 0.4 to about 1.0, or about 0.5 to about 0.9, or about 0.6 to about 0.8.

In some embodiments involving the silk fibroin particle described above and herein, the silk fibroin particle can comprise a plasticizer. Examples of a plasticizer include, but are not limited to an alcohol, a sugar, a polyol, or any combinations thereof. In one embodiment, the plasticizer is glycerol.

In some embodiments involving the silk fibroin particle described above and herein, the porous structure of the silk fibroin particle is characterized by interconnected pores having an average pore size of about 1 μm to about 100 μm. In some embodiments, the silk fibroin particle can have an average porosity of at least about 90% or higher.

The silk fibroin particles described herein can exist in different states, e.g., in hydrated state or dried state. In some embodiments involving the silk fibroin particle described above and herein, the silk fibroin particles are lyophilized silk fibroin particles.

In some embodiments involving the silk fibroin particle described above and herein, the silk fibroin particle may comprise residual chemical(s). For example, in some embodiments, the silk fibroin particles (having an average particle size of about 300 microns to 450 microns) can possess no more than 250 micrograms of residual lithium in an about 1 mL dose containing about 40% v/v silk fibroin particles. In some embodiments, the silk fibroin particles (having an average particle size of about 300 microns to 450 microns) can possess no more than 250 micrograms of residual bromide in about 1 mL dose containing about 40% v/v silk fibroin particles. In some embodiments, the silk fibroin particles (having an average particle size of about 300 microns to 450 microns) can possess no more than 30 mg of residual methanol in an about 1 mL dose containing about 40% v/v silk fibroin particles.

In some embodiments involving the porous silk fibroin particle described above and herein, the porous silk fibroin particle may have an average density (when the particles in dried form, e.g., dried and non-compressed silk fibroin particles) of about 0.05 g/mL particles to about 0.2 g/mL particles, or about 0.08 g/mL particles to about 0.15 g/mL particles, or about 0.1 g/mL particles to about 0.13 g/mL particles.

In some embodiments involving the silk fibroin particle described above and herein, the silk fibroin particle may be hydrated, e.g., in an aqueous solution, including, e.g., but not limited to water, saline, and/or a buffered solution such as a phosphate buffered solution. In these embodiments, the hydrated silk fibroin particle may have an average density (when the particles are in hydrated form, e.g., hydrated and non-compressed silk fibroin particles) of about 0.4 g/mL particles to about 1.0 g/mL particles, or about 0.6 g/mL particles to about 0.8 g/mL particles.

In some embodiments involving the porous silk fibroin particle described above and herein, the porous structure may be characterized by interconnected pores having an average circle equivalent diameter of about 25 µm to about 55 µm, or about 30 µm to about 50 µm.

In some embodiments involving the porous silk fibroin particle described above and herein, the porous structure may be characterized by no more than 10% (including, e.g., no more than about 9%, no more than about 8%, no more than about 7%, no more than about 6%, no more than about 5% or lower) of interconnected pores having a circle equivalent diameter of about 100 µm or greater.

In some embodiments involving the porous silk fibroin particle described above and herein, the porous structure may be characterized by interconnected pores having an average circle equivalent diameter of about 25 µm to about 55 µm, or about 30 µm to about 50 µm.

In some embodiments involving the porous silk fibroin particle described above and herein, the porous structure may be characterized by no more than 10% (including, e.g., no more than about 9%, no more than about 8%, no more than about 7%, no more than about 6%, no more than about 5% or lower) of interconnected pores having a circle equivalent diameter of about 100 µm or greater.

In some embodiments involving the porous silk fibroin particle described above and herein, the porous structure may be characterized by at least about 60% (including, e.g., at least about 70%, at least about 80%, at least about 90% or more) of interconnected pores having a circle equivalent diameter of about 75 µm or lower.

In some embodiments involving the porous silk fibroin particle described above and herein, the porous structure may be characterized by at least about 80% (including, e.g., at least about 85%, at least about 90%, at least about 95% or more and up to 100%) of interconnected pores having a circle equivalent diameter of about 15 µm to about 100 µm.

Also provided herein are compositions comprising one or more silk fibroin particles as described above and herein and a carrier. In some embodiments, the silk fibroin particles and the carrier are in a volume ratio of about 5:95 to about 95:5. In some embodiments, the silk fibroin particles are substantially monodispersed.

The carrier can comprise a single carrier or a mixture of two or more carriers (e.g., a first carrier and a second carrier of the same different weight average molecular weights). Non-limiting examples of the carrier include glycosaminoglycan polymers (e.g., hyaluronic acid, crosslinked hyaluronic acid, keratan sulfate, chondroitin sulfate, and/or heparin), extracellular matrix protein polymers (e.g., collagen, elastin, and/or fibronectin), polysaccharides (e.g., cellulose), fibrous protein polymers, a fat material (e.g., derived from a lipoaspirate), and a combination of two or more thereof.

In some embodiments involving the compositions described above and herein, the carrier comprises non-crosslinked or crosslinked hyaluronic acid polymer. In some embodiments, the hyaluronic acid polymer may have a weight average molecular weight of about 200 kDa to about 5 MDa. In some embodiments where there are at least two carriers, the first carrier may comprise hyaluronic acid with a weight average molecular weight of about 200 kDa to about 1 MDa, and optionally wherein the second carrier comprises hyaluronic acid with a weight average molecular weight of about 200 kDa to about 5 MDa. In some embodiments, the hyaluronic acid polymer may have a concentration of about 0.1% w/v to 10% w/v.

In some embodiments involving the compositions described above and herein, where the carrier comprises crosslinked hyaluronic acid, the composition may comprise residual chemical(s). For example, in some embodiments, about 1 mL dose of the composition comprising 40% v/v silk fibroin particles (having an average particle size of about 300 microns to 450 microns) and 60% v/v hyaluronic acid can possess no more than 250 micrograms of residual lithium. In some embodiments, about 1 mL dose of the composition comprising silk fibroin particles (having an average particle size of about 300 microns to 450 microns) can possess no more than 250 micrograms of residual bromide. In some embodiments, about 1 mL dose of the composition comprising 40% v/v silk fibroin particles (having an average particle size of about 300 microns to 450 microns) and 60% v/v hyaluronic acid can possess no more than 30 mg of residual methanol. In some embodiments, the crosslinked hyaluronic acid in the composition can comprise no more than 2 ppm residual crosslinking agent (e.g., 1,4-butanediol diglycidyl ether (BDDE)).

The average particle size of the silk fibroin particles in some embodiments involving the compositions described herein may be selected to suit the need of each application. For example, smaller average particle size may be desirable for treatment of fine lines and wrinkles, while larger average particle size may be more suitable for vocal fold augmentation or even large volume reconstruction (e.g., breast reconstruction). Accordingly, in some embodiments, the silk fibroin particles have an average particle size of about 250 µm to about 450 µm, or about 300 µm to about 400 µm. In alternative embodiments, the silk fibroin particles may have an average particle size of about 400 µm to about 600 µm or about 450 µm to about 550 µm. In some embodiments, the silk fibroin particles may have an average particle size of about 50 µm to about 200 µm. In some embodiments, the silk fibroin may have an average particle size of about 75 µm to about 125 µm. In some embodiments involving the compositions described above and herein, a plurality of the particles (e.g., silk fibroin particles in a carrier matrix) may be delivered through a tube having an inside diameter that allows particles to be delivered at a low extrusion force. In some embodiments, the tube may have an inside diameter of at least about 0.5 mm, at least about 0.7 mm, at least about 0.8 mm, at least about 0.85 mm, at least about 0.9 mm, at least about 0.95 mm, at least about 1 mm, at least about 1.05 mm, at least about 1.1 mm, at least about 1.15 mm, or at least about 1.2 mm. In some embodiments, the tube may have an inside diameter of less than or equal to about 1.5 mm, less than or equal to about 1.3 mm, less than or equal to about 1.2 mm, less than or equal to about 1.15 mm, less than or equal to about 1.1 mm, less than or equal to about 1.05 mm, less than or equal to about 1 mm, less than or equal to about 0.95 mm, less than or equal to about 0.9 mm, or less than or equal to about 0.8 mm. Combinations of the above-referenced ranges are also possible. For example, in some embodiments, the tube may have an inside diameter of about 0.5 mm to about 1.5 mm, or about 0.7 mm to about 1.3 mm, or about 0.9 mm to about 1.1 mm.

The composition may be characterized in that a standard deviation of extrusion force of the composition through a 18-30 gauge needle into air, as determined between about 50% extrusion volume and about 90% extrusion volume, is less than about 40%, less than about 30%, less than about 20%, or less than about 10%, of an average extrusion force for the corresponding range of the extrusion volume. The needle may be designed to further reduce the extrusion force of the composition.

In some embodiments involving the compositions described above and herein, the composition is characterized in that stiffness of the composition is decreased by at least about 10%, at least about 20%, at least about 30%, at least about 40%, or at least about 50% as measured between about 10% strain and about 90% strain.

In some embodiments involving the compositions described above and herein, the composition is characterized in that an average force of extruding about 1 mL of the composition through an 18-30 gauge needle into air is about 5 N to about 40 N.

In some embodiments involving the compositions of any aspects described above and herein, the injectable composition may be pre-loaded in a syringe. In some embodiments, the syringe is coupled to a tube via a handle so that the composition may be injected through the tube. This tube may further be coupled to an endoscope or laryngoscope during a procedure. The needle may be a hollow needle that is attached to the tube. The tube may be positioned within and moveable within an outer sheath tube. The needle may be moveable between a retracted position within the outer sheath tube and an extended position in which the needle tip is outside the outer sheath tube to control injection of the compositions. In some embodiments, the outer sheath tube, with the needle and inner tube inside the outer sheath tube, is inserted into the channel of an endoscope. The delivery device may include a handle that can be actuated by a user to move the inner tube distally relative to the outer tube sheath, thereby advancing the needle distally through the outer sheath tube toward an extended position in which the needle tip is exposed for injection of the compositions into a tissue or region of interest.

In some embodiments involving the compositions of any aspects described above and herein, the compositions may include any suitable inactive ingredient included in U.S. Food & Drug Administration (FDA)'s database for Generally Recognized as Safe (GRAS) substances, which is accessible online at accessdata.fda.gov/scripts/fdcc/?set=SCOGS.

The compositions and injectable compositions described above and herein can be implanted or injected to a subject in need thereof. For example, the compositions and injectable compositions described herein can be used for treating a target site in a soft tissue of a subject, e.g., for soft tissue augmentation and/or ingrowth. Accordingly, methods for augmenting or regenerating different soft tissues are provided herein. In some embodiments, such a method comprises injecting to a target site (e.g., a site of defect or a void) in a soft tissue a composition comprising silk fibroin particles of any embodiments or aspects described herein and a carrier, or a composition as described above or herein. The silk particles provide a bulking effect to the soft tissue by maintaining up to about 80% (including, e.g., up to about 50%, up to about 60%, up to about 70% or up to about 80%) of the particles' original volume for at least about 3 months or longer after the injection. In some embodiments, the composition can be injected through an 18-30 needle using an average extrusion force of no more than 60 N, including, e.g., no more than 50 N, no more than 40 N, or lower.

The methods described herein and/or compositions described herein can be applied to treat different soft tissues for small volume bulking or large volume bulking applications, including but not limited to, a skin tissue, e.g., a facial skin tissue, a bladder tissue, a cervical tissue, a vocal fold tissue, a breast tissue, or a buttock tissue. For example, in some embodiments, particle size of the particles used in the methods and/or compositions described herein can be tuned to meet requirements of the volume bulking site. Additionally or alternatively, the injection volume of the compositions described herein can also be tuned to meet requirements of the volume bulking site. For example, in some embodiments for large volume bulking applications (e.g., but not limited to breast reconstruction, buttock reconstruction, and treatment of lipodystrophy), the composition can be injected in an amount of at least about 3 cm$^3$ or more. In these embodiments, the composition can be injected in an amount that is sufficient to fill and conform to the shape of a void at the target site. In these embodiments, the method may optionally further comprise allowing cells from tissue surrounding the target site to interact with the silk fibroin particles, wherein the silk fibroin particles maintain at least about 30% of their volume for at least about 9 months or longer after the injection, thereby augmenting or regenerating the soft tissue. In some embodiments, the silk fibroin particles maintain at least about 30% of their volume for at least about 12 months or longer after the injection.

In some embodiments involving large volume bulking applications, the composition is injected through a 18-21 gauge needle using an average extrusion force of no more than 60 N, including, e.g., no more than 50 N, no more than 40 N, or lower.

In other embodiments for small volume bulking applications, the composition may be injected with a 21-30 gauge needle using an average extrusion force of no more than about 30 N. Examples of small volume bulking applications include, but are not limited to a dermal filler for skin tissue (e.g., treatment of facial skin tissue having a facial line, or wrinkle, or a scar to be filled), bulking of urethra (e.g., treatment for stress-urinary incontinence), bulking of cervical tissue (e.g., treatment for cervical insufficiency), and bulking of vocal fold (e.g., correction of vocal fold paralysis or other causes of vocal fold insufficiency). In these embodiments, the composition can be injected in an amount of about 3 cm$^3$ or less.

In some aspects, methods of augmenting a vocal fold in a subject in need thereof are also provided herein. For example, in one aspect, the method comprises injecting to a target site (e.g., a glottal gap) in the vocal fold of the subject a composition comprising a crosslinked matrix carrier and porous silk fibroin particles, wherein the composition is characterized in that:
  (i) the crosslinked matrix carrier has a crosslink density of about 4 mol % to about 30 mol %;
  (ii) the porous silk fibroin particles and the crosslinked matrix carrier are present in a volume ratio of about 80% (v/v) silk fibroin particles: about 20% (v/v) HA, to about 20% (v/v) silk fibroin particles: about 80% (v/v) HA; and (iii) a standard deviation of extrusion force of the composition through a 18-21 gauge needle into air, as determined between about 50% extrusion volume and about 90% extrusion volume, is less than about 40% (including, e.g., less than about 30%, less than about 20% or lower) of an average extrusion force for the corresponding range of the extrusion volume.

In some embodiments, the porous silk fibroin particles and the crosslinked matrix carrier are present in a volume ratio of about 60% (v/v) silk fibroin particles: about 40% (v/v) HA.

In another aspect, the method comprises injecting to a target site (e.g., a glottal gap) in the vocal fold of the subject a composition comprising a crosslinked matrix carrier and porous silk fibroin particles, wherein the composition is characterized in that:

(i) the crosslinked matrix carrier has a crosslink density of about 4 mol % to about 30 mol %;

(ii) the porous silk fibroin particles and the crosslinked matrix carrier are present in a volume ratio of about 60:40 to about 20:80; and (iii) a stiffness of the composition is decreased by at least about 10% (including, e.g., at least about 20%, at least about 30%, at least about 40%, at least about 50%, at least about 60%, or more) as measured between about 10% strain and about 90% strain.

In some embodiments, the stiffness of the composition is measured when the composition is in a fully water saturated state.

In any aspects described herein involving methods for augmenting vocal folds, the porous silk fibroin particles provide bulking effect to the vocal fold by maintaining up to about 80% (including, e.g., up to about 50%, up to about 60%, up to about 70% or up to about 80%) of the particles' original volume for at least about 3 months or longer after the injection.

In some embodiments involving vocal fold augmentation, the crosslinked matrix carrier comprises crosslinked glycosaminoglycan polymers (e.g., crosslinked hyaluronic acid), crosslinked extracellular matrix protein polymers (e.g., crosslinked collagen, crosslinked elastin, and/or crosslinked fibronectin), crosslinked polysaccharides (e.g., crosslinked cellulose), crosslinked fibrous protein polymers, and a combination of two or more thereof. In some embodiments, the crosslinked matrix carrier (e.g., crosslinked hyaluronic acid) has a concentration of about 0.1% w/v to 10% w/v.

Any porous silk fibroin particles described herein can be used for the methods described herein for vocal fold augmentation. In some embodiments, the porous silk fibroin particles can comprise a plasticizer, examples of which include, but are not limited to an alcohol, a sugar, and/or a polyol (e.g., glycerol). In some embodiments, the porous silk fibroin particles have an average particle size of about 50 μm to about 500 μm, or about 300 μm to about 450 μm. In some embodiments, the porous silk fibroin particles have a porous structure characterized by interconnected pores having an average pore size of about 20 μm to about 100 μm. In some embodiments, the porous silk fibroin particles have an average porosity of at least 90%. In some embodiments, the porous silk fibroin particles and the crosslinked matrix carrier are present in a volume ratio of about 30:70 to about 70:30 or about 30:70 to about 50:50.

In some embodiments involving the compositions and/or methods described above and herein, the subject in need thereof has vocal cord paresis, paralysis, or glottic insufficiency. In some embodiments, the injection can comprise trans-oral injection, trans-nasal injection, percutaneous injection, or thyroid injection. In some embodiments, the injection is trans-oral or trans-nasal injection, which, for example, may be performed with a device for delivering the composition to the site of defect in the vocal fold.

According to one aspect, a method of administering a composition to a subject is provided. The method can comprise, in some embodiments, inserting a needle and a catheter of a delivery device into the subject, the needle being coupled to and in fluid communication with the catheter. The method may also include moving the needle toward an injection site of the subject. The method may also include actuating a handle of the delivery device to move the needle from a retracted position to an extended position, where actuating the handle comprises sliding a first portion of the handle relative to a second portion of the handle from a first discrete position to a second discrete position. The method may also include inserting the needle into the injection site and delivering a composition comprising silk fibroin particles through the catheter and the needle into the injection site.

According to another aspect, a method of administering a composition to a subject is provided. The method can comprise, in some embodiments, inserting a needle and a catheter trans-orally or trans-nasally into the subject, the needle being coupled to and in fluid communication with the catheter. The method may also include moving the needle toward a vocal fold of the subject, inserting the needle into the vocal fold and delivering a composition comprising particles through the catheter and the needle into the vocal fold.

According to yet another aspect, a device for delivering a composition to a subject is provided. The device can comprise, in some embodiments, a hollow needle, an outer sheath tube and an inner tube. The inner tube and the needle may be movable within the outer sheath tube, a proximal end of the inner tube being configured to couple to a container for holding composition. A distal end of the inner tube may be coupled to and in fluid communication with the needle. The device may also include a handle coupled to the outer sheath tube. The handle may be configured to couple the outer sheath tube to the container. A length of the inner tube from the proximal end to the distal end may be 20 cm to 60 cm.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention.

FIG. 3A shows that hydrogels are generally more suitable for spreading because they are easily deformed, e.g., due to the nanoparticle sliding effect. FIG. 3B shows that the silk fibroin foam or sponge are generally more suitable for elasticity, control, and maintenance of a fixed particle size. In one set of the embodiments described herein, the silk fibroin particles are produced from a silk fibroin bulk foam or sponge described in the International Patent Publication No. WO 2016/145281 entitled "Shape Memory Silk Materials," which claims the benefit of U.S. Provisional Application No. 62/132,429 filed Mar. 12, 2015, the contents of each of which is incorporated herein.

FIGS. 4A-4C are scanning electron microscopic (SEM) images of freeze-dried silk fibroin materials without glycerol. FIG. 4A shows the entire cross-section of the silk fibroin bulk material. FIG. 4B shows a zoomed-in cross section of the silk fibroin bulk material. FIG. 4C depicts silk fibroin particles produced from the silk fibroin bulk material of FIG. 4A or 4B.

FIGS. 5A-5C are scanning electron microscopic (SEM) images of freeze-dried silk fibroin materials with glycerol. FIG. 5A shows the entire cross-section of the silk fibroin bulk material. FIG. 5B shows a zoomed-in cross section of the silk fibroin bulk material. FIG. 5C depicts silk fibroin particles produced from the silk fibroin bulk material of FIG. 5A or 5B. The silk fibroin bulk materials in FIGS. 4A-4C and FIGS. 5A-5C were produced from a silk fibroin solution at a concentration of about 10% w/v. The silk fibroin solution of FIGS. 5A-5C has glycerol at a concentration of about 3.33% w/w. The silk fibroin solution (with or without glycerol) was subjected to freeze-drying to fabricate a sponge-like material, which was then immersed in an alcohol (e.g., methanol) to induce β-sheet formation. As compared to the silk fibroin material of FIG. 5B (comprising glycerol), the silk fibroin material of FIG. 4B (without glycerol) contained a combination of porous silk fibroin materials and larger non-porous crystals, which could be attributed to irregularities in freezing. Without wishing to be bound by theory, glycerol may delay or slow freezing such that silk fibroin is not exposed to extreme temperatures in such a rapid timeframe.

FIG. 7A: force of extruding lipoaspirate alone through a 16G needle. FIG. 7B: force of extruding a mixture of 30% silk fibroin particles and lipoaspirate through a 16G needle. FIG. 7C: average extrusion forces of indicated compositions using a 1 mL syringe, 14G needle system. FIG. 7D: average extrusion forces of indicated compositions using a 1 mL syringe, 16G needle system. The percentages associated with silk fibroin particles in the figures correlate to the volume ratio of silk fibroin particles and human lipoaspirate in the mixture. For example, 30% silk refers to a volume ratio of the silk fibroin particles to lipoaspirate being 30:70. The silk fibroin particles were extruded through 14G or 16G needles without clogging, and the rate of compressing the plunger of the syringe was 5.5 mm/s, which corresponds to extrusion of 1 mL of material in 10 seconds.

FIG. 8A: force of extruding HA alone through a 14G needle. FIG. 8B: force of extruding HA alone through a 16G needle. FIG. 8C: force of extruding a mixture of silk fibroin particles and HA in a volume ratio of 50:50 through a 14G needle. The concentration of HA was about 4% w/v. FIG. 8D: force of extruding a mixture of silk fibroin particles and HA in a volume ratio of 50:50 through a 16G needle. The concentration of HA was about 4% w/v. The percentages associated with silk fibroin particles in the figures correlate to the volume ratio of silk fibroin particles and non-crosslinked HA in the mixture. For example, 50% particles refers to a volume ratio of the silk fibroin particles to 4% non-crosslinked HA being 50:50. The silk fibroin particles were extruded through 14G needles without no or no incidence of clogging. The rate of compressing the plunger of the syringe was 5.5 mm/s, which corresponds to extrusion of 1 mL of material in 10 seconds.

FIG. 9A is a SEM image of porous silk fibroin particles according to one embodiment described herein. Average particle diameter is 500-600 μm. Scale bar is 200 μm. FIG. 9B is a graph showing pore size distribution of the porous silk fibroin sponge by mercury intrusion porosimetry. Lyophilized silk fibroin sponge have an average pore diameter of 40-50 μm (e.g., 44 μm), with 93% total porosity. Pores as small as 4 microns in diameter or as large as 200 microns in diameter were also detected, but at very low frequency. "-dV/dlog(D)" is a measure of infiltrated mercury into silk fibroin pores. It is contemplated that particles reduced from the silk fibroin sponge have comparable pore size. FIG. 9C shows extrusion forces of formulations comprising prior art particles (e.g., HFIP, salt-leached porous particles, and aqueous derived non-porous particles) at 20% and 50% v/v concentrations in a silk-based gel carrier. The formulations were extruded through 1 mL syringes with a 14 or 16G needle. The full 1 mL volume was unable to be extruded due to frequent clogging at the needle. Clogging is denoted by extrusion forces exceeding 100N. FIG. 9D shows compositions comprising aqueous—derived porous silk fibroin particles according to some embodiments described herein in lipoaspirate. Such formulations were shown to be injectable via 1 mL syringes with a 14 or 16G needle when mixed with lipoaspirate at volume concentrations up to 50% v/v. Compared to lipoaspirate only (darkest curve), silk particle/lipoaspirate mixtures were extruded at similar forces within the optimal range of 15-30N.

FIGS. 13A-13F show additional experimental data showing aspect ratios of pores present in the silk fibroin sponge produced by the method described in the International Patent Publication No. WO 2016/145281. The aspect ratios were determined from SEM images of cross sections of silk fibroin sponges. FIGS. 13A and 13D are SEM images of cross-sections of the silk fibroin sponges. Contrast was manipulated using image analysis tool such that silk fibroin are presented as white pixels and pores are presented as black pixels. FIGS. 13B and 13E show the outline of the pores by ellipses fit. FIGS. 13C and 13F are distribution graphs showing aspect ratios of the pores.

FIGS. 14A and 14D are SEM images of cross-sections of the silk fibroin sponges. Contrast was manipulated using image analysis tool such that silk fibroin are presented as white pixels and pores are presented as black pixels. FIGS. 14B and 14E show the outline of the pores by ellipses fit. FIGS. 14C and 14F are distribution graphs showing aspect ratios of the pores.

FIG. 15A shows stress-strain profile of the silk fibroin sponges in hydrated state. The elastic modulus (at 6-10% axial strain) of the silk fibroin sponges was found to be 72.4±5.2 kPa. FIG. 15B shows compressive recovery for the silk fibroin sponges in hydrated state. FIG. 15C shows the compressive mechanics measured from a population of silk fibroin particles according to some embodiments described herein.

FIG. 16A: extrusion of crosslinked HA gel carrier only, FIG. 16B: extrusion of crosslinked HA with silk fibroin particles.

FIG. 17A: extrusion of the composition in which crosslinked HA was prepared with a crosslinking agent (CA), e.g., BDDE, and hyaluronic acid disaccharides (HAD) in a CA:HAD mole ratio of about 22%. FIG. 17B: extrusion of the composition in which crosslinked HA was prepared with a crosslinking agent (CA), e.g., BDDE, and hyaluronic acid disaccharides (HAD) in a CA:HAD mole ratio of about 30%.

FIGS. 20A-20D is a set of graphs showing rheometry data describing the shear properties for compositions comprising a crosslinked HA carrier in combination with silk fibroin particles according to one set of embodiments described herein. The silk fibroin particles were about 355 to about 425 microns in size, and 40% v/v silk fibroin particles were mixed with crosslinked HA gel. FIG. 20A: storage modulus (G') and loss modulus (G") of the composition were measured as a function of oscillatory frequency sweeps from 0.1-10 Hz. FIG. 20B: dynamic viscosity was measured as a function of oscillatory frequency sweeps from 0.1-10 Hz. FIG. 20C: storage modulus (G') and loss modulus (G") of the composition were measured as a function of strain from 0.1-100. FIG. 20D: elasticity of the composition was measured as a function of frequencies of 1 and 10 Hz.

DETAILED DESCRIPTION OF EXEMPLARY EMBODIMENTS

Figure 1:
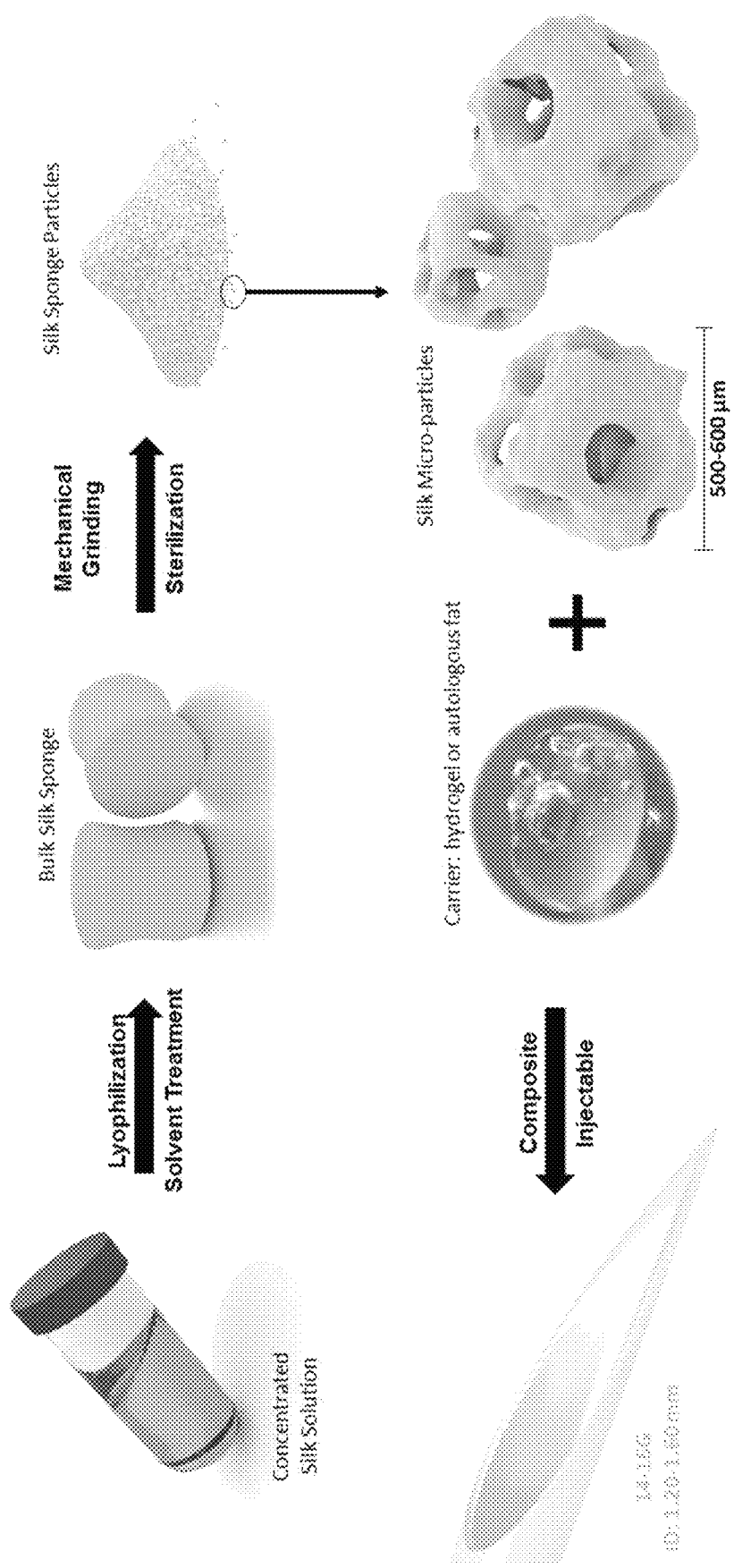
FIG. 1 is a schematic representation of an exemplary method for making silk fibroin particles according to one set of embodiments described herein.

Some aspects of the present disclosure provide injectable compositions comprising a highly crosslinked matrix carrier (e.g., highly crosslinked hyaluronic acid, but not limited to such) and biocompatible particles dispersed therein, methods of manufacturing and using such compositions, and delivery devices and kits for applying such compositions. Such compositions are generally stiffer and more resistant to in vivo degradation than those comprising a low-crosslinked matrix carrier, yet these compositions are injectable through a needle with smoother extrusion profiles than those observed for the same concentration of highly-crosslinked carrier alone without particles (e.g., highly crosslinked hyaluronic acid alone).

In some aspects, the present disclosure provides novel silk fibroin particles and compositions comprising the same, and a carrier such that (i) the particles and/or compositions exhibit little or minimal plastic deformation; (ii) the particles and/or compositions are biocompatible with cells and/or tissues (e.g., soft tissues) with minimal complications such as formation of granulomas at tissue injection site; (iii) the particles and/or compositions are tunable to match as close as possible at least one or more mechanical properties (e.g., elasticity) of tissue to be treated; (iv) the particles and/or compositions are tunable to degrade at a rate appropriate for a particular biomedical application (e.g., are tunable to degrade at a rate that is slow enough to provide a long lasting bulking effect, e.g., can fill up wrinkles for cosmetic purposes or bulk vocal cord so as to minimize frequent treatment); and (v) the particles and/or compositions are injectable with low extrusion forces. The compositions described herein can be adjusted for any suitable biomedical applications such as soft tissue augmentation and/or regeneration (e.g., breast reconstruction, lumpectomy reconstruction, correction of glottic (vocal cord) insufficiency, treatment of urinary incontinence, injectable fillers and dermal fillers, e.g., for wrinkles), wound sealing or clotting, and/or drug delivery such as controlled release applications. Methods of using these silk fibroin particles and/or compositions as well as delivery devices and kits for applying such compositions are also provided herein.

Appropriate combination of silk fibroin particles and a carrier, as described herein, provides advantages of material and degradation tunability of the compositions herein as well as clinically acceptable extrusion force of the compositions. For example, addition of silk fibroin particles prolongs a bulking effect of a composition injected into a tissue, without increasing the concentration and/or crosslink density of the carrier to achieve the same effect. Generally, increasing the concentration and/or crosslink density of a carrier would result in an undesirable increase in the extrusion force during the course of injection. However, the compositions described herein may be formulated to have favorable extrusion characteristics while also providing comparable soft tissue bulking. Accordingly, the compositions described herein may provide desirable material and mechanical properties without adversely affecting their injectability.

Injectable Compositions Comprising a Crosslinked Matrix Carrier and Particles

One aspect provided herein relates to an injectable composition comprising a matrix carrier (e.g., crosslinked or non-crosslinked) and particles, wherein a standard deviation of extrusion force of the composition through a 18-30 (e.g., 18, 19, 20, 21, 22, 23, 24, 25, 26, 27, 28, 29, or 30) gauge needle into air, as determined between about 50% extrusion volume and about 90% extrusion volume, is at least about 30% lower (including, e.g., at least about 20% lower, at least about 10% lower, at least about 5% lower, at least about 1% lower) than a standard deviation of extrusion force of a corresponding matrix carrier alone (e.g., without particles) through a needle of the same gauge. In some embodiments, the matrix carrier is crosslinked.

Another aspect provided herein relates to an injectable composition comprising a matrix carrier (e.g., crosslinked or non-crosslinked) and particles, wherein a reduction in stiffness of the composition as measured between about 10% strain and about 90% strain is at least about 10% larger, at least about 20% larger, at least about 30% larger, at least about 40% larger, at least about 50% larger (including, e.g., at least about 60% larger, at least about 70% larger, at least about 80% larger, at least about 90% larger, at least about 1.1-fold larger, at least about 1.5-fold larger, at least about 2-fold larger, at least about 3-fold larger, at least about 4-folder larger) than a change in stiffness of the corresponding matrix carrier alone (e.g., without particles) as measured between the about 10% strain and about 90% strain. In some embodiments, a reduction in stiffness of the composition as measured between about 10% strain and about 90% strain is about 5-fold or less, about 4-fold or less, about 3-fold or less, about 2-fold or less, or about 1-fold or less) than a change in stiffness of the corresponding matrix carrier alone (e.g., without particles) as measured between the about 10% strain and about 90% strain. Combinations of the above-referenced ranges are also possible. In some embodiments, the matrix carrier is crosslinked.

Figure 16A:
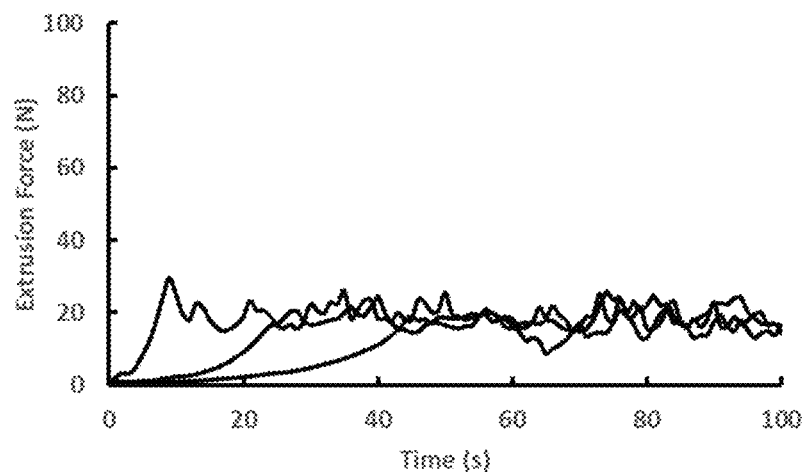
FIGS. 16A-16B is a set of graphs showing extrusion force data using a 1 mL syringe (21 gauge needle) for compositions comprising a crosslinked HA carrier, alone or in combination with silk fibroin particles, according to one set of embodiments described herein. The silk fibroin particles were about 355 to about 425 microns in diameter, and were about 40% v/v when mixed with crosslinked HA gel.

The inventors unexpectedly discovered that addition of silk fibroin particles to a viscous carrier, e.g., a crosslinked matrix carrier such as crosslinked hyaluronic acid, improves the smoothness of the extrusion profile, compared to the viscous carrier without the silk fibroin particles, all other factors being equal. In addition, the inventors discovered that such compositions provide the same or similar immediate soft tissue bulking and are easily sculpted, but are longer-lasting and promote regeneration of soft tissue into the porous silk fibroin particles while the carrier slowly degrades. For example, Example 9 shows that when silk fibroin particles were combined with a highly crosslinked hyaluronic acid carrier, the addition of silk fibroin particles improved smoothness of the extrusion force profile. The crosslinked hyaluronic acid (HA) carrier by itself typically has an extrusion profile that is not as smooth, e.g., the extrusion force fluctuates over the course of the injection as shown in FIG. 16A. Example 10 shows that the addition of silk fibroin particles to a crosslinked HA carrier reduces the strain required to cause the composition to yield to flow, while the crosslinked HA alone is more strain-resistant and does not yield as early as the silk fibroin/crosslinked HA composition. The strain-induced yielding property observed in the silk fibroin/crosslinked HA composition may aid in the ability of the material to naturally spread better once implanted or injected, conforming to difficult geometries, e.g., of a void space or wound, better than crosslinked HA gels alone. It may also allow the material to flow better, e.g., smoother (compared to crosslinked HA carrier without silk fibroin particles), when extruded through, for example, a 21 gauge needle, resulting in a smoother extrusion profile. It was also observed that crosslinked HA gels alone result in tough gels that are tacky, but do not cohere well to itself in a bulk volume (e.g., 1 cc extruded). The compositions comprising crosslinked HA and silk fibroin particles according to some embodiments described herein, on the other hand, exhibit high cohesion and may be sculpted easily. Accordingly, by addition of an appropriate amount of silk fibroin particles (e.g., a specific volume ratio of silk fibroin particles to a carrier as described herein, e.g., about 30% v/v to about 60% v/v silk fibroin particles), a viscous carrier with a high crosslink density (e.g., highly crosslinked HA) can be used to benefit from longer in vivo lifetime while maintaining a smooth extrusion force profile that is suitable for injection.

The viscous carrier may be crosslinked or non-crosslinked. In some embodiments, the viscous carrier is a crosslinked matrix carrier. The crosslinked matrix carrier may comprise crosslinked glycosaminoglycan polymers (e.g., crosslinked hyaluronic acid), crosslinked extracellular matrix protein polymers (e.g., crosslinked collagen, crosslinked elastin, and/or crosslinked fibronectin), crosslinked polysaccharides (e.g., crosslinked cellulose), crosslinked fibrous protein polymers, or a combination of two or more thereof. In one set of embodiments of the compositions or injectable compositions described herein, the crosslinked matrix carrier is crosslinked hyaluronic acid.

In some embodiments, the viscous carrier is a non-crosslinked (interchangeably used with "uncrosslinked") matrix carrier. Examples of uncrosslinked matrix carriers include, but are not limited to HA, uncrosslinked chondroitin sulfate polymers, uncrosslinked dermatan sulfate polymers, uncrosslinked keratan sulfate polymers, uncrosslinked heparan polymers, uncrosslinked heparan sulfate polymers, uncrosslinked hyaluronan polymers, uncrosslinked glycosaminoglycan polymers, uncrosslinked elastin and/or fibronectin, and any combinations thereof.

Accordingly, one aspect relates to an injectable composition comprising crosslinked hyaluronic acid (HA) and particles, wherein the composition is characterized in that a standard deviation of extrusion force of the composition through a 18-30 (e.g., 18, 19, 20, 21, 22, 23, 24, 25, 26, 27, 28, 29, or 30) gauge needle into air, as determined between about 50% extrusion volume and about 90% extrusion volume, is less than about 40% of an average extrusion force for the corresponding range of the extrusion volume.

Figure 16B:
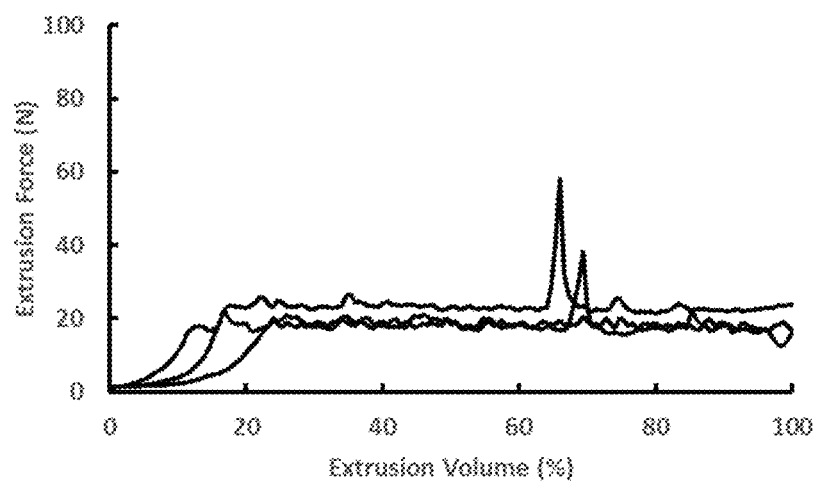

In some embodiments of any compositions or injectable compositions described herein (e.g., including a crosslinked matrix carrier and particles), the standard deviation of extrusion force of the composition through a 18-30 (e.g., 18, 19, 20, 21, 22, 23, 24, 25, 26, 27, 28, 29, or 30) gauge needle into air, as determined between about 50% extrusion volume and about 90% extrusion volume, is less than about 35%, less than about 30%, less than about 25%, less than about 20%, less than about 15%, less than about 10%, less than about 5%, or less than about 1%, of an average extrusion force for the corresponding range of the extrusion volume (i.e., about 50%-about 90% extrusion volume). In some embodiments, the standard deviation of extrusion force of the composition through a 18-30 (e.g., 18, 19, 20, 21, 22, 23, 24, 25, 26, 27, 28, 29, or 30) gauge needle into air, as determined between about 50% extrusion volume and about 90% extrusion volume, is at least about 0.1%, at least about 0.5%, at least about 1%, at least about 5%, at least about 10%, at least about 15%, or at least about 20%, of an average extrusion force for the corresponding range of the extrusion volume (i.e., about 50%-about 90% extrusion volume). Combinations of the above-referenced ranges are also possible. For example, in some embodiments, the standard deviation of extrusion force of the composition through a 18-30 (e.g., 18, 19, 20, 21, 22, 23, 24, 25, 26, 27, 28, 29, or 30) gauge needle into air, as determined between about 50% extrusion volume and about 90% extrusion volume, is about 0.1% to about 40%, or about 1% to about 20%, or about 1% to about 15%, of an average extrusion force for the corresponding range of the extrusion volume (i.e., about 50%-about 90% extrusion volume). For example, as shown in FIG. 16B, the standard deviation of extrusion force of the composition (according to one set of embodiments described herein) through a 21 gauge needle into air, as determined between about 50% extrusion volume and about 90% extrusion volume, is about 1% to about 15%, of an average extrusion force for the corresponding range of the extrusion volume (i.e., about 50%-about 90% extrusion volume). By contrast, as shown in FIG. 16A for crosslinked HA gel alone, the standard deviation of extrusion force through a 21 gauge needle into air, as determined between about 50% extrusion volume and about 90% extrusion volume, is at least about 10% or higher of an average extrusion force for the corresponding range of the extrusion volume (i.e., about 50%-about 90% extrusion volume).

Also provided herein is an injectable composition cotruprising crosslinked HA and particles, wherein the composition is characterized in that a stiffness of the composition decreases with respect to increasing strain. For instance, the injectable composition comprising crosslinked HA and particles may be characterized in that a stiffness of the composition is decreased by at least about 10% as measured within a pre-determined range of strain (e.g., about 0.1% strain to about 1% strain, or about 0.1% strain to about 10% strain, or about 0.1% strain to about 100% strain, or about 10% strain and about 90% strain). The stiffness values may be measured at the endpoints of the pre-determine range (e.g., at about 0.1% strain and at about 100% strain for a pre-determined range of about 0.1% strain and about 100% strain) and the percent difference in the stiffness at these two points can be used for the calculation, based on the value of stiffness at the lowest % strain (e.g., 0.1% strain). The stiffness of the composition may be determined by shear storage modulus (G') of the composition.

In some embodiments of any compositions or injectable compositions described herein (e.g., including a crosslinked matrix carrier and particles), the stiffness of the composition is decreased by at least about 15%, at least about 20%, at least about 30%, at least about 40%, at least about 50%, at least about 60%, at least about 70%, at least about 80%, at least about 90%, or higher, as measured between about 0.1% strain and about 1% strain. In some embodiments, the stiffness of the composition is decreased by no more than about 95%, no more than about 90%, no more than about 80%, no more than about 70%, no more than about 60%, no more than about 50%, no more than about 40%, no more than about 30%, or no more than about 20%, as measured between about 0.1% strain and about 1% strain. Combinations of the above-referenced ranges are also possible. In some embodiments, the stiffness of the composition is decreased by about 10% to about 90% or about 15% to about 80%, or about 10% to about 40% or about 10% to about 30%, as measured between about 0.1% strain and about 1% strain.

In some embodiments of any compositions or injectable compositions described herein (e.g., including a crosslinked matrix carrier and particles), the stiffness of the composition is decreased by at least about 15%, at least about 20%, at least about 30%, at least about 40%, at least about 50%, at least about 60%, at least about 70%, at least about 80%, at least about 90%, or higher, as measured between about 0.1% strain and about 10% strain. In some embodiments, the stiffness of the composition is decreased by no more than about 95%, no more than about 90%, no more than about 80%, no more than about 70%, no more than about 60%, no more than about 50%, no more than about 40%, no more than about 30%, or no more than about 20%, as measured between about 0.1% strain and about 10% strain. Combinations of the above-referenced ranges are also possible. In some embodiments, the stiffness of the composition is decreased by about 10% to about 90% or about 15% to about 80%, or about 10% to about 40% or about 10% to about 30%, as measured between about 0.1% strain and about 10% strain.

In some embodiments of any compositions or injectable compositions described herein (e.g., including a crosslinked matrix carrier and particles), the stiffness of the composition is decreased by at least about 15%, at least about 20%, at least about 30%, at least about 40%, at least about 50%, at least about 60%, at least about 70%, at least about 80%, at least about 90%, or higher, as measured between about 0.1% strain and about 100% strain. In some embodiments, the stiffness of the composition is decreased by no more than about 95%, no more than about 90%, no more than about 80%, no more than about 70%, no more than about 60%, no more than about 50%, no more than about 40%, no more than about 30%, or no more than about 20%, as measured between about 0.1% strain and about 100% strain. Combinations of the above-referenced ranges are also possible. In some embodiments, the stiffness of the composition is decreased by about 10% to about 90% or about 15% to about 80%, or about 10% to about 40% or about 10% to about 30%, as measured between about 0.1% strain and about 100% strain.

In some embodiments of any compositions or injectable compositions described herein (e.g., including a crosslinked matrix carrier and particles), the stiffness of the composition is decreased by at least about 15%, at least about 20%, at least about 30%, at least about 40%, at least about 50%, at least about 60%, at least about 70%, at least about 80%, at least about 90%, or higher, as measured between about 10% strain and about 90% strain. In some embodiments, the stiffness of the composition is decreased by no more than about 95%, no more than about 90%, no more than about 80%, no more than about 70%, no more than about 60%, no more than about 50%, no more than about 40%, no more than about 30%, or no more than about 20%, as measured between about 10% strain and about 90% strain. Combinations of the above-referenced ranges are also possible. In some embodiments, the stiffness of the composition is decreased by about 10% to about 90% or about 15% to about 80%, or about 10% to about 40% or about 10% to about 30%, as measured between about 10% strain and about 90% strain.

As shown in FIG. 20C, the stiffness of the composition according to one set of embodiments described herein (a) is decreased by about 25%, as measured between about 0.1% strain and about 1% strain; (b) is decreased by about 35-40%, as measured between about 0.1% strain and about 10% strain; (c) is decreased by about 75-80% as measured between about 0.1% strain and about 100% strain; or (d) is decreased by about 30-35% as measured between about 10% strain and about 90% strain. By contrast, the stiffness of a corresponding crosslinked carrier alone (e.g., crosslinked HA carrier alone) is substantially constant until about 40% strain. The stiffness of the crosslinked carrier alone (e.g., crosslinked HA carrier alone) is decreased by only about 10-15%, as measured between about 0.1% strain and about 100% strain.

In some embodiments of any compositions or injectable compositions described herein (e.g., including a crosslinked matrix carrier and particles), the average force of extruding 1 mL of the composition through a 18-30 gauge needle (e.g., 18, 19, 20, 21, 22, 23, 24, 25, 26, 27, 28, 29, or 30 gauge) is at least about 30%, at least about 40%, at least about 50%, at least about 60%, at least about 70%, lower than that of extruding 1 mL of the crosslinked matrix carrier (e.g., crosslinked HA) alone through a needle of the same gauge number. In some embodiments, the average force of extruding 1 mL of the composition through a 18-30 gauge needle is no more than 80%, no more than 70%, no more than 60%, no more than 50%, no more than 40%, or no more than 30%, lower than that of extruding 1 mL of the crosslinked matrix carrier (e.g., crosslinked HA) alone through a needle of the same gauge number. Combinations of the above-referenced ranges are also possible. For example, in some embodiments of any one of compositions or injectable compositions provided herein, the average force of extruding 1 mL of the composition through a 18-30 gauge needle is about 30% to about 80%, or about 40% to about 70%, lower than that of extruding 1 mL of the crosslinked matrix carrier (e.g., crosslinked HA) alone through a needle of the same gauge number.

In some embodiments involving the compositions or injectable compositions described herein, the crosslinked matrix carrier (e.g., crosslinked hyaluronic acid) may have a concentration of at least about 0.1% (w/v), at least about 0.5% (w/v), at least about 1% (w/v), at least about 2% (w/v), at least about 3% (w/v), at least about 4% (w/v), at least about 5% (w/v), at least about 6% (w/v), at least about 7% (w/v), at least about 8% (w/v), at least about 9% (w/v), at least about 10% (w/v). In some embodiments, the crosslinked matrix carrier (e.g., crosslinked hyaluronic acid) may have a concentration of no more than 10% (w/v), no more than 9% (w/v), no more than 8% (w/v), no more than 7% (w/v), no more than 6% (w/v), no more than 5% (w/v), no more than 4% (w/v), no more than 3% (w/v), no more than 2% (w/v), no more than 1% (w/v), no more than 0.5% (w/v), or no more than 0.1% (w/v). Combinations of the above-referenced ranges are also possible. For example, in some embodiments, the crosslinked matrix carrier (e.g., crosslinked HA) have a concentration of about 0.1% (w/v) to about 10% (w/v) or 0.5% (w/v) to about 10% (w/v), or 1% (w/v) to about 10% (w/v), or about 2% (w/v) to about 8% (w/v), or about 3% (w/v) to about 6% (w/v).

In addition to the needle gauge size and/or concentration of the crosslinked matrix carrier (e.g., crosslinked HA), the average extrusion force of the compositions of any aspects described herein may also vary with the crosslink density of a crosslinked matrix carrier. As used herein, the term "crosslink density" describes the final crosslink density of a crosslinked carrier, which is determined as a ratio of the total number of molecules (or moles) of a crosslinking agent incorporated into the crosslinked carrier to the total number of repeating entity molecules (or moles) of the carrier present in the crosslinked carrier, multiplied by 100. For example, the crosslink density of crosslinked hyaluronic acid is a ratio of the total number of molecules (or moles) of a crosslinking agent (e.g., BDDE) incorporated into the crosslinked HA to the total number of disaccharide units (repeating entity molecules) of hyaluronic acid present in the crosslinked HA, multiplied by 100. The crosslink density of a crosslinked carrier can be determined, for example, by proton nuclear magnetic resonance (1 H NMR) as described in Example 11. Examples of cross-linking agents include, but are not limited to epichlorohydrin, divinyl sulfone, 1,4-bis(2,3-epoxypropoxy)butane (or 1,4-bisglycidoxybutane or 1,4-butanediol diglycidyl ether (BDDE)), 1,2-bis(2,3-epoxypropoxy)ethylene, 1-(2,3-epoxypropyl)-2,3-epoxycyclohexane, and aldehydes such as formaldehyde, glutaraldehyde and crotonaldehyde, taken by themselves or in a mixture. In one embodiment, the cross-linking agent comprises 1,4-butanediol diglycidyl ether (BDDE).

In one set of embodiments described herein, the crosslinked carrier (e.g., a crosslinked HA) has a crosslink density of at least about 4 mol %, at least about 5 mol %, at least about 6 mol %, at least about 7 mol %, at least about 8 mol %, at least about 9 mol %, at least about 10 mol %, at least about 11 mol %, at least about 12 mol %, at least about 13 mol %, at least about 14 mol %, at least about 15 mol %, at least about 16 mol %, at least about 17 mol %, at least about 18 mol %, at least about 19 mol %, at least about 20 mol %, at least about 25 mol %, at least about 30 mol %, at least about 35 mol %, at least about 40 mol %, or higher. In some embodiments, the crosslinked carrier (e.g., a crosslinked HA) has a crosslink density of no more than about 40 mol %, no more than about 35 mol %, no more than about 30 mol %, no more than about 25 mol %, or no more than about 20 mol %. Combinations of the above-referenced ranges are also possible. For example, in some embodiments, the crosslinked carrier (e.g., a crosslinked HA) may have a crosslink density of about 4 mol % to about 30 mol %, about 4 mol % to about 25 mol %, or about 4 mol % to about 20 mol %.

In one set of embodiments of the compositions or injectable compositions described herein where the crosslinked matrix carrier (e.g., crosslinked HA) has a crosslink density of about 4 mol % to about 30 mol % (including combinations of the above-referenced ranges), the composition is characterized in that an average force of extruding about 1 mL of the composition through a 18-30 gauge needle (e.g., 18, 19, 20, 21, 22, 23, 24, 25, 26, 27, 28, 29, or 30 gauge) into air is less than 60 N, including, for example less than 50 N, less than 40 N, less than 30 N, less than 20 N, less than 15 N, less than 10 N, or less than 5 N. In some embodiments, the composition is characterized in that an average force of extruding about 1 mL of the composition through a 18-30 gauge needle (e.g., 18, 19, 20, 21, 22, 23, 24, 25, 26, 27, 28, 29, or 30 gauge) into air is equal to or more than 5 N, equal to or more than 10 N, equal to or more than 15 N, equal to or more than 20 N, equal to or more than 30 N, equal to or more than 40 N, equal to more than 50 N, equal to or more than 60 N. Combinations of the above-referenced ranges are also possible. For example, in some embodiments, the composition is characterized in that an average force of extruding about 1 mL of the composition through a 18-30 gauge needle (e.g., 18, 19, 20, 21, 22, 23, 24, 25, 26, 27, 28, 29, or 30 gauge) into air is about 5 N to about 60 N, about 10 N to about 50 N, or about 15 N to about 50 N, or about 20 N to about 50 N, or about 5 N to about 60 N.

Generally, the extrusion force is lower if needles with smaller gauge numbers (corresponding to larger needle diameters) are used; and the extrusion force is higher if needles with higher gauge numbers (corresponding to smaller needle diameters) are used.

As used herein, the term "average force of extruding" or "average extrusion force" generally refers to the average force required to sustain extrusion of a composition described herein through a needle. In other words, in an extrusion force profile (i.e., a graph of a force or pressure required to extrude a composition as a function of extruded volume or length), the "average extrusion force" is determined from a portion of the graph where sustained extrusion occurs, typically preceded by an initial increasing force required to displace a plunger (plunger break-loose force). As used herein, the term "sustained extrusion" refers to a substantially continuous extrusion of a material through a needle with a substantially constant force, after the motion of the plunger is initiated and before the plunger presses against the end of a syringe body. In some embodiments, the sustained extrusion refers to a portion of an extrusion force profile (i.e., a graph of a force or pressure required to extrude a composition as a function of extruded volume or length) where the standard deviation of the extrusion force of a material as determined from the profile portion is less than about 40% (including, e.g., less than about 30%, less than about 25%, less than about 20%, less than about 15%, less than about 10%, or less than about 5%) of the average extrusion force determined from the same profile portion. In one set of embodiments described herein, the sustained extrusion refers to a portion of an extrusion force profile between about 50% extrusion volume and about 90% extrusion volume. The smaller the standard deviation of the extrusion force is, the smoother the profile of the sustained extrusion is, e.g., represented by a relatively smooth plateau. On the other hand, the profile of the sustained extrusion appears less smooth, e.g., a spiky profile, when the standard deviation of the extrusion force is too large, e.g., more than 50% of the average extrusion force for the corresponding range of extrusion volume. In some embodiments, the average extrusion force is measured based on a 1 mL of a composition described herein through a 21 gauge needle into air (e.g., under atmospheric pressure) at a cross-speed of 5.5 mm/seconds. In some embodiments, the term "average extrusion force" may be equivalent to "dynamic glide force" as used in the art.

In some embodiments, the force required to sustain extrusion of any one of the compositions described herein at any point during the course of injection deviates from the average extrusion force by no more than about 40% or lower, including, no more than about 30%, no more than about 25%, no more than about 20%, no more than about 15%, no more than about 10%, no more than about 5% or lower.

In some embodiments involving the compositions or injectable compositions described herein, the particles and the crosslinked matrix carrier (e.g., crosslinked HA) are present in a volume ratio of about 5:95 to about 95:5.

The crosslinked matrix carrier (e.g., crosslinked HA) and the particles can be present in any volume ratio that yields properties of the compositions suitable for the need of a particular application. In some embodiments of any one of the compositions or injectable compositions described herein, the total amounts of crosslinked matrix carrier (e.g., crosslinked HA) and the particles are in a volume ratio (HA: particle) of at least about 5:95, at least about 10:90, at least about 15:85, at least about 20:80, at least about 25:75, at least about 30:70, at least about 35:65, at least about 40:60, at least about 45:55, at least about 50:50, at least about 55:45, at least about 60:40, at least about 65:35, at least about 70:30, at least about 75:25, at least about 80:20, at least about 85:15, at least about 90:10, or at least about 95:5. In some embodiments, the total amounts of crosslinked matrix carrier (e.g., crosslinked HA) and the particles are in a volume ratio of less than or equal to about 99:1, less than or equal to about 95:5, less than or equal to about 90:10, less than or equal to about 85:15, less than or equal to about 80:20, less than or equal to about 75:25, less than or equal to about 70:30, less than or equal to about 65:35, less than or equal to about 60:40, less than or equal to about 55:45, less than or equal to about 50:50, less than or equal to about 45:55, less than or equal to about 40:60, less than or equal to about 35:65, less than or equal to about 30:70, less than or equal to about 25:75, less than or equal to about 20:80, less than or equal to about 15:85, less than or equal to about 10:90, or less than or equal to about 5:95. Combinations of the above-referenced ranges are also possible. For example, in some embodiments of any one of the compositions or injectable compositions described herein, the total amounts of crosslinked matrix carrier (e.g., crosslinked HA) and the particles are in a volume ratio of about 5:95 to about 95:5, or about 10:90 to about 90:10, or about 20:80 to about 80:20, or about 25:75 to about 75:25, or about 30:70 to about 70:30, or about 40:60 to about 60:40. In some embodiments, the total amounts of crosslinked matrix carrier (e.g., crosslinked HA) and the particles are in a volume ratio of about 50:50; about 40:60; about 30:70; about 25:75; about 20:80, or about 10:90, or as low as about 5:95. In some embodiments, the total amounts of crosslinked matrix carrier (e.g., crosslinked HA) and the particles are in a volume ratio of about 60:40, about 70:30, about 75:25; about 80:20, about 90:10 or up to about 95:5.

In some embodiments involving the compositions or injectable compositions described herein where the total amounts of the crosslinked matrix carrier (e.g., crosslinked HA) and the particles are in a volume ratio of about 80:20 to about 40:60, an average force of extruding about 1 mL of the composition through a 18-21 gauge (e.g., 18, 19, 20, 21 gauge) needle into air is about 40 N or lower. Alternatively, an average force of extruding about 1 mL of the composition through a 25-30 gauge (e.g., 22, 23, 24, 25, 26, 27, 28, 29, or 30) gauge needle into air is less than 50 N. In some embodiments, when the total amounts of the crosslinked matrix carrier (e.g., crosslinked HA) and the particles are in a volume ratio of 70:30 to about 50:50, an average force of extruding about 1 mL of the composition through a 21 gauge needle into air is about 40 N or lower. In some embodiments having any of the above-referenced extrusion forces described herein, the particles may have an average particle size of about 300 μm to about 500 μm, or about 200 μm to about 600 μm, or less than about 200 μm.

The particles present in any embodiments of the compositions or injectable compositions described herein may comprise any biocompatible material that is suitable for soft tissue augmentation and/or drug delivery in vivo. For example, in some embodiments, the particles may comprise a biocompatible and/or biodegradable polymer, a silk fibroin, a peptide, or any combinations thereof. Examples of biocompatible and/or biodegradable polymers include, but are not limited to polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid and other biocompatible and/or biodegradable polymers. See, e.g., International Application Nos.: WO 04/062697; WO 05/012606.

In one set of embodiments of the compositions or injectable compositions described herein, the particles dispersed in the crosslinked matrix carrier (e.g., crosslinked HA) are silk fibroin particles, e.g., as known in the art or as described herein.

While the particles (e.g., silk fibroin particles) described herein can be of any shape, e.g., a spherical shape, polygonal-shaped, elliptical-shaped, in some embodiments, the particles (e.g., silk fibroin particles) are substantially spherical. In some embodiments, at least about 80% or higher (including, e.g., at least about 85%, at least about 90%, at least about 95%, at least about 98%, or higher, up to 100%) of the particles (e.g., silk fibroin particles) in the compositions described herein are substantially spherical particles. In some embodiments, the substantially spherical particles have a circularity value of greater than or equal to about 0.65, greater than or equal to about 0.7, greater than or equal to about 0.8, greater than or equal to about 0.9, or greater than or equal to about 0.96. In some embodiments, the substantially spherical particles have a circularity value of about 0.65 to about 1.0.

In some embodiments, the particles described herein may have an aspect ratio of (a ratio of the major axis to the minor axis) of less than or equal to about 4.0, including, e.g., less than or equal to about 3.0, less than or equal to about 2.0, or less than or equal to about 1.0. In some embodiments, the particles described herein may have an aspect ratio of (a ratio of the major axis to the minor axis) of at least about 1.0, at least about 1.5, at least about 2.0, at least about 3.0, or at least about 4.0. Combinations of the above-referenced ranges are possible. For example, in some embodiments, the particles described herein may have an aspect ratio of about 1.0 to about 4.0, or about 1.0 to about 3.0. To determine the aspect ratio of a particle, the dimensions of the particles can be determined from high-resolution images of particles, e.g., scanning electron microscopic images.

The particles (e.g., silk fibroin particles) present in any embodiment of the compositions or injectable compositions described herein can exhibit a distribution of particle sizes. The particle size can vary with a number of factors including, without limitations, the size of defect in a tissue (e.g., soft tissue) to be repaired or augmented and/or desired properties of the particles, e.g., volume retention or degradation profile. The particles in any one of the compositions or injectable compositions described herein can have any particle size that suits the need of a particular application.

In some embodiments, the particle size of the particles (e.g., silk fibroin particles) is characterized by the average or mean value of a size distribution of the particles. The terms "average" and "mean" are interchangeably used herein. The average or mean value is generally associated with the basis of the size distribution calculation (e.g., number, surface, or volume). Accordingly, the average size of the particles (e.g., silk fibroin particles) can correspond to a number average size, a surface average size, or a volume average size. In one embodiment, the average size refers to volume mean diameter. In some embodiments, the particle size of the particles (e.g., silk fibroin particles) in any one of the compositions described herein is characterized by the mode of a size distribution of particles (e.g., silk fibroin particles), i.e., the value that occurs most frequently in the size distribution.

In some embodiments, the average particle size of the particles (e.g., silk fibroin particles) within a composition or an injectable composition described herein is at least about 50 µm, at least about 75 µm, at least about 100 µm, at least about 125 µm, at least about 150 µm, at least about 175 µm, at least about 200 µm, at least about 250 µm, at least about 300 µm, at least about 350 µm, at least about 400 µm, at least about 450 µm, at least about 500 µm, at least about 550 µm, at least about 600 µm, at least about 650 µm, at least about 700 µm, at least about 750 µm, at least about 800 µm, at least about 850 µm, at least about 900 µm, at least about 950 µm, or at least about 1000 µm. In some embodiments, the average particle size of the particles (e.g., silk fibroin particles) within a composition or an injectable composition described herein is less than or equal to about 1000 µm, less than or equal to about 950 µm, less than or equal to about 900 µm, less than or equal to about 850 µm, less than or equal to about 800 µm, less than or equal to about 750 µm, less than or equal to about 700 µm, less than or equal to about 650 µm, less than or equal to about 600 µm, less than or equal to about 550 µm, less than or equal to about 500 µm, less than or equal to about 450 µm, less than or equal to about 400 µm, less than or equal to about 350 µm, less than or equal to about 300 µm, less than or equal to about 250 µm, less than or equal to about 200 µm, less than or equal to about 175 µm, less than or equal to about 150 µm, less than or equal to about 125 µm, less than or equal to about 100 µm, less than or equal to about 75 µm, or less than or equal to about 50 µm. Combinations of the above-referenced ranges are also possible. In some embodiments, the average particle size of the particles (e.g., silk fibroin particles) within a composition or an injectable composition described herein may be about 50 µm to about 1000 µm. In some embodiments, the average particle size of the particles (e.g., silk fibroin particles) can be about 250 µm to about 850 µm. In some embodiments, the average particle size of the particles (e.g., silk fibroin particles) can be about 300 µm to about 800 µm. In some embodiments, the average particle size of the particles (e.g., silk fibroin particles) can be about 400 µm to about 600 µm. In some embodiments, the average particle size of the particles (e.g., silk fibroin particles) can be about 250 µm to about 450 µm. In some embodiments, the average particle size of the particles (e.g., silk fibroin particles) can be about 200 µm to about 500 µm. In some embodiments, the average particle size of the particles (e.g., silk fibroin particles) can be about 300 µm to about 450 µm. In some embodiments, the average particle size of the particles (e.g., silk fibroin particles) can be about 50 µm to about 200 µm. In some embodiments, the average particle size of the particles (e.g., silk fibroin particles) can be about 75 µm to about 150 µm. In some embodiments, the average particle size of the particles (e.g., silk fibroin particles) can be about 75 µm to about 125 µm. In some embodiments of any average particle size ranges described herein, the average particle size of silk fibroin particles may refer to volume mean diameter of silk fibroin particles. In some embodiments, smaller particles or larger particles may be used provided that the average force extruding about 1 mL of the composition through a 18G-30G gauge needle into air remains less than 60N (including, e.g., less than 50 N, less than 40 N, or less than 30 N).

Methods for measuring particle size are known to a skilled artisan, e.g., by dynamic light scattering, light obscuration methods (such as Coulter analysis method), or other techniques (such as rheology, and light or electron microscopy). In some embodiments, laser diffraction is used to measure particle size of the compositions described herein.

In some embodiments, the particles (e.g., silk fibroin particles) can comprise porous structures, e.g., to mimic the structural morphology of a native tissue, to modulate the degradation rate/volume retention rate of the particles (e.g., silk fibroin particles), and/or to module modulate release profile of an active agent embedded therein, if any. As used herein, the terms "porous" and "porosity" are generally used to describe a structure having an interconnected network of pores or void spaces (which can, for example, be openings, interstitial spaces or other channels) throughout its volume. The term "porosity" is a measure of void spaces in a material, and is a fraction of volume of voids over the total volume, as a percentage between 0 and 100% (or between 0 and 1).

The porous particles (e.g., porous silk fibroin particles) can have pores and/or cervices that are accessible to cells, media, and/or solutes. The pores can be at the surface of the particles (e.g., silk fibroin particles) and/or within the bulk structure of the particles (e.g., silk fibroin particles). In some embodiments, the porous particles (e.g., silk fibroin particles) may have an average porosity of at least about 1%, at least about 3%, at least about 5%, at least about 10%, at least about 15%, at least about 20%, at least about 30%, at least about 40%, at least about 50%, at least about 60%, at least about 70%, at least about 80%, at least about 90%, at least about 93%, at least about 95%, at least about 97%, or higher. In some embodiments, the porous particles (e.g., silk fibroin particles) may have an average porosity of less than or equal to about 99%, less than or equal to about 95%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, less than or equal to about 15%, less than or equal to about 10%, less than or equal to about 5%, less than or equal to about 3%, or less than or equal to about 1%. Combinations of the above-referenced ranges are also possible. In some embodiments, the average porosity may range from about 50% to about 99%, about 70% to about 99%, or from about 80% to about 98%. The pore size and total porosity values can be quantified using conventional methods and models known to those of skill in the art. For example, the pore size and porosity can be measured by standardized techniques, such as mercury porosimetry and nitrogen adsorption.

In some embodiments, the porous particles (e.g., silk fibroin particles) may have a porosity such that the average density of the particles when in dried form (e.g., dried and non-compressed silk fibroin particles) is at least about 0.05 g/mL particles, at least about 0.1 g/mL particles, at least about 0.15 g/mL particles, at least about 0.2 g/mL particles, at least about 0.25 g/mL particles, at least about 0.3 g/mL particles, at least about 0.35 g/mL particles, at least about 0.4 g/mL particles, at least about 0.45 g/mL particles, at least about 0.5 g/mL particles, at least about 0.55 g/mL particles, at least about 0.6 g/mL particles, at least about 0.65 g/mL particles, at least about 0.7 g/mL particles, at least about 0.75 g/mL particles, at least about 0.8 g/mL particles, at least about 0.85 g/mL particles, at least about 0.9 g/mL particles, at least about 0.9 g/mL particles, or at least about 1.0 g/mL particles. In some embodiments, the porous particles (e.g., silk fibroin particles) may have a porosity such that the average density of the particles when in dried form (e.g., dried and non-compressed silk fibroin particles) is no more than 1.0 g/mL particles, no more than 0.95 g/mL particles, no more than 0.9 g/mL particles, no more than 0.85 g/mL particles, no more than 0.8 g/mL particles, no more than 0.75 g/mL particles, no more than 0.7 g/mL particles, no more than 0.65 g/mL particles, no more than 0.6 g/mL particles, no more than 0.55 g/mL particles, no more than 0.5 g/mL particles, no more than 0.45 g/mL particles, no more than 0.4 g/mL particles, no more than 0.35 g/mL particles, no more than 0.3 g/mL particles, no more than 0.25 g/mL particles, or no more than 0.2 g/mL particles. Combinations of the above-referenced ranges are also possible. In some embodiments, the porous particles (e.g., silk fibroin particles) may have a porosity such that the average density of the particles when in dried form (e.g., dried and non-compressed silk fibroin particles) is about 0.05 g/mL particles to about 1.0 g/mL particles, or about 0.1 g/mL particles to about 1 g/mL particles, or about 0.2 g/mL particles to about 1.0 g/mL particles, or about 0.4 g/mL particles to about 0.8 g/mL particles, or about 0.5 g/mL particles to about 0.7 g/mL particles, or about 0.1 g/mL particles to about 0.3 g/mL particles, or about 0.08 g/mL particles to about 0.15 g/mL particles, or about 0.1 g/mL particles to about 0.12 g/mL particles.

In some embodiments, the porous particles (e.g., silk fibroin particles) may be hydrated (e.g., in an aqueous solution, including, e.g., but not limited to water, saline, and/or a buffered solution such as a phosphate buffered solution) such that the average density of the hydrated particles (e.g., hydrated and non-compressed silk fibroin particles) is at least about 0.4 g/mL particles, at least about 0.5 g/mL particles, at least about 0.6 g/mL particles, at least about 0.7 g/mL particles, at least about 0.8 g/mL particles, at least about 0.9 g/mL particles, or at least about 1 g/mL particles. In some embodiments, the porous particles (e.g., silk fibroin particles) may be hydrated such that the average density of the hydrated particles (e.g., hydrated and non-compressed silk fibroin particles) is no more than 1.5 g/mL particles, no more than 1.4 g/mL particles, no more than 1.3 g/mL particles, no more than 1.2 g/mL particles, no more than 1.1 g/mL particles, no more than 1 g/mL particles, no more than 0.9 g/mL particles, no more than 0.8 g/mL particles, no more than 0.7 g/mL particles, no more than 0.6 g/mL particles, or no more than 0.5 g/mL particles. Combinations of the above-referenced ranges are also possible. In some embodiments, the porous particles (e.g., silk fibroin particles) may be hydrated such that the average density of the hydrated particles (e.g., hydrated and non-compressed silk fibroin particles) is about 0.4 g/mL particles to about 1.2 g/mL particles, or about 0.5 g/mL particles to about 1 g/mL particles, or about 0.6 g/mL particles to about 0.8 g/mL particles, or about 0.65 g/mL particles to about 0.75 g/mL particles.

The pores of the particles can be of any suitable shape, e.g., circular, elliptical, or polygonal. The porous particles (e.g., silk fibroin particles) can have an average pore size of less than or equal to about 100 μm, less than or equal to about 95 μm, less than or equal to about 90 μm, less than or equal to about 85 μm, less than or equal to about 80 μm, less than or equal to about 75 µm, less than or equal to about 70 µm, less than or equal to about 65 µm, less than or equal to about 60 µm, less than or equal to about 55 µm, less than or equal to about 50 µm, less than or equal to about 45 µm, less than or equal to about 40 µm, less than or equal to about 35 µm, less than or equal to about 30 µm, less than or equal to about 25 µm, less than or equal to about 20 µm, less than about 15 µm, less than about 10 µm, less than about 5 µm, or less than about 1 µm. In some embodiments, the porous particles (e.g., silk fibroin particles) may have an average pore size of at least about 0.1 µm, at least about 0.5 µm, at least about 1 µm, at least about 5 µm, at least about 10 µm, at least about 15 µm, at least about 20 µm, at least about 25 µm, at least about 30 µm, at least about 35 µm, at least about 40 µm at least about 45 µm at least about 50 µm at least about 55 µm at least about 60 µm at least about 65 µm at least about 70 µm at least about 75 µm at least about 80 µm at least about 85 µm at least about 90 µm at least about 95 µm or at least about 100 µm. Combinations of the above-referenced ranges are also possible. In some embodiments, the porous particles (e.g., silk fibroin particles) may have an average pore size of about 0.1 µm to about 100 or about 15 µm to about 100 µm or about 20 µm to about 100 µm about 30 µm to about 80 µm or about 30 µm to about 60 µm or about 0.1 µm to about 10 or about 25 µm to about 55 µm or about 30 µm to about 50 µm. In some embodiments, the porous particles (e.g., silk fibroin particles) can comprise pores that are too small to be detected by methods known in the art. The term "pore size" as used herein refers to a dimension of a pore. In some embodiments, the pore size can refer to the longest dimension of a pore, e.g., a diameter of a pore having a circular cross section, or the length of the longest cross-sectional chord that can be constructed across a pore having a non-circular cross-section. In other embodiments, the pore size can refer to the shortest dimension of a pore. As used herein, the term "average pore size" refers to an average or mean value of a size distribution of pores of a population of particles (e.g., silk fibroin particles) based on measurements of a selected dimension of a pore (e.g., the longest dimension of a pore such as diameter, or a characteristic length of a pore such as circle equivalent diameter).

In some embodiments, the average pore size can refer to an average circle equivalent diameter. A "circle equivalent diameter"(also known as "area equivalent diameter") is the diameter of a circular pore that gives the same cross-section area as an equivalent pore (e.g., an equivalent non-circular pore) present in a test sample. The cross-section area of a pore in a test sample can be determined, e.g., by SEM analysis of cross-sections of a porous scaffold to determine the cross-section area ($A_{pore}$) of pores and then determine the circle equivalent diameter ($D_{circular}$) using the equation: $D_{circular} = (4A_{pore}/\pi)^{1/2}$.

In some embodiments involving the particles (e.g., silk fibroin particles) described herein, at least about 40% (including, e.g., at least about 50%, at least about 60%, at least about 70%, at least about 80%, at least about 90% or more and up to 100%) of the pores have an aspect ratio of about 1.0 to about 3.

In some embodiments involving the particles (e.g., silk fibroin particles) described herein, no more than about 10% (including, e.g., no more than about 9%, no more than about 8%, no more than about 7%, no more than about 6%, no more than about 5%, or lower) of the pores have an aspect ratio of at least about 2.5 or higher (e.g., including, e.g., at least about 3.0, at least about 3.5, at least about 4.0, or higher).

In some embodiments involving the particles (e.g., silk fibroin particles) described herein, the pores of the particles (e.g., silk fibroin particles) have an average aspect ratio of at least about 1.5, at least about 1.6, at least about 1.7, at least about 1.8, at least about 1.9, at least about 2.0. In some embodiments, the pores of the particles (e.g., silk fibroin particles) have an average aspect ratio of no more than about 2.5, no more than about 2.4, no more than about 2.3, no more than about 2.2, no more than about 2.1, no more than about 2.0, no more than about 1.9, no more than about 1.8, no more than about 1.7, no more than about 1.6, or lower. Combinations of the above-referenced ranges are possible. For example, in some embodiments, the pores of the particles (e.g., silk fibroin particles) have any average aspect ratio of about 1.5 to about 2.5, or about 1.8 to about 2.0.

In some embodiments involving the particles (e.g., silk fibroin particles) described above and herein, the pores of the particles (e.g., silk fibroin particles) have an average circularity of about 0.4 to about 1.0, or about 0.5 to about 0.9, or about 0.6 to about 0.8.

The porosity (including, e.g., pore shape and/or pore size) of the particles can be controlled during synthesis and/or preparation of particles. See, e.g., the compositions and/or methods of making silk fibroin particles as described in International Patent Application filed Oct. 31, 2017, by Brown, J. et al., entitled "Compositions Comprising Low Molecular Weight Silk Fibroin Fragments and Plasticizers," the content of which is incorporated herein by reference.

The particles (e.g., silk fibroin particles) can be in any suitable format, e.g., dry particles, hydrated particles, lyophilized particles (e.g., particles that have been subject to lyophilization), gel particles, or viscous liquid particles. In some embodiments of any one of the compositions described herein, the particles (e.g., silk fibroin particles) are in the form of lyophilized, spongy particles which are hydrated in their final, packaged form. Such particles may be soft, compressible, and have a low density which may be suitable for mimicking soft tissue mechanics and allowing tissue ingrowth.

In some embodiments, the particles (e.g., silk fibroin particles) are not transparent to light, or only allow minimal transmission of light. For example, the particles (e.g., silk fibroin particles) may permit light (e.g., visible light, e.g., with a wavelength of about 390 nm to about 700 nm) transmission of at least about 5%, at least about 10%, at least about 15%, at least about 20%, at least about 30%, at least about 40%, at least about 50%, or higher. In some embodiments, the particles (e.g., silk fibroin particles) may permit light (e.g., visible light, e.g., with a wavelength of about 390 nm to about 700 nm) transmission of less than or equal to about 50%, less than or equal to about 40%, less than or equal to 30%, less than or equal to 25%, less than or equal to 20%, less than or equal to 15%, less than or equal to 10%, or lower. In some embodiments, the particles (e.g., silk fibroin particles) can permit light (e.g., visible light, e.g., with a wavelength of about 390 nm to about 700 nm) transmission of about 5% to about 30%, about 7% to about 30%, or about 10% to 20%. For example, in some embodiments, the optical transparency of 600 nm light in silk fibroin particles alone (1-2 particle layer thick) is about 7.0% or higher.

Silk Fibroin Particles that Exhibit Little or Minimal Plastic Deformation

Another aspect described herein relates to a novel porous silk fibroin particle that exhibits little or minimal plastic deformation and its pores exhibit more rounded morphology. For example, the silk fibroin particle has an average particle size of about 50 μm to about 1000 μm and a porous structure characterized in that:

no more than about 10% of pores within the porous structure have an aspect ratio of about 4.0 or higher; and when a population of the silk fibroin particles is exposed to a compressive strain of at least about 20%, the silk fibroin particles recover at least about 90% of their original volume after release of the compression.

As used herein, the phrase "silk fibroin particles" generally refers to particles comprising silk fibroin. In some embodiments, the phrase "silk fibroin particles" refers to particles in which silk fibroin constitutes at least about 30% of the total particle composition, including at least about 40%, at least about 50%, at least about 60%, at least about 70%, at least about 80%, at least about 90%, at least about 95% or up to 100%, of the total particle composition. In certain embodiments, the silk fibroin particles can be substantially formed from silk fibroin. In one embodiment, the silk fibroin particles consist essentially of silk fibroin.

In some embodiments, the silk fibroin particles are substantially depleted of its native sericin content (e.g., about 5% (w/w) or less residual sericin in the final extracted silk). Alternatively, higher concentrations of residual sericin can be left on the silk following extraction or the extraction step can be omitted. In some embodiments, the silk fibroin particles have, e.g., about 0.1% (w/w) residual sericin (or more), about 1% (w/w) residual sericin (or more), about 2% (w/w) residual sericin (or more), about 3% (w/w) residual sericin (or more), about 4% (w/w) (or more), or about 5% (w/w) residual sericin (or more). In some embodiments, the silk fibroin particles have, e.g., at most 1% (w/w) residual sericin, at most 2% (w/w) residual sericin, at most 3% (w/w) residual sericin, at most 4% (w/w), or at most 5% (w/w) residual sericin. Combinations of the above-referenced ranges are also possible. In some other embodiments, the silk fibroin particles have, e.g., about 1% (w/w) to about 2% (w/w) residual sericin, about 1% (w/w) to about 3% (w/w) residual sericin, about 1% (w/w) to about 4% (w/w), or about 1% (w/w) to about 5% (w/w) residual sericin. In some embodiments, the silk fibroin particles are entirely free of its native sericin content. As used herein, the term "entirely free" means that within the detection range of the instrument or process being used, the substance cannot be detected or its presence cannot be confirmed. In some embodiments, the silk fibroin is essentially free of its native sericin content. As used herein, the term "essentially free" means that only trace amounts of the substance can be detected, is present in an amount that is below detection, or is absent.

Silk fibroin is a particularly appealing biopolymer candidate to be used for various embodiments described herein, e.g., because of its versatile processing, e.g., all-aqueous processing (Sofia et al., 54 J. Biomed. Mater. Res. 139 (2001); Perry et al., 20 Adv. Mater. 3070-72 (2008)), relatively easy functionalization (Murphy et al., 29 Biomat. 2829-38 (2008)), and biocompatibility (Santin et al., 46 J. Biomed. Mater. Res. 382-9 (1999)). For example, silk has been approved by U.S. Food and Drug Administration as a tissue engineering scaffold in human implants. See Altman et al., 24 Biomaterials: 401 (2003).

As used herein, the term "silk fibroin" includes silkworm fibroin and insect or spider silk protein. See e.g., Lucas et al., 13 Adv. Protein Chem. 107 (1958). Any type of silk fibroin can be used in different embodiments described herein. Silk fibroin produced by silkworms, such as Bornbyx rnori, is the most common and represents an earth-friendly, renewable resource. For instance, silk fibroin may be attained by extracting sericin from the cocoons of Bornbyx rnori. Silkworm cocoons are commercially available. There are many different silks, however, including spider silk (e.g., obtained from Nephila clavipes), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used.

In any one of the embodiments described herein, silk fibroin can be modified for desired mechanical or chemical properties. One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interactions. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic—inorganic composite. See WO 2006/076711.

In some embodiments, silk fibroin can be chemically modified to enhance hydrophilicity (or hydrophobicity), making it more or less hydrophilic in the presence of media. Hydrophilic silk fibroin particles are more likely to take up aqueous media and swell after injection into a tissue to be treated compared to silk fibroin particles that are less hydrophilic.

While silk fibroin particles can be of any shape, e.g., a spherical shape, polygonal-shaped, elliptical-shaped, in some embodiments, the silk fibroin particles are substantially spherical. A substantially spherical particle may have an aspect ratio of (a ratio of the major axis to the minor axis) of less than or equal to about 1.5, e.g., about 0.5 to about 1.5, about 0.6 to about 1.4, about 0.7 to about 1.3, about 0.8 to about 1.2, about 0.9 to about 1.1, or about 1.0 to about 1.1, while a non-spherical particle (e.g., an elongated particle) may have an aspect ratio of more than about 1.5 or higher (e.g., more than about 2, more than about 3, more than about 4, more than about 5 or higher).

In some embodiments involving the silk fibroin particles of this aspect described herein, the average particle size of the silk fibroin particles is at least about 50 μm, at least about 100 μm, at least about 150 μm, at least about 200 μm, at least about 250 μm, at least about 300 μm, at least about 350 μm, at least about 400 μm, at least about 450 μm, at least about 500 μm, at least about 550 μm, at least about 600 μm, at least about 650 μm, at least about 700 μm, at least about 750 μm, at least about 800 μm, at least about 850 μm, at least about 900 μm, at least about 950 μm, or at least about 1000 μm. In some embodiments, the average particle size of the silk fibroin particles is less than or equal to about 1000 μm, less than or equal to about 950 μm, less than or equal to about 900 μm, less than or equal to about 850 μm, less than or equal to about 800 μm, less than or equal to about 750 μm, less than or equal to about 700 μm, less than or equal to about 650 μm, less than or equal to about 600 μm, less than or equal to about 550 μm, less than or equal to about 500 μm, less than or equal to about 450 μm, less than or equal to about 400 μm, less than or equal to about 350 μm, less than or equal to about 300 μm, less than or equal to about 250 μm, less than or equal to about 200 μm, less than or equal to about 150 μm, less than or equal to about 100 μm, or less than or equal to about 50 μm. Combinations of the above-referenced ranges are also possible. In some embodiments, the average particle size of the silk fibroin particles may be about 50 μm to about 1000 μm. In some embodiments, the average particle size of the silk fibroin particles can be about 250 μm to about 850 μm. In some embodiments, the average particle size of the silk fibroin particles can be about 300 μm to about 800 μm. In some embodiments, the average particle size of the silk fibroin particles can be about 400 μm to about 600 μm. In some embodiments, the average particle size of the silk fibroin particles can be about 250 μm to about 450 μm. In some embodiments, the average particle size of the silk fibroin particles can be about 200 μm to about 500 μm. In some embodiments, the average particle size of the silk fibroin particles can be about 300 μm to about 450 μm. In some embodiments of any average particle size ranges described herein, the average particle size of silk fibroin particles may refer to volume mean diameter of silk fibroin particles.

The silk fibroin particles of this aspect have pores and/or cervices that are accessible to cells, media, and/or solutes. The pores can be at the surface of the silk fibroin particles and/or within the bulk structure of the silk fibroin particles. In some embodiments, the porous silk fibroin particles may have an average porosity of at least about 50%, at least about 55%, at least about 60%, at least about 65%, at least about 70%, at least about 75%, at least about 80%, at least about 85%, at least about 90%, at least about 93%, at least about 95%, at least about 97%, or higher. In some embodiments, the porous silk fibroin particles may have an average porosity of less than or equal to about 99%, less than or equal to about 98%, less than or equal to about 95%, less than or equal to about 90%, less than or equal to about 85%, less than or equal to about 80%, less than or equal to about 75%, less than or equal to about 70%, less than or equal to about 65%, less than or equal to about 60%, less than or equal to about 55%, or less than or equal to about 50%. Combinations of the above-referenced ranges are also possible. In some embodiments, the average porosity may range from about 50% to about 99%, about 70% to about 99%, or from about 80% to about 98%.

In some embodiments, the porous silk fibroin particles have a porosity such that the average density of the dried silk fibroin particles (silk fibroin particles in dried and non-compressed form) is at least about 0.05 g/mL particles, at least about 0.1 g/mL particles, at least about 0.15 g/mL particles, at least about 0.2 g/mL particles, at least about 0.25 g/mL particles, at least about 0.3 g/mL particles, at least about 0.35 g/mL particles, at least about 0.4 g/mL particles, at least about 0.45 g/mL particles, at least about 0.5 g/mL particles, at least about 0.55 g/mL particles, at least about 0.6 g/mL particles, at least about 0.65 g/mL particles, at least about 0.7 g/mL particles, at least about 0.75 g/mL particles, at least about 0.8 g/mL particles, at least about 0.85 g/mL particles, at least about 0.9 g/mL particles, at least about 0.9 g/mL particles, or at least about 1.0 g/mL particles. In some embodiments, the porous silk fibroin particles may have a porosity such that the average density of the dried silk fibroin particles (silk fibroin particles in dried and non-compressed form) is no more than 1.0 g/mL particles, no more than 0.95 g/mL particles, no more than 0.9 g/mL particles, no more than 0.85 g/mL particles, no more than 0.8 g/mL particles, no more than 0.75 g/mL particles, no more than 0.7 g/mL particles, no more than 0.65 g/mL particles, no more than 0.6 g/mL particles, no more than 0.55 g/mL particles, no more than 0.5 g/mL particles, no more than 0.45 g/mL particles, no more than 0.4 g/mL particles, no more than 0.35 g/mL particles, no more than 0.3 g/mL particles, no more than 0.25 g/mL particles, no more than 0.2 g/mL particles, no more than 0.15 g/mL particles, no more than 0.1 g/mL particles, or no more than 0.05 g/mL particles. Combinations of the above-referenced ranges are also possible. In some embodiments, the porous silk fibroin particles may have a porosity such that the average density of the dried silk fibroin particles (silk fibroin particles in dried and non-compressed form) is about 0.05 g/mL particles to about 1.0 g/mL particles, or about 0.1 g/mL particles to about 1 g/mL particles, or about 0.2 g/mL particles to about 1.0 g/mL particles, or about 0.4 g/mL particles to about 0.8 g/mL particles, or about 0.5 g/mL particles to about 0.7 g/mL particles, or about 0.1 g/mL particles to about 0.3 g/mL particles, or about 0.08 g/mL particles to about 0.15 g/mL particles. In one embodiment, the porous silk fibroin particles may have a porosity such that the average density of the dried and non-compressed silk fibroin particles is about 0.1 g/mL particles. In one embodiment, the porous silk fibroin particles may have a porosity such that the average density of the dried and non-compressed silk fibroin particles is about 0.1 g/mL particles to about 0.12 g/mL particles.

In some embodiments, the porous particles (e.g., silk fibroin particles) may be hydrated such that the average density of the hydrated particles (e.g., hydrated and non-compressed silk fibroin particles) is at least about 0.4 g/mL particles, at least about 0.5 g/mL particles, at least about 0.6 g/mL particles, at least about 0.7 g/mL particles, at least about 0.8 g/mL particles, at least about 0.9 g/mL particles, or at least about 1 g/mL particles. In some embodiments, the porous particles (e.g., silk fibroin particles) may be hydrated such that the average density of the hydrated particles (e.g., hydrated and non-compressed silk fibroin particles) is no more than 1.5 g/mL particles, no more than 1.4 g/mL particles, no more than 1.3 g/mL particles, no more than 1.2 g/mL particles, no more than 1.1 g/mL particles, no more than 1 g/mL particles, no more than 0.9 g/mL particles, no more than 0.8 g/mL particles, no more than 0.7 g/mL particles, no more than 0.6 g/mL particles, or no more than 0.5 g/mL particles. Combinations of the above-referenced ranges are also possible. In some embodiments, the porous particles (e.g., silk fibroin particles) may be hydrated such that the average density of the hydrated particles (e.g., hydrated and non-compressed silk fibroin particles) is about 0.4 g/mL particles to about 1.2 g/mL particles, or about 0.5 g/mL particles to about 1 g/mL particles, or about 0.6 g/mL particles to about 0.8 g/mL particles, or 0.65 g/mL particles to about 0.75 g/mL particles.

In some embodiments involving the silk fibroin particles described herein, at least about 40% (including, e.g., at least about 50%, at least about 60%, at least about 70%, at least about 80%, at least about 90% or more and up to 100%) of the pores have an aspect ratio of about 1.0 to about 2.5.

In some embodiments involving the silk fibroin particles described herein, no more than about 10% (including, e.g., no more than about 9%, no more than about 8%, no more than about 7%, no more than about 6%, no more than about 5%, or lower) of the pores have an aspect ratio of at least about 2.5 or higher (e.g., including, e.g., at least about 3.0, at least about 3.5, at least about 4.0, or higher).

In some embodiments involving the silk fibroin particles described herein, the pores have an average aspect ratio of at least about 1.5, at least about 1.6, at least about 1.7, at least about 1.8, at least about 1.9, at least about 2.0. In some embodiments, the pores have an average aspect ratio of no more than about 2.5, no more than about 2.4, no more than about 2.3, no more than about 2.2, no more than about 2.1, no more than about 2.0, no more than about 1.9, no more than about 1.8, no more than about 1.7, no more than about 1.6, or lower. Combinations of the above-referenced ranges are possible. For example, in some embodiments, the pores have any average aspect ratio of about 1.5 to about 2.5, or about 1.8 to about 2.0.

In some embodiments involving the silk fibroin particle described herein, the pores of the silk fibroin particle have an average circularity of about 0.4 to about 1.0, or about 0.5 to about 0.9, or about 0.6 to about 0.8.

In some embodiments, no more than 10% pores within the porous silk fibroin particle have an aspect ratio of about 4.0 or higher. For example, in some embodiments, no more than about 10% pores, no more than about 9% pores, no more than about 8% pores, no more than about 7% pores, no more than about 6% pores, no more than about 5% pores, no more than about 4% pores, no more than about 3% pores, no more than about 2% pores, or no more than about 1% pores, within the porous silk fibroin particle have an aspect ratio of about 4.0, about 4.5, about 5.0, about 5.5, about 6.0, or higher. In some embodiments, the porous silk fibroin particles are substantially free of pores that have an aspect ratio of about 4.0, about 4.5, about 5.0, about 5.5, about 6.0, or higher.

In some embodiments of this aspect described herein, at least about 40% of the pores, including, e.g., at least about 50%, at least about 60%, at least about 70%, at least about 80%, at least about 90%, or at least about 95% or higher (e.g., up to 100%), of the pores, have an aspect ratio of about 1.0 to about 2.0 (inclusive). In these embodiments, at least about 20% or about 30% of the pores may have an aspect ratio of about 1.0 to about 1.5 (inclusive).

Figure 13C:
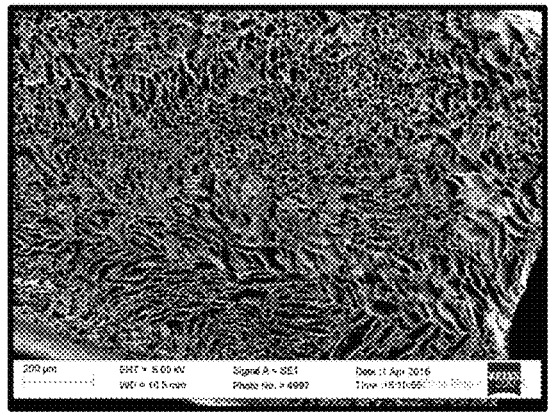
Figure 13C:
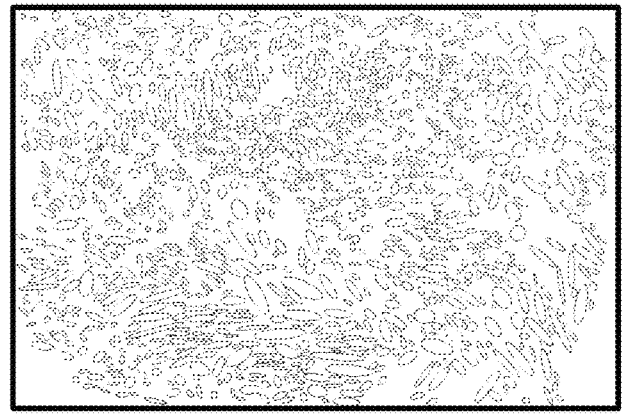
Figure 13C:
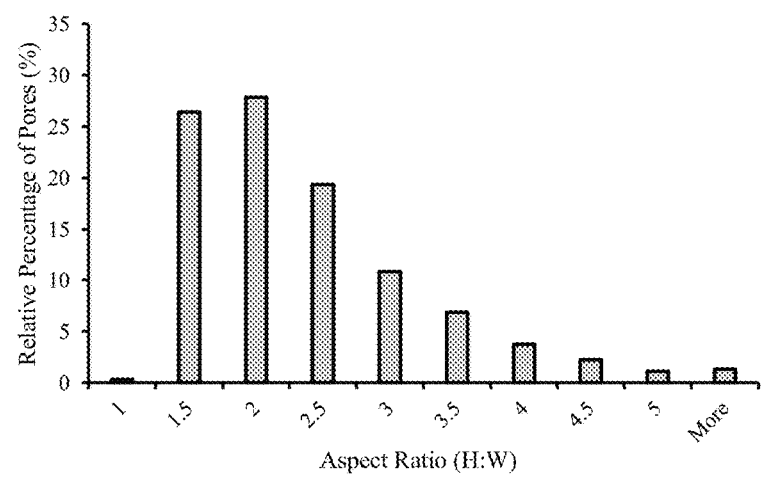

As used herein with respect to a pore, the term "aspect ratio" refers to a ratio of the longest dimension of a pore to the shortest dimension of the pore. Rounded pores (e.g., pores having a round cross-section) generally have an aspect ratio of about 1.0 to about 1.5. Perfectly round cross-section has an aspect ratio of about 1.0. Example 6 provides an exemplary method to determine aspect ratios of pores present in a silk fibroin material. For example, in some embodiments where the silk fibroin particles are produced from a bulk silk fibroin sponge, SEM analysis of a cross-section of the bulk silk fibroin sponge (prior to reducing it to particles) can be performed. The contrast of the SEM images of the cross-section composite can be manipulated using any art-recognized image analysis tool (e.g., ImageJ or Phenom Porometric software) such that pores of the bulk silk fibroin sponge are distinguishable from the silk fibroin bulk material. Using an image analysis tool, the pores are then outlined, for example, using ellipses fitting, and the longest and shortest dimensions of the pores are measured to determine an aspect ratio of a pore. The aspect ratios of a representative number of the pores (e.g., at least 100 or more) are measured to create a distribution graph showing percentages of pores with respect to aspect ratios, for example, as shown in FIGS. 13C and 13F. Alternatively, the silk fibroin particles can be embedded in a substrate material (e.g., a hydrogel) to form a silk fibroin/substrate composite and then an SEM analysis of a cross-section of the composite can be performed.

In some embodiments of any one of the silk fibroin particles described herein, the porous structure of the silk fibroin particles is characterized by interconnected pores having an average pore size of less than or equal to about 100 µm, less than or equal to about 95 µm, less than or equal to about 90 µm, less than or equal to about 85 µm, less than or equal to about 80 µm, less than or equal to about 75 µm, less than or equal to about 70 µm, less than or equal to about 65 µm, less than or equal to about 60 µm, less than or equal to about 55 µm, less than or equal to about 50 µm, less than or equal to about 45 µm, less than or equal to about 40 µm, less than or equal to about 35 µm, less than or equal to about 30 µm, less than or equal to about 25 µm, less than or equal to about 20 µm, less than or equal to about 15 µm, less than or equal to about 10 µm, less than or equal to about 5 µm, less than or equal to about 1 µm, or less than or equal to about 0.5 µm. In some embodiments, the porous silk fibroin particles may have an average pore size of at least about 0.1 µm, at least about 0.5 µm, at least about 1 µm, at least about 5 µm, at least about 10 µm, at least about 15 µm, at least about 20 µm, at least about 25 µm, at least about 30 µm, at least about 35 µm, at least about 40 µm, at least about 45 µm, at least about 50 µm, at least about 55 µm, at least about 60 µm, at least about 65 µm, at least about 70 µm, at least about 75 µm, at least about 80 µm, at least about 85 µm, at least about 90 µm, at least about 95 µm, or at least about 100 µm. Combinations of the above-referenced ranges are also possible. For example, in some embodiments, the porous structure of the silk fibroin particles may be characterized by interconnected pores having an average pore size of about 0.1 µm to about 100 µm, or about 0.1 µm to about 10 µm, or about 15 µm to about 100 µm, or about 20 µm to about 100 µm, about 30 µm to about 80 µm, or about 30 µm to about 60 µm, or about 25 µm to about 55 µm, or about 30 µm to about 50 µm. In some embodiments, the pores of the silk fibroin particles may be too small to be detected by methods known in the art.

In some embodiments involving the porous silk fibroin particles described herein, the porous structure may be characterized by no more than 10% (including, e.g., no more than about 9%, no more than about 8%, no more than about 7%, no more than about 6%, no more than about 5% or lower) of interconnected pores having a circle equivalent diameter of about 100 µm or greater.

In some embodiments involving the porous silk fibroin particles described herein, the porous structure may be characterized by no more than 15% (including, e.g., no more than about 14%, no more than about 13%, no more than 12%, no more than 11%, no more than 10%, no more than about 9%, no more than about 8%, no more than about 7%, no more than about 6%, no more than about 5% or lower) of interconnected pores having a circle equivalent diameter of about 75 µm or greater.

In some embodiments involving the porous silk fibroin particles described herein, the porous structure may be characterized by at least about 50% (including, e.g., at least about 60%, at least about 70%, at least about 80%, at least about 90%, or above) of interconnected pores having a circle equivalent diameter of about 5 µm to about 75 µm, or about 15 µm to about 60 µm, or about 15 µm to about 55 µm.

In some embodiments of any one of the silk fibroin particles described herein, the population of the silk fibroin particles exhibit an elastic modulus (as measured at about 6-10% strain) of at least about 1 kPa, at least about 2 kPa, at least about 3 kPa, at least about 4 kPa, at least about 5 kPa, at least about 10 kPa, at least about 20 kPa, at least about 30 kPa, at least about 40 kPa, at least about 50 kPa, at least about 60 kPa, at least about 70 kPa, at least about 80 kPa, at least about 90 kPa, or at least about 100 kPa. In some embodiments of any one of the silk fibroin particles described herein, the population of the silk fibroin particles exhibit an elastic modulus (as measured at about 6-10% strain) of less than or equal to about 100 kPa, less than or equal to about 90 kPa, less than or equal to about 80 kPa, less than or equal to about 70 kPa, less than or equal to about 60 kPa, less than or equal to about 50 kPa, less than or equal to about 40 kPa, less than or equal to about 30 kPa, less than or equal to about 20 kPa, less than or equal to about 10 kPa, or less than or equal to about 5 kPa. Combinations of the above-referenced ranges are also possible. For example, in some embodiments, the population of the silk fibroin particles exhibit about 1 kPa to about 100 kPa, about 1 kPa to about 50 kPa, about 1 kPa to about 30 kPa, about 1 kPa to about 20 kPa, or about 5 kPa to about 20 kPa, or about 40 kPa to about 100 kPa, about 50 kPa to about 90 kPa, or about 60 kPa to about 80 kPa (as measured at about 6% axial strain). The elastic modulus can be measured using the method as described in Example 8.

When a population of the silk fibroin particles of this aspect described herein is exposed to a compressive strain of at least about 10% (e.g., including, e.g., at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or higher), the silk fibroin particles recover at least about 50%, at least about 55%, at least about 60%, at least about 65%, at least about 70%, at least about 75%, at least about 80%, at least about 85%, at least about 90%, at least about 95%, at least about 98%, at least about 99%, or up to 100%, of their original volume (e.g., hydrated state such as fully saturated with water) after release of the compression. In some embodiments, the silk fibroin particles recover no more than 100%, no more than 95%, no more than 90%, no more than 85%, no more than 80%, no more than 75%, no more than 70%, no more than 65%, no more than 60%, no more than 55%, no more than 50%, no more than 45%, or more than 40%, of their original volume (e.g., hydrated state such as fully saturated with water) after release of the compression. Combinations of the above-referenced ranges are also possible. For example, in some embodiments, when a population of the silk fibroin particles is exposed to a compressive strain of at least about 10% (e.g., including, e.g., at least about 20%, at least about 30%, at least about 40%, at least about 50%, at least about 60%, at least about 70%, at least about 80%, at least about 90% or higher), the silk fibroin particles recover about 40%-100%, about 50-100%, about 60-99%, about 70-99%, about 80-99%, or about 90-100%, or about 90-99% of their original volume (e.g., hydrated state such as fully saturated with water) after release of the compression. The compression recovery of the material can be measured using the method as described in Example 8.

The mechanics (e.g., elastic modulus and/or compression recovery) of individual silk fibroin particles can also be determined by atomic force microscope or other microscopic methods.

In some embodiments, the silk fibroin particles that exhibit compression recovery and/or elastic modulus as described above and herein comprise a plasticizer, for example, in the amount of about 0.001% (w/w) to about 30% (w/w), about 0.01% (w/w) to about 30% (w/w), about 0.1% (w/w) to about 30% (w/w), or about 1% (w/w) to about 30% (w/w). In some embodiments, the silk fibroin particles that exhibit compression recovery and/or elastic modulus as described above and herein comprise a plasticizer, for example, in the amount of about 0.001% (w/w) to about 20% (w/w), about 0.01% (w/w) to about 20% (w/w), about 0.1% (w/w) to about 20% (w/w), or about 1% (w/w) to about 20% (w/w). In some embodiments, the silk fibroin particles that exhibit compression recovery and/or elastic modulus as described above and herein comprise a plasticizer, for example, in the amount of about 0.001% (w/w) to about 10% (w/w), about 0.01% (w/w) to about 10% (w/w), about 0.1% (w/w) to about 10% (w/w), or about 1% (w/w) to about 10% (w/w). Examples of a plasticizer include, but are not limited to alcohols containing at least one hydroxyl group (including, e.g., methanol; ethanol; propanol isomers, e.g., 1-propanol, isopropyl alcohol; butanol isomers, e.g., n-butanol, sec-butanol, isobutanol, tert-butanol; pentanol isomers (amyl alcohol), e.g., n-pentanol, isobutyl carbinol, active amyl alcohol, tertiary butyl carbinol, 3-pentanol, methyl (n) propyl carbinol, methyl isopropyl carbinol, dimethyl ethyl carbinol; hexanol, e.g., n-hexanol and related isomers; heptanol and related isomers; octanol and related isomers; nonanol and related isomers; and decanol and related isomers); sugars or simple sugars (including, e.g., sucrose, glucose; fructose; ribose; galactose; maltose; lactose; triose; tetrose; pentose; hexose; trehalose; and any other monosaccharides, disaccharides, oligosaccharides, and polysaccharides); polyols containing multiple hydroxyl groups (including, e.g., diols; vicinal diols (hydroxyl groups attached to adjacent atoms: examples include but are not limited to: propane-1,2-diol; ethylene glycol; propylene glycol); 1,3 diols (e.g., propane-1,3-diol; 2,2-dimethyl-1,3-propanediol; 1,3 butanediol; 1,4 diols (e.g., 1,4-butanediol, 1,4-pentanediol); 1,5 diols and longer; triols (e.g., Glycerol, Benzenetriol, Pyrogallol, 1,2,6 Hexanetriol, 1,3,5-pentanetriol; Phenols (e.g., hydroquinone, resorcinol, meta-cresol, eugenol, thymol, pyrogallol); sugar alcohols or polyhydric alcohols; arabitol; erythritol; fucitol; galactitol; iditol; inositol; isomalt; lactitol; maltitol; maltotetraitol; maltotriitol; mannitol; ribitol (adonitol); sorbitol; threitol; volemitol; xylitol; and any combinations thereof. In one set of embodiments of the silk fibroin particles of this aspect, the plasticizer is glycerol, for example, in the amount of about 1% (w/w) to about 10% (w/w). See, e.g., WO 2010/042798, Modified Silk Films Containing Glycerol.

The silk fibroin particles described herein can exist in different states, e.g., in hydrated state or dried state. In some embodiments involving the silk fibroin particle described above and herein, the silk fibroin particles are lyophilized silk fibroin particles.

Compositions or Injectable Compositions Comprising the Silk Fibroin Particles Described Herein Also provided herein are compositions comprising one or more silk fibroin particles as described above and herein and a carrier (which may comprise a single carrier or a mixture of two or more carriers (e.g., a first carrier and a second carrier of the same or different weight average molecular weights). In some embodiments, the carrier is not a mixture of two HA components of different weight average molecular weights. The silk fibroin particles and the carrier can be present in any volume ratio that yields properties of the compositions suitable for the need of a particular application. In some embodiments of any one of the compositions or injectable compositions described herein, the silk fibroin particles and the carrier (e.g., total amount of carrier) are present in a volume ratio of at least about 5:95, at least about 10:90, at least about 15:85, at least about 20:80, at least about 25:75, at least about 30:70, at least about 35:65, at least about 40:60, at least about 45:55, at least about 50:50, at least about 55:45, at least about 60:40, at least about 65:35, at least about 70:30, at least about 75:25, at least about 80:20, at least about 85:15, at least about 90:10, or at least about 95:5. In some embodiments, the silk fibroin particles and the carrier (e.g., total amount of carrier) are present in a volume ratio of less than or equal to about 100:1, less than or equal to about 95:5, less than or equal to about 90:10, less than or equal to about 85:15, less than or equal to about 80:20, less than or equal to about 75:25, less than or equal to about 70:30, less than or equal to about 65:35, less than or equal to about 60:40, less than or equal to about 55:45, less than or equal to about 50:50, less than or equal to about 45:55, less than or equal to about 40:60, less than or equal to about 35:65, less than or equal to about 30:70, less than or equal to about 25:75, less than or equal to about 20:80, less than or equal to about 15:85, less than or equal to about 10:90, or less than or equal to about 5:95. Combinations of the above-referenced ranges are also possible. For example, in some embodiments of any one of the compositions or injectable compositions described herein, the silk fibroin particles and the carrier (e.g., total amount of carrier) are present in a volume ratio of about 5:95 to about 95:5, or about 10:90 to about 90:10, or about 20:80 to about 80:20, or about 25:75 to about 75:25, or about 30:70 to about 70:30, or about 40:60 to about 60:40. In some embodiments, the silk fibroin particles and the carrier are present in a volume ratio of about 50:50; about 40:60; about 30:70; about 25:75; about 20:80, or about 10:90, or as low as about 5:95. In some embodiments, the silk fibroin particles and the carrier are present in a volume ratio of about 60:40, about 70:30, about 75:25; about 80:20, about 90:10 or up to about 95:5.

One or more mechanical properties of any one of the compositions or injectable compositions described herein can be tuned to substantially match (e.g., within about 30% or less, within about 20% or less, within about 15% or less, within about 10% or less, within about 9% or less, within about 8% or less, within about 7% or less, within about 6% or less, within about 5% or less, within about 4% or less, within about 3% or less, within about 2% or less, within about 1% or less, or lower) the corresponding mechanical property of a soft tissue to which the compositions are injected. By way of example only, the stiffness of any one of the compositions or injectable compositions described herein can be tuned to substantially match (e.g., within about 30% or less, within about 20% or less, within about 15% or less, within about 10% or less, within about 9% or less, within about 8% or less, within about 7% or less, within about 6% or less, within about 5% or less, within about 4% or less, within about 3% or less, within about 2% or less, within about 1% or less, or lower) the stiff tissue of a soft tissue to which the compositions are injected.

In some embodiments, the compositions described herein exhibit shear thinning behavior with increasing frequency.

In some embodiments of any one of the compositions or injectable compositions described herein, the composition has a stiffness that is characterized by shear storage modulus (G') of a soft tissue to be treated, e.g., within the range of 0.1-10 kPa. In some embodiments of any one of the compositions or injectable compositions described herein, the composition has a stiffness that is characterized by shear storage modulus (G') of human vocal fold tissue, e.g., within the range of 0.01-1 kPa for the frequency range of 1-100 Hz (10 rad/s=1.59 Hz). See, e.g., Miri, A., "Mechanical Characterization of Vocal Fold Tissue: A Review Study," 2014, Journal of Voice. In some embodiments of any one of the compositions or injectable compositions described herein, the composition has a stiffness that is characterized by shear storage modulus (G') of at least about 100 Pa, at least about 150 Pa, at least about 200 Pa, at least about 250 Pa, at least about 300 Pa, at least about 350 Pa, at least about 400 Pa, at least about 450 Pa, at least about 500 Pa, at least about 550 Pa, at least about 600 Pa, at least about 650 Pa, at least about 700 Pa, at least about 750 Pa, at least about 800 Pa, at least about 850 Pa, at least about 900 Pa, at least about 950 Pa, at least about 1000 Pa, at least about 1050 Pa, at least about 1100 Pa, at least about 1150 Pa, at least about 1200 Pa, at least about 1250 Pa, at least about 1300 Pa, at least about 1350 Pa, at least about 1400 Pa, at least about 1450 Pa, at least about 1500 Pa, at least about 2000 Pa, at least about 3000 Pa, at least about 4000 Pa, or at least about 5000 Pa. In some embodiments, the composition has a stiffness that is characterized by G' of less than or equal to about 5,000 Pa, less than or equal to about 4,000 Pa, less than or equal to about 2,000 Pa, less than or equal to about 1500 Pa, less than or equal to about 1450 Pa, less than or equal to about 1400 Pa, less than or equal to about 1350 Pa, less than or equal to about 1300 Pa, less than or equal to about 1250 Pa, less than or equal to about 1200 Pa, less than or equal to about 1150 Pa, less than or equal to about 1100 Pa, less than or equal to about 1050 Pa, less than or equal to about 1000 Pa, less than or equal to about 950 Pa, less than or equal to about 900 Pa, less than or equal to about 850 Pa, less than or equal to about 800 Pa, less than or equal to about 750 Pa, less than or equal to about 700 Pa, less than or equal to about 650 Pa, less than or equal to about 600 Pa, less than or equal to about 550 Pa, less than or equal to about 500 Pa, less than or equal to about 450 Pa, less than or equal to about 400 Pa, less than or equal to about 350 Pa, less than or equal to about 300 Pa, less than or equal to about 250 Pa, less than or equal to about 200 Pa, less than or equal to about 150 Pa, or less than or equal to about 100 Pa. Combinations of the above-referenced ranges are also possible. For example, in some embodiments of any one of the compositions or injectable compositions provided herein, the composition has a stiffness that is characterized by shear storage modulus (G') of about 100 Pa to about 1500 Pa, or about 150 Pa to about 1250 Pa, or about 200 Pa to about 1000 Pa, or about 250 Pa to about 950 Pa, or about 300 Pa to about 900 Pa. In some embodiments, the composition can have a shear storage modulus (G') of about 400 Pa to about 1000 Pa, or about 500 Pa to about 900 Pa. In some embodiments, the composition can have a shear storage modulus (G') of about 100 Pa to about 500 Pa or about 100 Pa to about 400 Pa. In some embodiments, the shear storage modulus provided herein correspond to the value obtained at an angular frequency (or a shear frequency) of about 1Hz. Without wishing to be bound by theory, the shear storage modulus may gradually increase with increasing frequency. For example, for silk fibroin particles suspended in a cross-linked hyaluronic acid (HA) carrier, the storage modulus of the suspension is about 1 kPa measured at a frequency of about 0.1 Hz and up to about 6 kPa measured at a frequency of about 10 Hz.

In some embodiments of any one of the compositions or injectable compositions described herein, the composition is characterized by shear loss modulus (G") of a soft tissue to be treated, e.g., within the range of 0.01-1 kPa. In some embodiments of any one of the compositions or injectable compositions described herein, the composition is characterized by shear loss modulus (G") of human vocal fold tissue, e.g., within the range of 0.05-0.7 kPa for the frequency range of 1-100 Hz. See, e.g., Miri, A., "Mechanical Characterization of Vocal Fold Tissue: A Review Study," 2014, Journal of Voice. In some embodiments of any one of the compositions or injectable compositions described herein, the composition is characterized by shear loss modulus (G") of at least about 25 Pa, at least about 50 Pa, at least about 75 Pa, at least about 100 Pa, at least about 150 Pa, at least about 200 Pa, at least about 250 Pa, at least about 300 Pa, at least about 350 Pa, at least about 400 Pa, at least about 450 Pa, at least about 500 Pa, at least about 550 Pa, at least about 600 Pa, at least about 650 Pa, at least about 700 Pa, at least about 750 Pa, at least about 800 Pa, at least about 850 Pa, at least about 900 Pa, at least about 950 Pa, at least about 1000 Pa, at least about 1050 Pa, at least about 1100 Pa, at least about 1150 Pa, at least about 1200 Pa, at least about 1250 Pa, at least about 1300 Pa, at least about 1350 Pa, at least about 1400 Pa, at least about 1450 Pa, or at least about 1500 Pa. In some embodiments, the composition is characterized by G" of less than or equal to about 1500 Pa, less than or equal to about 1450 Pa, less than or equal to about 1400 Pa, less than or equal to about 1350 Pa, less than or equal to about 1300 Pa, less than or equal to about 1250 Pa, less than or equal to about 1200 Pa, less than or equal to about 1150 Pa, less than or equal to about 1100 Pa, less than or equal to about 1050 Pa, less than or equal to about 1000 Pa, less than or equal to about 950 Pa, less than or equal to about 900 Pa, less than or equal to about 850 Pa, less than or equal to about 800 Pa, less than or equal to about 750 Pa, less than or equal to about 700 Pa, less than or equal to about 650 Pa, less than or equal to about 600 Pa, less than or equal to about 550 Pa, less than or equal to about 500 Pa, less than or equal to about 450 Pa, less than or equal to about 400 Pa, less than or equal to about 350 Pa, less than or equal to about 300 Pa, less than or equal to about 250 Pa, less than or equal to about 200 Pa, less than or equal to about 150 Pa, less than or equal to about 100 Pa, less than or equal to about 75 Pa, less than or equal to about 50 Pa, or less than or equal to about 25 Pa. Combinations of the above-referenced ranges are also possible. For example, in some embodiments of any one of the compositions or injectable compositions provided herein, the composition is characterized by shear loss modulus (G") of about 25 Pa to about 1500 Pa, or about 50 Pa to about 1250 Pa, or about 100 Pa to about 1000 Pa, or about 150 Pa to about 950 Pa, or about 200 Pa to about 900 Pa. In some embodiments, the shear loss modulus provided herein correspond to the value obtained at an angular frequency (or a shear frequency) of about 1Hz. Both shear storage and shear loss moduli can be measured simultaneously using the same testing set-up, e.g., a parallel plate set-up. Similar to shear storage modulus, shear loss modulus can slightly increase with increasing frequencies.

An exemplary method of assessing certain mechanical properties (e.g., the shear storage modulus and shear loss modulus) of the compositions described herein (e.g., a suspension of silk fibroin particles in a carrier described herein) is shear rheometry with parallel plate set-up at a temperature of 25° C. For example, test protocols for oscillatory strain sweeps, frequency sweeps and steady state shear measurements can be adapted from Malvern Instruments Application Notes: "Evaluating the rheological properties of hyaluronic acid hydrogels for dermal filler applications," 2015; and Stocks et al., "Rheological Evaluation of the physical properties of hyaluronic acid dermal fillers," 2011, Journal of Drugs in Dermatology, the contents of each of which are incorporated herein by reference in their entireties. See Example 10 for exemplary methods for determination of such mechanical property measurements.

In some embodiments of any one of the compositions or injectable compositions described herein, the composition is characterized by complex shear modulus (G*) of a soft tissue to be treated, e.g., within the range of 0.1-10 kPa. In some embodiments of any one of the compositions or injectable compositions described herein, the composition is characterized by complex shear modulus (G*) of human vocal fold tissue, e.g., within the range of 0.01-1 kPa for the frequency range of 1-100 Hz. In some embodiments of any one of the compositions or injectable compositions described herein, the composition is characterized by complex shear modulus (G*) of human vocal fold tissue, e.g., within the range of 1-10 kPa for the frequency range of 0.1-10 Hz. In some embodiments of any one of the compositions or injectable compositions described herein, the composition is characterized by complex shear modulus (G*) of at least about 100 Pa, at least about 150 Pa, at least about 200 Pa, at least about 250 Pa, at least about 300 Pa, at least about 350 Pa, at least about 400 Pa, at least about 450 Pa, at least about 500 Pa, at least about 550 Pa, at least about 600 Pa, at least about 650 Pa, at least about 700 Pa, at least about 750 Pa, at least about 800 Pa, at least about 850 Pa, at least about 900 Pa, at least about 950 Pa, at least about 1000 Pa, at least about 1050 Pa, at least about 1100 Pa, at least about 1150 Pa, at least about 1200 Pa, at least about 1250 Pa, at least about 1300 Pa, at least about 1350 Pa, at least about 1400 Pa, at least about 1450 Pa, or at least about 1500 Pa, at least about 2000 Pa, at least about 3000 Pa, at least about 4000 Pa, at least about 5000 Pa, at least about 6000 Pa, or at least about 7000 Pa. In some embodiments, the composition is characterized by G* of less than or equal to about 7000 Pa, less than or equal to about 6,000 Pa, less than or equal to about 5,000 Pa, less than or equal to about 4,000 Pa, less than or equal to about 2,000 Pa, less than or equal to about 1500 Pa, less than or equal to about 1450 Pa, less than or equal to about 1400 Pa, less than or equal to about 1350 Pa, less than or equal to about 1300 Pa, less than or equal to about 1250 Pa, less than or equal to about 1200 Pa, less than or equal to about 1150 Pa, less than or equal to about 1100 Pa, less than or equal to about 1050 Pa, less than or equal to about 1000 Pa, less than or equal to about 950 Pa, less than or equal to about 900 Pa, less than or equal to about 850 Pa, less than or equal to about 800 Pa, less than or equal to about 750 Pa, less than or equal to about 700 Pa, less than or equal to about 650 Pa, less than or equal to about 600 Pa, less than or equal to about 550 Pa, less than or equal to about 500 Pa, less than or equal to about 450 Pa, less than or equal to about 400 Pa, less than or equal to about 350 Pa, less than or equal to about 300 Pa, less than or equal to about 250 Pa, less than or equal to about 200 Pa, less than or equal to about 150 Pa, or less than or equal to about 100 Pa. Combinations of the above-referenced ranges are also possible. For example, in some embodiments of any one of the compositions or injectable compositions provided herein, the composition may be characterized by complex shear modulus (G*) of about 100 Pa to about 1500 Pa, or about 150 Pa to about 1250 Pa, or about 200 Pa to about 1000 Pa, or about 250 Pa to about 950 Pa, or about 300 Pa to about 900 Pa. In some embodiments, the composition may have a complex shear modulus (G*) of about 400 Pa to about 1000 Pa, or about 500 Pa to about 900 Pa. In some embodiments, the composition may have a complex shear modulus (G*) of about 100 Pa to about 500 Pa or about 100 Pa to about 400 Pa. In some embodiments, the complex shear modulus provided herein correspond to the value obtained at an angular frequency (or a shear frequency) of about 0.1-10 Hz (e.g., 1Hz). In some embodiments, the composition may have a complex shear modulus (G*) of about 1 kPa to about 10 kPa, or about 2 kPa to about 8 kPa, or about 2 kPa to about 7 kPa measured within a frequency range of about 0.1 Hz to 10 Hz. Without wishing to be bound by theory, the complex shear modulus may gradually increase with increasing frequency. G* is a derived value from the measured G' and G". Therefore, G* can be computed from the equation G*=G'+iG". In some embodiments, the ranges and trends of G* mimic closely the values and ranges of the shear storage modulus, G', e.g., when G" is an order of magnitude less than G', so the value of G* is primarily dictated by G'.

In some embodiments, the compositions described herein are elastic across a frequency of 0.1-10 Hz (e.g., the value of G' is greater than the value G" for all frequencies between 0.1-10 Hz by at least 10-fold, at least 20-fold, at least 30-fold, at least 40-fold, at least 50-fold, at least 100-fold, or higher). Furthermore, it is contemplated that at frequencies lower than the range presented (<0.1 Hz), the compositions described herein would continue to exhibit elastic behavior. Only at very high frequencies, e.g., well above 100 Hz, and well outside the physiologically relevant range that the compositions would experience in the body, the compositions may begin to yield and may exhibit a significant reduction in elastic behavior.

In some embodiments of any one of the compositions described herein, the composition is characterized by elasticity of at least about 50% or more, including, e.g., at least about 55%, at least about 60%, at least about 65%, at least about 70%, at least about 75%, at least about 80%, at least about 85%, at least about 90%, at least about 95%, or more. In some embodiments, the composition is characterized by an elasticity of less than or equal to about 99%, less than or equal to about 95%, less than or equal to about 90%, less than or equal to about 85%, less than or equal to about 80%, less than or equal to about 75%, less than or equal to about 70%, or less than or equal to about 60%. Combinations of the above-referenced ranges are also possible, In some embodiments, the composition is characterized by elasticity of about 50% to about 95%, or about 60% to about 90% or about 70% to about 85%. In some embodiments, the composition exhibits such elasticity at a shear frequency of at least 5 rad/s or higher, e.g., at least about 10 rad/s, at least about 20 rad/s, at least about 25 rad/s, at least about 50 rad/s, at least about 75 rad/s, or at least about 100 rad/s. In some embodiments, the compositions described herein are elastic across a frequency of 0.1-10 Hz (e.g., the value of G' is greater than the value G" for all frequencies between 0.1-10 Hz by at least 10-fold, at least 20-fold, at least 30-fold, at least 40-fold, at least 50-fold, at least 100-fold, or higher). Furthermore, it is contemplated that at frequencies lower than the range presented (<0.1 Hz), the compositions described herein would continue to exhibit elastic behavior. Only at very high frequencies, e.g., well above 100 Hz, and well outside the physiologically relevant range that the compositions would experience in the body, the compositions may begin to yield and may exhibit a significant reduction in elastic behavior.

As used herein, the term "elasticity" or "elastic" describes the elastic property of a material or composition, e.g., the ability of a material or composition to deform reversibly under applied stress, or to recover its pre-stressed shape and/or volume after removal of the applied stress. In some embodiments, the values of elasticity provided herein can be determined by rheometry at an angular frequency (or shear frequency) of 10 rad/s and computed as follows:

$$\text{Elasticity} = 100\% \times G'/(G'+G''),$$

where G' is the shear storage modulus; and G" is the shear loss modulus. In one set of embodiments, the values of elasticity provided herein can be determined by rheometry at an angular frequency of 10 rad/s.

The carrier may be selected from the examples of carriers discussed in the section "Carriers" below or otherwise as described herein. In some embodiments, the carrier may comprise glycosaminoglycan polymers (e.g., crosslinked or non-crosslinked hyaluronic acid, keratan sulfate, chondroitin sulfate, and/or heparin), extracellular matrix protein polymers (e.g., collagen, elastin, and/or fibronectin), polysaccharides (e.g., cellulose), fibrous protein polymers, a fat material (e.g., derived from a lipoaspirate), and a combination of two or more thereof.

In some embodiments of any compositions and/or injectable compositions described herein, the carrier may have a concentration of at least about 0.1% (w/v), at least about 0.5% (w/v), at least about 1% (w/v), at least about 2% (w/v), at least about 3% (w/v), at least about 4% (w/v), at least about 5% (w/v), at least about 6% (w/v), at least about 7% (w/v), at least about 8% (w/v), at least about 9% (w/v), or at least about 10% (w/v). In some embodiments, the carrier may have a concentration of less than or equal to about 10% (w/v), less than or equal to about 9% (w/v), less than or equal to about 8% (w/v), less than or equal to about 7% (w/v), less than or equal to about 6% (w/v), less than or equal to about 5% (w/v), less than or equal to about 4% (w/v), less than or equal to about 3% (w/v), less than or equal to about 2% (w/v), less than or equal to about 1% (w/v), less than or equal to about 0.5% (w/v), or less than or equal to about 0.1% (w/v). Combinations of the above-referenced ranges are also possible. For example, in some embodiments, the carrier may have a concentration of about 0.1% (w/v) to about 10% (w/v), about 1% (w/v) to about 10% (w/v), about 1% (w/v) to about 8% (w/v), about 1% (w/v) to about 6% (w/v), or about 1% (w/v) to about 5% (w/v). In some embodiments, the hyaluronic acid polymer may have a concentration of about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v).

In some embodiments of any compositions and/or injectable compositions described herein where the carrier is a single carrier, the carrier is hyaluronic acid (e.g., crosslinked hyaluronic acid). In these embodiments, the density of hydrated (e.g., fully saturated with water) silk fibroin particles/hyaluronic acid composition is at least about 0.5 g/mL composition, at least about 0.55 g/mL composition, at least about 0.6 g/mL composition, at least about 0.65 g/mL composition, at least about 0.7 g/mL composition, at least about 0.75 g/mL composition, at least about 0.8 g/mL composition, at least about 0.85 g/mL composition, at least about 0.9 g/mL composition, at least about 0.95 g/mL composition, at least about 1.0 g/mL composition, at least 1.1 g/mL composition, at least 1.2 g/mL composition, at least 1.3 g/mL composition, at least 1.4 g/mL composition, or at least 1.5 g/mL composition. In some embodiments, the density of hydrated (e.g., fully saturated with water) silk fibroin particles/hyaluronic acid composition is no more than 1.5 g/mL composition, no more than 1.4 g/mL composition, no more than 1.3 g/mL composition, no more than 1.2 g/mL composition, no more than 1.1 g/mL, no more than 1.0 g/mL composition, no more than 0.95 g/mL composition, no more than 0.9 g/mL composition, no more than 0.85 g/mL composition, no more than 0.8 g/mL composition, no more than 0.75 g/mL composition, no more than 0.7 g/mL composition, no more than 0.65 g/mL composition, no more than 0.6 g/mL composition, no more than 0.55 g/mL composition, or no more than 0.5 g/mL composition. Combinations of the above-referenced ranges are also possible. In some embodiments, the density of hydrated (e.g., fully saturated with water) silk fibroin particles/hyaluronic acid composition is about 0.5 g/mL composition to about 1.5 g/mL composition, or about 0.7 g/mL composition to about 1.3 g/mL composition, or about 0.8 g/mL composition to about 1.2 g/mL composition, or about 1.0 g/mL composition to about 1.2 g/mL composition, or about 1.1 g/mL composition.

In some embodiments, the density of hydrated (e.g., fully saturated with an aqueous solution, including, e.g., but not limited to water, saline, and/or a buffered solution such as a phosphate buffered solution) silk fibroin particles/hyaluronic acid composition being about 1.1 g/mL composition corresponds to a composition in which hyaluronic acid has a weight average molecular weight of about 800 kDa to about 900 kDa (e.g., about 823 kDa to about 884 kDa) and the crosslinked HA has a crosslink density of about 4 mol % to about 15 mol % (e.g., about 13 mol %).

In some embodiments of any compositions and/or injectable compositions described herein, the carrier may comprise two or more carriers (e.g., a first carrier and a second carrier). Thus, in these embodiments, the composition comprises silk fibroin particles, a first carrier, and a second carrier. The first carrier and the second carrier can each independently be selected from the examples of carriers discussed in the section "Carriers" below or otherwise as described herein. In some embodiments, the first carrier and the second carrier can each independently comprise glycosaminoglycan polymers (e.g., crosslinked or non-crosslinked hyaluronic acid, keratan sulfate, chondroitin sulfate, and/or heparin), extracellular matrix protein polymers (e.g., collagen, elastin, and/or fibronectin), polysaccharides (e.g., cellulose), fibrous protein polymers, a fat material (e.g., derived from a lipoaspirate), and a combination of two or more thereof. In one set of embodiments, at least one or both of the first carrier and the second carrier is/are a hyaluronic acid polymer (crosslinked and/or non-crosslinked).

In some embodiments, the carrier (e.g., the first carrier and optionally the second carrier), e.g., for soft tissue filling applications, can be independently a material that satisfies one or more (e.g., 1, 2, 3, 4) of the following conditions:
  a highly viscous material with a predominantly elastic behavior (via oscillatory rheology);
    These two features are generally applicable for properly suspending particles. Low viscosity materials generally cause particles to settle over time, which can affect performance and storage.
  biocompatibility, minimal to no cytotoxicity;
  tunable mechanical features (either by controlling molecular weight, crosslinking, and/or concentration of particles and/or carriers, or other parameters); and
  biodegradability, which is mediated by the surrounding tissues/cells, or can be triggered by addition of a specific protease or enzyme (e.g. hyaluronidase).
There may be additional criteria involving other types of mechanical features which may be used for selecting first and/or second carriers in other embodiments.

In some embodiments where there are more than one types of carriers in a composition, the first carrier and the second carrier may have different average molecular weights. In some embodiments where the first carrier is HA, the second carrier is not HA of a different average molecular weight. Using at least two carriers of different average molecular weights may provide flexibility to control injectability and/or degradation tunability of the composition. In some embodiments, the second carrier may have a higher average molecular weight than that of the first carrier. For example, the average molecular weight of the second carrier may be higher than that of the first carrier by at least about 50% or higher, including, e.g., by at least about 55%, at least about 60%, at least about 65%, at least about 70%, at least about 75%, at least about 80%, at least about 85%, at least about 90%, at least about 95%, or higher. In some embodiments, the average molecular weight of the second carrier can be higher than that of the first carrier by at least 1.1-fold or higher, including, e.g., at least 1.5-fold, 2-fold, 2.5-fold, 3-fold, 3.5-fold, 4-fold, 4.5-fold, 5-fold, or higher, e.g., up to 10-fold or less. In some embodiments, the average molecular weight of the second carrier can be higher than that of the first carrier by less than or equal to about 500%, less than or equal to about 450%, less than or equal to about 400%, less than or equal to about 350%, less than or equal to about 300%, less than or equal to about 250%, less than or equal to about 200%, less than or equal to about 150%, less than or equal to about 100%, less than or equal to about 95%, less than or equal to about 90%, less than or equal to about 80%, less than or equal to about 70%, less than or equal to about 60%, or less than or equal to about 50%. Combinations of the above-referenced ranges are also possible. The presence of more than one carriers (e.g., two or more, or three or more) of different average molecular weights may result in the carrier having a multimodal (e.g., a bimodal) molecular weight distribution. The average molecular weights provided herein and below for the first carrier and second carrier can correspond to weight average molecular weights, number average molecular weights, or peak average molecular weights. The average molecular weights provided herein and below for the first carrier and second carrier can be determined by any known methods in the art, including, e.g., but not limited to, gel electrophoresis (e.g., sodium dodecyl sulfate polyacrylamide gel electrophoresis (SDS-PAGE), size exclusion gel chromatography, mass spectroscopy (e.g., MALDI or ESI), or high performance liquid chromatography (HPLC), refractive index detection, light scattering, or any combinations thereof.

In one set of the embodiments described herein, the average molecular weights provided herein and below for the first carrier and second carrier correspond to weight average molecular weights, for example, as determined by size exclusion chromatography.

The volume ratio of the first carrier to the second carrier can vary according to the need of an application, e.g., to achieve a particular extrusion force and/or degradation rate. In some embodiments of any one of the compositions or injectable compositions described herein where there are more than one types of carriers, the volume ratio of the first carrier to the second carrier is at least about 5:95; at least about 10:90, at least about 15:85, at least about 20:80, at least about 25:75, at least about 30:70, at least about 35:65, at least about 40:60, at least about 45:55, at least about 50:50, at least about 55:45, at least about 60:40, at least about 65:35, at least about 70:30, at least about 75:25, at least about 80:20, at least about 85:15, at least about 90:10, or at least about 95:5. In some embodiments, the volume ratio of the first carrier to the second carrier is less than or equal to about 90:10, less than or equal to about 85:15, less than or equal to about 80:20, less than or equal to about 75:25, less than or equal to about 70:30, less than or equal to about 65:35, less than or equal to about 60:40, less than or equal to about 55:45, less than or equal to about 50:50, less than or equal to 45:55, less than or equal to 40:60, less than or equal to 35:65, less than or equal to 30:70, less than or equal to 25:75, less than or equal to 20:80, less than or equal to 15:85, less than or equal to 10:90, less than or equal to 5:95. Combinations of the above-referenced ranges are also possible. In some embodiments, the volume ratio of the first carrier to the second carrier can be about 50:50 to about 90:10, or about 60:40 to 90:10, or about 70:30 to about 90:10, or about 80:20 to about 90:10. In some embodiments, the volume ratio of the first carrier to the second carrier can be about 5:95 to about 50:50, about 5:95 to about 40:60 or about 10:90 to about 30:70.

In some embodiments of any one of the compositions described above or herein, the composition is an injectable composition. As used herein, the term "injectable composition" generally refers to a composition that can be delivered or administered into a tissue with a minimally invasive procedure. The term "minimally invasive procedure" refers to a procedure that is carried out by entering a subject's body through the skin or through a body cavity or an anatomical opening, but with the smallest damage possible (e.g., a small incision, injection). In some embodiments, the injectable composition can be administered or delivered into a tissue by injection. In some embodiments, the injectable composition can be delivered into a tissue through a small incision into a tissue or skin followed by insertion of a needle, a cannula, and/or tubing, e.g., a catheter.

In some embodiments of any one of the compositions described herein, the composition is characterized in that a standard deviation of extrusion force of the composition through a 18-30 (e.g., 18, 19, 20, 21, 22, 23, 24, 25, 26, 27, 28, 29, or 30) gauge needle into air, as determined between about 50% extrusion volume and about 90% extrusion volume, is less than about 40%, less than about 35%, less than about 30%, less than about 25%, less than about 20%, less than about 15%, less than about 10%, less than about 5%, or less than about 1%, of an average extrusion force for the corresponding range of the extrusion volume (i.e., about 50%-about 90% extrusion volume). In some embodiments, the standard deviation of extrusion force of the composition through a 18-30 (e.g., 18, 19, 20, 21, 22, 23, 24, 25, 26, 27, 28, 29, or 30) gauge needle into air, as determined between about 50% extrusion volume and about 90% extrusion volume, is at least about 0.1%, at least about 0.5%, at least about 1%, at least about 5%, at least about 10%, at least about 15%, or at least about 20%, of an average extrusion force for the corresponding range of the extrusion volume (i.e., about 50%-about 90% extrusion volume). Combinations of the above-referenced ranges are also possible. For example, in some embodiments, the standard deviation of extrusion force of the composition through a 18-30 (e.g., 18, 19, 20, 21, 22, 23, 24, 25, 26, 27, 28, 29, or 30) gauge needle into air, as determined between about 50% extrusion volume and about 90% extrusion volume, is about 0.1% to about 40%, or about 1% to about 20%, or about 1% to about 15%, of an average extrusion force for the corresponding range of the extrusion volume (i.e., about 50%-about 90% extrusion volume).

In some embodiments of any compositions or injectable compositions described herein, the stiffness of the composition is decreased by at least about 10%, at least about 15%, at least about 20%, at least about 30%, at least about 40%, at least about 50%, at least about 60%, at least about 70%, at least about 80%, at least about 90%, or higher, as measured between about 0.1% strain and about 1% strain, or between about 0.1% strain and about 10% strain, or between about 1% strain and about 100% strain, or between about 10% strain and about 90% strain. In some embodiments, the stiffness of the composition is decreased by no more than about 95%, no more than about 90%, no more than about 80%, no more than about 70%, no more than about 60%, no more than about 50%, no more than about 40%, no more than about 30%, or no more than about 20%, as measured between about 0.1% strain and about 1% strain, or between about 0.1% strain and about 10% strain, or between about 1% strain and about 100% strain, or between about 10% strain and about 90% strain. Combinations of the above-referenced ranges are also possible. In some embodiments, the stiffness of the composition is decreased by about 10% to about 90% or about 15% to about 80%, or about 10% to about 40% or about 10% to about 30%, as measured between about 0.1% strain and about 1% strain, or between about 0.1% strain and about 10% strain, or between about 1% strain and about 100% strain, or between about 10% strain and about 90% strain.

In some embodiments of any one of the compositions described herein, the composition is characterized in that an average force of extruding about 1 mL of the composition (e.g., using a 1-mL syringe) through a 18-30 gauge needle (e.g., 18, 19, 20, 21, 22, 23, 24, 25, 26, 27, 28, 29, or 30 gauge) into air (e.g., under atmospheric pressure) is less than 60 N, including, for example less than 50 N, less than 40 N, less than 30 N, less than 20 N, less than 15 N, less than 10 N, or less than 5 N. In some embodiments, the composition is characterized in that an average force of extruding about 1 mL of the composition through a 18-30 gauge needle (e.g., 18, 19, 20, 21, 22, 23, 24, 25, 26, 27, 28, 29, or 30 gauge) into air is equal to or more than 5 N, equal to or more than 10 N, equal to or more than 15 N, equal to or more than 20 N, equal to or more than 30 N, equal to or more than 40 N, equal to more than 50 N, equal to or more than 60 N. Combinations of the above-referenced ranges are also possible. For example, in some embodiments, the composition is characterized in that an average force of extruding about 1 mL of the composition through a 18-30 gauge needle (e.g., 18, 19, 20, 21, 22, 23, 24, 25, 26, 27, 28, 29, or 30 gauge) into air is about 5 N to about 60 N, about 10 N to about 50 N, or about 15 N to about 50 N, or about 20 N to about 50 N, or about 5 N to about 60 N.

In some embodiments where the total amounts of the silk fibroin particles and the carrier are in a volume ratio of about 5:95 to about 95:5 (inclusive), an average force of extruding about 1 mL of the composition (e.g., using a 1-mL syringe) through a 18-30 gauge needle (e.g., 18, 19, 20, 21, 22, 23, 24, 25, 26, 27, 28, 29, or 30 gauge) into air (e.g., under atmospheric pressure) is less than 60 N, including, for example less than 50 N, less than 40 N, less than 30 N, less than 20 N, less than 15 N, less than 10 N, or less than 5 N. In some embodiments, the composition is characterized in that an average force of extruding about 1 mL of the composition through a 18-30 gauge needle (e.g., 18, 19, 20, 21, 22, 23, 24, 25, 26, 27, 28, 29, or 30 gauge) into air is equal to or more than 5 N, equal to or more than 10 N, equal to or more than 15 N, equal to or more than 20 N, equal to or more than 30 N, equal to or more than 40 N, equal to more than 50 N, equal to or more than 60 N. Combinations of the above-referenced ranges are also possible. For example, in some embodiments, the composition is characterized in that an average force of extruding about 1 mL of the composition through a 18-30 gauge needle (e.g., 18, 19, 20, 21, 22, 23, 24, 25, 26, 27, 28, 29, or 30 gauge) into air is about 5 N to about 60 N, about 10 N to about 50 N, or about 15 N to about 50 N, or about 20 N to about 50 N, or about 5 N to about 60 N.

In some embodiments where the total amounts of the silk fibroin particles and the carrier are in a volume ratio of less than or equal to about 50:50 (e.g., e.g., less than or equal to about 40:60, or less than or equal to about 30:70, less than or equal to about 20:80, or lower, inclusive), an average force of extruding about 1 mL of the composition described herein through a 18-25 gauge (e.g., 18, 19, 20, 21, 22, 23, 24, or 25 gauge) needle into air (e.g., atmospheric pressure) is about 30 N or lower (e.g., about 25 N or lower, about 20 N or lower, about 15 N or lower, about 10 N or lower, or about 5 N or lower). Alternatively, an average force of extruding about 1 mL of the composition through a 25-30 gauge (e.g., 25G, 26G, 27G, 28G, 29G, or 30G) gauge needle into air is less than 40N (e.g., about 35 N or lower, about 30 N or lower, about 25 N or lower, about 20 N or lower, about 15 N or lower, about 10 N or lower, or about 5 N or lower). In some embodiments, when the total amounts of the particles and the carrier are in a volume ratio of 40:60 or lower (e.g., 30:70), an average force of extruding about 1 mL of the composition through a 21 gauge needle into air is about 30 N or lower.

In some embodiments, at least about 80% or higher (including, e.g., at least about 85%, at least about 90%, at least about 95%, at least about 98%, or higher, up to 100%) of the silk fibroin particles in the compositions described herein are substantially spherical particles (e.g., having an aspect ratio of less than or equal to about 1.5, such as about 0.9 to about 1.1 or about 1.0 to about 1.1).

In some embodiments, the silk fibroin particles in any one of the compositions described herein are substantially monodispersed. As used therein, the term "substantially monodispersed" refers to a population of silk fibroin particles having a narrow particle size distribution. For example, the particle size distribution can be characterized by particle size uniformity as defined below, $$\text{Uniformity} = \frac{\sum X_i |d(x, 0.5) - di|}{d(x, 0.5) \sum X_i}$$

where d is the mean diameter and X is the frequency/percentage. The values of uniformity range from 0-1 where 0 represents completely monodisperse populations. In some embodiments, the particle size uniformity of the silk fibroin particles is at least about 0, at least about 0.1, at least about 0.2, at least about 0.3, at least about 0.4, or at least about 0.5. In some embodiments, the particle size uniformity of the silk fibroin particles is no more than 0.5, no more than 0.4, no more than 0.3, no more than 0.2, no more than 0.1, or no more than 0.05. Combinations of the above-referenced ranges are also possible. For example, in some embodiments, the particle size uniformity of the silk fibroin particles may be about 0-0.4, or about 0-0.5. In some embodiments, the particle size uniformity of the silk fibroin particles is about 0, about 0.1, about 0.2, about 0.3, or about 0.4 (inclusive). The particle size can be measured by any methods known in the art or as described herein.

The average particle size of the silk fibroin particles in some embodiments involving the compositions described herein may be selected to suit the need of each application. For example, smaller average particle size may be desirable for vocal fold augmentation, while larger average particle size may be more suitable for large volume reconstruction (e.g., breast reconstruction). Accordingly, in some embodiments, the silk fibroin particles have an average particle size of about 250 µm to about 450 µm, or about 300 µm to about 400 µm. In alternative embodiments, the silk fibroin particles may have an average particle size of about 400 µm to about 600 µm or about 450 µm to about 550 µm. In some embodiments, the silk fibroin particles may have an average particle size of about 50 µm to about 200 µm. In some embodiments, the silk fibroin may have an average particle size of about 75 µm to about 125 µm.

In some embodiments involving the compositions of any aspects described above and herein, the compositions may include any suitable inactive ingredient included in U.S. Food & Drug Administration (FDA)'s database for Generally Recognized as Safe (GRAS) substances, which is accessible online at accessdata.fda.gov/scripts/fdcc/?set=SCOGS.

In some embodiments involving the compositions described above and herein, where the carrier comprises crosslinked hyaluronic acid, the composition may comprise residual chemical(s). For example, in some embodiments, about 1 mL dose of the composition comprising silk fibroin particles (having an average particle size of about 300 microns to 450 microns) can possess no more than about 250 micrograms of residual lithium, including, e.g., no more than 200 micrograms, no more than about 150 micrograms, no more than about 100 micrograms, no more than about 50 micrograms, no more than about 25 micrograms, no more than about 10 micrograms, no more than about 5 micrograms, of residual lithium. In some embodiments, about 1 mL dose of the composition comprising silk fibroin particles (having an average particle size of about 300 microns to 450 microns) can possess no more than about 250 micrograms, including, e.g., no more than about 200 micrograms, no more than about 150 micrograms, no more than about 100 micrograms, no more than about 50 micrograms, no more than about 25 micrograms, no more than about 10 micrograms, no more than about 5 micrograms, of residual bromide. In some embodiments, about 1 mL dose of the composition comprising silk fibroin particles (having an average particle size of about 300 microns to 450 microns) can possess no more than about 30 mg, including, e.g., no more than about 20 mg, no more than about 10 mg, no more than about 5 mg, no more than about 1 mg, no more than about 0.5 mg, no more than about 0.1 mg, or no more than about 0.01 mg, of residual methanol. In some embodiments, the crosslinked hyaluronic acid in the composition can comprise no more than about 2 ppm, including, e.g., no more than about 1 ppm, no more than about 0.5 ppm, no more than about 0.1 ppm, or no more than about 0.05 ppm, of residual crosslinking agent (e.g., 1,4-butanediol diglycidyl ether (BDDE)).

In some embodiments involving the compositions of any aspects described above and herein, the injectable composition may be pre-loaded in a delivery device, e.g., a syringe or any embodiment of the delivery devices described herein.

Delivery Devices

In some embodiments, a delivery device may be used to deliver a composition to a subject. In some embodiments, the device may be coupled to a laryngoscope or other endoscope.

In some embodiments, the device may include tubing that may include an inner tube and an outer sheath tube. In some embodiments, the device may include a hollow needle that is connected to the inner tube and in fluid communication with the inner tube. In some embodiments, the inner tube may be positioned inside the outer sheath tube. The outer sheath tube may have an inside diameter that is larger than the outside diameter of the inner tube. In some cases, the outer sheath tube may help to prevent the needle from breaking as the device is coupled to an endoscope or laryngoscope. In some embodiments, a diameter-reduced portion, e.g., a taper, may be formed at the distal end of the outer sheath tube so as to enable control of how far the needle and inner tube may be distally extended relative to the outer sheath tube.

In some embodiments, the inner tube extends through a channel of a handle and is connected to and in fluid communication with a syringe that is attached to the handle. As such, a composition may be extruded from the syringe into the inner tube. The inner tube and needle may be moved through the outer sheath tube by actuating the handle. In some embodiments, the handled is actuated by sliding one portion of the handle relative to another portion of the handle.

Although the description herein is directed primarily to delivering the compositions described herein, in some embodiments, the delivery device described herein may be used to deliver other compositions. The device may be used to deliver compositions to the vocal folds, cervix, urinary tract, larynx, pelvis, or other parts of the body in other embodiments.

Figure 22:
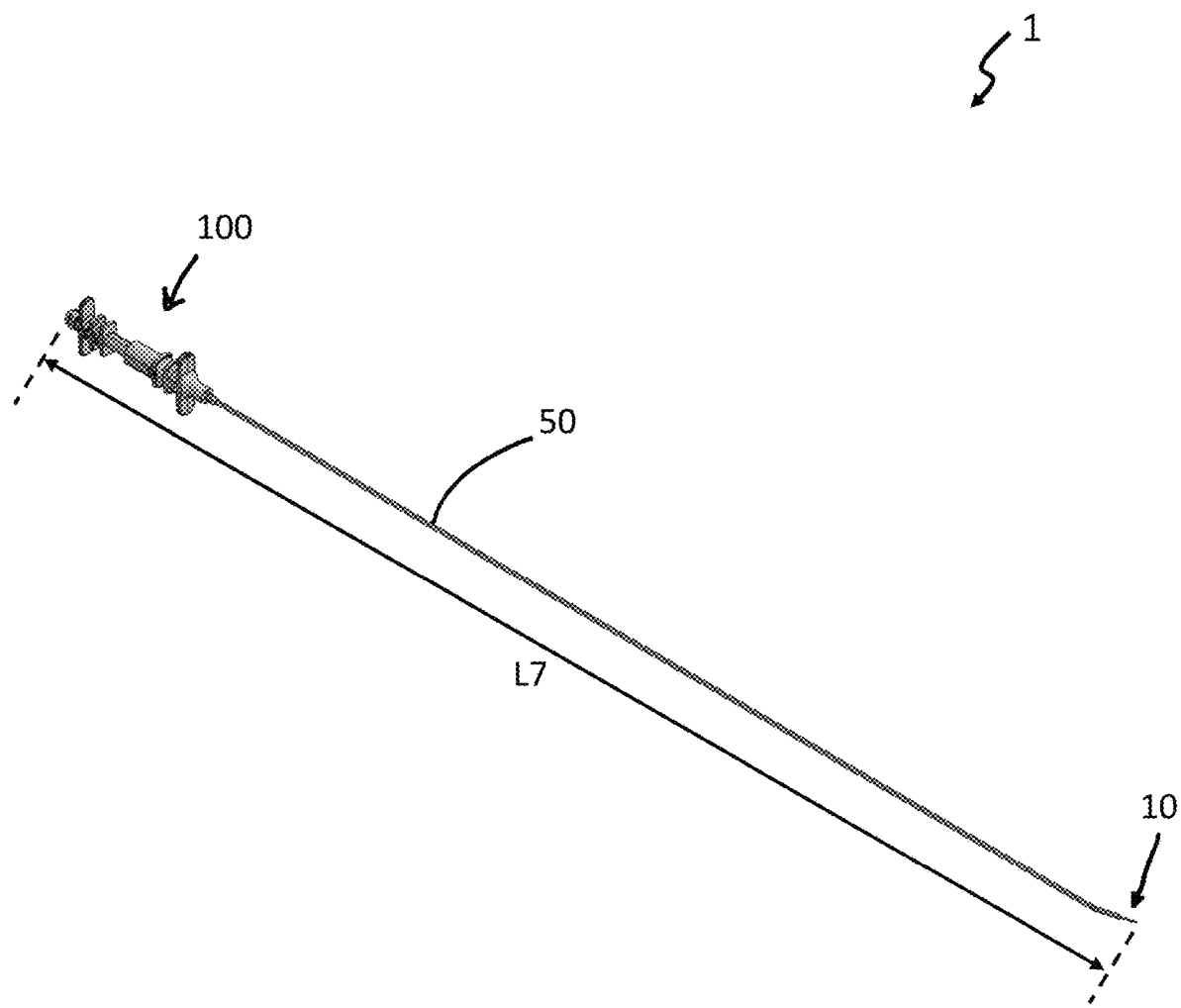
FIG. 22 depicts a device for delivering a composition to a subject according to some aspects.

FIG. 22 depicts an illustrative example of a delivery device 1 for delivering a composition to a subject according to one set of embodiments. The device 1 may include a needle 10, tubing 50, and a handle 100. The needle 10 may be hollow in order to deliver the composition through the needle to the patient. In some embodiments, the tubing 50 includes a tube that is connected to the needle such that movement of the inner tube also moves the needle. The inner tube may also be in fluid communication with the needle such that fluid can enter from the inner tube into the needle. In some embodiments, the inner tube may be referred to as a catheter or a needle catheter. In some embodiments, the tubing 50 may also include an outer sheath tube such that the tube connected to the needle may be positioned within the outer sheath tube. As such, the tube connected to the needle may also be referred to as an inner tube.

The needle may be moved through the outer sheath tube of the tubing such that the needle may be moved from a retracted position in which the needle is covered by the outer sheath tube to an extended, deployed position in which the needle tip is exposed outside of the outer sheath tube in order to pierce tissue and deliver composition to a target site. The outer sheath tube of the tubing may connect to a distal end of the handle 100, and the inner tube of the tubing may run through a channel within the handle. In some embodiments, the inner tube may connect to a container, such as a syringe, (not shown in FIG. 22) holding the composition. The inner tube may be in fluid communication with the syringe such that the composition may be moved from the syringe into the inner tube, and then into the needle. In some embodiments, the proximal end of the handle may connect to the syringe. In some embodiments, the handle may include an actuation mechanism that moves the needle from a retracted position to an extended, deployed position.

Figure 23:
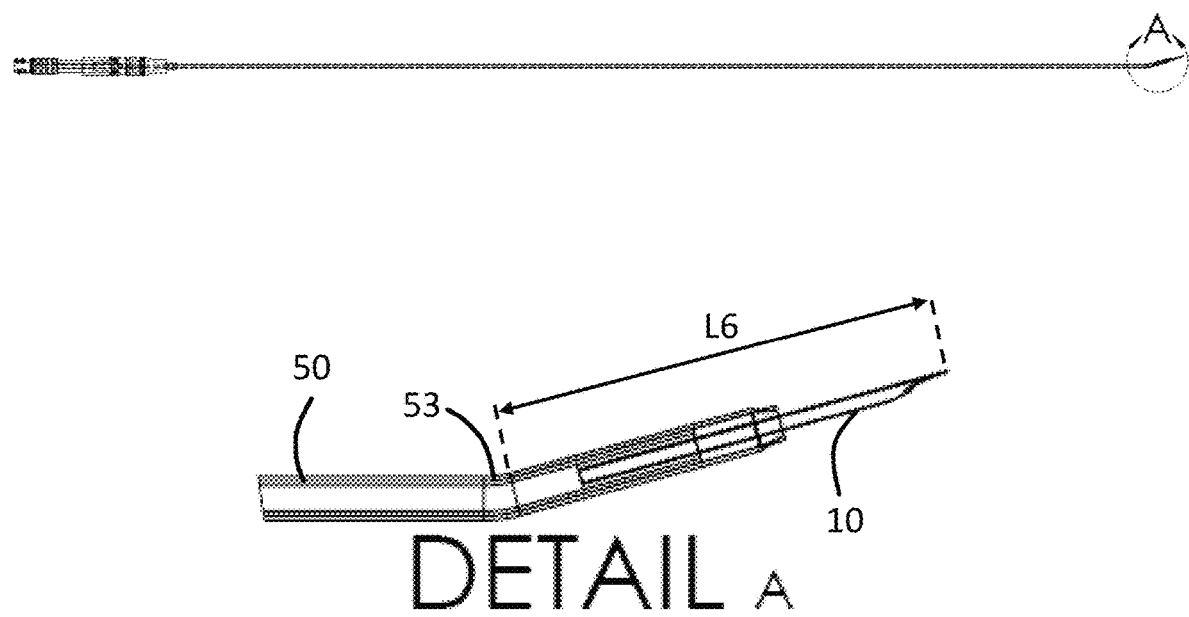
FIG. 23 depicts an enlargement of a distal portion of the device of FIG. 22 showing a needle of the device.

FIG. 23 depicts an enlarged view of the distal end of the device 1. In FIG. 23, a portion of the needle 10 may be located within the outer sheath tube of the tubing 50. The needle 10 is shown in the extended, deployed position in FIG. 23, in which the tip of the needle has been moved out of the outer sheath tube of tubing 50 and is exposed. In the extended, deployed position, the needle is able to penetrate into an injection site, such as tissue, in order to deliver composition.

Figure 24:
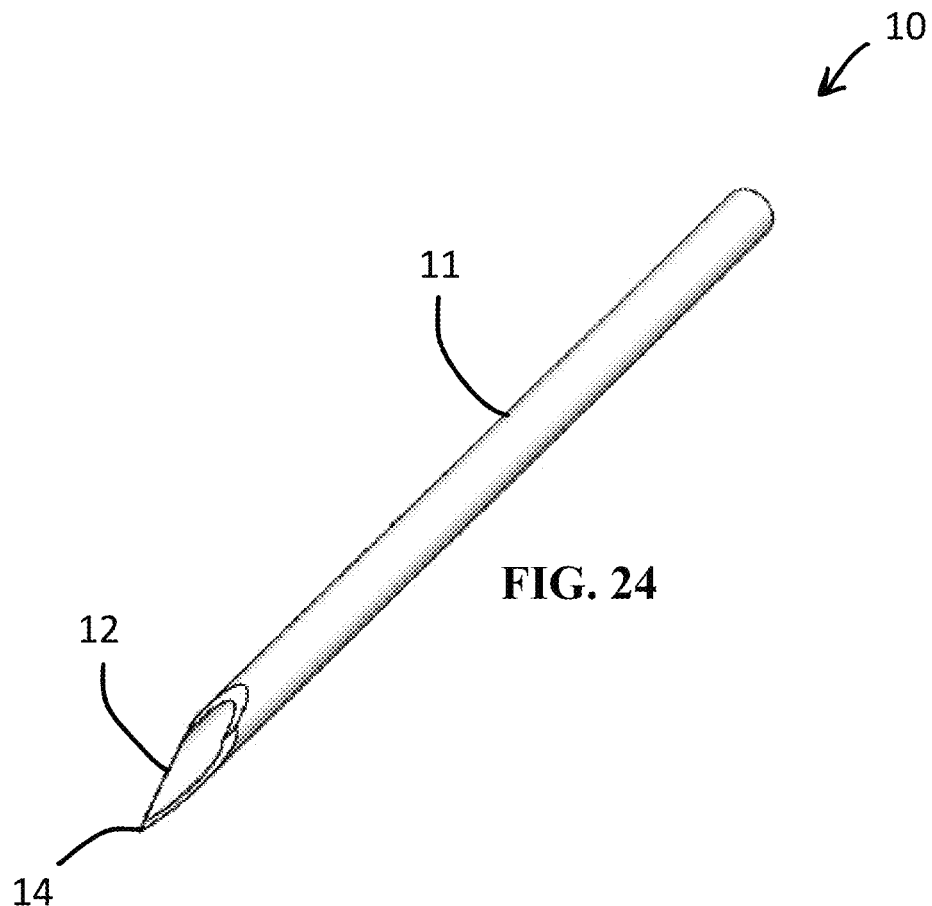
FIG. 24 depicts an enlarged view of the needle of FIG. 23.

FIG. 24 depicts an enlarged view of the needle 10. The needle 10 may include a needle body 11 and a needle tip 12.

Figure 25:
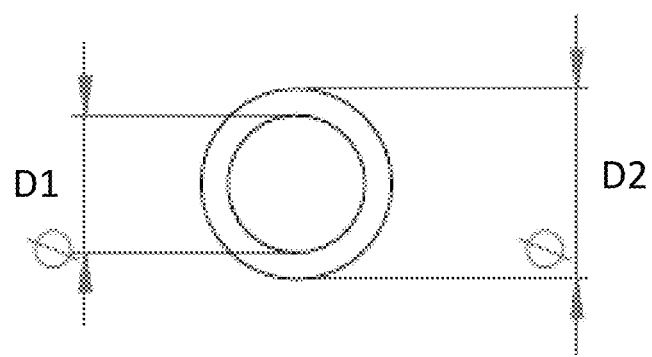
FIG. 25 is a cross-section of the needle of FIG. 24.

In some embodiments, the needle tip 12 may end in a point 14. As discussed above, the needle may be hollow. A cross-section of the needle body is shown in FIG. 25, which shows the inside diameter D1 and outside diameter D2 of the needle body 11.

In some embodiments, the needle body may have an inside diameter D1 of at least about 0.3 mm, at least about 0.4 mm, at least about 0.45 mm, at least about 0.5 mm, at least about 0.55 mm, at least about 0.6 mm, at least about 0.7 mm, at least about 0.8 mm or at least about 0.9 mm. In some embodiments, the needle body may have an inside diameter D1 of less than or equal to about 0.9 mm, less than or equal to about 0.8 mm, less than or equal to about 0.7 mm, less than or equal to about 0.6 mm, less than or equal to about 0.55 mm, less than or equal to about 0.5 mm, less than or equal to about 0.45 mm or less than or equal to about 0.4 mm. Combinations of the above-referenced ranges are also possible. For example, in some embodiments, the needle body may have an inside diameter D1 of about 0.3 mm to about 0.9 mm, or about 0.4 mm to about 0.8 mm, or about 0.45 mm to about 0.55 mm, or about 0.65 mm to about 0.75 mm.

In some embodiments, the needle body may have an outside diameter D2 of at least about 0.4 mm, at least about 0.5 mm, at least about 0.6 mm, at least about 0.65 mm, at least about 0.7 mm, at least about 0.75 mm, at least about 0.8 mm, at least about 0.9 mm, or at least about 1.0 mm. In some embodiments, the needle body may have an outside diameter D2 of less than or equal to about 1.0 mm, less than or equal to about 0.9 mm, less than or equal to about 0.8 mm, less than or equal to about 0.75 mm, less than or equal to about 0.7 mm, less than or equal to about 0.65 mm, less than or equal to about 0.6 mm, less than or equal to about 0.55 mm, less than or equal to about 0.5 mm, or less than or equal to about 0.4 mm. Combinations of the above-referenced ranges are also possible. For example, in some embodiments, the needle body may have an outside diameter D2 of about 0.4 mm to about 0.9 mm, or about 0.5 to about 0.8 mm, or about 0.55 to about 0.75 mm, or about 0.6 mm to about 0.7 mm, or about 0.63 mm to about 0.68 mm, or about 0.6 mm to about 1.0 mm, or about 0.7 mm to about 0.9 mm, or about 0.75 mm to about 0.85 mm, or about 0.7 mm.

In some embodiments, the needle body may have a thickness, i.e., the difference between D1 and D2, of at least about 0.03 mm, at least about 0.04 mm, at least about 0.045 mm, at least about 0.05 mm, at least about 0.065 mm, at least about 0.07 mm, at least about 0.085 mm, at least about 0.1 mm, at least about 0.125 mm, at least about 0.15 mm, at least about 0.175 mm, at least about 0.2 mm, at least about 0.25 mm, or at least about 0.3 mm. In some embodiments, the needle body may have a thickness of less than or equal to about 0.3 mm, less than or equal to about 0.25 mm, less than or equal to about 0.2 mm, less than or equal to about 0.175 mm, less than or equal to about 0.16 mm, less than or equal to about 0.15 mm, less than or equal to about 0.125 mm, less than or equal to about 0.1 mm, less than or equal to about 0.09 mm, less than or equal to about 0.085, less than or equal to about 0.065 mm, less than or equal to about 0.05 mm, or less than or equal to about 0.045 mm. Combinations of the above-referenced ranges are also possible. For example, in some embodiments, the needle body may have a thickness of about 0.03 mm to about 0.3 mm, or about 0.04 mm to about 0.1 mm, or about 0.04 mm to about 0.25 mm, or about 0.4 mm to about 0.2 mm, or about 0.125 to about 0.175 mm, or about 0.14 mm to about 0.16 mm, or about 0.045 mm to about 0.085 mm, or about 0.8 mm.

In some embodiments, having a thin needle body thickness may have the benefit of having a large enough needle inside diameter to allow passage of material such as viscous material, and yet having a small enough needle outside diameter to allow the needle to fit within an outer sheath tube that is small enough to be endoscopically delivered. In some embodiments, the needle is formed from a hypotube. In some embodiments, the needle may be made of stainless steel or other metal or metal alloy, or other suitable material.

In some embodiments, the needle may have a needle gauge of 18-30 (e.g., 18, 19, 20, 21, 22, 23, 24, 25, 26, 27, 28, 29, or 30) gauge. In some embodiments, the needle may have a needle gauge of 23XX gauge.

The needle may be movable within the outer sheath tube between a fully extended state, as shown in FIG. 23, and a retracted state in which the entire needle is located within the outer sheath tube. In some embodiments, when the hollow needle is in the fully extended state, a distance from a distal end of the hollow needle to a distal end of the outer sheath tube may be at least about 4 mm, at least about 5 mm, at least about 5.5 mm, at least about 6 mm, or at least about 7 mm. In some embodiments, when the hollow needle is in the fully extended state, a distance from a distal end of the hollow needle to a distal end of the outer sheath tube may be less than or equal to about 10 mm, less than or equal to about 9 mm, less than or equal to about 8.5 mm, less than or equal to about 8 mm, or less than or equal to about 7 mm. Combinations of the above-referenced ranges are also possible. For example, in some embodiments, when the hollow needle is in the fully extended state, a distance from a distal end of the hollow needle to a distal end of the outer sheath tube may be about 4 mm to about 10 mm, or about 5 mm to about 9 mm, or about 5.5 mm to about 8.5 mm, or about 6 mm to about 8 mm.

In some embodiments, the needle 10 may include a needle tip 12, which may end in a point 14. In some embodiments, a frontside triple point cut is used to form the needle tip 12. Detailed views of the needle tip geometry are shown in the top view of FIG. 26A and the side view of FIG. 26B.

Figures 26A, 26B:
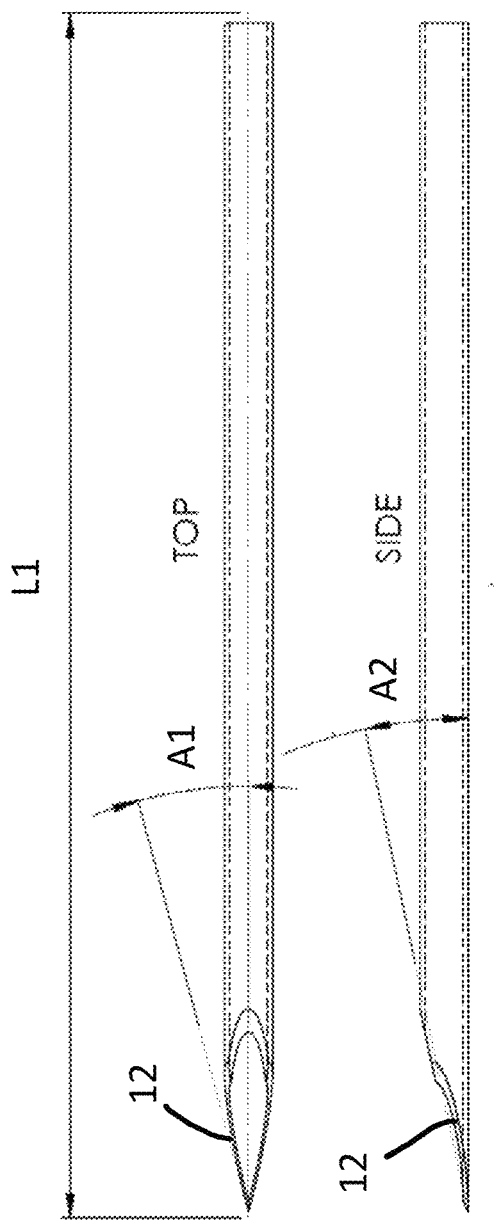
FIG. 26A is a top view of the needle of FIG. 24.
FIG. 26B is a side view of the needle of FIG. 24.

In some embodiments, such as that shown in FIG. 26A, the needle tip 12 has a tip point angle A1. In some embodiments, the angle A1 may be at least about 10 degrees, at least about 12 degrees, at least about 14 degrees, at least about 14.5 degrees, at least about 15 degrees, at least about 15.5 degrees, at least about 16 degrees, or at least about 18 degrees. In some embodiments, angle A1 may be less than or equal to about 20 degrees, less than or equal to about 18 degrees, less than or equal to about 17 degrees, less than or equal to about 16 degrees, less than or equal to about 15.5 degrees, less than or equal to about 15 degrees, less than or equal to about 14.5 degrees, less than or equal to about 14 degrees, or less than or equal to about 12 degrees. Combinations of the above-referenced ranges are also possible. For example, in some embodiments, angle A1 may be about 10 degrees to about 20 degrees, or about 12 degrees to about 18 degrees, or about 13 degrees to about 17 degrees, or about 14 degrees to about 16 degrees, or about 14.5 degrees to about 15.5 degrees, or about 14.8 degrees to about 15.2 degrees.

In some embodiments, such as that shown in FIG. 26B, the needle tip has a bevel angle A2. In some embodiments, the angle A2 may be at least about 10 degrees, at least about 11 degrees, at least about 11.5 degrees, at least about 12 degrees, at least about 12.5 degrees, at least about 13 degrees, at least about 13.5 degrees, at least about 14 degrees, at least about 14.5 degrees, or at least about 15 degrees. In some embodiments, angle A2 may be less than or equal to about 15 degrees, less than or equal to about 14.5 degrees, less than or equal to about 14 degrees, less than or equal to about 13.5 degrees, less than or equal to about 13 degrees, less than or equal to about 12.5 degrees, less than or equal to about 12 degrees, less than or equal to about 11.5 degrees, less than or equal to about 11 degrees, or less than or equal to about 10 degrees. Combinations of the above-referenced ranges are also possible. For example, in some embodiments, angle A1 may be about 10 degrees to about 15 degrees, about 12 degrees to about 15 degrees, about 10 degrees to about 14 degrees, about 11 degrees to about 13 degrees, about 11.5 degrees to about 12.5 degrees, or about 11.8 degrees to about 12.2 degrees.

In some embodiments, the needle tip geometry may be formed into a tube of material, e.g., by starting with a tube of material and grinding the needle tip geometry into the tubing.

In some embodiments, such as that shown in FIG. 26A, the needle has a total length L1. In some embodiments, the length L1 may be at least about 10 mm, at least about 12 mm, at least about 14 mm, at least about 15 mm, at least about 15 0.5 mm, at least about 16 mm, at least about 17 mm, at least about 18 mm, at least about 20 mm, or at least about 22 mm. In some embodiments, length L1 may be less than or equal to about 30 mm, less than or equal to about 28 mm, less than or equal to about 26 mm, less than or equal to about 24 mm, less than or equal to about 22 mm, less than or equal to about 20 mm, less than or equal to about 18 mm, less than or equal to about 17 mm, less than or equal to about 16.5 mm, less than or equal to about 16 mm, less than or equal to about 15.5 mm, less than or equal to about 15 mm, less than or equal to about 14 mm, less than or equal to about 12 mm, or less than or equal to about 10 mm. Combinations of the above-referenced ranges are also possible. For example, in some embodiments, length L1 may be about 10 mm to about 20 mm, or about 14 mm to about 18 mm, or about 15 mm to about 17 mm, or about 15.5 to about 16.5 mm.

Figure 27:
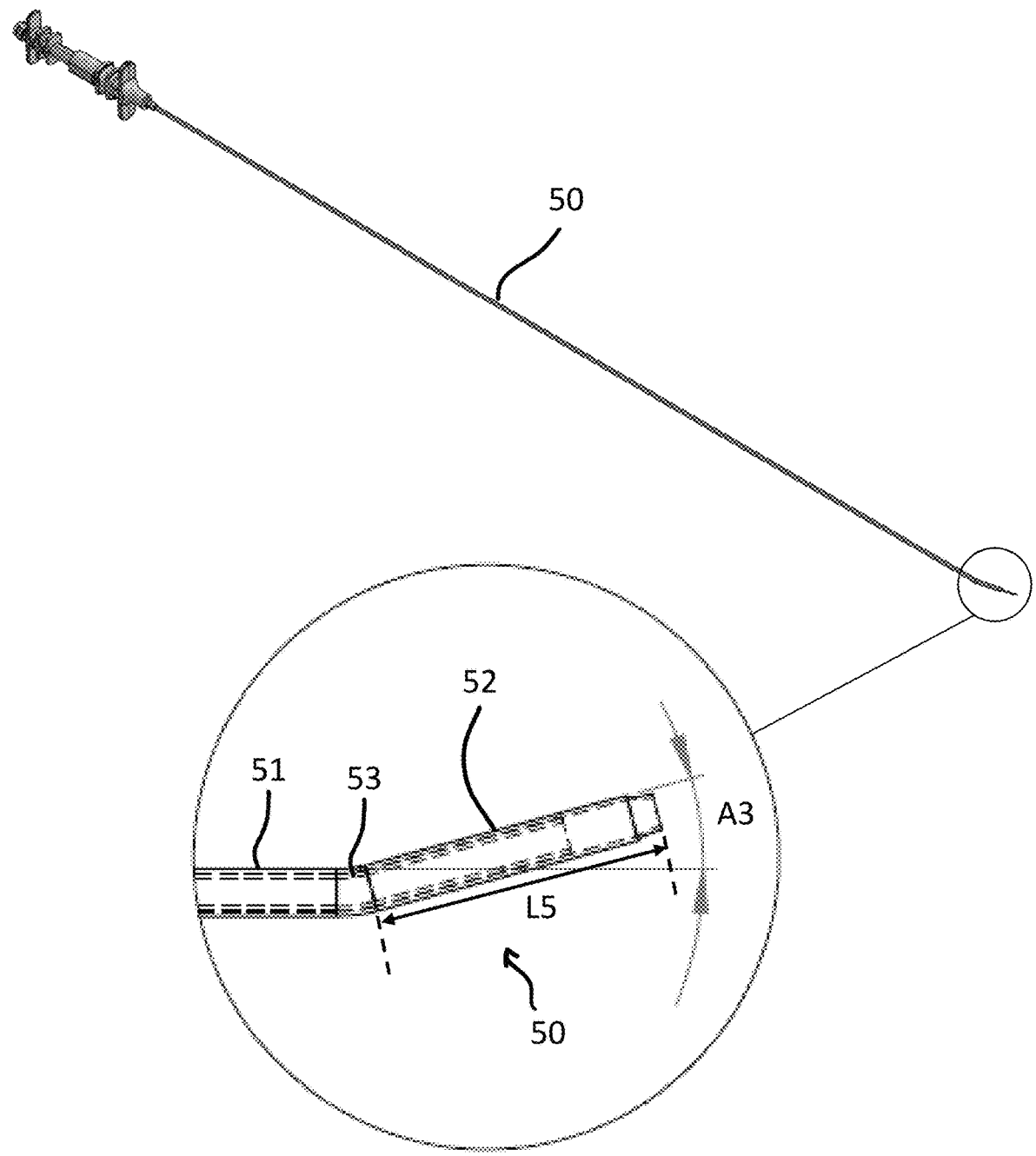
FIG. 27 depicts an enlargement of a distal portion of the device of FIG. 22 showing an angled bend in tubing of the device.

According to one aspect, the device tubing may have an angled bend at a distal portion of the tubing. The inventors have recognized that creating a bend in the tubing at the distal portion of the tubing may aid in visualization of the needle during an endoscopic procedure. One illustrative embodiment is shown in FIG. 27, which depicts an enlarged view of a distal portion of the tubing 50. As shown in FIG. 27, the tubing 50 may have a main body 51 and a distal portion 52. The distal portion 52 may be angled relative to the main body 51 by angle A3 due to bend 53.

In some embodiments, the angle A3 may be at least about 8 degrees, at least about 10 degrees, at least about 12 degrees, at least about 14 degrees, at least about 14.5 degrees, at least about 15 degrees, at least about 15.5 degrees, at least about 16 degrees, at least about 18 degrees, at least about 20 degrees, or at least about 22 degrees. In some embodiments, angle A3 may be less than or equal to about 20 degrees, less than or equal to about 18 degrees, less than or equal to about 16 degrees, less than or equal to about 15.5 degrees, less than or equal to about 15 degrees, less than or equal to about 14.5 degrees, less than or equal to about 14 degrees, less than or equal to about 12 degrees, or less than or equal to about 10 degrees. Combinations of the above-referenced ranges are also possible. For example, in some embodiments, angle A3 may be about 10 degrees to about 20 degrees, or about 12 degrees to about 18 degrees, or about 14 degrees to about 16 degrees, or about 14.5 degrees to about 15.5 degrees, or about 14.8 degrees to about 15.2 degrees.

In some embodiments, the bend 53 may be located at a distance L5 away from the tip of the distal portion 52 of the tubing 50. In some embodiments, the distance L5 may be at least about 10 mm, at least about 11 mm, at least about 12 mm, at least about 13 mm, at least about 14 mm, at least about 15 mm, at least about 16 mm, at least about 17 mm, at least about 18 mm, at least about 19 mm, at least about 20 mm, at least about 21 mm, at least about 22 mm, at least about 23 mm, or at least about 23 mm. In some embodiments, the distance L5 may be less than or equal to about 24 mm, less than or equal to about 23 mm, less than or equal to about 22 mm, less than or equal to about 21 mm, less than or equal to about 20 mm, less than or equal to about 19 mm, less than or equal to about 18 mm, less than or equal to about 17 mm, less than or equal to about 16 mm, less than or equal to about 15 mm, less than or equal to about 14 mm, less than or equal to about 13 mm, less than or equal to about 12 mm, less than or equal to about 11 mm, or less than or equal to about 10 mm. Combinations of the above-referenced ranges are also possible. For example, in some embodiments, distance L5 may be about 10 mm to about 24 mm, or about 11 mm to about 23 mmm, or about 12 mm to about 22 mm, or about 13 mm to about 21 mm, or about 14 mm to about 20 mm, or about 16 mm to about 18 mm.

In some embodiments, as shown in FIG. 23, with the needle 10 fully extended, the bend 53 may be located at a distance L6 away from the tip of the needle. In some embodiments, the distance L6 may be at least about 15 mm, at least about 18 mm, at least about 20 mm, at least about 22 mm, at least about 24 mm, at least about 26 mm, at least about 28 mm, at least about 30 mm, at least about 32 mm, at least about 34 mm, or at least about 36 mm. In some embodiments, the distance L6 may be less than or equal to about 36 mm, less than or equal to about 34 mm, less than or equal to about 32 mm, less than or equal to about 30 mm, less than or equal to about 28 mm, less than or equal to about 26 mm, less than or equal to about 24 mm, less than or equal to about 22 mm, less than or equal to about 20 mm, less than or equal to about 18 mm, or less than or equal to about 16 mm. Combinations of the above-referenced ranges are also possible. For example, in some embodiments, distance L6 may be about 15 mm to about 36 mm, or about 16 mm to about 34 mm, or about 18 mm to about 32 mm, or about 20 mm to about 30 mm, or about 22 mm to about 28 mm, or about 24 mm to about 26 mm.

Figure 28:
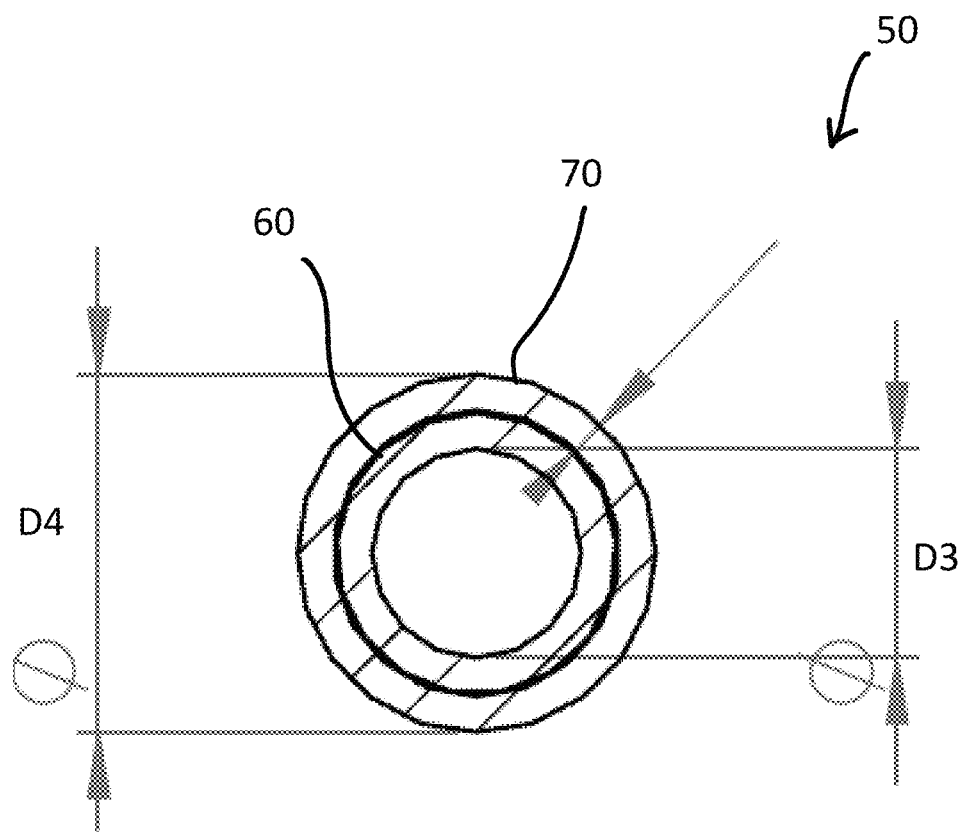
FIG. 28 depicts a cross-section of the tubing of the device, showing that the tubing includes an inner tube and an outer sheath tube.

As discussed above, in some embodiments, the tubing may comprise an inner tube and an outer sheath tube. In some embodiments, the tubes are positioned and dimensioned such that the inner tube is able to slide within the outer sheath tube. A cross-section of the tubing 50 is shown in FIG. 28, which depicts an inner tube 60 and an outer sheath tube 70. In some embodiments, the outer sheath tube 70 and/or the inner tube 60 may have an angled distal portion relative to a main body of the tube as described above with respect to angle A3.

In some embodiments, the inner tube may have an inside diameter D3 of at least about 0.7 mm, at least about 0.8 mm, at least about 0.85 mm, at least about 0.9 mm, at least about 0.95 mm, at least about 1 mm, at least about 1.05 mm, at least about 1.1 mm, at least about 1.15 mm, or at least about 1.2 mm. In some embodiments, the inner tube may have an inside diameter of less than or equal to about 1.3 mm, less than or equal to about 1.2 mm, less than or equal to about 1.15 mm, less than or equal to about 1.1 mm, less than or equal to about 1.05 mm, less than or equal to about 1 mm, less than or equal to about 0.95 mm, less than or equal to about 0.9 mm, or less than or equal to about 0.8 mm. Combinations of the above-referenced ranges are also possible. For example, in some embodiments, the inner tube may have an inside diameter of about 0.7 mm to about 1.2 mm, or about 0.8 mm to about 1.1 mm, or about 0.85 mm to about 1.15 mm, or about 0.9 mm to about 1.1 mm, or about 0.95 to about 1.05 mm.

In some embodiments, the inner tube may have an outside diameter of at least about 1 mm, at least about 1.2 mm, at least about 1.35 mm, at least about 1.4 mm, at least about 1.45 mm, at least about 1.5 mm, at least about 1.55 mm, at least about 1.6 mm, or at least about 1.65 mm. In some embodiments, the inner tube may have an outside diameter of less than or equal to about 1.8 mm, less than or equal to about 1.7 mm, less than or equal to about 1.65 mm, less than or equal to about 1.6 mm, less than or equal to about 1.55 mm, less than or equal to about 1.5 mm, less than or equal to about 1.45 mm, less than or equal to about 1.4 mm, less than or equal to about 1.2 mm, or less than or equal to about 1 mm. Combinations of the above-referenced ranges are also possible. For example, in some embodiments, the inner tube may have an outside diameter of about 1 mm to about 1.8 mm, or about 1.1 mm to about 1.7 mm, or about 1.2 mm to about 1.6 mm, or about 1.3 mm to about 1.5 mm, or about 1.3 mm to about 1.4 44, or about 1.35 mm to about 1.45 mm, or about 1.6 mm to about 1.8 mm.

In some embodiments, the outer sheath tube may have an inside diameter of at least about 1.2 mm, at least about 1.3 mm, at least about 1.4 mm, at least about 1.5 mm, at least about 1.55 mm, at least about 1.6 mm, at least about 1.7 mm, at least about 1.8 mm or at least about 1.9 mm. In some embodiments, the outer sheath tube may have an inside diameter of less than or equal to about 1.9 mm, less than or equal to about 1.8 mm, less than or equal to about 1.7 mm, less than equal to about 1.65 mm, less than or equal to about 1.6 mm, less than or equal to about 1.5 mm, less than or equal to about 1.45 mm, or less than or equal to about 1.4 mm. Combinations of the above-referenced ranges are also possible. For example, in some embodiments, the outer sheath tube may have an inside diameter of about 1.2 mm to about 1.7 mm, or 1.3 mm to about 1.6 mm, or about 1.4 mm to about 1.5 mm, or about 1.42 mm to about 1.47 mm.

In some embodiments, the outer sheath tube may have an outside diameter D4 of at least about 1.5 mm, at least about 1.6 mm, at least about 1.7 mm, at least about 1.75 mm, at least about 1.8 mm, at least about 1.85 mm, at least about 1.9 mm, at least about 2 mm, at least about 2.1 mm, or at least about 2.2 mm. In some embodiments, the outer sheath tube may have an outside diameter of less than or equal to about 2.2 mm, less than or equal to about 2.1 mm, less than or equal to about 2 mm, less than or equal to about 1.95 mm, less than or equal to about 1.9 mm, less than or equal to about 1.85 mm, less than or equal to about 1.8 mm, less than or equal to about 1.7 mm, less than or equal to about 1.6 mm, or less than or equal to about 1.5 mm. Combinations of the above-referenced ranges are also possible. For example, in some embodiments, the outer sheath tube may have an outside diameter of about 1.5 mm to about 2.2 mm, or about 1.6 mm to about 2.1 mm, or about 1.65 to about 2 mm, or about 1.7 mm to about 1.9 mm, or about 1.75 mm to about 1.85 mm.

In some embodiments, the outer sheath tube may have an inside diameter that is larger than the outside diameter of the inner tube by at least about 0.08 mm, at least about 0.09 mm, at least about 0.1 mm, at least about 0.11 mm, or at least about 0.12 mm. In some embodiments, the outer sheath tube may have an inside diameter that is larger than the outside diameter of the inner tube by less than or equal to about 0.14 mm, less than or equal to about 0.12 mm, less than or equal to about 0.11 mm, less than or equal to about 0.1 mm, or less than or equal to about 0.09 mm, or less than or equal to about 0.08 mm. Combinations of the above-referenced ranges are also possible. For example, in some embodiments, the outer sheath tube may have an inside diameter that is larger than the outside diameter of the inner tube by at least about 0.08 mm to about 0.12 mm, or about 0.09 mm to about 0.11 mm, or about 0.095 mm to about 0.11 mm.

In some embodiments, the inner tube and/or the outer sheath tube may have a total length from a proximal end to a distal end of at least about 10 cm, at least about 20 cm, at least about 30 cm, at least about 40 cm, at least about 45 cm, at least about 50 cm, at least about 55 cm, at least about 60 cm, or at least about 70 cm. In some embodiments, the inner tube and/or the outer sheath tube may have a total length from a proximal end to a distal end of less than or equal to about 70 cm, less than or equal to about 60 cm, less than or equal to about 55 cm, less than or equal to about 50 cm, less than or equal to about 45 cm, less than or equal to about 40 cm, less than or equal to about 30 cm, less than or equal to about 20 cm, or less than or equal to about 10 cm. Combinations of the above-referenced ranges are also possible. For example, in some embodiments, the inner tube and/or the outer sheath tube may have a total length from a proximal end to a distal end of about 20 cm to about 60 cm, or about 10 cm to about 70 cm, or about 30 cm to about 50 cm, or about 40 cm to about 50 cm, or about 45 cm to about 55 cm, or about 48 to about 52 cm, or about 50 to about 60 cm.

In some embodiments, the inner tube and/or the outer sheath tube may be made from PTFE, other polymer, fluoropolymer or plastic material, or other suitable material that can be used to provide appropriate tubing strength and/or torque transferences. In some embodiments, the inner tube and/or the outer sheath tube may be made from a braided (steel or otherwise) PTFE tubing.

According to one aspect, in some embodiments, the device may include a component that may help to reinforce the connection between the needle and the inner tube. In one illustrative embodiment, shown in FIG. 29, the device includes a needle sheath 60 that receives the needle 10. In some embodiments, the needle sheath 60 may serve to connect the needle to the inner tube and/or reinforce the connection between the needle and the inner tube.

Figure 30A:
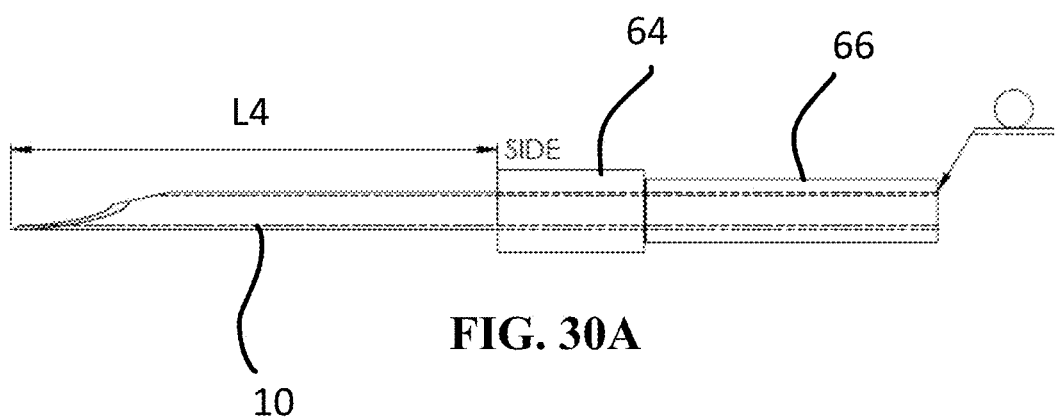
FIG. 30A depicts a side view of the needle and needle sheath assembly of FIG. 29.
Figure 30B:
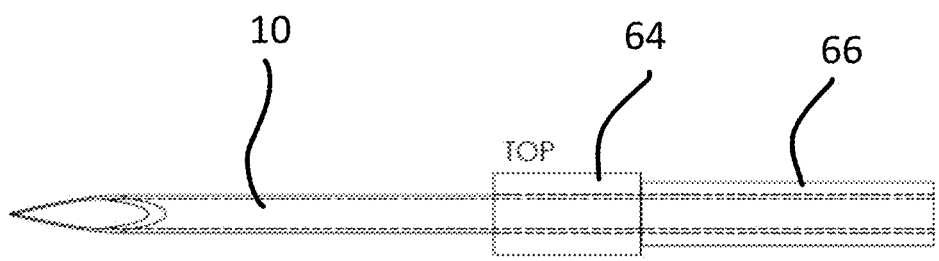
FIG. 30B depicts a top view of the needle and needle sheath assembly of FIG. 29.

In some embodiments, the needle sheath 60 may include a needle sheath body 66 and a collar 64. The outside diameter of the collar 64 may be larger than the outside diameter of the needle sheath body 66. As seen in FIGS. 30A and 30B, the needle 10 may extend through the needle sheath 60. In some embodiments, the distal portion of the outer sheath tube may be tapered in the distal direction to have a reduced inside diameter. In some embodiments, the inside diameter of the outer sheath tube at the distal end of the outer sheath tube may be smaller than the outside diameter of the collar 64. As a result, due to contact between the collar and the tapered inside diameter at the distal portion of the outer sheath tube, the collar may prevent the needle from further distal movement relative to the outer sheath tube beyond a certain point. In some cases, such an arrangement may help to prevent overextension of the needle.

In some embodiments, the needle may be attached to the needle sheath by laser welding, adhesive bonding, ultrasonic welding, or by any other suitable attachment means. The needle may be attached to the collar and/or to the needle sheath body.

In some embodiments, such as that shown in FIG. 30A, the needle 10 has an exposed portion having length L4 extending from the sheath 64. In some embodiments, the length L4 may be at least about 5 mm, at least about 6 mm, at least about 7 mm, at least about 7.5 mm, at least about 8 mm, at least about 8.5 mm, at least about 9 mm, at least about 10 mm, at least about 11 mm, or at least about 12 mm. In some embodiments, length L4 may be less than or equal to about 15 mm, less than or equal to about 12 mm, less than or equal to about 11 mm, less than or equal to about 10 mm, less than or equal to about 9 mm, less than or equal to about 8.5 mm, less than or equal to about 8 mm, less than or equal to about 7.5 mm, less than or equal to about 7 mm, less than or equal to about 6 mm, or less than or equal to about 5 mm. Combinations of the above-referenced ranges are also possible. For example, in some embodiments, length L4 may be about 5 mm to about 11 mm, or about 6 mm to about 10 mm, or about 7 mm to about 9 mm, or about 7.5 to about 8.5 mm.

Figure 31A:
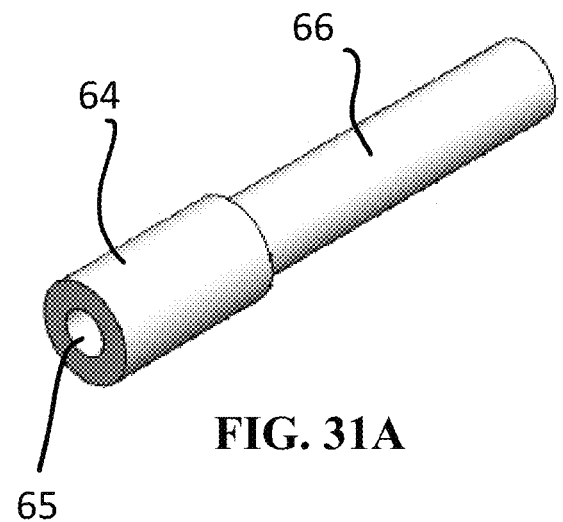
FIG. 31A depicts a perspective view of the needle sheath of FIG. 29.
Figure 31B:
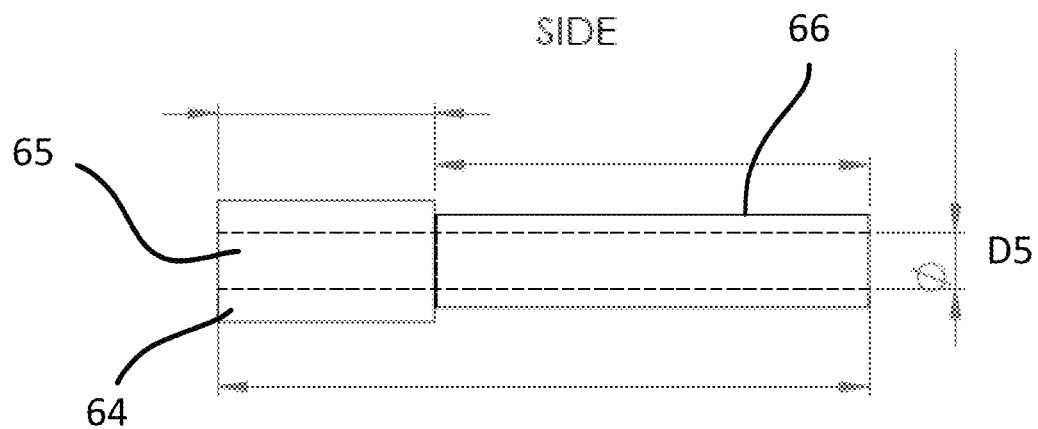
FIG. 31B depicts a side view of the needle sheath of FIG. 31A.

In some embodiments, as seen in FIGS. 31A and 31B, the needle sheath 60 may have a channel 65 to receive the needle, the channel having a diameter D5. In some embodiments, the diameter D5 may be at least about 0.45 mm, at least about 0.5 mm, at least about 0.55 mm, at least about 0.6 mm, at least about 0.65 mm, at least about 0.7 mm, at least about 0.75 mm, or at least about 0.8 mm. In some embodiments, the channel 65 may have a diameter D5 of less than or equal to about 0.9 mm, less than or equal to about 0.8 mm, less than or equal to about 0.7 mm, less than or equal to about 0.65 mm, less than or equal to about 0.6 mm, or less than or equal to about 0.5 mm. Combinations of the above-referenced ranges are also possible. For example, in some embodiments, the channel may have a diameter D5 of about 0.45 mm to about 0.8 mm, or about 0.55 mm to about 0.75 mm, or about 0.6 to about 0.7 mm.

The collar 64 and needle sheath body 66 may be a single monolithic component. For example, the collar and needle sheath body may be welded together or may be molded together. In some embodiments, the collar and needle sheath body are formed separately and then attached together.

In some embodiments, the needle sheath may be attached to the inner tube. In some embodiments, a distal end of the inner tube may be received within the channel of the needle sheath. In other embodiments, the proximal end of the needle sheath may be received within the inner tube. The needle sheath may be attached to the inner tube by laser welding, adhesive bonding, ultrasonic welding, or by any other suitable attachment means. In some embodiments, an intermediate coupling may be used to attach the inner tube to the needle sheath.

According to one aspect, the device handle may be used to actuate the needle between a retracted position and an extended position. In some embodiments, the handle comprises two portions that cooperate with one another to actuate the needle. In some embodiments, the two portions of the handle are moveable relative to one another. In one embodiment, the first handle portion may be attached to the outer tube sheath, and the inner tube may extend through channels in both portions of the handle. The inner tube may attach to a syringe that connects to the second portion of the handle. Movement of the second handle portion relative to the first handle portion may move the inner tube relative to the outer sheath tube, which may cause the inner tube and needle to move from a retracted position in which the needle is covered by the outer sheath, to an extended position in which the needle is exposed. As such, in some embodiments, the portions of the handle are moved relative to one another to actuate deployment of the needle.

Figure 32:
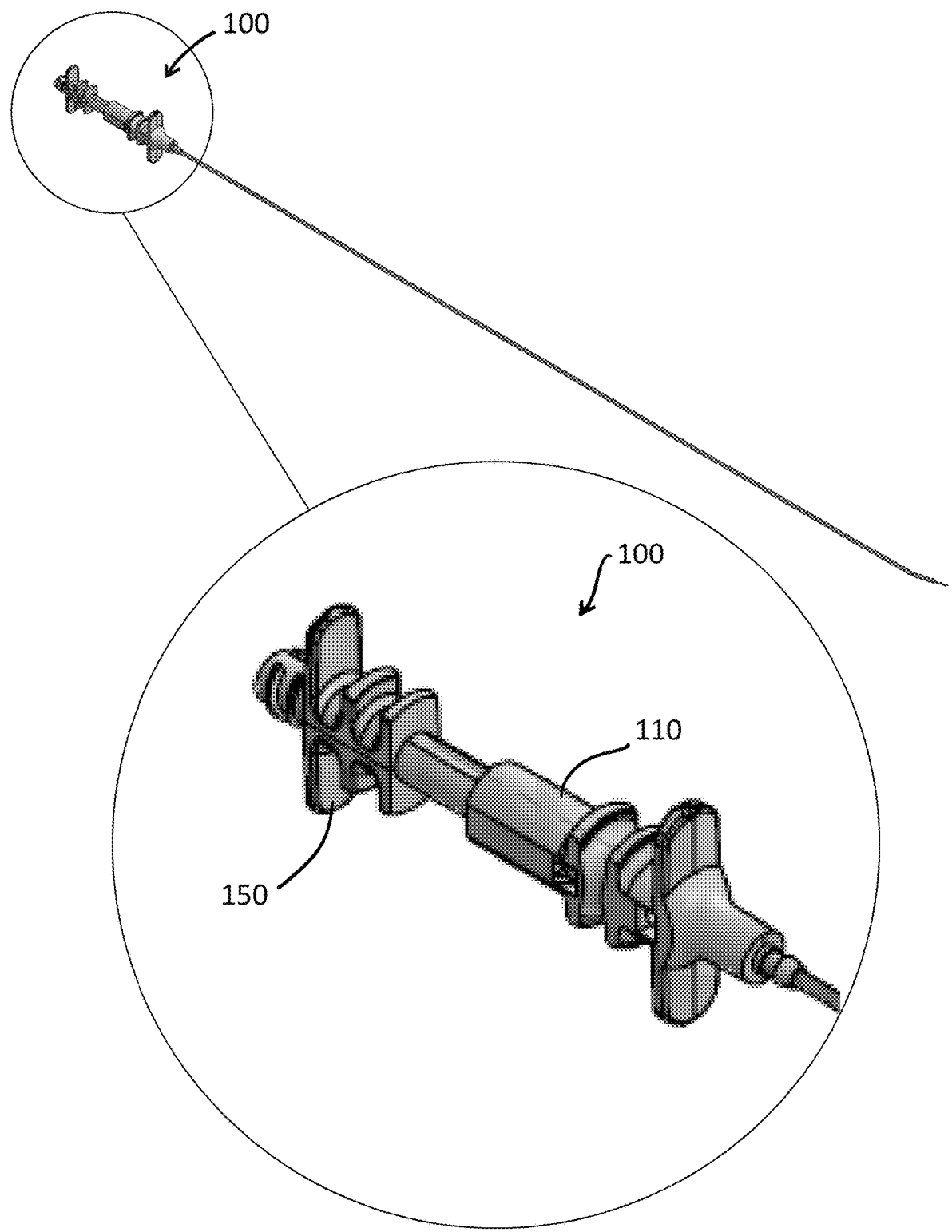
FIG. 32 depicts an enlarged view of a handle of the device of FIG. 22.

One illustrative embodiment of a device handle is shown in FIG. 32, which depicts an enlarged view of the handle 100. The handle 100 may include two portions, a leading portion 110 and a back portion 150. In some embodiments, the leading portion 110 may have an opening that receives the back portion 150. As shown in FIG. 32, the distal end of the leading portion 110 receives the proximal end of back portion 150. Alternatively, in some embodiments, the back portion may have an opening that receives the leading portion.

Figure 33A:
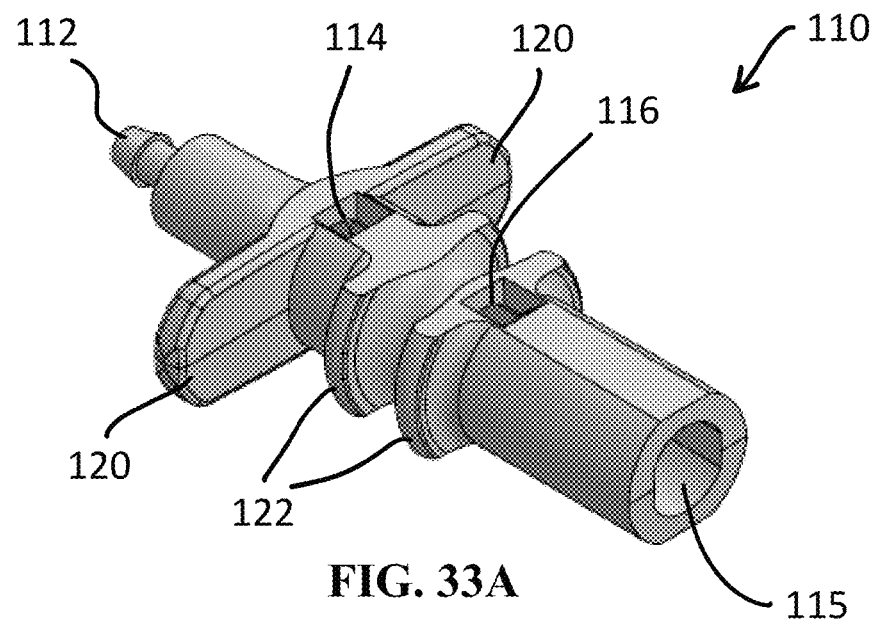
FIG. 33A depicts an enlarged view of a leading portion of the handle of FIG. 32.
Figure 33B:
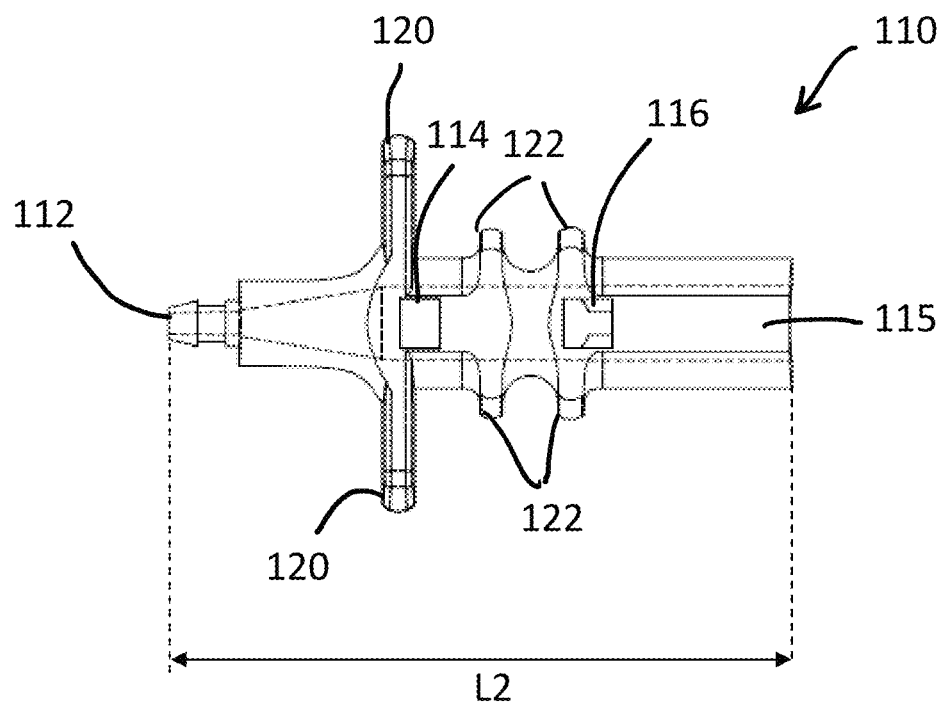
FIG. 33B depicts a top down view of the leading portion of the handle of FIG. 33A.

A perspective view of the leading portion 110 is shown in FIG. 33A and a top-down view of the leading portion 110 is shown in FIG. 33B. In some embodiments, the leading portion 110 may attach to the outer tube sheath. The leading portion 110 may have a tubing connector 112 that couples the outer tube sheath to the leading portion 110. The tubing connector 112 may be inserted into the proximal end of the outer tube sheath and may create a fluid-tight connection via an interference fit. Alternatively or in addition, a fluid-tight connection may be provided by or further supplemented by adhesive bonding, UV welding or other suitable attachment means. As best seen in FIG. 33B, the leading portion 110 may have a channel 115. The inner tube may be positioned within the channel 115, and may be able to slide within the channel 115 relative to the leading portion 110 and relative to the outer tube sheath. The proximal end of the channel 115 may be sized and shaped to receive the back portion 150 of the handle. In FIG. 32, the handle is shown in an assembled state where the back portion 150 is received in the leading portion 110.

Figure 34A:
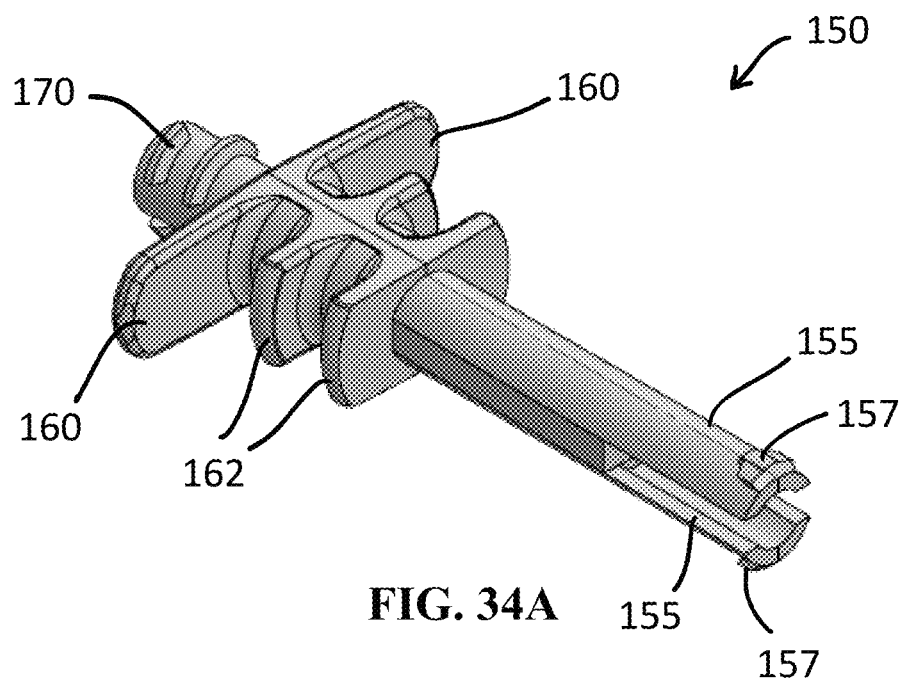
FIG. 34A depicts an enlarged view of a back portion of the handle of FIG. 32.
Figure 34B:
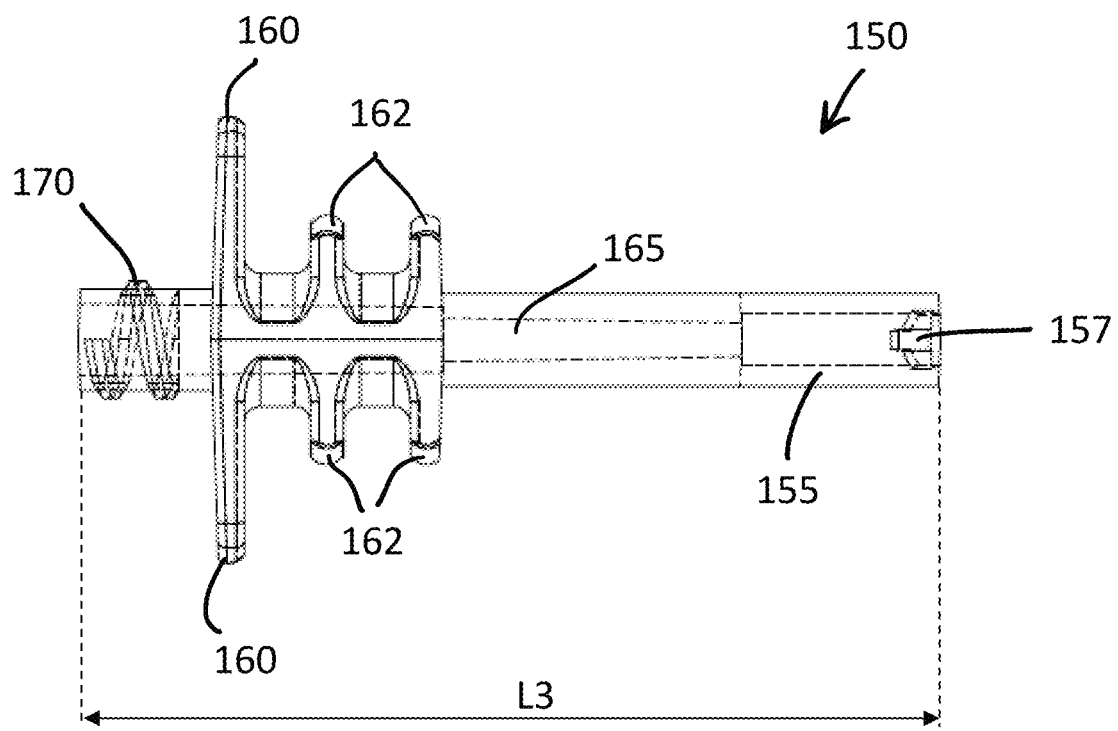
FIG. 34B depicts a top down view of the back portion of the handle of FIG. 34A.

A perspective view of the back portion 150 is shown in FIG. 34A and a top-down view of the back portion 150 is shown in FIG. 34B. As best seen in FIG. 34B, in some embodiments, the back portion 150 includes a channel 165 through which the inner tube may extend. The back portion 150 may include a luer fitting 170 or other connecting feature that serves to connect the handle to a syringe or other composition-holding container. In some embodiments, an intermediate coupling between the handle and the syringe is used to connect the handle to the syringe. In other embodiments, the handle may directly connect to a syringe.

In some embodiments, the distal end of the back portion 150 is sized and shaped to fit within the channel 115 of the leading portion 110. The distal end of the back portion 150 may have arms 155 that can move relative to one another. Each of the arms 155 may include a protrusion 157. When the arms 155 are slid into the channel 115 of the leading portion 110, the arms may be pressed radially inwardly toward one another due to contact between the protrusions 157 and the inner surface of the channel 115. As the arms proceed further into the channel 115, they may arrive at a pair of proximal openings 116 in the leading portion 110 (the second proximal opening is not visible in FIG. 33A, as it is on the underside of the component). The proximal openings 116 may be sized and shaped to receive the protrusions 157. When the protrusions 157 reach the openings 116, the protrusions may snap into place into the openings, as the arms 155 may be biased to return from its inwardly pressed state to an unstressed state. In some embodiments, during manufacturing, the device may be placed in this orientation, in which the protrusions of the arms are located within the proximal openings 116.

A user may apply a force on the leading portion 110 and/or on the back portion 150 of the handle to force the protrusions 157 of the arms out of the openings 116 and move the leading portion 110 proximally towards the back portion 150. The arms 155 may be pressed radially inwardly toward one another due to contact between the protrusions 157 and the inner surface of the channel 115. As the leading portion 110 is moved toward the back portion 150, the protrusions 157 may encounter a pair of distal openings 114. As the openings 114 near the protrusions, the protrusions 157 may snap into place into the openings 114, as the arms 155 may be biased to return from its inwardly pressed state to an unstressed state.

In some embodiments, when the protrusions 157 are located within the proximal openings 116, the needle may be in the retracted position in which the needle is covered by the outer sheath tube. Pushing the back portion 150 of the handle distally forward further into the leading portion 110 of the handle such that the protrusions 157 are moved into the distal openings 114 may move the needle into the extended position in which the needle is exposed and can penetrate into an injection site. A user may manipulate the portions of the handle to move the protrusions 155 back and forth between the distal and proximal holes 114, 116 by applying a threshold amount of force on one or both portions of the handle in order to actuate the needle between retracted and extended positions.

According to one aspect, the handle may include features that aid in actuation and/or gripping of the handle. Such features may aid in one-handed operation of the handle.

As seen in FIG. 33A, in some embodiments, the leading portion 110 may include protruding gripping features 122. In some embodiments, the leading portion 110 may include outwardly extending wings 120. Such wings 120 may provide one or more surfaces against which a user may pull or push on to move the leading portion 110 distally away from the back portion 150 or proximally toward the back portion 150.

In some embodiments, the back portion 150 of the handle may have features that aid in actuation and/or gripping of the handle. As seen in FIG. 34A, the back portion 150 may include protruding gripping features 162, as well as outwardly extending wings 160. In some cases, a user may hold onto the back portion 150 of the handle by gripping these features with a portion of one hand, and the rest of the hand may be used to manipulate the leading portion 110. For example, the middle, ring and pinky fingers may wrap around the back portion 150, while the thumb and index finger may be used to push and pull on the leading portion 110 relative to the back portion 150. In some cases, the middle finger may be used to interact with the leading portion 110 instead. As a result, a user may actuate the handle using one hand.

In some embodiments, as seen in FIG. 33B, the leading portion 110 of the handle may have a total length L2 from proximal end to distal end. In some embodiments, length L2 may be at least about 30 mm, at least about 40 mm, at least about 45 mm, at least about 47 mm, at least about 50 mm, at least about 55 mm, or at least about 60 mm. In some embodiments, length L2 may be less than or equal to about 60 mm, less than or equal to about 55 mm, less than or equal to about 50 mm, less than or equal to about 45 mm, less than or equal to about 40 mm, or less than or equal to about 30 mm. Combinations of the above-referenced ranges are also possible. For example, in some embodiments, length L2 may be about 30 mm to about 60 mm, or about 40 mm to about 50 mm, or about 45 mm to about 50 mm.

In some embodiments, as seen in FIG. 34B, the back portion 150 of the handle may have a total length L3 from proximal end to distal end. In some embodiments, length L3 may be at least about 30 mm, at least about 40 mm, at least about 45 mm, at least about 50 mm, at least about 55 mm, or at least about 60 mm. In some embodiments, length L2 may be less than or equal to about 60 mm, less than or equal to about 55 mm, less than or equal to about 50 mm, less than or equal to about 45 mm, less than or equal to about 40 mm, or less than or equal to about 30 mm. Combinations of the above-referenced ranges are also possible. For example, in some embodiments, length L3 may be about 30 mm to about 60 mm, or about 40 mm to about 50 mm, or about 45 mm to about 55 mm.

In some embodiments, the handle may have a first overall length when the needle is retracted, and a second overall length when the needle is exposed. In some embodiments, the first overall length may be at least about 6 cm, at least about 7 cm, at least about 8 cm, at least about 8.2 cm, at least about 8.5 cm, at least about 9 cm or at least about 10 cm. In some embodiments, the first overall length may be less than or equal to about 10 cm, less than or equal to about 9 cm, less than or equal to about 8.5 cm, less than or equal to about 8.2 cm, less than or equal to about 8 cm, less than or equal to about 7 cm, or less than or equal to about 6 cm. Combinations of the above-referenced ranges are also possible. For example, in some embodiments, the first overall length may be about 6 cm to about 10 cm, or about 7 cm to about 9 cm, or about 8 cm to about 8.5 cm, or about 8.2 cm.

In some embodiments, the second overall length may be at least about 4 cm, at least about 5 cm, about 6 cm, at least about 7 cm, at least about 8 cm, at least about 8.2 cm, at least about 8.5 cm, or at least about 9 cm. In some embodiments, the second overall length may be less than or equal to about 9 cm, less than or equal to about 8 cm, less than or equal to about 7.5 cm, less than or equal to about 7.3 cm, less than or equal to about 7 cm, or less than or equal to about 6 cm. Combinations of the above-referenced ranges are also possible. For example, in some embodiments, the second overall length may be about 4 cm to about 9 cm, or about 6 cm to about 8 cm, or about 6.5 cm to about 7.5 cm, or about 7 cm.

In some embodiments, the difference between the first overall length and the second overall length may be at least about 2 cm, at least about 4 cm, or at least about 6 cm. In some embodiments, the difference between the first overall length and the second overall length may be less than or equal to about 6 cm, less than or equal to about 4 cm, or less than or equal to about 2 cm. Combinations of the above-referenced ranges are also possible. For example, in some embodiments, the difference between the first overall length and the second overall length may be about 2 to 6 cm, or about 3 to 5 cm, or about 4 to 4.5 cm.

In some embodiments, the first overall length is greater than the second overall length.

In some embodiments, as seen in FIG. 22, the delivery device 1 has a total working length L7, which is the combined length of handle, tubing and needle when all assembled together and the needle is fully extended. In some embodiments, the total working length L7, is at least about 40 cm, at least about 45 cm, at least about 50 cm, at least about 54 cm, at least about 55 cm, at least about 60 cm, at least about 65 cm, or at least about 70 cm. In some embodiments, the total working length L7 is less than or equal to about 70 cm, less than or equal to about 65 cm, less than or equal to about 60 cm, less than or equal to about 55 cm, less than or equal to about 54 cm, less than or equal to about 50 cm, less than or equal to about 45 cm, or less than or equal to about 40 cm.

In some embodiments, the delivery device has a priming volume of at least about 600 µL, at least about 700 µL, at least about 750 µL, at least about 800 µL, or at least about 850 µL. In some embodiments, the priming volume is less than or equal to about 900 µL, less than or equal to about 850 µL, less than or equal to about 800 µL, less than or equal to about 750 µL, less than or equal to about 700 µL, or less than or equal to about 600 µL. Combinations of the above-referenced ranges are also possible. For example, in some embodiments, the priming volume is about 600 µL, to about 900 µL, or about 650 µL, to about 850 µL, or about 700 µL, to about 800, or about 740 µL, to about 760 µL.

In some embodiments, the handle may be made from acrylonitrile butadiene styrene (ABS), other plastic, or other suitable material. In some embodiments, the handle is formed via injection molding.

Figure 35:
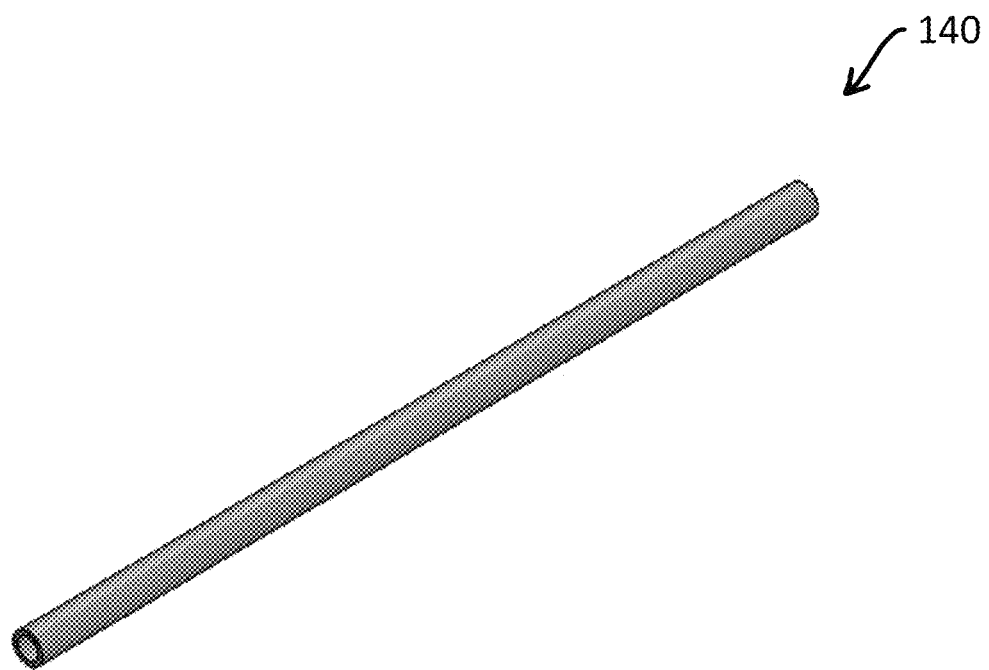
FIG. 35 depicts a perspective view of a connecting tube.

In some embodiments, the delivery device may include a connecting tube connecting a proximal end of the inner tube to the syringe. The tube may be sized to be received within the handle. In some cases, the connecting tube may help to facilitate flow of material from the syringe into the inner tubing. In some embodiments, the connecting tube is made of a material having a higher rigidity than that of the inner tube. For example, in some embodiments, the connecting tube is made of stainless steel or other metal or metal alloy. In some embodiments, the connecting tube comprises a hypotube. One illustrative embodiment of a connecting tube 140 is shown in FIG. 35.

In some embodiments, the connecting tube may have a total length from a proximal end to a distal end of at least about 30 mm, at least about 40 mm, at least about 45 mm, at least about 50 mm, at least about 55 mm, at least about 60 mm, or at least about 70 mm. In some embodiments, the connecting tube may have a total length from a proximal end to a distal end of less than or equal to about 70 mm, less than or equal to about 60 mm, less than or equal to about 55 mm, less than or equal to about 50 mm, less than or equal to about 45 mm, less than or equal to about 40 mm, or less than or equal to about 30 mm. Combinations of the above-referenced ranges are also possible. For example, in some embodiments, the connecting tube may have a total length from a proximal end to a distal end of about 30 mm to about 60 mm, or about 40 mm to about 50 mm, or about 42 mm to about 48 mm, or about 43 mm to about 47 mm.

In some embodiments, a connecting tube or a channel of the back portion and/or the leading portion of the handle may be tapered in the distal direction. Without wishing to be bound by theory, a tapered connecting tube or channel may help to reduce shear stress of viscous material as the material moves from the syringe to the inner tube.

In some embodiments, to administer an injectable composition, the tubing of a delivery device may be first threaded onto an endoscope or laryngoscope. Once the endoscope or laryngoscope is positioned next to a region of interest, the sliding portion of the handle may be moved to extend the inner tube and insert the needle into the region of interest. A syringe containing an injectable composition may then be attached to the handle of the delivery device. A channel within the handle may connect the injectable composition to the inner tube for extrusion. After extrusion, the syringe may be removed from the handle and the sliding portion of the handle may be moved to retract the inner tube and remove the hollow needle from the region of interest. The delivery device and endoscope may then be removed.

Kit Comprising Delivery Device and any One of the Silk Fibroin Particles or Compositions Described Herein Further provided herein is a kit comprising any embodiment of the delivery devices described herein and any embodiment of the compositions or injectable compositions described herein. In some embodiments, the composition may be pre-loaded in or separately packaged from a syringe.

In some embodiments, a topical anesthetic can be blended with any embodiment of the compositions or injectable compositions described herein. In alternative embodiments, a topical anesthetic can be packaged in a separate container or in a separate syringe. For example, in some embodiments, it may be desirable to apply a topical anesthetic to a target tissue to be treated prior to further treatment. An exemplary anesthetic includes, but is not limited to, lidocaine. Dependent upon application, the kit can include syringes sizes from about 0.5 mL to about 3 mL, or about 0.5 mL to about 1.5 mL, or about 0.5 mL to about 1 mL.

In some embodiments, needle gauge can be adjusted according to the particular injection site with an acceptable range of 18 to 30 gauge needles. For example, 26 to 30 gauge needles can be used for intradermal injections.

In some embodiments, the kit can further comprise a plurality of syringes (each with a corresponding needle) containing any embodiment of the compositions or injectable compositions described herein. Each syringe can be individually packaged.

In some embodiments, the kit can further comprise a container containing a buffered solution or an injection carrier.

In some embodiments, the kit can further comprise at least one additional empty syringe. In some embodiments, the kit can further comprise at least one additional needle. In some embodiments, the kit can further comprise at least one catheter or cannula.

The one or more syringes of the kit may contain an injectable composition comprising crosslinked hyaluronic acid and biocompatible particles having an average particle size of about 50 μm to about 1000 μm, wherein the crosslinked hyaluronic acid has a crosslink density of about 4 mol % to about 30 mol %, wherein the biocompatible particles and the crosslinked hyaluronic acid are present in a volume ratio of about 5:95 to about 95:5 (e.g., about 60:40 to about 20:80).

In some embodiments, the composition is characterized in that a standard deviation of extrusion force of the composition through a 18-30 gauge needle into air, as determined between about 50% extrusion volume and about 90% extrusion volume, is less than about 40% of an average extrusion force for the corresponding range of the extrusion volume.

In some embodiments, the composition is characterized in that a stiffness of the composition is decreased by at least about 10% as measured between about 10% strain and about 90% strain.

Carriers

Any suitable carrier (e.g., first carrier, second carrier) that is biocompatible with the particles (e.g., silk fibroin particles) or any other components, if any, dispersed therein can be used. The particular carrier(s) used may be chosen based on its ability to carry or deliver the particles as described herein (e.g., silk fibroin particles). In some embodiments, a carrier (e.g., first carrier, second carrier) is selected such that the combination of the particles or silk fibroin particles and the carrier is injectable as described above, e.g., having a particular average extrusion force as discussed above.

In some embodiments, a carrier (e.g., first carrier, second carrier) for use in any one of the compositions described herein is a pharmaceutically acceptable carrier. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or stearic acid), or solvent encapsulating material, involved in maintaining the stability, solubility, or activity of, silk fibroin particles and/or an active agent, if any, dispersed therein. Each carrier must be "acceptable" in the sense of being compatible with the other ingredients of the formulation and not injurious to the patient.

In some embodiments, the carrier (e.g., first carrier, second carrier) can be a biological carrier. Examples of such carriers suitable for use in any one of the compositions described herein include, but are not limited to a glycosaminoglycan polymer (e.g., hyaluronic acid, crosslinked hyaluronic acid, keratan sulfate, chondroitin sulfate, heparin, and the like), an extracellular matrix such as a globular or fibrous protein polymer (e.g., collagen, elastin, fibronectin, etc.), or a biological fluid or concentrate (e.g., lipoaspirate, a bone marrow aspirate).

In some embodiments, the carrier (e.g., first carrier, second carrier) comprises a hyaluronic acid polymer (crosslinked and/or non-crosslinked). In some embodiments, the carrier essentially consists of a hyaluronic acid polymer (crosslinked and/or non-crosslinked). In some embodiments, the hyaluronic acid polymer (non-crosslinked) may have an average molecular weight of at least about 200 kDa, at least about 300 kDa, at least about 400 kDa, at least about 500 kDa, at least about 600 kDa, at least about 700 kDa, at least about 800 kDa, at least about 900 kDa, at least about 1 MDa, at least about 2 MDa, at least about 3 MDa, at least about 4 MDa, or at least about 5 MDa. In some embodiments, the hyaluronic acid polymer (non-crosslinked) may have an average molecular weight of less than or equal to about 5 MDa, less than or equal to about 4 MDa, less than or equal to about 3 MDa, less than or equal to about 2 MDa, less than or equal to about 1 MDa, less than or equal to about 900 kDa, less than or equal to about 800 kDa, less than or equal to about 700 kDa, less than or equal to about 600 kDa, less than or equal to about 500 kDa, less than or equal to about 400 kDa, less than or equal to about 300 kDa, or less than or equal to about 200 kDa. Combinations of the above-referenced ranges are also possible. For example, in some embodiments, In some embodiments, the hyaluronic acid polymer (non-crosslinked) may have an average molecular weight of about 200 kDa to about 5 MDa, or about 300 kDa to about 4 MDa, or about 400 kDa to about 3 MDa, or about 500 kDa to about 2 MDa. In some embodiments, the hyaluronic acid polymer (non-crosslinked) may have an average molecular weight of about 1 MDa or greater, e.g., 1 MDa, 1.5 MDa, 2 MDa, 2.5 MDa, 3 MDa, 3.5 MDa, 4 MDa, 4.5 MDa, 5 MDa or higher. In some embodiments, the hyaluronic acid polymer (crosslinked and/or non-crosslinked) may have an average molecular weight of about 1 MDa or lower, e.g., 0.9 MDa, 0.8 MDa, 0.7 MDa, 0.6 MDa, 0.5 MDa, 0.4 MDa, 0.3 MDa, 0.2 MDa, 0.1 MDa, or lower.

In some embodiments, the crosslinked matrix carrier (e.g., crosslinked hyaluronic acid polymer) has an average molecular weight that is at least about 2-fold, at least about 3-fold, at least about 4-fold, at least about 5-fold, at least about 10-fold, at least about 25-fold, at least about 50-fold, at least about 75-fold, or at least about 100-fold, higher than any of the average molecular weights provided herein for a corresponding non-crosslinked carrier (e.g., non-crosslinked hyaluronic acid polymer) used to form the crosslinked matrix carrier in the composition.

The average molecular weights provided herein for the carrier (e.g., first carrier, second carrier) and/or hyaluronic acid polymer (crosslinked or non-crosslinked) can correspond to weight average molecular weights, number average molecular weights, or peak average molecular weights. In one set of the embodiments described herein, the average molecular weights provided herein for the carrier (e.g., first carrier, second carrier) and/or hyaluronic acid polymer (crosslinked or non-crosslinked) correspond to weight average molecular weights.

In some embodiments, the carrier (e.g., first carrier, second carrier) can be a polymeric or a synthetic carrier. Examples of such carriers suitable for use in any one of the compositions described herein include, but are not limited to biocompatible polymers such as polyesters, poly(lactic acid) (PLA), poly(lactic-co-glycolic acid) (PLGA), poly(ethylene glycol) (PEG), and the like.

In some embodiments, the carrier is a shear-thinning material, e.g., a hyaluronic acid polymer. As used herein, the term "shear thinning" has an ordinary meaning associated with the term, i.e., an effect where a material or fluid's viscosity decreases with an increasing strain or shear rate. For example, the viscosity of the carrier can be measured at varying strain or shear rates, e.g., between about 2 $s^{-1}$ and about 30 $s^{-1}$, or between about 3 $s^{-1}$ and about 25 $s^{-1}$, or between about 5 $s^{-1}$ and about 25 $s^{-1}$.

The concentration of the carrier (e.g., first carrier, second carrier) can vary with the desired viscosity of the composition comprising silk fibroin particles and the carrier. Desirable ranges of dynamic viscosity can vary with different applications. For example, the compositions described herein for use in vocal fold tissue can have dynamic viscosity ranging from about 10,000 Pas to about 1 Pas. Soft tissues in general follow similar trends. See, e.g., Borzacchiello, A. "Rheological Characterization of Vocal Folds after Injection Augmentation in a Preliminary Animal Study," 2004, Journal of Bioactive and Compatible Polymers; and Caton T., "Viscoelasticity of hyaluronan and nonhyaluronan based vocal fold injectables: implications for mucosal versus muscle use," 2007, The Laryngoscope, the contents of each of which is incorporated herein by reference in their entireties. Viscosity of a composition can be measured, for example, by a parallel plate, shear rheology test, in which steady state shear rate is varied, e.g., from 0-23 $s^{-1}$, to observe changes in viscosity.

In some embodiments where a hyaluronic acid polymer is selected as the carrier, the concentration of the hyaluronic acid polymer can vary with the desired viscosity of the composition as described above. For example, the hyaluronic acid polymer may have a concentration of at least about 0.1% (w/v), at least about 0.5% (w/v), at least about 1% (w/v), at least about 2% (w/v), at least about 3% (w/v), at least about 4% (w/v), at least about 5% (w/v), at least about 6% (w/v), at least about 7% (w/v), at least about 8% (w/v), at least about 9% (w/v), or at least about 10% (w/v). In some embodiments, the hyaluronic acid polymer may have a concentration of less than or equal to about 10% (w/v), less than or equal to about 9% (w/v), less than or equal to about 8% (w/v), less than or equal to about 7% (w/v), less than or equal to about 6% (w/v), less than or equal to about 5% (w/v), less than or equal to about 4% (w/v), less than or equal to about 3% (w/v), less than or equal to about 2% (w/v), less than or equal to about 1% (w/v), less than or equal to about 0.5% (w/v), or less than or equal to about 0.1% (w/v). Combinations of the above-referenced ranges are also possible. For example, in some embodiments, the hyaluronic acid polymer may have a concentration of about 0.1% (w/v) to about 10% (w/v), about 1% (w/v) to about 10% (w/v), about 1% (w/v) to about 8% (w/v), about 1% (w/v) to about 6% (w/v), or about 1% (w/v) to about 5% (w/v). In some embodiments, the hyaluronic acid polymer may have a concentration of about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v).

In some embodiments where the carrier comprises more than two types of carriers, and the first carrier comprises hyaluronic acid of any molecular weight described above or within a range described above, the second carrier comprises hyaluronic acid with an average molecular weight (e.g., weight average molecular weight) of at least about 200 kDa, at least about 300 kDa, at least about 400 kDa, at least about 500 kDa, at least about 600 kDa, at least about 700 kDa, at least about 800 kDa, at least about 900 kDa, or at least about 1 MDa. In some embodiments, the second carrier comprises hyaluronic acid with an average molecular weight (e.g., weight average molecular weight) of less than or equal to about 1 MDa, less than or equal to about 900 kDa, less than or equal to about 800 kDa, less than or equal to about 700 kDa, less than or equal to about 600 kDa, less than or equal to about 500 kDa, less than or equal to about 400 kDa, less than or equal to about 300 kDa, or less than or equal to about 200 kDa. Combinations of the above-referenced ranges are also possible. In some embodiments, the second carrier can comprise hyaluronic acid with a molecular weight (e.g., weight average molecular weight) of about 200 kDa to about 1 MDa, or about 300 kDa to about 1 MDa, or about 400 kDa to about 1 MDa, or about 500 kDa to about 1 MDa. In some embodiments, the second carrier can comprise hyaluronic acid with a molecular weight (e.g., weight average molecular weight) of less than 1 MDa or lower, including, e.g., 1 MDa, 0.9 MDa, 0.8 MDa, 0.7 MDa, 0.6 MDa, 0.5 MDa, 0.4 MDa, 0.3 MDa, 0.2 MDa, 0.1 MDa, or lower. The concentration of hyaluronic acid in the first carrier and/or the second carrier can be the same or different, for example, within the ranges as described above for a single carrier.

In other embodiments, one or more additional carriers (e.g., a third carrier) may be present in the composition. For example, the third carrier may comprise hyaluronic acid of an average molecular weight that is different from that of the first carrier and the second carrier. Alternatively, the third carrier may comprise a polymer that is different from that of the first carrier and/or the second carrier, or a tissue. In such embodiments, the first and second carriers may be ones present in the highest amounts with respect to all carriers in the composition.

Active Agents

In some embodiments, the compositions or injectable compositions and/or the particles (e.g., silk fibroin particles) as described herein can further comprise at least one active agent. The active agent can be mixed, dispersed, or suspended in any embodiment of the compositions or injectable compositions described herein, including the particles (e.g., silk fibroin particles) and/or the carrier, and/or the active agent can be distributed or embedded in any embodiment of the particles (e.g., silk fibroin particles). In some embodiments, the active agent can be distributed, embedded or encapsulated in the particles (e.g., silk fibroin particles). In some embodiments, the active agent can be coated on surfaces of the particles (e.g., silk fibroin particles). In some embodiments, the active agent can be mixed with the particles (e.g., silk fibroin particles) to form an injectable composition. The term "active agent" can also encompass combinations or mixtures of two or more active agents, as described below. Examples of active agents include, but are not limited to, a biologically active agent (e.g., an therapeutic agent, an anesthetic, a cell growth factor, a peptide, a peptidomimetic, an antibody or a portion thereof, an antibody-like molecule, nucleic acid, a polysaccharide, and any combinations, cells, stem cells, biological fluids, immune suppressors, antibacterial agents, anti-inflammatory agents, analgesics, etc.), a cosmetically active agent (e.g., an anti-aging agent, an anti-free radical agent, an anti-oxidant, a hydrating agent, a whitening agent, a colorant, a depigmenting agent, a sun-blocking agent, a muscle relaxant, etc.), a cell attachment agent (e.g., collagen, crosslinked hyaluronic acid/collagen, integrin-binding molecules, chitosan, elastin, fibronectin, vitronectin, laminin, proteoglycans, any derivatives thereof, any peptide or oligosaccharide variants), and any combinations thereof.

The term "biologically active agent" as used herein refers to any molecule which exerts at least one biological effect in vivo. For example, the biologically active agent can be a therapeutic agent to treat or prevent a disease state or condition in a subject. Examples of biologically active agents include, without limitation, peptides, peptidomimetics, aptamers, antibodies or a portion thereof, antibody—like molecules, nucleic acids (DNA, RNA, siRNA, shRNA), polysaccharides, enzymes, receptor antagonists or agonists, hormones, growth hormones, growth factors, cell signaling factors, autogenous bone marrow, antibiotics, antimicrobial agents, small molecules and therapeutic agents. The biologically active agents can also include, without limitations, anti-inflammatory agents, anesthetics, and active agents that stimulate tissue healing, formation, and/or ingrowth, cell recruitment, integration into surrounding tissue matrix, and/or regrowth of natural tissues, and any combinations thereof. Cells, living tissues or tissue components such as lipoaspirate, extracellular matrix components can be included in any embodiment of the compositions, injectable compositions and/or particles (e.g., silk fibroin particles) described herein.

Anti-inflammatory agents can include, but are not limited to, naproxen, sulindac, tolmetin, ketorolac, celecoxib, ibuprofen, diclofenac, acetylsalicylic acid, nabumetone, etodolac, indomethacin, piroxicam, cox-2 inhibitors, ketoprofen, antiplatelet medications, salsalate, valdecoxib, oxaprozin, diflunisal, flurbiprofen, corticosteroids, MMP inhibitors and leukotriene modifiers or combinations thereof.

Agents that increase formation of new tissues and/or stimulates healing or regrowth of native tissue at the site of injection can include, but are not limited to, fibroblast growth factor (FGF), transforming growth factor-beta (TGF-β, platelet-derived growth factor (PDGF), epidermal growth factors (EGFs), connective tissue activated peptides (CTAPs), osteogenic factors including bone morphogenic proteins, heparin, angiotensin II (A-II) and fragments thereof, insulin-like growth factors, tumor necrosis factors, interleukins, colony stimulating factors, erythropoietin, nerve growth factors, interferons, biologically active analogs, fragments, and derivatives of such growth factors, and any combinations thereof.

Anesthetics can include, but are not limited to, those used in caudal, epidural, inhalation, injectable, retrobulbar, and spinal applications, such as bupivacaine, lidocaine, benzocaine, cetacaine, ropivacaine, and tetracaine, or combinations thereof.

In some embodiments, the one or more active agents included in the compositions and/or particles (e.g., silk fibroin particles) described herein may be cosmetically active agents. By the term "cosmetically active agent" is meant a compound that has a cosmetic or therapeutic effect on the skin, hair, or nails, e.g., anti-aging agents, anti-free radical agents, lightening agents, whitening agents, depigmenting agents, darkening agents such as self-tanning agents, colorants, anti-acne agents, shine control agents, anti-microbial agents, anti-inflammatory agents, anti-mycotic agents, anti-parasite agents, external analgesics, sun-blocking agents, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, muscle relaxants, agents for hair, nail, and/or skin conditioning, and any combination thereof.

In one embodiment, the cosmetically active agent can be selected from, but not limited to, the group consisting of hydroxy acids, benzoyl peroxide, sulfur resorcinol, ascorbic acid, D-panthenol, hydroquinone, octyl methoxycinnamate, titanium dioxide, octyl salicylate, homosalate, avobenzone, polyphenolics, carotenoids, free radical scavengers, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, feverfew, and soy, and derivatives and mixtures thereof. Examples of vitamins include, but are not limited to, vitamin A, vitamin Bs (such as vitamin B3, vitamin B5, and vitamin B12), vitamin C, vitamin K, and vitamin E, and derivatives thereof.

In one embodiment, the one or more cosmetically active agents included in the compositions and/or particles (e.g., silk fibroin particles) may be antioxidants. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid, and ascorbic acid derivatives (e.g., ascorbyl palmitate and ascorbyl polypeptide). Oil-soluble antioxidants suitable for use in the compositions described herein include, but are not limited to, butylated hydroxytoluene, tocopherols (e.g., tocopheryl acetate), tocotrienols, and ubiquinone. Natural extracts containing antioxidants suitable for use in the injectable compositions described herein, include, but not limited to, extracts containing flavonoids and isoflavonoids and their derivatives (e.g., genistein and diadzein), and extracts containing resveratrol. Examples of such natural extracts include grape seed, green tea, pine bark, and propolis.

In some embodiments, the active agents can be cell attachment agents. Examples of cell attachment agents include, but are not limited to, hyaluronic acid, collagen, crosslinked hyaluronic acid/collagen, an integrin-binding molecule, chitosan, elastin, fibronectin, vitronectin, laminin, proteoglycans, any derivatives thereof, and any combinations thereof.

In some embodiments, the compositions or injectable compositions and/or particles (e.g., silk fibroin particles) can further comprise at least one additional material for soft tissue augmentation, e.g., additional filler materials, including, but not limited to, poly(methyl methacrylate) microspheres, hydroxyapatite, poly(L-lactic acid), collagen, elastin, and glycosaminoglycans, and/or hyaluronic acid.

In some embodiments where the compositions or injectable compositions are formulated for use as dermal fillers, the compositions or injectable compositions may further comprise a commercial dermal filler product such as DYSPORT®, COSMODERM®, EVOLENCE®, RADIESSE®, RESTYLANE®, JUVEDERM® (from Allergan), SCULPTRA®, PERLANE®, and CAPTIQUE®, and any combinations thereof.

In some embodiments, the compositions or injectable composition and/or silk fibroin particles can comprise metallic nanoparticles (e.g., but not limited to, gold nanoparticles), optical molecules (e.g., but not limited to, fluorescent molecules, and/or quantum dots), and any other art—recognized contrast agent, e.g., for biomedical imaging.

Exemplary Methods of Use

The compositions and/or injectable compositions described herein can be used in a variety of medical uses, including, without limitation, fillers for tissue space, templates for tissue reconstruction or ingrowth, scaffolds for cells in tissue engineering applications, and/or as a vehicle/carrier for drug delivery. Any embodiment of the compositions or injectable compositions injected into a tissue to be repaired or augmented can act as a scaffold to mimic the extracellular matrices (ECM) of the body, and/or promote tissue ingrowth. The scaffold can serve as both a physical support and/or an adhesive template for cells to proliferate therein. In some embodiments, the compositions or injectable compositions do not comprise cells. However, in those embodiments, the compositions or injectable compositions can comprise cell attachment agents, e.g., collagen, and/or chemotactants, e.g., growth factors, that can attract host cells and support the cell proliferation. Such cell attachment agents can be dispersed in the carrier and/or silk fibroin particles of the compositions or injectable compositions. In alternative embodiments, the silk fibroin particles can be seeded with cells prior to administration to a target tissue to be repaired or augmented.

In some embodiments, provided herein are compositions and/or injectable compositions that can be used to fill, volumize, and/or regenerate a tissue in need thereof. The injectable compositions can generally be used for tissue filling or volumizing, soft tissue augmentation, replacement, cosmetic enhancement and/or tissue repair in a subject. Additionally, the injectable compositions can be used for filling of any tissue void or indentation that are either naturally formed (e.g., aging) or created by surgical procedure for removal of tissue (e.g., a dermal cyst or a solid tumor), corticosteroid treatment, immunologic reaction resulting in lipoatrophy, tissue damage resulting from impact injuries or therapeutic treatment (e.g., radiotherapy or chemotherapy). The injectable compositions can also be used to raise scar depressions.

In certain embodiments, the injectable compositions can be used for soft tissue augmentation. As used herein, by the term "augmenting" or "augmentation" is meant increasing, filling in, restoring, enhancing or replacing a tissue. In some embodiments, the tissue can lose its elasticity, firmness, shape and/or volume. In some embodiments, the tissue can be partially or completely lost (e.g., removal of a tissue) or damaged. In those embodiments, the term "augmenting" or "augmentation" can also refer to decreasing, reducing or alleviating at least one symptom or defect in a tissue (for example, but not limited to, loss of elasticity, firmness, shape and/or volume in a tissue; presence of a void or an indentation in a tissue; loss of function in a tissue) by injecting into the tissue with at least one injectable composition described herein. In such embodiments, at least one symptom or defect in a tissue can be decreased, reduced or alleviated by at least about 30%, at least about 40%, at least about 50%, at least about 60%, at least about 70%, at least about 80% or higher, as compared to no treatment. In some embodiments, at least one symptom or defect in a tissue can be decreased, reduced or alleviated by at least about 90%, at least about 95%, at least about 97%, or higher, as compared to no treatment. In some embodiments, at least one symptom or defect in a tissue can be decreased, reduced or alleviated by 100% (defect-free or the defect is undetectable by one of skill in the art), as compared to no treatment. In other embodiments, the tissue can be augmented to prevent or delay the onset of defect manifestation in a tissue, e.g., loss of elasticity, firmness, shape and/or volume in a tissue, or signs of wrinkles. As used herein, the phrase "soft tissue augmentation" is generally used in reference to altering a soft tissue structure, including but not limited to, increasing, filling in, restoring, enhancing or replacing a tissue, e.g., to improve the cosmetic or aesthetic appearance of the soft tissue. Examples of soft tissue augmentation include, but are not limited to, dermal tissue augmentation; filling of lines, folds, wrinkles, minor facial depressions, and cleft lips, especially in the face and neck; correction of minor deformities due to aging or disease, including in the hands and feet, fingers and toes; augmentation of the vocal cords or glottis to rehabilitate speech; dermal filling of sleep lines and expression lines; replacement of dermal and subcutaneous tissue lost due to aging; lip augmentation; filling of crow's feet and the orbital groove around the eye; chin augmentation; augmentation of the cheek and/or nose; bulking agent for periurethral support, filling of indentations in the soft tissue, dermal or subcutaneous, due to, e.g., overzealous liposuction or other trauma; filling of acne or traumatic scars; filling of nasolabial lines, nasoglabellar lines and intraoral lines. In some embodiments, the compositions or injectable compositions described herein can be used to treat facial lipodystrophies.

In some embodiments, the compositions or injectable compositions can be used for soft tissue repair. The term "repair" or "repairing" as used herein, with respect to a tissue, refers to any correction, reinforcement, reconditioning, remedy, regenerating, filling of a tissue that restores volume, shape and/or function of the tissue. In some embodiments "repair" includes full repair and partial repair. For example, the volume, shape and/or function of a tissue to be repaired can be restored by at least about 30%, at least about 40%, at least about 50%, at least about 60%, at least about 70%, at least about 80% or higher within a certain period of time (e.g., within about 12 months, within about 9 months, within about 6 months, within about 3 months or shorter), as compared to no treatment. In some embodiments, the volume, shape and/or function of a tissue to be repaired can be restored by at least about 90%, at least about 95%, at least about 97%, or higher, within a certain period of time (e.g., within about 12 months, within about 9 months, within about 6 months, within about 3 months or shorter), as compared to no treatment. In some embodiments, the volume, shape and/or function of a tissue to be repaired can be restored by 100% (defect—free or the defect is undetectable by one of skill in the art) within a certain period of time (e.g., within about 12 months, within about 9 months, within about 6 months, within about 3 months or shorter), as compared to no treatment. In various embodiments, the injectable compositions can be used to repair any soft tissues discussed earlier, e.g., skin, and any soft tissues amenable for soft tissue augmentation. Without wishing to be bound by theory, the injectable compositions described herein can promote tissue ingrowth, which may ultimately shorten repair time. For example, tissue or cellular ingrowth into the pores of the silk fibroin particles described herein can improve the healing response.

The compositions and/or injectable compositions described herein can also be used for filling a tissue located at or near a prosthetic implant, for example, but not limited to, a conventional breast implant or knee replacement implant. In some embodiments, the compositions and/or injectable compositions can be used to interface between a prosthetic implant and a tissue, e.g., to fill a void between the prosthetic implant and the tissue, and/or to prevent the tissue in direct contact with the prosthetic implant. By way of example only, after placing a prosthetic implant (e.g., a breast implant) in a subject, an injectable composition described herein can be introduced at or adjacent to the implant to fill any void between the implant and the tissue (e.g., breast tissue) and/or "sculpt" the tissue for a more natural look.

In any of the uses described herein, the compositions and/or injectable compositions described herein can be combined with cells for purposes of a biologically enhanced augmentation and/or tissue ingrowth. Cells can be dispersed in the carrier and/or silk fibroin particles. Cells can be collected from a multitude of hosts including but not limited to human autograft tissues, or transgenic mammals. More specifically, human cells used can comprise cells selected from stem cells (e.g., adipocyte—derived stem cells), fibroblasts, lipocytes, assorted immunocytes, cells from lipoaspirate or any combinations thereof.

In some embodiments, administering the cells (e.g., stem cells) with any embodiment of the compositions and/or injectable compositions described herein can enhance or accelerate host integration and/or tissue formation over time. The cells can be dispersed in any embodiment of the compositions and/or injectable compositions described herein, or they can be administered prior to, concurrently with, or after the composition is introduced into a target site. Without wishing to be bound by theory, the cells can secrete pro-angiogenic factors and/or growth factors at the target site. As the tissue regenerates or remodels to fill up a void or repair a defect, the silk fibroin particles and/or carrier matrix can degrade accordingly. In some embodiments, the silk fibroin particles and/or carrier matrix can integrate with the regenerated host tissue.

In some aspects, the compositions and/or injectable compositions described herein can be used as tissue space fillers or bulking agents for treating a defect in a soft tissue of a subject, e.g., for soft tissue augmentation and/or ingrowth. Accordingly, methods for augmenting or regenerating different soft tissues are provided herein. In some embodiments, such a method comprises injecting to a site of defect in a soft tissue a composition comprising silk fibroin particles of any embodiments or aspects described herein and a carrier, or a composition of any embodiments or as aspects described herein.

In some embodiments, a method of administering a composition to a subject may include
inserting a needle and a catheter of a delivery device into the subject, where the needle is coupled to and in fluid communication with the catheter. The method may include moving the needle toward an injection site of the subject and actuating a handle of the delivery device to move the needle from a retracted position to an extended position, where actuating the handle comprises sliding a first portion of the handle relative to a second portion of the handle from a first discrete position to a second discrete position. The method may include inserting the needle into the injection site, and the method may include delivering a composition comprising silk fibroin particles through the catheter and the needle into the injection site.

In some embodiments, a method of administering a composition to a subject may include inserting a needle and a catheter trans-orally or trans-nasally into the subject, the needle being coupled to and in fluid communication with the catheter. The method may include moving the needle toward a vocal fold of the subject, inserting the needle into the vocal fold, and delivering a composition comprising particles through the catheter and the needle into the vocal fold.

In some embodiments involving the methods of soft tissue augmentation described herein, the compositions or injectable compositions are injected through a 18-30 gauge needle (e.g., 18, 19, 20, 21, 22, 23, 24, 25, 26, 27, 28, 29, or 30) such that a standard deviation of extrusion force of the composition through a 18-30 (e.g., 18, 19, 20, 21, 22, 23, 24, 25, 26, 27, 28, 29, or 30) gauge needle, as determined between about 50% extrusion volume and about 90% extrusion volume, is less than about 40%, less than about 35%, less than about 30%, less than about 25%, less than about 20%, less than about 15%, less than about 10%, less than about 5%, or less than about 1%, of an average extrusion force for the corresponding range of the extrusion volume (i.e., about 50%-about 90% extrusion volume). In some embodiments, the standard deviation of extrusion force of the composition through a 18-30 (e.g., 18, 19, 20, 21, 22, 23, 24, 25, 26, 27, 28, 29, or 30) gauge needle, as determined between about 50% extrusion volume and about 90% extrusion volume, is at least about 0.1%, at least about 0.5%, at least about 1%, at least about 5%, at least about 10%, at least about 15%, or at least about 20%, of an average extrusion force for the corresponding range of the extrusion volume (i.e., about 50%-about 90% extrusion volume). Combinations of the above-referenced ranges are also possible. For example, in some embodiments, the standard deviation of extrusion force of the composition through a 18-30 (e.g., 18, 19, 20, 21, 22, 23, 24, 25, 26, 27, 28, 29, or 30) gauge needle, as determined between about 50% extrusion volume and about 90% extrusion volume, is about 0.1% to about 40%, or about 1% to about 20%, or about 1% to about 15%, of an average extrusion force for the corresponding range of the extrusion volume (i.e., about 50%-about 90% extrusion volume).

In some embodiments involving the methods of soft tissue augmentation described herein, the compositions or injectable compositions are injected through a 18-30 gauge needle (e.g., 18, 19, 20, 21, 22, 23, 24, 25, 26, 27, 28, 29, or 30) using an average extrusion force of no more than about 60 N, e.g., no more than about 55 N, no more than about 50 N, no more than about 45 N, no more than about 40 N, no more than about 35 N, no more than about 30 N, no more than about 25 N, no more than about 20 N, no more than about 15 N, no more than about 10 N, or no more than about 5 N. In some embodiments, the average extrusion force can be at least about 5 N, at least about 6 N, at least about 7 N, at least about 8 N, at least about 9 N, at least about 10 N, at least about 15 N, at least about 20 N, at least about 25 N, at least about 30 N, at least about 35 N, at least about 40 N, at least about 45 N, at least about 50 N, at least about 55 N, or at least about 60 N. Combinations of the above-referenced ranges are also possible. For example, in some embodiments, the average extrusion force can range from about 5 N to about 60 N, from about 10 N to about 60 N, or from about 5N to about 30N, or from about 5N to about 25N, or about 5 N to about 20 N, or about 5N to about 15N, or about 5N to about 10 N.

In some embodiments of any one of the methods and/or compositions described herein, the silk fibroin particles provide a bulking effect (e.g., increasing the elasticity, stiffness, and/or density of a soft tissue) to the soft tissue by maintaining up to about 90%, or up to about 85%, or up to about 80%, or up to about 75%, or up to about 70%, or up to about 60%, or up to about 50%, of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 24 months after injection). In some embodiments, the silk fibroin particles can maintain at least about 20%, at least about 30%, at least about 40%, at least about 50%, at least about 60%, at least about 70%, at least about 80%, or at least about 90%, of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 36 months after injection). Combinations of the above-referenced ranges are also possible. For example, in some embodiments, the silk fibroin particles can maintain about 20% to about 90% or about 30% to about 80%, or about 40% to about 70% of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after the injection (e.g., up to about 36 months after injection).

In some embodiments of any one of the methods described herein, the composition and or injectable composition comprises (i) silk fibroin particles and (ii) a carrier comprising any one or more of a glycosaminoglycan polymer (e.g., crosslinked HA or non-crosslinked HA), an extracellular matrix, a polysaccharide, or a fibrous protein polymer described herein (including specific examples of each as described herein).

In some embodiments of any one of the methods described herein, the silk fibroin particles have an average particle size in one or more ranges described herein, e.g., about 200 µm to about 1000 µm, about 250 µm to about 850 µm, about 300 µm to about 800 µm, about 400 µm to about 600 µm, about 250 µm to about 450 µm, 200 µm to about 500 µm, or about 300 µm to about 450 µm. In some embodiments of any one of the methods described herein, the silk fibroin particles have an average size of about 200 µm, 300 µm, 400 µm, 500 µm, 600 µm, 700 µm, 800 µm, 900 µm, or 1000 µm. Different sized particles can be chosen depending the volume of a void to be filled or a defect to be treated. In general, small particles can be used for small defects, while larger particles can be used for larger defects.

The methods described herein can be applied to treat different soft tissues for small volume bulking or large volume bulking applications, including but not limited to, a skin tissue, e.g., a facial skin tissue, a bladder tissue (e.g., a urethra), a cervical tissue, a vocal fold tissue, a breast tissue, or a buttock tissue. Other applications are also possible, for example, stationary phases for liquid chromatography and/or embolization therapy (occlusion of vessels to prevent hemorrhaging).

For example, in some embodiments for large volume bulking applications (e.g., but not limited to breast reconstruction, buttock reconstruction, and treatment of lipodystrophy), the composition of any embodiment described herein can be injected in an amount of at least about 3 cm$^3$ or larger (including, e.g., at least about 5 cm$^3$, at least about 10 cm$^3$, at least about 20 cm$^3$, at least about 30 cm$^3$, at least about 40 cm$^3$, at least about 50 cm$^3$, at least about 60 cm$^3$, at least about 70 cm$^3$, at least about 80 cm$^3$, at least about 90 cm$^3$, at least about 100 cm$^3$, at least about 200 cm$^3$, at least about 300 cm$^3$, at least about 400 cm$^3$, at least about 500 cm$^3$, or at least about 600 cm$^3$. In some embodiments, the composition may be injected in an amount of no more than about 600 cm$^3$, no more than about 500 cm$^3$, no more than about 400 cm$^3$, no more than about 300 cm$^3$, no more than about 200 cm$^3$, no more than about 100 cm$^3$, no more than about 90 cm$^3$, no more than about 80 cm$^3$, no more than about 70 cm$^3$, no more than about 60 cm$^3$, no more than about 50 cm$^3$, no more than about 40 cm$^3$, no more than about 30 cm$^3$, no more than about 20 cm$^3$, no more than about 10 cm$^3$, or no more than about 5 cm$^3$. Combination of the above-referenced are also possible. For example, the amount of the composition injected into a target site may be of about 3 cm$^3$ to about 600 cm$^3$, or about or 3 cm$^3$ to about 500 cm$^3$, or about 5 cm$^3$ to about 500 cm$^3$, or about 10 cm$^3$ to about 500 cm$^3$. In these embodiments, the composition can be injected in an amount that is sufficient to fill and conform to the shape of a void at the target site. In these embodiments, the method may optionally further comprise allowing cells from tissue surrounding the target site to interact with the silk fibroin particles, wherein the silk fibroin particles maintain at least about 30% (including, e.g., at least about 40%, at least about 50%, at least about 60%, at least about 70% or higher) of their original volume (e.g., injected volume) for at least about 9 months (including, e.g., at least about 10 months, at least about 11 months, at least about 12 months, at least about 1.5 years, at least about 2 years or longer) after the injection, thereby augmenting or regenerating the soft tissue. In some embodiments, the silk fibroin particles maintain at least 30% (including, e.g., at least about 40%, at least about 50%, at least about 60%, at least about 70% or higher) of their original volume (e.g., injected volume) of their volume for at least 12 months or longer after the injection.

In some embodiments involving large volume bulking applications, the composition is injected through a 18-21 gauge needle (e.g., 18, 19, 20, or 21 gauge needle) using an average extrusion force of no more than 60 N. For example, in some embodiments, the average extrusion force can range from about 5 N to about 60 N, from about 10 N to about 60 N, or from about 5N to about 30N, or from about 5N to about 25N, or about 5 N to about 20 N, or about 5N to about 15N, or about 5N to about 10 N.

In other embodiments for small volume bulking applications, e.g., where the site of defect is not more than 3 cm$^3$, the composition is injected with a 21-30 gauge needle using an average extrusion force of no more than 30 N. For example, in some embodiments, the average extrusion force can range from about 5 N to about 30 N, from about 10 N to about 30 N, or from about 10N to about 25N, or from about 5N to about 25N, or about 5 N to about 20 N, or about 5N to about 15N, or about 5N to about 10 N. Examples of small volume bulking applications include, but are not limited to a dermal filler for skin tissue (e.g., treatment of facial skin tissue having a facial line, or wrinkle, or a scar to be filled), bulking of urethra (e.g., treatment for stress-urinary incontinence), bulking of cervical tissue (e.g., treatment for cervical insufficiency), and bulking of a vocal fold tissue (e.g., correction of vocal fold paralysis or other causes of vocal fold insufficiency).

In some embodiments, any of the methods and/or compositions or injectable compositions described herein are used to treat a facial skin tissue. For example, any embodiment of the compositions or injectable compositions described herein can be injected to a facial line or wrinkle, or a scar. Thus, in some embodiments, the compositions and/or injectable compositions described herein can be used as a dermal filler. The dermal filler comprising any embodiment of the compositions and/or injectable composition can be modulated for particle compressibility, elasticity, softness, and/or opacity through alteration of silk fibroin concentration and/or carrier matrix. The dermal filler can be used to improve skin appearance or condition, including, but not limited to, rehydrating the skin, providing increased elasticity to the skin, reducing skin roughness, making the skin tauter, reducing or eliminating stretch lines or marks, giving the skin better tone, shine, brightness, and/or radiance, reducing or eliminating wrinkles in the skin, providing wrinkle resistance to the skin and replacing loss of soft tissue.

Accordingly, another aspect described herein provides a method of improving a condition and/or appearance of skin in a subject in need thereof. Non-limiting examples of a skin condition or and/or appearance include dehydration, lack of skin elasticity, roughness, lack of skin tautness, skin stretch line and/or marks, skin paleness, and skin wrinkles. The method comprises injecting any embodiment of the compositions or injectable compositions described herein into a dermal region of the subject, wherein the injection improves the skin condition and/or appearance. For example, improving a skin appearance may include, but is not limited to, rehydrating the skin, providing increased elasticity to the skin, reducing skin roughness, making the skin tauter, reducing or eliminating stretch lines or marks, giving the skin better tone, shine, brightness and/or radiance to reduce paleness, reducing or eliminating wrinkles in the skin, and providing wrinkle resistance to the skin.

As used herein, the term "dermal region" refers to the region of skin comprising the epidermal-dermal junction and the dermis, including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis include, but are not limited to, keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Stretch marks from pregnancy are also located in the dermis.

The hypodermis is not part of the skin, and lies below the dermis. Its purpose is to attach the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In one set of embodiments, methods of treatment are provided. In one embodiment, a method of treating a lack of skin elasticity comprises injecting to a dermal region suffering from a lack of skin elasticity any embodiment of the compositions or injectable compositions described herein, wherein the injection of the composition increases the elasticity of the skin, thereby treating a lack of skin elasticity.

In another embodiment, a method of treating skin roughness comprises injecting to a dermal region suffering from skin roughness any embodiment of the compositions or injectable compositions described herein, wherein the injection of the composition decreases skin roughness, thereby treating skin roughness.

In still another embodiment, a method of treating a lack of skin tautness comprises injecting to a dermal region suffering from a lack of skin tautness any embodiment of the compositions or injectable compositions described herein, wherein the injection of the composition makes the skin tauter, thereby treating a lack of skin tautness.

In a further embodiment, a method of treating a skin stretch line or mark comprises injecting to a dermal region suffering from a skin stretch line or mark any embodiment of the compositions or injectable compositions described herein, wherein the injection of the composition reduces or eliminates the skin stretch line or mark, thereby treating a skin stretch line or mark.

In another embodiment, a method of treating skin wrinkles comprises injecting to a dermal region suffering from skin wrinkles any embodiment of the compositions or injectable compositions described herein, wherein the injection of the composition reduces or eliminates skin wrinkles, thereby treating skin wrinkles.

In yet another embodiment, a method of treating, preventing or delaying the formation of skin wrinkles comprises injecting to a dermal region susceptible to, or showing signs of wrinkles any embodiment of the compositions or injectable compositions described herein, wherein the injection of the composition makes the skin resistant to skin wrinkles, thereby treating, preventing or delaying the formation of skin wrinkles.

In some embodiments of the methods and/or compositions and/or injectable compositions described herein, the compositions and/or injectable compositions can be used to treat a target site (e.g., a target site of no more than 3 cm³, no more than 2 cm³, or no more than 1 cm³) for urogenital applications (e.g., a target site, e.g., a defect, in a bladder tissue). For example, urethral bulking—where bulking material is injected into the bladder neck and urethra—is used to treat incontinence due to sphincter deficiency. In some embodiments, the compositions and/or injectable compositions described herein can bulk urethra walls, restoring the sealing mechanism, and be programmed for long term volume retention for lasting effect. For example, the silk fibroin particles can maintain up to about 90%, or up to about 85%, or up to about 80%, or up to about 75%, or up to about 70%, or up to about 60%, or up to about 50%, of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 24 months after injection). In some embodiments, the silk fibroin particles can maintain at least about 20%, at least about 30%, at least about 40%, at least about 50%, at least about 60%, at least about 70%, at least about 80%, or at least about 90%, of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 36 months after injection). Combinations of the above-referenced ranges are also possible. For example, in some embodiments, the silk fibroin particles can maintain about 20% to about 90% or about 30% to about 80%, or about 40% to about 70% of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after the injection (e.g., up to about 36 months after injection).

In some embodiments of the methods and/or compositions and/or injectable compositions described herein, the compositions and/or injectable compositions can be used to treat cervical insufficiency, a disease which is known to increase the risk of preterm labor. An injectable bulking agent into the walls of cervix can enhance the mechanical properties of the cervical canal to reduce the risk of early pregnancy. Current treatments for cervical insufficiency include cervical cerclage, which is often associated with hemorrhage, tearing, and difficult implantation procedures. A minimally invasive injectable alternative using compositions and/or injectable compositions described herein may improve tissue mechanics without the drawbacks associated with sutures. In some embodiments, the compositions and/or injectable compositions described herein can bulk the walls of cervix to reduce the risk of early pregnancy.

In some embodiments of the methods and/or compositions and/or injectable compositions described herein, the compositions and/or injectable compositions can be used to augment vocal fold in subjects in need thereof, e.g., a subject having vocal cord paresis, paralysis or glottic insufficiency. In these embodiments, the method comprises injecting to a target site (e.g., a glottal gap) in the vocal fold a subject in need thereof any embodiment of the compositions or injectable compositions described herein, with a 18-30 gauge needle (e.g., 18, 19, 20, 21, 22, 23, 24, 25, 26, 27, 28, 29, 30) such that a standard deviation of extrusion force of the composition through a 18-30 (e.g., 18, 19, 20, 21, 22, 23, 24, 25, 26, 27, 28, 29, or 30) gauge needle, as determined between about 50% extrusion volume and about 90% extrusion volume, is less than about 40%, less than about 35%, less than about 30%, less than about 25%, less than about 20%, less than about 15%, less than about 10%, less than about 5%, or less than about 1%, of an average extrusion force for the corresponding range of the extrusion volume (i.e., about 50%-about 90% extrusion volume). In some embodiments, the standard deviation of extrusion force of the composition through a 18-30 (e.g., 18, 19, 20, 21, 22, 23, 24, 25, 26, 27, 28, 29, or 30) gauge needle, as determined between about 50% extrusion volume and about 90% extrusion volume, is at least about 0.1%, at least about 0.5%, at least about 1%, at least about 5%, at least about 10%, at least about 15%, or at least about 20%, of an average extrusion force for the corresponding range of the extrusion volume (i.e., about 50%-about 90% extrusion volume). Combinations of the above-referenced ranges are also possible. For example, in some embodiments, the standard deviation of extrusion force of the composition through a 18-30 (e.g., 18, 19, 20, 21, 22, 23, 24, 25, 26, 27, 28, 29, or 30) gauge needle, as determined between about 50% extrusion volume and about 90% extrusion volume, is about 0.1% to about 40%, or about 1% to about 20%, or about 1% to about 15%, of an average extrusion force for the corresponding range of the extrusion volume (i.e., about 50%-about 90% extrusion volume).

In some embodiments, the method comprises injecting to a target site (e.g., a glottal gap) in the vocal fold of a subject in need thereof any embodiment of the compositions or injectable compositions described herein, with a 18-30 gauge needle (e.g., 18, 19, 20, 21, 22, 23, 24, 25, 26, 27, 28, 29, or 30) using an average extrusion force of no more than 60 N, e.g., no more than 55 N, no more than 50 N, no more than 45 N, no more than 40 N, no more than 35 N, no more than 30 N, no more than 25 N, no more than 20 N, no more than 15 N, no more than 10 N, or no more than 5 N. In some embodiments, the average extrusion force can be at least about 5 N, at least about 6 N, at least about 7 N, at least about 8 N, at least about 9 N, at least about 10 N, at least about 15 N, at least about 20 N, at least about 25 N, at least about 30 N, at least about 40 N, at least about 50 N, or at least about 60 N. Combinations of the above-referenced ranges are also possible. In some embodiments, the average extrusion force can range from 5 N to about 60 N, from about 10 N to about 60 N, or from about 5N to about 30N, or from about 5N to about 25N, or about 5 N to about 20 N, or about 5N to about 15N, or about 5N to about 10 N. In some embodiments, the injection can comprise trans-oral injection, trans-nasal injection, percutaneous injection, or thyroid injection. In some embodiments, the injection is trans-oral or trans-nasal injection, for example, which can be performed with the injection tube described herein for coupling to a laryngoscope or other endoscope and delivering the composition to the site of defect in the vocal fold.

In some embodiments involving the methods for augmenting a vocal fold, the composition and/or injectable composition can comprise (i) silk fibroin particles and (ii) a carrier comprising any one or more examples of a glycosaminoglycan polymer, an extracellular matrix, a polysaccharide, or a fibrous protein polymer described herein. For example, in one embodiment, the composition comprises silk fibroin particles and a hyaluronic acid carrier (crosslinked and/or non-crosslinked). In some embodiments, the silk fibroin particles have an average particle size in one or more ranges described herein, e.g., about 300 µm to about 450 µm, or about 200 µm to about 500 µm. In some embodiments, the hyaluronic acid (HA) in the composition for augmenting vocal fold has a molecular weight range of about 750 kDa to about 1000 kDa (with a weighted average of about 800 kDa to about 850 kDa, e.g., about 823 kDa), and a crosslink density of about 4 mol % to about 15 mol % (e.g., 13 mol %), wherein the crosslink density is computed as the total number of molecules (or moles) of a crosslinking agent (e.g., BDDE) incorporated into the crosslinked carrier (e.g., crosslinked HA) to the total number of repeating entity molecules (or moles) (e.g., diasaccharides repeats) of the carrier (e.g., HA) present in the crosslinked carrier (e.g., crosslinked HA), multiplied by 100.

In some embodiments, the composition and/or injectable composition for augmenting a vocal fold can comprise a crosslinked matrix carrier (e.g., as described herein) and porous silk fibroin particles (e.g., as described herein), wherein the composition is characterized in that: (i) the crosslinked matrix carrier has a crosslink density of about 4 mol % to about 30 mol % (including the ranges described herein); (ii) the porous silk fibroin particles and the crosslinked matrix carrier are present in a volume ratio of about 5:95 to about 95:5 (including the ranges described herein); and (iii) an average force of extruding about 1 mL of the composition through a 18G-30G needle into air is less than 60 N (including, e.g., less than 50 N, less than 40 N, or less than 30 N, or the ranges described herein). The porous silk fibroin particles provide bulking effect to the vocal fold by maintaining up to 80% (e.g., about 10% to about 80% or about 20% to about 80%, or about 30% to about 70%) of the particles' original volume for at least 3 months or longer (including, e.g., at least 6 months, at least 9 months or longer) after the injection. The crosslinked matrix carrier may comprise crosslinked glycosaminoglycan polymers (e.g., crosslinked hyaluronic acid), crosslinked extracellular matrix protein polymers (e.g., crosslinked collagen, crosslinked elastin, and/or crosslinked fibronectin), crosslinked polysaccharides (e.g., crosslinked cellulose), crosslinked fibrous protein polymers, and a combination of two or more thereof. In some embodiments, the crosslinked matrix carrier (e.g., crosslinked hyaluronic acid) has a concentration of about 0.1% w/v to 10% w/v, including the ranges described herein.

In some embodiments, the composition and/or injectable composition for augmenting a vocal fold is characterized in that the stiffness of the composition is decreased by at least about 15%, at least about 20%, at least about 30%, at least about 40%, at least about 50%, at least about 60%, at least about 70%, at least about 80%, at least about 90%, or higher, as measured between about 0.1% strain and about 1% strain, or between about 0.1% strain and about 10% strain, or between about 0.1% strain and about 100% strain, or between about 10% strain and about 90% strain. In some embodiments, the stiffness of the composition is decreased by no more than about 95%, no more than about 90%, no more than about 80%, no more than about 70%, no more than about 60%, no more than about 50%, no more than about 40%, no more than about 30%, or no more than about 20%, as measured between about 0.1% strain and about 1% strain, or between about 0.1% strain and about 10% strain, or between about 0.1% strain and about 100% strain, or between about 10% strain and about 90% strain. Combinations of the above-referenced ranges are also possible. In some embodiments, the stiffness of the composition is decreased by about 10% to about 90% or about 15% to about 80%, or about 10% to about 40% or about 10% to about 30%, as measured between about 0.1% strain and about 1% strain, or between about 0.1% strain and about 10% strain, or between about 0.1% strain and about 100% strain, or between about 10% strain and about 90% strain.

Any porous silk fibroin particles described herein can be used for the methods for vocal fold augmentation described herein. In some embodiments, the porous silk fibroin particles can comprise a plasticizer, examples of which include, but are not limited to an alcohol, a sugar, and/or a polyol (e.g., glycerol) including other examples of plasticizers described herein. In some embodiments, the porous silk fibroin particles have an average particle size of about 200 µm to about 500 µm, or about 300 µm to about 450 µm. In some embodiments, the porous silk fibroin particles have a porous structure characterized by interconnected pores having an average pore size of about 20 µm to about 100 µm (including the ranges described herein). In some embodiments, the porous silk fibroin particles have an average porosity of at least 90% (e.g., about 90% to about 99%, or about 90% to about 98%). In some embodiments, the porous silk fibroin particles and the crosslinked matrix carrier are present in a volume ratio of about 30:70 to about 70:30 or about 30:70 to about 50:50. Other volume ratios as described herein are also possible.

In some embodiments of any methods for augmenting vocal fold described herein, the silk fibroin particles provide a bulking effect such that it closes the glottal gap by maintaining up to about 90%, or up to about 85%, or up to about 80%, or up to about 75%, or up to about 70%, or up to about 60%, or up to about 50%, of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 24 months after injection). In some embodiments, the silk fibroin particles can maintain at least about 20%, at least about 30%, at least about 40%, at least about 50%, at least about 60%, at least about 70%, at least about 80%, or at least about 90%, of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 36 months after injection). Combinations of the above-referenced ranges are also possible. For example, in some embodiments, the silk fibroin particles can maintain about 20% to about 90% or about 30% to about 80%, or about 40% to about 70% of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after the injection (e.g., up to about 36 months after injection).

In another aspect, any embodiment of the methods, compositions, and/or injectable compositions described herein can be used for applications, including, e.g., fistula occlusion or similar wounds caused by injury or surgery. For example, any embodiment of the compositions and/or injectable compositions described herein can be used to seal the abnormal connection between two or more tissues, allowing epithelium to develop around the silk implant, reforming a natural epithelial barrier and preventing the exchange of substances that may cause further infection or inflammation.

In some embodiments, any embodiment of the compositions, and/or injectable compositions described herein can be used as scaffolds to support cell growth for tissue engineering. For example, any embodiment of the compositions, and/or injectable compositions described herein can be administered into an incision or wound site to promote wound healing or wound disclosure. The methods generally comprise administering any embodiment of the compositions, and/or injectable compositions described herein, at the wound or incision site and allowing the wound or incision to heal while the silk fibroin particles is eroded or absorbed in the body and is replaced with the individual's own viable tissue. The methods can further comprise seeding the silk fibroin particles or mixing the composition with viable cellular material, either from the individual or from a donor, prior to or during administration.

For any methods of use described herein, the effective amount and administration schedule of any embodiment of the compositions and/or injectable compositions described herein injected into a soft tissue (e.g., a dermal tissue, a bladder tissue, a cervical tissue, or a vocal fold tissue) can be determined by a person of ordinary skill in the art taking into account various factors, including, without limitation, the size, condition, and/or location of a defect to be treated, and the duration of treatment desired, the properties (e.g., degradation rate, and/or pharmacodynamics) of selected compositions and/or injectable compositions for treatment, history and risk factors of the individual, such as, e.g., age, weight, general health, and any combinations thereof. In some embodiments, any embodiment of the compositions and/or injectable compositions described herein can be injected into a defect to be treated every about 3 months, every about 6 months, every about 9 months, every about one year, every about two years or longer.

In some embodiments of any methods, compositions, and/or injectable compositions described herein, the compositions or injectable compositions comprising at least one active agent can be used as a platform for drug delivery. For example, the silk fibroin particles can be formed with a pharmaceutical agent either entrained in or bound to the particles and then administered into the body (e.g., injection, implantation or even oral administration). In some embodiments, an active agent can be mixed with silk fibroin particles and/or injectable compositions and then administered into the body (e.g., injection, implantation or even oral administration). For extended or sustained release, silk fibroin particles can manipulated, e.g., to modulate its beta-sheet content, for its volume retention and/or degradation rate. The therapeutic-bound silk fibroin particles can also be further crosslinked to enhance the stability to extend the release period. In an alternative approach, silk fibroin particles can be mixed with other polymers, for examples, hyaluronic acid, to prolong the release of certain growth factors or cytokines and to stabilize the functionality.

As used herein, the term "sustained release" refers to the release of a pharmaceutically-active drug over a period of about seven days or more. In aspects of this embodiment, a drug delivery platform comprising any embodiment of the compositions or injectable compositions described herein releases a pharmaceutically-active drug over a period of, e.g., at least about 7 days after administration, at least about 15 days after administration, at least about 30 days after administration, at least about 45 days after administration, at least about 60 days after administration, at least about 75 days after administration, or at least about 90 days after administration (and/or up to 360 days or up to 120 days after administration).

As used herein, the term "extended release" refers to the release of a pharmaceutically-active drug over a period of time of less than about seven days. In such embodiments, a drug delivery platform comprising any embodiment of the compositions or injectable compositions described herein can release a pharmaceutically-active drug over a period of, e.g., about 1 day after administration, about 2 days after administration, about 3 days after administration, about 4 days after administration, about 5 days after administration, or about 6 days after administration.

Depending on the formulation and processing methods of the compositions and the associated applications, any embodiment of the compositions or injectable compositions described herein can be administered (e.g., by injection) periodically, for example, every about 3 months, every about 4 months, every about 5 months, every about 6 months, every about 7 months, every about 8 months, every about 9 months, every about 10 months, every about 11 months, every about 1 year, every about 2 years or longer.

In some embodiments of any of the applications described herein, any embodiment of the compositions or injectable compositions described herein can be injected subcutaneously, submuscularly, or intramuscularly. In some embodiments, the methods and/or compositions described herein can be used in the dermal region. In some embodiments, the methods and/or compositions described herein can be used in the epidermal layer, dermal layer, hypodermis layer, or any combinations thereof.

Exemplary Methods of Making the Compositions Described Herein

Silk fibroin particles are mixed with or suspended in at least one carrier as described herein in an appropriate volume ratio to form the compositions described herein. In some embodiments, the carrier (e.g., first carrier, second carrier) can be crosslinked, e.g., prior to mixing with the silk fibroin particles. For example, hyaluronic acid as a carrier can be chemically crosslinked using a crosslinking agent, prior to mixing with silk fibroin particles to form the compositions described herein. Examples of crosslinking agents that can be used to chemically crosslink hyaluronic acid include, but are not limited to divinyl sulfone, diepoxyoctane, epoxypropoxy butane, epoxypropoxy ethylene, and 1,4-butanediol-diglycidylether.

Silk fibroin particles can be modified through controlled partial removal of silk sericin or deliberate enrichment of source silk with sericin. This can be accomplished by varying the conditions, such as time, temperature, concentration, and the like for the silk degumming process.

Degummed silk can be prepared by any conventional method known to one skilled in the art. For example, *B. mori* cocoons are boiled for a period of pre-determined time in an aqueous solution. Generally, a long degumming time generates low molecular silk fibroin fragments. See WO 2014/145002 for methods of making low molecular weight silk fibroin fragments, the content of which is incorporated herein by reference in its entirety. In some embodiments, the silk cocoons are boiled for at least about 10 minutes, at least about 20 minutes, at least about 30 minutes, at least about 40 minutes, at least about 50 minutes, at least about 60 minutes, at least about 70 minutes, at least about 80 minutes, at least about 90 minutes, at least about 100 minutes, at least about 110 minutes, at least about 120 minutes, or longer (e.g., up to about 180 minutes). In some embodiments, the silk cocoons may be boiled for no more than about 180 minutes, no more than about 170 minutes, no more than about 160 minutes, no more than about 150 minutes, no more than about 140 minutes, no more than about 130 minutes, no more than about 120 minutes, no more than about 110 minutes, no more than about 100 minutes, no more than about 90 minutes, no more than about 80 minutes, no more than about 70 minutes, no more than about 60 minutes, no more than about 50 minutes, no more than about 40 minutes, no more than about 30 minutes, no more than about 20 minutes, no more than about 10 minutes. Combinations of the above-referenced ranges are also possible. For example, in some embodiments, the silk cocoons may be boiled for about 10 minutes to about 180 minutes, about 15 minutes to about 160 minutes, about 20 minutes to about 140 minutes, or about 30 minutes to about 120 minutes. In some embodiments, silk cocoons can be heated or boiled at an elevated temperature (e.g., for an amount of time described above). For example, in some embodiments, silk cocoons may be heated or boiled at a temperature of at least about 95° C., at least about 100° C., at least about 101.0° C., at least about 101.5° C., at least about 102.0° C., at least about 102.5° C., at least about 103.0° C., at least about 103.5° C., at least about 104.0° C., at least about 104.5° C., at least about 105.0° C., at least about 105.5° C., at least about 106.0° C., at least about 106.5° C., at least about 107.0° C., at least about 107.5° C., at least about 108.0° C., at least about 108.5° C., at least about 109.0° C., at least about 109.5° C., at least about 110.0° C., at least about 110.5° C., at least about 111.0° C., at least about 111.5° C., at least about 112.0° C., at least about 112.5° C., at least about 113.0° C., at least about 113.5° C., at least about 114.0° C., at least about 114.5° C., at least about 115.0° C., at least about 115.5° C., at least about 116.0° C., at least about 116.5° C., at least about 117.0° C., at least about 117.5° C., at least about 118.0° C., at least about 118.5° C., at least about 119.0° C., at least about 119.5° C., at least about 120.0° C., or higher (e.g., up to about 130° C.). In some embodiments, silk cocoons may be heated or boiled a temperature of no more than about 130° C., no more than about 125° C., no more than about 120° C., no more than about 105° C., or no more than about 100° C. Combinations of the above-referenced ranges are also possible. In some embodiments, silk cocoons may be heated or boiled at a temperature of about 95° C. to about 110° C., or about 100° C. to about 105° C.

In some embodiments, the elevated temperature at any of the above-referenced ranges can be achieved by carrying out at least portion of the heating process (e.g., boiling process) under suitable pressure. For example, the suitable pressure under which silk fibroin fragments are produced are typically between about 10-40 psi, between about 10-35 psi, between about 10-30 psi, or between about 10-20 psi. In some embodiments, the pressure may be at least about 10 psi, at least about 11 psi, at least about 12 psi, at least about 13 psi, at least about 14 psi, at least about 15 psi, at least about 20 psi, at least about 25 psi, at least about 30 psi, at least about 35 psi, or at least about 40 psi. In some embodiments, the pressure may be no more than 40 psi, no more than 35 psi, no more than 30 psi, no more than 25 psi, no more than 20 psi, no more than 15 psi, or no more than 10 psi. Combinations of the above-referenced ranges are also possible.

In one embodiment, the aqueous solution used in the process of degumming silk cocoons is about 0.001 M to about 0.5 M $Na_2CO_3$ (e.g., about 0.02 M $Na_2CO_3$ in one embodiment). The cocoons are rinsed, for example, with water to extract the sericin proteins. The degummed silk can be then dissolved, e.g., in an aqueous salt solution. Salts useful for this purpose include lithium bromide, lithium thiocyanate, calcium nitrate or other chemicals capable of solubilizing silk. In some embodiments, the degummed silk can be dissolved by maintaining the silk fibers in about 8M-12 M LiBr solution, or in about 8.5M-11.5M LiBr solution, or in about 9M-11M LiBr solution for up to 6 hours (including, e.g., up to 5 hours, up to 4 hours, up to 3 hours, up to 2 hours, up to 1 hr) at an average temperature of about 55° C. to about 65° C. In some embodiments, the average temperature is about 60° C. The salt is consequently removed using, for example, dialysis. In most cases dialysis for about 2-12 hours can be sufficient. However, in some embodiments, dialysis can be performed for more than about 12 hours, e.g., at least about 12 hours, at least about 24 hours, at least about 2 days, at least about 3 days, at least about 4 days, at least about 5 days or longer (e.g., up to about 1 week). See, for example, International Patent Application Publication Number. WO 2005/012606, the content of which is incorporated herein by reference in its entirety.

If necessary, the solution can then be concentrated using, for example, dialysis against a hygroscopic polymer, for example, PEG, a polyethylene oxide, or amylose. In some embodiments, the PEG is of a molecular weight of 8,000-10,000 g/mol and has a concentration of about 10% to about 50% (w/v). A slide-a-lyzer dialysis cassette (Pierce, MWCO 3500) can be used. However, any suitable dialysis system can be used. The dialysis can be performed for a time period sufficient to result in a final concentration of aqueous silk solution between about 10% to about 30%. In most cases dialysis for about 2-12 hours can be sufficient. See, for example, International Patent Application Publication Number. WO 2005/012606, the content of which is incorporated herein by reference in its entirety.

In some embodiments, the silk fibroin solution can be purified, e.g., by centrifugation or filtration, e.g., using a 0.2 μm filter.

Silk fibroin particles can be produced from aqueous-based or organic solvent-based silk fibroin solutions. In some embodiments, silk fibroin particles produced from organic solvent-based silk fibroin solution (e.g., silk fibroin dissolved in hexafluoroisopropanol (HFIP), see, for example, International Application No. WO2004/000915, content of which is incorporated herein by reference in its entirety) can maintain the particles' original volume for a longer period of time (or degrade at a slower rate) than that of aqueous-based silk fibroin particles. The aqueous- or organic solvent-based silk fibroin solution used for making silk fibroin particles described herein can be prepared using any techniques known in the art.

The concentration of silk fibroin in solutions can be suited to a particular volume retention or degradation requirement. For example, higher concentrations of silk fibroin solutions can be used when longer volume retention or slower degradation rate of the silk fibroin particles is desired upon injection into a tissue to be repaired or augmented. In some embodiments, the silk fibroin solution for making the silk fibroin particles described herein can vary from about 4% (w/v) to about 30% (w/v), inclusive, or about 4% (w/v) to about 20% (w/v), inclusive. In some embodiments, the silk fibroin solution can vary from about 6% (w/v) to about 20% (w/v). In some embodiments, the silk fibroin solution can vary from about 6% (w/v) to about 17% (w/v). Suitable processes for preparing silk fibroin solution are disclosed, for example, in U.S. Pat. No. 7,635,755; and International Application Numbers: WO/2005/012606; and WO/2008/127401. A micro-filtration step can be used herein. For example, the prepared silk fibroin solution can be processed further, e.g., by centrifugation and/or syringe based microfiltration before further processing into silk fibroin particles described herein.

In some embodiments, one or more biocompatible and/or biodegradable polymers (e.g., two or more biocompatible polymers) including the ones described herein, can be added to the silk fibroin solution to form silk fibroin particles. In some embodiments, one or more polymeric plasticizers, carriers, and/or protein additives that enhance cellular response, immune response, and/or regeneration/tissue regrowth, can be added to the silk fibroin solution to form silk fibroin particles.

In some embodiments, at least one active agent described herein can be added to the silk fibroin solution before further processing into silk fibroin particles described herein. In some embodiments, the active agent can be dispersed homogeneously or heterogeneously within the silk fibroin, dispersed in a gradient, e.g., using the carbodiimide-mediated modification method described in the U.S. Patent Application No. US 2007/0212730. In some embodiments, the silk fibroin particles can be first formed and then contacted with (e.g., dipped into) at least one active agent such that the open surface of the particles can be coated with at least one active agent.

The silk fibroin particles can be produced by any methods known in the art. In some embodiments, the silk fibroin particles can be reduced from a solid-state silk fibroin matrix by a mechanical means. Exemplary mechanical means to obtain silk fibroin particles include micronizing, milling, pulverizing, crushing, grinding, freeze-drying or any combination thereof. Methods of forming a solid-state silk fibroin from a silk fibroin solution may involve, e.g., using a solvent-based or an aqueous-based silk fibroin solution. See, e.g., Wang Y. et al. (2008) 29 Biomaterials 3415, U.S. Pat. No. 7,635,755; and International Application Nos: WO/2005/012606; and WO/2008/127401.

In some embodiments, the silk fibroin particles are derived from a bulk silk fibroin sponge produced according to one embodiment of the method described in the International Patent Publication No. WO 2016/145281, the content of which is incorporated herein by reference in its entirety. For example, as described in Example 1, a concentrated silk fibroin solution (e.g., 8-12% w/v) mixed with a plasticizer (e.g., glycerol) at a concentration of about 3-30% w/w (including, e.g., about 3-20% w/w or about 3-10% w/w) is prepared and then frozen at a freezing temperature of about −30° C. to about −10° C. in a lyophilizer under controlled slow freezing rate (about −0.1° C./min to about −0.01° C./min), followed by vacuum at about 50 mTorr to about 200 mTorr for about 36 hours to about 100 hours, to produce a sponge-like material. The bulk silk fibroin sponge can then be reduced to particles (e.g., round particles) using any mechanical means, e.g., grinding, milling, and cutting. In some embodiments, particles of a desired size range can be separated from others, e.g., by sieving.

In some embodiments, the silk fibroin particles can be lyophilized prior to mixing with a carrier as described herein.

Methods for generating porous structures within silk fibroin matrix, e.g., freeze-drying, salt-leaching, and gas foaming methods, may be used, as described in, e.g., U.S. Pat. No. 7,842,780; and US Patent Application Nos: US 2010/0279112; and US 2010/0279112, the contents of which are incorporated herein by reference in their entirety.

In some embodiments, silk fibroin particles or a solid-state silk fibroin described herein can be subjected to a post-treatment that will affect at least one silk fibroin property. For example, post-treatment of silk fibroin particles or a solid-state silk fibroin can affect silk fibroin properties including β-sheet content, solubility, active agent loading capacity, degradation time, drug permeability, or any combinations thereof. Silk post-processing options include controlled slow drying (Lu et al., 10 Biomacromolecules 1032 (2009)), water annealing (Jin et al., Water—Stable Silk Films with Reduced β-Sheet Content, 15 Adv. Funct. Mats. 1241 (2005)), stretching (Demura & Asakura, Immobilization of glucose oxidase with *Bombyx mori* silk fibroin by only stretching treatment and its application to glucose sensor, 33 Biotech & Bioengin. 598 (1989)), compression, and solvent immersion, including methanol (Hofmann et al., 2006), ethanol (Miyairi et al., 1978), glutaraldehyde (Acharya et al., 2008) and N-ethyl-N'-(3-dimethyl aminopropyl) carbodiimide (EDC) (Bayraktar et al., 2005).

In some embodiments, post-treatment of the solid-state silk fibroin or silk fibroin particles, e.g., water—annealing or solvent immersion, can modulate the degradation or solubility properties of the silk fibroin particles described herein. In some embodiments, post-treatment of the solid-state silk fibroin or silk fibroin particles, e.g., water-annealing or solvent immersion, can modulate the volume retention properties of the silk fibroin particles described herein.

In some embodiments, the silk fibroin particles described herein can be coated with at least one layer of a biocompatible and/or biodegradable polymer described herein, e.g., to modulate the degradation and/or volume retention properties of the silk fibroin particles upon injection into a tissue to be treated and/or to modulate the rate of active agents, if any, released from the silk fibroin particles. In such embodiments, the biocompatible and/or biodegradable polymer can comprise at least one active agent.

In some embodiments, the silk fibroin particles described herein can be coated with cell adhesion molecules, e.g., but not limited to, fibronectin, vitronectin, laminin, collagen, any art-recognized extracellular matrix molecules, and any combinations thereof.

In some embodiments, the silk fibroin particles described herein can be sterilized. In some embodiments, compositions comprising silk fibroin particles and a matrix carrier (e.g., but not limited to HA) are sterilized. In some embodiments, a delivery device (e.g., but not limited to a syringe) comprising silk fibroin particles and a matrix carrier (e.g., but not limited to HA) are sterilized. Sterilization methods for biomaterials and/or biomedical devices are well known in the art, including, but not limited to, gamma or ultraviolet radiation, autoclaving (e.g., heat/steam); alcohol sterilization (e.g., ethanol and methanol); gas sterilization (e.g., ethylene oxide sterilization) and heat sterilization.

In some embodiments, compositions comprising silk fibroin particles and a matrix carrier (e.g., but not limited to HA) are subject to heat sterilization. In some embodiments, a delivery device (e.g., but not limited to a syringe) comprising silk fibroin particles and a matrix carrier (e.g., but not limited to HA) are subject to heat sterilization.

In some embodiments involving the silk fibroin particles and/or compositions described herein, the silk fibroin particles and/or compositions may be sterilized (e.g., heat sterilized) such that the sterility assurance level (SAL) is sufficiently low, e.g., to comply with the regulatory requirement. In some embodiments, the sterilized silk fibroin particles and/or compositions described herein has a SAL of about $10^{-6}$ or lower.

In some embodiments involving the silk fibroin particles and/or compositions described herein, the silk fibroin solution used to make the silk fibroin particles can be sterilized, e.g., by sterile filtration, prior to forming silk fibroin particles from the silk fibroin solution.

Further, the silk fibroin particles described herein can take advantage of the many techniques developed to functionalize silk fibroin (e.g., active agents such as dyes and sensors). See, e.g., U.S. Pat. No. 6,287,340, Bioengineered anterior cruciate ligament; WO 2004/000915, Silk Biomaterials & Methods of Use Thereof; WO 2004/001103, Silk Biomaterials & Methods of Use Thereof; WO 2004/062697, Silk Fibroin Materials & Use Thereof; WO 2005/000483, Method for Forming inorganic Coatings; WO 2005/012606, Concentrated Aqueous Silk Fibroin Solution & Use Thereof; WO 2011/005381, Vortex-Induced Silk fibroin Gelation for Encapsulation & Delivery; WO 2005/123114, Silk-Based Drug Delivery System; WO 2006/076711, Fibrous Protein Fusions & Uses Thereof in the Formation of Advanced Organic/Inorganic Composite Materials; U.S. Application Pub. No. 2007/0212730, Covalently immobilized protein gradients in three-dimensional porous scaffolds; WO 2006/042287, Method for Producing Biomaterial Scaffolds; WO 2007/016524, Method for Stepwise Deposition of Silk Fibroin Coatings; WO 2008/085904, Biodegradable Electronic Devices; WO 2008/118133, Silk Microspheres for Encapsulation & Controlled Release; WO 2008/108838, Microfluidic Devices & Methods for Fabricating Same; WO 2008/127404, Nanopatterned Biopolymer Device & Method of Manufacturing Same; WO 2008/118211, Biopolymer Photonic Crystals & Method of Manufacturing Same; WO 2008/127402, Biopolymer Sensor & Method of Manufacturing Same; WO 2008/127403, Biopolymer Optofluidic Device & Method of Manufacturing the Same; WO 2008/127401, Biopolymer Optical Wave Guide & Method of Manufacturing Same; WO 2008/140562, Biopolymer Sensor & Method of Manufacturing Same; WO 2008/127405, Microfluidic Device with Cylindrical MicroChannel & Method for Fabricating Same; WO 2008/106485, Tissue-Engineered Silk Organs; WO 2008/140562, Electroactive Biopolymer Optical & Electro-Optical Devices & Method of Manufacturing Same; WO 2008/150861, Method for Silk Fibroin Gelation Using Sonication; WO 2007/103442, Biocompatible Scaffolds & Adipose-Derived Stem Cells; WO 2009/155397, Edible Holographic Silk Products; WO 2009/100280, 3-Dimensional Silk Hydroxyapatite Compositions; WO 2009/061823, Fabrication of Silk Fibroin Photonic Structures by Nanocontact Imprinting; WO 2009/126689, System & Method for Making Biomaterial Structures.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: Fabrication of Silk Particles

FIG. 1 is a schematic representation of an exemplary method of making silk particles and compositions according to some embodiments described herein. The silk fibroin particles are derived from a bulk silk fibroin sponge produced according to one embodiment of the method described in the International Patent Publication No. WO 2016/145281, the content of which is incorporated herein by reference in its entirety. A concentrated silk fibroin solution (e.g., 8-12% w/v) mixed with a plasticizer (e.g., glycerol) at a concentration of about 3-30% w/w (including, e.g., about 3-20% w/w or about 3-10% w/w) is prepared and then frozen at a freezing temperature of about −30° C. to about −10° C. in a lyophilizer under controlled slow freezing rate (about −0.1° C./min to about −0.01° C./min), followed by vacuum at about 50 mTorr to about 200 mTorr for about 36 hours to about 100 hours, to produce a sponge-like material.

After lyophilization, the silk fibroin/plasticizer material is subjected to solvent treatment, e.g., immersion in methanol for about 6-24 hours, and air drying for at least about 1 hour to form a bulk silk fibroin sponge. Formation of β-sheet structure in silk fibroin can be evaluated via Fourier Transform Infrared Spectroscopy (FTIR), which is well established in the art. Measurement of β-sheet content is typically performed by FTIR spectral deconvolution and peak fitting. This method is a manipulation of the data, and meant to represent comparative data, rather than empirical values. In some embodiments, an increase in β-sheet content by FTIR analysis from 20-30% β-sheet before methanol (MeOH) treatment, to approx. 45-55% β-sheet after MeOH treatment is contemplated. This change would be enough to greatly reduce the solubility of dried silk materials in aqueous media (e.g. PBS, $H_2O$), and extend in vivo volume retention.

Figure 2:
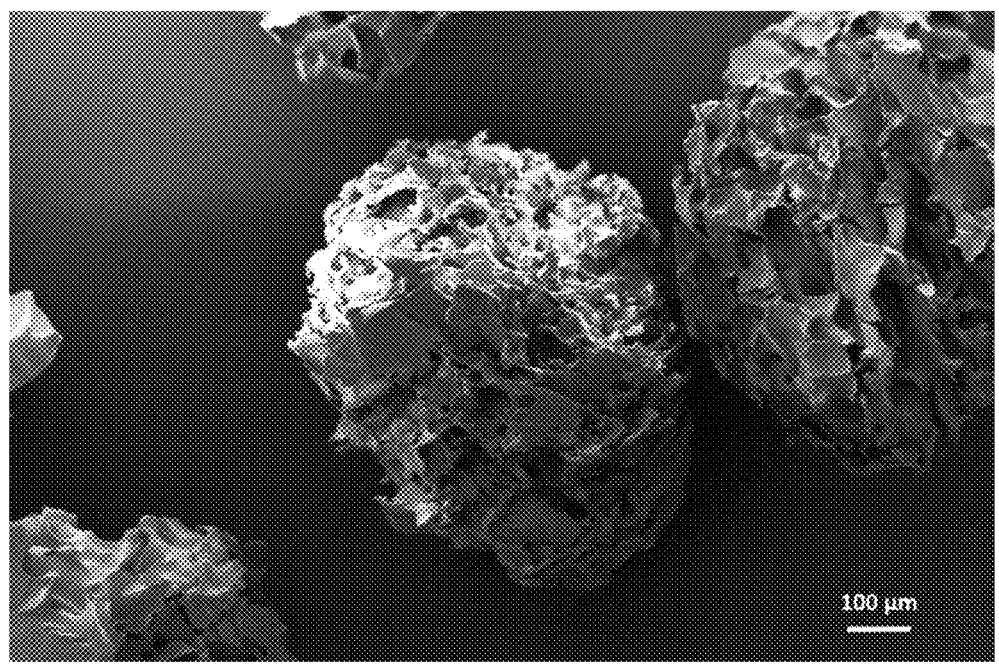
FIG. 2 is a microscopic image of individual silk fibroin particles according to one set of embodiments described herein. The porous silk fibroin particle have an average particle size of about 500 microns to about 600 microns in diameter and an average pore size of about 40 μm in diameter.
Figure 3A:
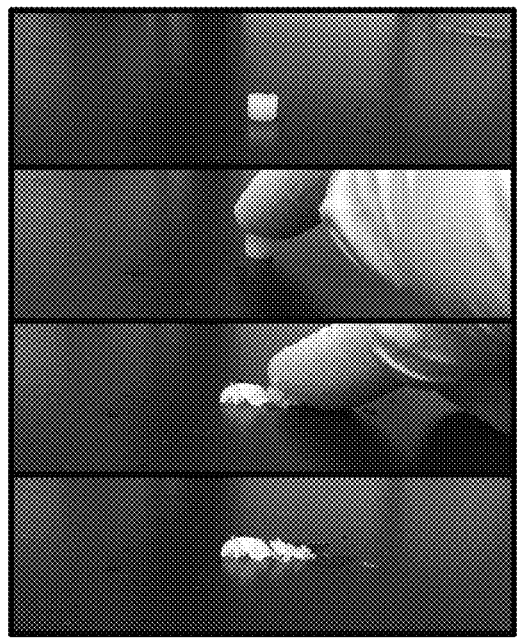
FIGS. 3A-3B are two sets of photographs depicting responses of an exemplary silk fibroin bulk foam or sponge (FIG. 3B), from which silk fibroin particles of one set of embodiments described herein are produced, to a compressive strain and after release of the compressive strain, as compared to those of a silk hydrogel (FIG. 3A).
Figure 3B:
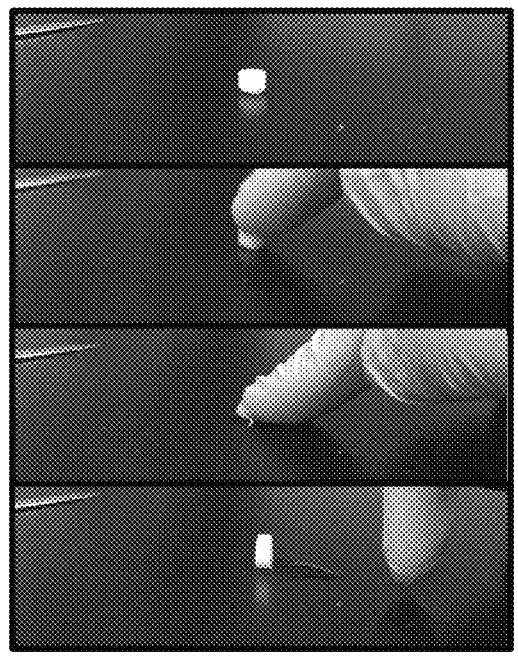

The silk fibroin sponge is then subjected to mechanical grinding and sterilization to form silk fibroin particles according to one set of embodiments described herein. FIG. 2 is a microscopic image of individual silk fibroin particles according to one set of embodiments described herein. The porous silk fibroin particle have an average particle size of about 500 microns to about 600 microns in diameter and an average pore size of about 40 μm in diameter. Such particle size can provide mechanical support to a carrier for tissue bulking, e.g., to retain tissue volume over a specified duration, e.g., of one year or longer. In addition, the porous, three-dimensional structure of the silk fibroin particles promotes cell attachment and migration, which in turns promotes interactions with the surrounding matrix for cell proliferation. Additionally, the slow degradation rate of the particles in vivo offers long-term scaffolding and support.

Figure 51A:
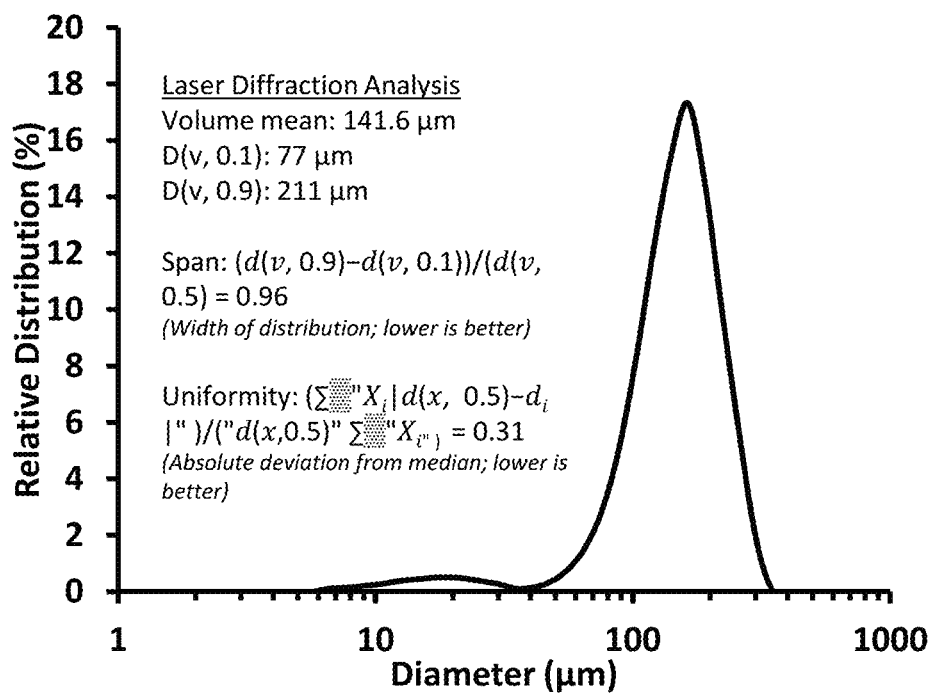
FIG. 51A-51B show a particle size distribution (FIG. 51A) of silk fibroin particles according to one set of embodiments described herein, as determined by laser diffraction analysis, with a representative image of silk fibroin particles (FIG. 51B).
Figure 51B:
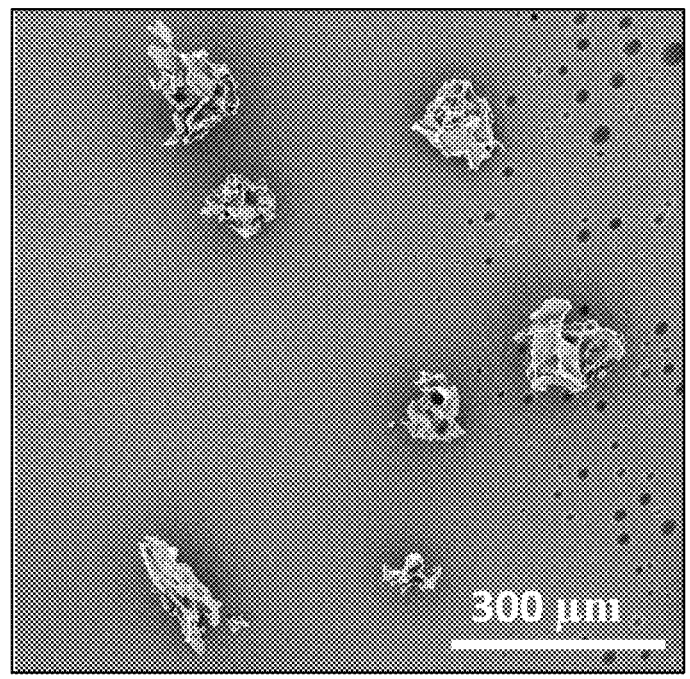

In some embodiments, silk fibroin particles of a desired size range can be separated from other particles, e.g., by sieving. For example, FIG. 51A shows a size distribution of silk fibroin particles produced by the method described above and sieved to about 75 μm to about 125 μm, and FIG. 51B is a representative image of silk fibroin particles according to one set of embodiments described herein.

The concentration of silk fibroin in the silk fibroin particles is at least about 95% w/v or higher, including, e.g., at least about 96% w/v, at least about 97% w/v, at least about 98% w/v, at least about 99% w/v, or up to 100% w/v. The resulting silk fibroin particles can then be mixed with a carrier (e.g., but not limited to hydrogel or autologous fat) in a desired ratio. For example, in one embodiment, the final silk concentration relative to the carrier is about 40% (w/v).

FIGS. 5A-5C are scanning electron microscopic (SEM) images of freeze-dried silk fibroin materials with glycerol. As compared to the silk fibroin material of FIG. 4B (without glycerol), which contained larger non-porous crystals, which, without wishing to be bound by theory, could be attributed to irregularities in freezing, the silk fibroin particles described herein had a more uniform size and contained more evenly distributed, rounded pores. These results show that addition of a plasticizer, e.g., glycerol, can reduce or prevent inconsistent, non-homogenous freezing patterns.

Example 2: Delivery Device Hollow Needle

Figure 29:
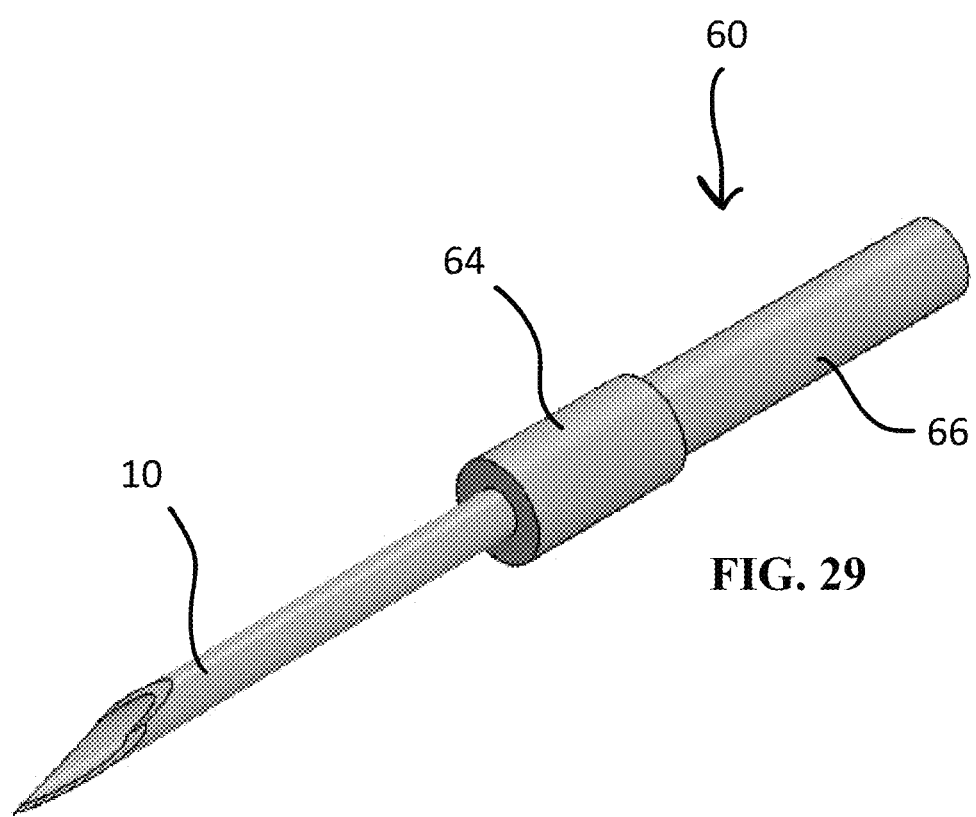
FIG. 29 depicts a needle coupled to a needle sheath according to one embodiment.

The hollow needle is fabricated from a 23XX gauge stainless steel hypotube with a frontside triple point cut as seen in FIGS. 24, 26A and 26B. A wire cut electrical discharge machining (EDM) machine is used to fashion the lancet cut tip and form the needle. As seen in FIGS. 29, 30A and 30B, the rear end of the needle is laser welded to a collar which is designed to prevent the needle from moving distally beyond the diameter-reduced portion of the outer sheath tube.

Example 3: Delivery Device Handle and Tubing

The handle is fabricated in two portions, a leading portion and a back portion. As seen in FIG. 34B, the back portion of the handle is designed to accommodate attachment of a Luer lock syringe. When the plunger on the syringe is depressed, the material held within the syringe is pushed out of the syringe, through a hypotube, and into the inner tube. The handle includes an actuation mechanism that moves the needle between a retracted position where the needle is positioned within and covered by the outer sheath tube and an extended position where the needle tip has been moved outside the outer sheath tube and is exposed. The two portions of the handle can move relative to one another, where one portion of the handle can slide relative to the other portion. Sliding of one portion of the handle relative to the other moves the needle between the retracted and extended positions.

The handle is made from ABS plastic and is formed via injection molding. The inner tube and outer sheath tube is made from PTFE.

Example 4: Injection Delivery of the Silk Fibroin Particles According to One Embodiment Described Herein The silk particles produced by the method as described in Example 1 were mixed with a carrier (e.g., lipoaspirate, hyaluronic acid, polylactic acid, collagen, or combinations thereof) in a silk particle: carrier volume ratio of about 30:70 to about 50:50. When silk fibroin particles were mixed with human fat, they conformed to the shape of a container, enabling more aesthetic sculpting of volume defect.

Figure 6:
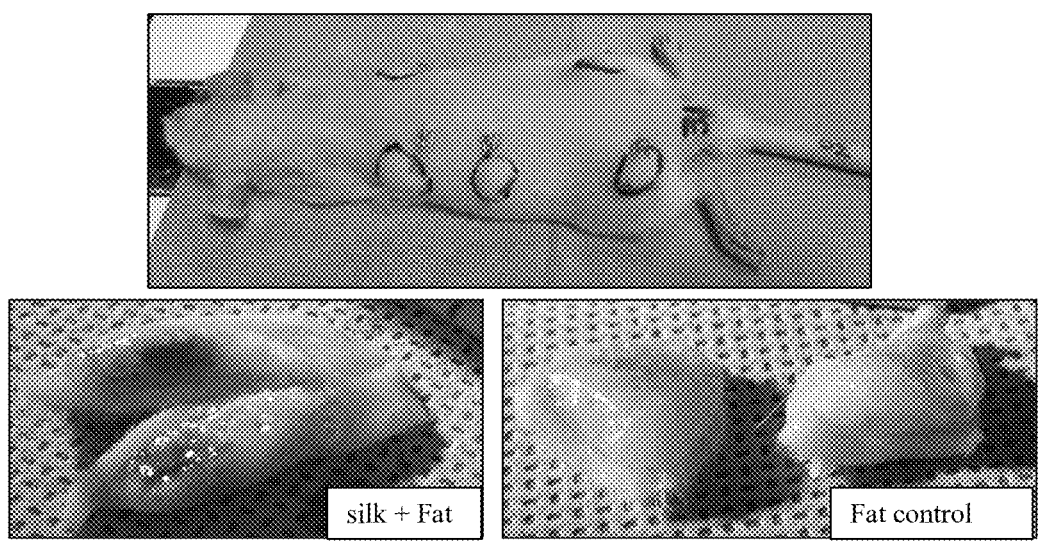
FIG. 6 shows subcutaneous delivery of a composition comprising silk fibroin particles according to one set of embodiments described herein and a carrier to an animal for soft tissue augmentation. (Top) a mouse was injected with control compositions and compositions according to one set of embodiments described herein; (bottom left) a biopsy of the tissue site injected with a mixture of silk fibroin particles and fat; and (bottom right) a biopsy of the tissue site injected with control (fat alone). In this example, about 30-50% silk fibroin particles were suspended in a carrier (e.g., fat).

FIG. 6 shows subcutaneous delivery of a composition comprising silk fibroin particles according to one set of embodiments described herein and a carrier to an animal for soft tissue augmentation. The top panel shows that a mouse was injected with control compositions and compositions according to one set of embodiments described herein. The bottom left panel shows a biopsy of the tissue site injected with a mixture of silk fibroin particles and fat; and the bottom right panel shows a biopsy of the tissue site injected with control (fat alone).

Example 5: Air Extrusion Force of Exemplary Compositions Comprising Silk Fibroin Particles and Lipoaspirate as a Carrier An exemplary extrusion force method is described as follows: pre-loaded syringes attached to a 14G or 16G needle are mounted vertically onto a custom syringe holder. A uniaxial mechanical tester (with a force transducer mounted to the top plate) depresses the plunger of the syringe, extruding material through the needle and recording force measurements via the attached transducer. The crosshead speed of the top plate is set to 5.5 mm/s (which extrudes 1 mL of material in 10 seconds) to achieve a constant rate of extrusion.

Samples of compositions (e.g., as described in Example 2) were extruded into air through a needle (e.g., 16G) of a syringe (e.g., with a volume of 1 mL) at a selected crosshead speed (e.g., at 5.5 mm/s).

Figure 7A:
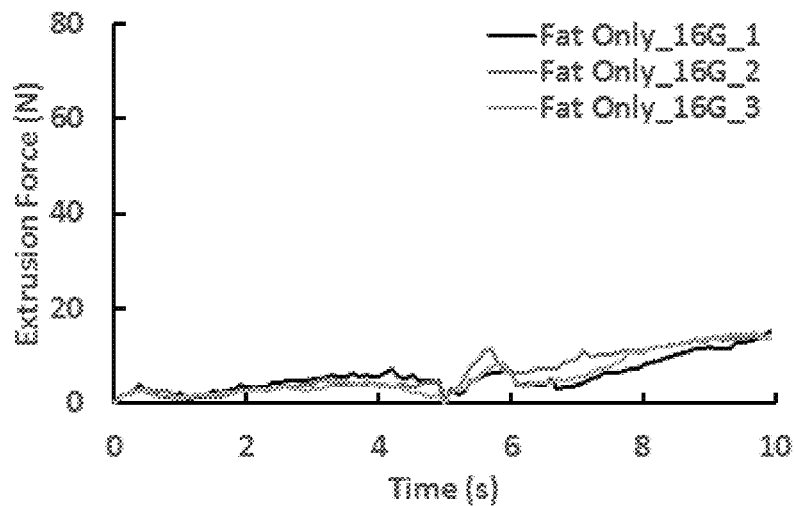
FIGS. 7A-7D are graphs showing extrusion forces resulting from injections of lipoaspirate alone or in combination with silk fibroin particles according to one set of embodiments described herein.
Figure 7B:
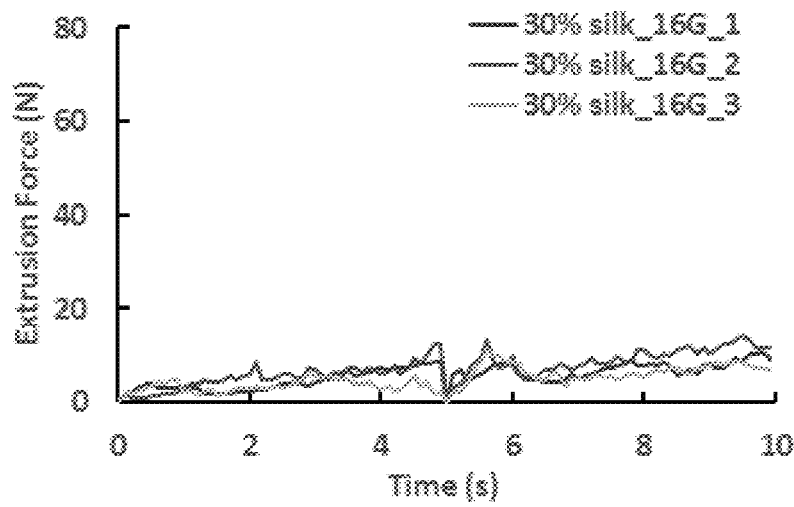
Figure 7C:
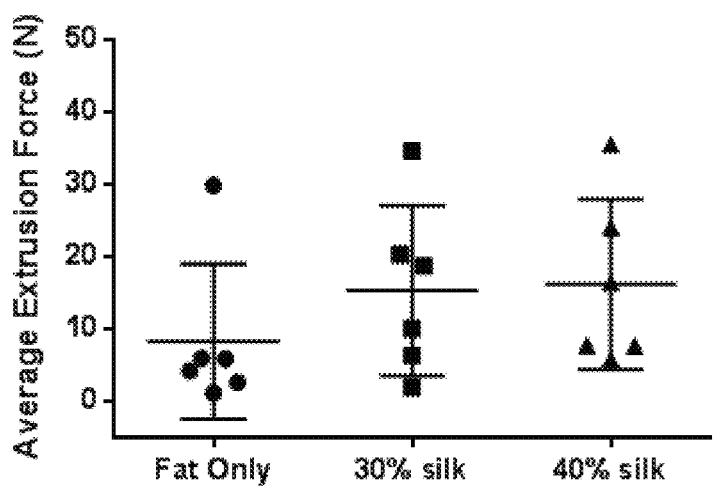
Figure 7D:
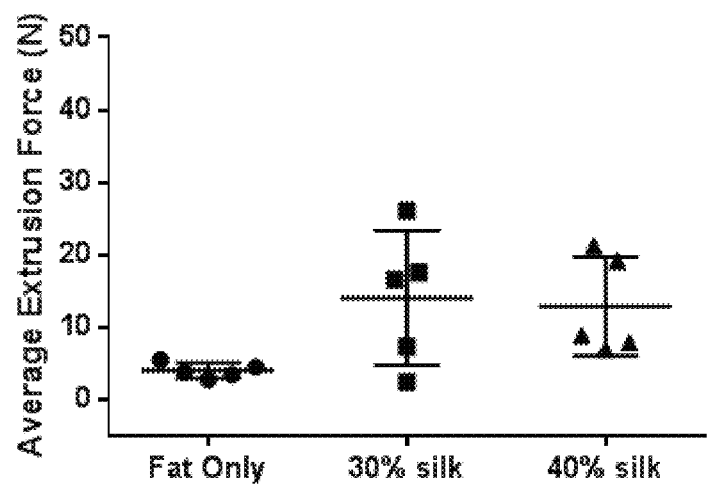

FIGS. 7A-7D are graphs showing extrusion forces resulting from injections of lipoaspirate alone or in combination with silk fibroin particles according to one set of embodiments described herein. FIG. 7A: force of extruding lipoaspirate alone through a 16G needle. FIG. 7B: force of extruding a mixture of 30% silk fibroin particles and lipoaspirate through a 16G needle. FIG. 7C: average extrusion forces of indicated compositions using a 1 mL syringe, 14G needle system. FIG. 7D: average extrusion forces of indicated compositions using a 1 mL syringe, 16G needle system. The compositions were extruded at a rate of 5.5 mm/s through 14G or 16G needles without clogging. Thus, in some embodiments, compositions comprising up to 40% volume of silk fibroin particles mixed with lipoaspirate can be extruded through 1 mL syringe appended with a 16G needle.

Example 6: Air Extrusion Force of Exemplary Compositions Comprising Silk Fibroin Particles and Hyaluronic Acid (HA) as a Carrier The HA at a concentration of 4% w/v was mixed with the silk particles in a volume ratio of 50:50. Extrusion forces of the composition were measured as described in Example 3. Samples were extruded through a 14G or 16G, 1 mL syringe system, at a crosshead speed of 5.5 mm/s, which would inject 1 mL of material in 10 seconds.

Figure 8A:
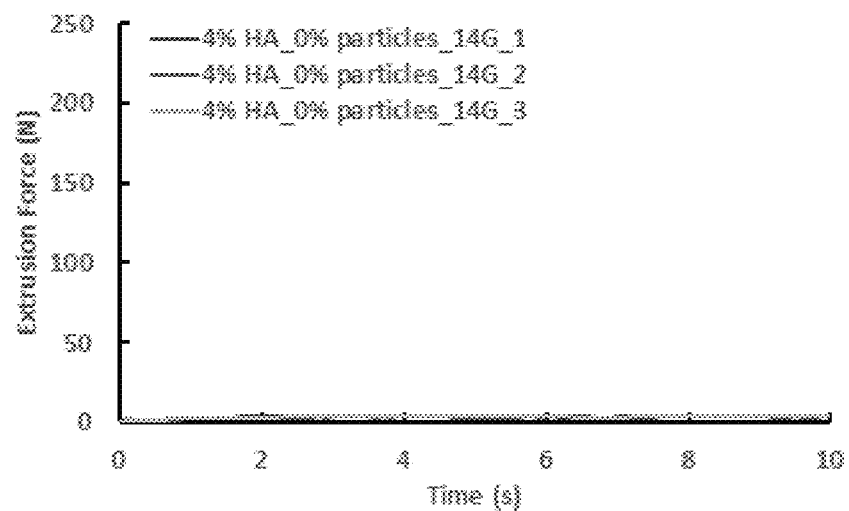
FIGS. 8A-8D are graphs showing extrusion forces resulting from injections of non-crosslinked hyaluronic acid (HA) alone or in combination with silk fibroin particles according to one set of embodiments described herein.
Figure 8B:
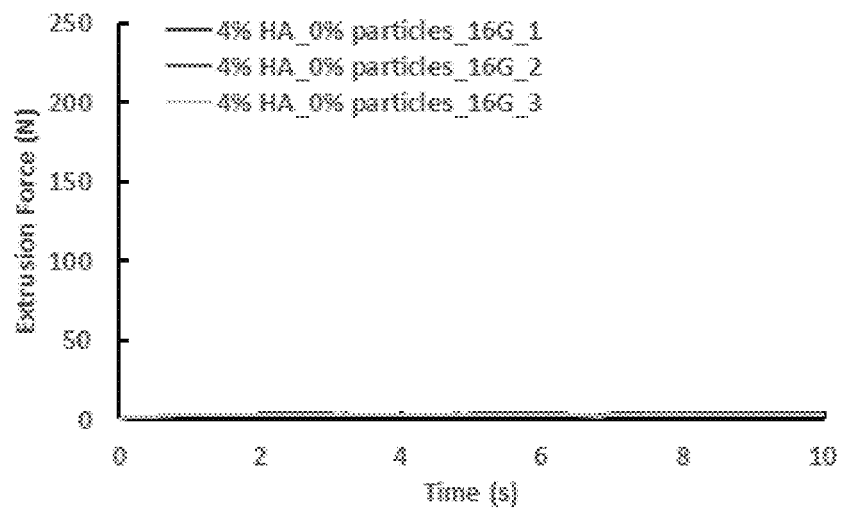
Figure 8C:
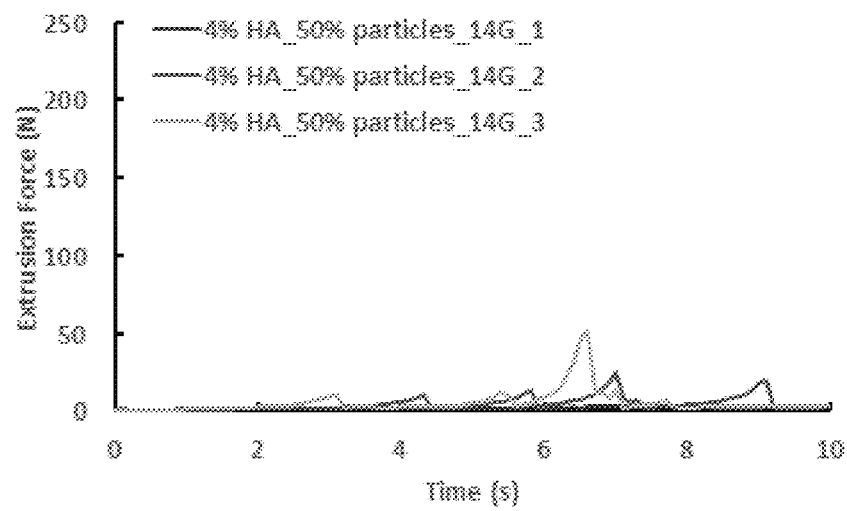
Figure 8D:
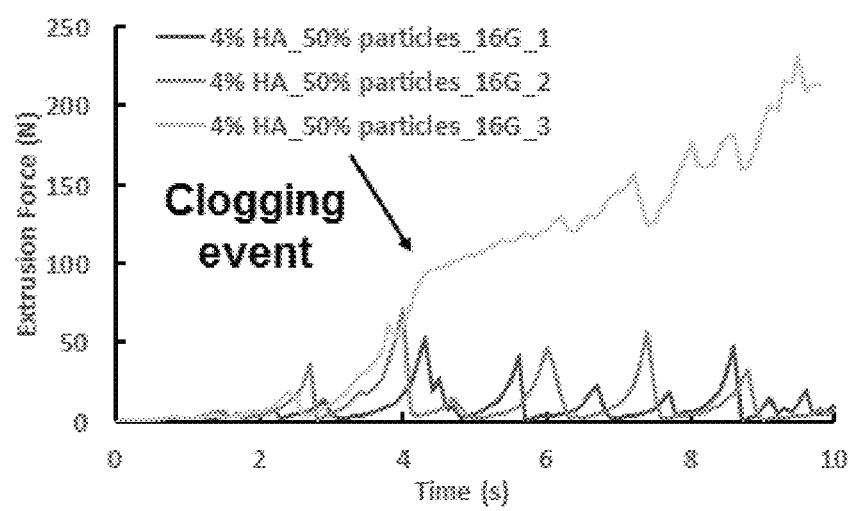

FIGS. 8A-8D are graphs showing extrusion forces resulting from injections of non-crosslinked hyaluronic acid (HA) alone or in combination with silk fibroin particles according to one set of embodiments described herein. FIG. 8A: force of extruding HA alone through a 14G needle. FIG. 8B: force of extruding HA alone through a 16G needle. FIG. 8C: force of extruding a mixture of silk fibroin particles and HA in a volume ratio of 50:50 through a 14G needle. FIG. 8D: force of extruding a mixture of silk fibroin particles and HA in a volume ratio of 50:50 through a 16G needle. The silk fibroin particles were extruded through 14G needles with no incidence of clogging. Thus, in some embodiments, compositions comprising up to 50% volume of silk fibroin particles mixed with non-crosslinked hyaluronic acid (e.g., autoclaved hyaluronic acid) can be extruded through 1 mL syringe appended with a 14G needle.

Example 7: Exemplary Injectable Formulations for Soft Tissue Repair Applications Scaffolds for soft tissue repair from *Bombyx mori* silk fibroin represent a unique opportunity to provide both cosmetic and therapeutic functions, demonstrating bioresorbable features. Silk fibroin materials are known to be used as cell scaffolds, and silk hydrogel and porous scaffold formulations have been fabricated using porogens. Implantable silk materials have shown resorption properties, while also promoting cell in-growth. Silk fibroin scaffolds can also be reinforced with hexafluoroisopropanol (HFIP) or particles to provide additional strength.

Figure 9A:
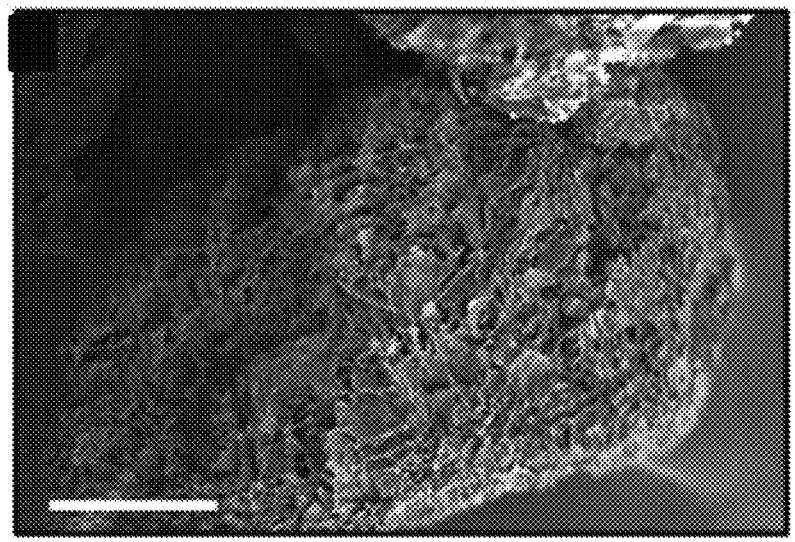
FIGS. 9A-9D show particle physical characterization and extrusion data.
Figure 9B:
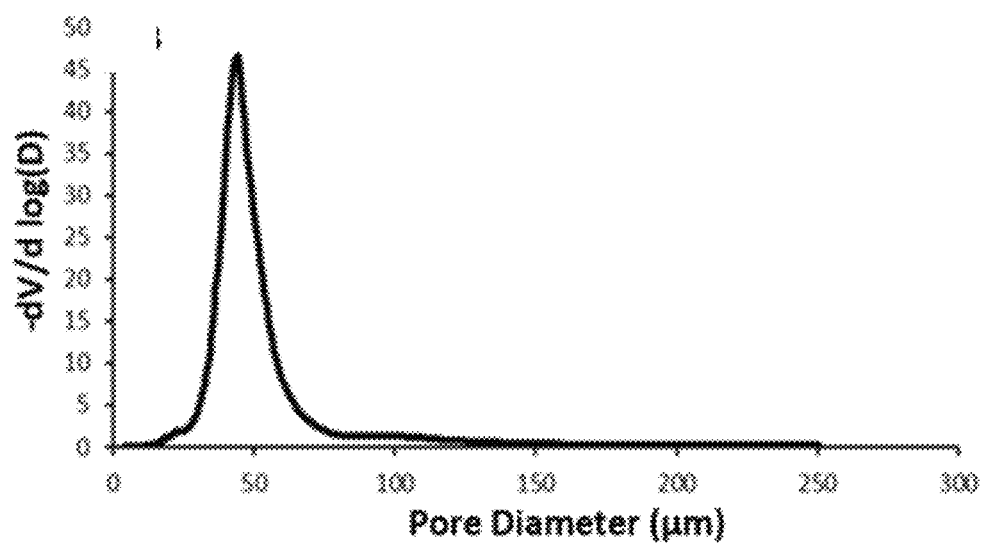

There is a need to develop injectable formulations for soft tissue repair applications, for example, comprising silk fibroin scaffold and a carrier such as lipoaspirate (fat). In one aspect, some embodiments provided herein relate to compositions comprising silk fibroin particles that uniformly have a volume mean diameter of about 500-600 um with a 44 um mean pore size (FIGS. 9A-9B). In these embodiments, the silk fibroin particles were produced as described below. A silk fibroin solution was prepared as described in Rockwood et al. (Nature Protocols (2011) 6: 1612-1631). Once generated, and diluted/concentrated to the desired wt % concentration, the silk fibroin solution was carefully lyophilized at −45° C. overnight to generate porous silk fibroin sponges with a 50-70 um mean pore size. These silk fibroin sponges were then treated with an alcohol (e.g., ethanol) to generate crosslinks within the silk protein matrix. The silk fibroin sponge was then mechanically ground to generate particles of 500-600 um in diameter. Finally, the silk fibroin particles were autoclaved and stored.

To prepare an injectable formulation comprising silk fibroin particles suspended in a carrier such as lipoaspirate, in some embodiments, the silk fibroin particles were mixed with fresh human fat, e.g., isolated from liposuction to generate a silk fibroin particle/lipoaspirate mixture, which can have from 5-50% vol/vol silk particles dispersed within the lipoaspirate.

Figure 9C:
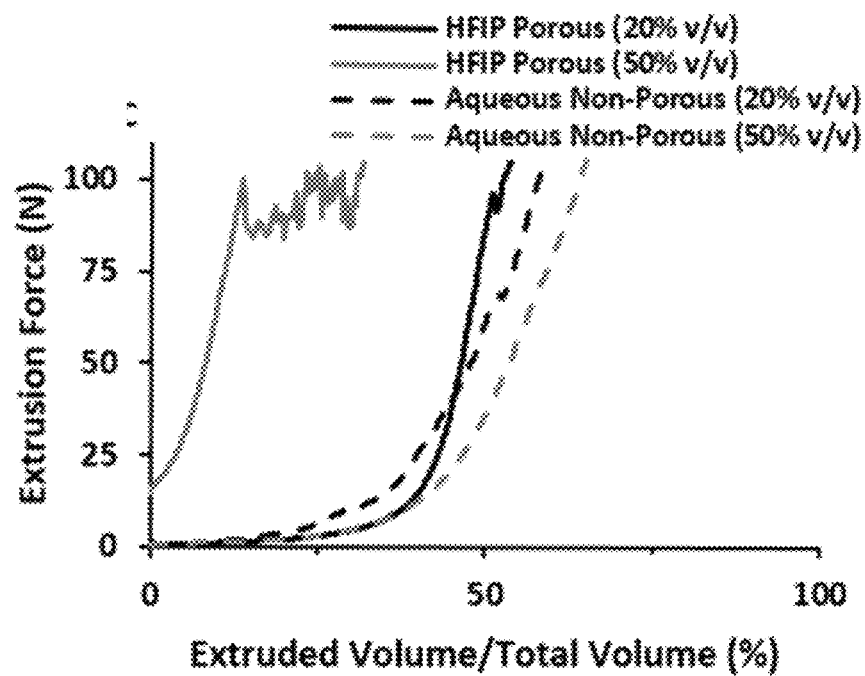
Figure 9D:
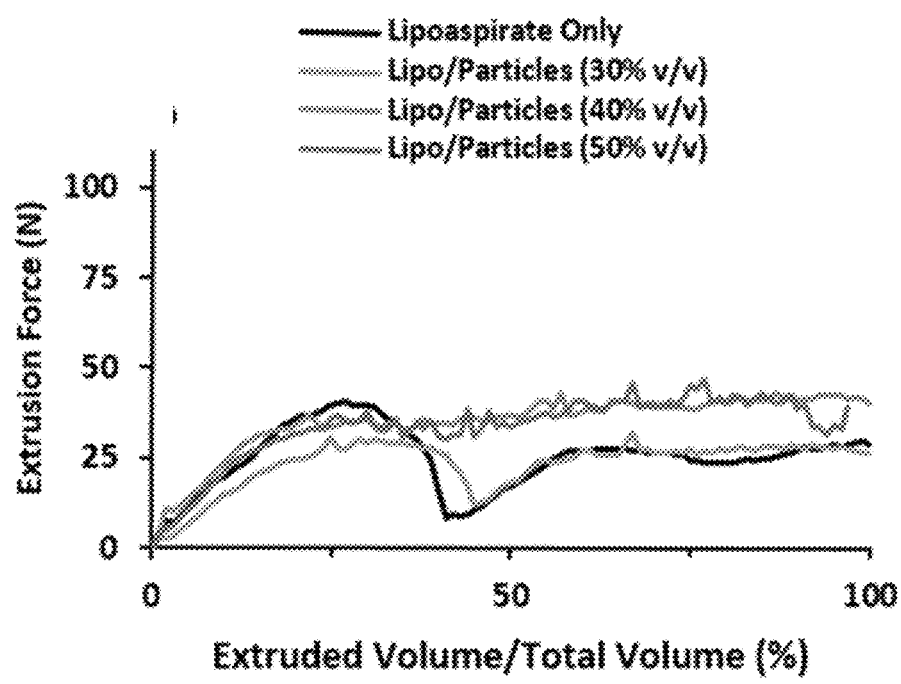

Unlike conventional silk fibroin particles, these silk fibroin particles are unique in that they can be extruded easily from a small gauge needle at concentrations of 5-50% vol/vol in a carrier such as human lipoaspirates. As seen in FIG. 9C, silk fibroin particles derived from both HFIP (as described in the International Patent Publication No. WO2013/071107) and aqueous processing (Rajkhowa et al. 2008) using an NaCl porogen leaching method were mixed with a 1.5% wt/vol silk hydrogel carrier for injection force testing. These two existing silk formulations exhibit strong back-pressure and difficulty extruding through a needle, resulting in frequent clogging events (injection force regularly exceeding 100N) before full extrusion of the material. By contrast, the silk fibroin particles described herein can be extruded from a 14 or 16 gauge needle (or larger gauge, e.g. 12G, 10G) at average forces between 15-30N without clogging (FIG. 9D and Table 1), which are suitable for clinical use in fat grafting applications.

TABLE 1

Average extrusion force of silk fibroin-lipoaspirate formulations

| Formulation | Syringe Size | Needle Gauge | Extrusion Force (N) [Average ± STD] |
|---|---|---|---|
| Lipoaspirate Only | 1 mL | 14 G | 29.8 ± 8.0 |
| 30% v/v Silk Particles in Lipo | 1 mL | 14 G | 34.5 ± 17.0 |
| 40% v/v Silk Particles in Lipo | 1 mL | 14 G | 35.5 ± 2.0 |
|  |  | 16 G | 28.4 ± 9.0 |
| 50% v/v Silk Particles in Lipo | 1 mL | 14 G | 36.2 ± 2.0 |
|  |  | 16 G | 50.4 ± 5.0 |
| Lipoaspirate Only | 20 mL | 14 G | 19.8 ± 9.0 |
| 15% v/v Silk Particles in Lipo | 20 mL | 14 G | 30.2 ± 15.0 |

Extrusion forces reported as the average of N = 3

In some embodiments, the silk fibroin particles described herein can be extruded with lipoaspirate at concentrations from 10% v/v and greater (e.g., 15% v/v or greater) with relatively low extrusion force (within the ideal range of 15-30N). There was no statistically significant difference between lipoaspirate control and lipoaspirate/silk fibroin particle formulations. Large volumes (e.g., 20 mL or greater) of 15% v/v silk fibroin particles in lipoaspirate can be extruded through 14G needles. Average extrusion force was not significantly increased by addition of silk fibroin particles. The lipoaspirate bulked with silk fibroin particles extruded smoothly and consistently without clogs or major spikes in extrusion force which may otherwise cause pain or discomfort to patients during injection.

Additionally, since these silk fibroin particles can be easily extruded at high concentrations, the high concentration of the silk fibroin particles provides structural bulkiness, which can enhance shape retention and malleability and allow for the formation of 3D structures upon injection. This is also a unique feature of these silk fibroin particles described herein over the conventional silk particle formulations that form a plug within the syringe and are difficult to be extruded from the needle. Such a unique feature of the silk fibroin particles described herein is useful for sculpting and spreading post-injection or post-implantation when a specific geometry is desired. Further, when human lipoaspirate ("fat") was extruded from the needle in the absence of the silk fibroin particles, no 3-dimensional shape was created. This novel aspect of the silk particle formulation has applications for both tissue augmentation and fat grafting. Silk fibroin particles described herein can be used as modifying materials for traditional fat grafting applications, such as breast, buttocks and facial enhancements, improving the predictability of volume retention and long term tissue viability. Cells or tissues other than human lipoaspirate could also be added, giving this formulation other unique utility.

Alternative applications beyond fat grafting may include fistula occlusion or similar wounds caused by injury or surgery. For example, an injectable silk particle formulation according to some embodiments described herein can seal the abnormal connection between two or more tissues, allowing epithelium to develop around the silk implant, reforming a natural epithelial barrier and preventing the exchange of substances that may cause further infection or inflammation. Alternatively, injectable silk particle based bulking agents can be used in urogenital applications. For example, urethral bulking—where bulking material is injected into the bladder neck and urethra—is used to treat incontinence due to sphincter deficiency. Injectable silk particles can bulk urethra walls, restoring the sealing mechanism, and be programmed for long term volume retention for lasting effect. Similarly, injectable silk particle formulations can be used to treat cervical insufficiency, a disease which is known to increase the risk of preterm labor. An injectable bulking agent comprising the silk fibroin particles described herein into the walls of cervix can enhance the mechanics of the cervical canal to reduce the risk of early pregnancy. Current treatments for cervical insufficiency include cervical cerclage, which is often associated with hemorrhage, tearing, and difficult implantation procedures. A minimally invasive injectable alternative may improve tissue mechanics without the drawbacks associated with sutures.

Example 8: Pore Characterization of a Silk Fibroin Material

To determine pore size and pore shape of a silk fibroin material, SEM analysis of silk fibroin material cross-sections was performed. Contrast was manipulated using image analysis tool (e.g., Phenom Porometric software/Nanoscience Instruments) such that silk fibroin are presented as one color pixels (e.g., white pixels) and pores are presented as a different color pixel (e.g., black pixels). Then ellipses fit using image analysis tool to outline the pore shape was performed to determine pore size and/or pore shape of the pores.

Figure 50A:
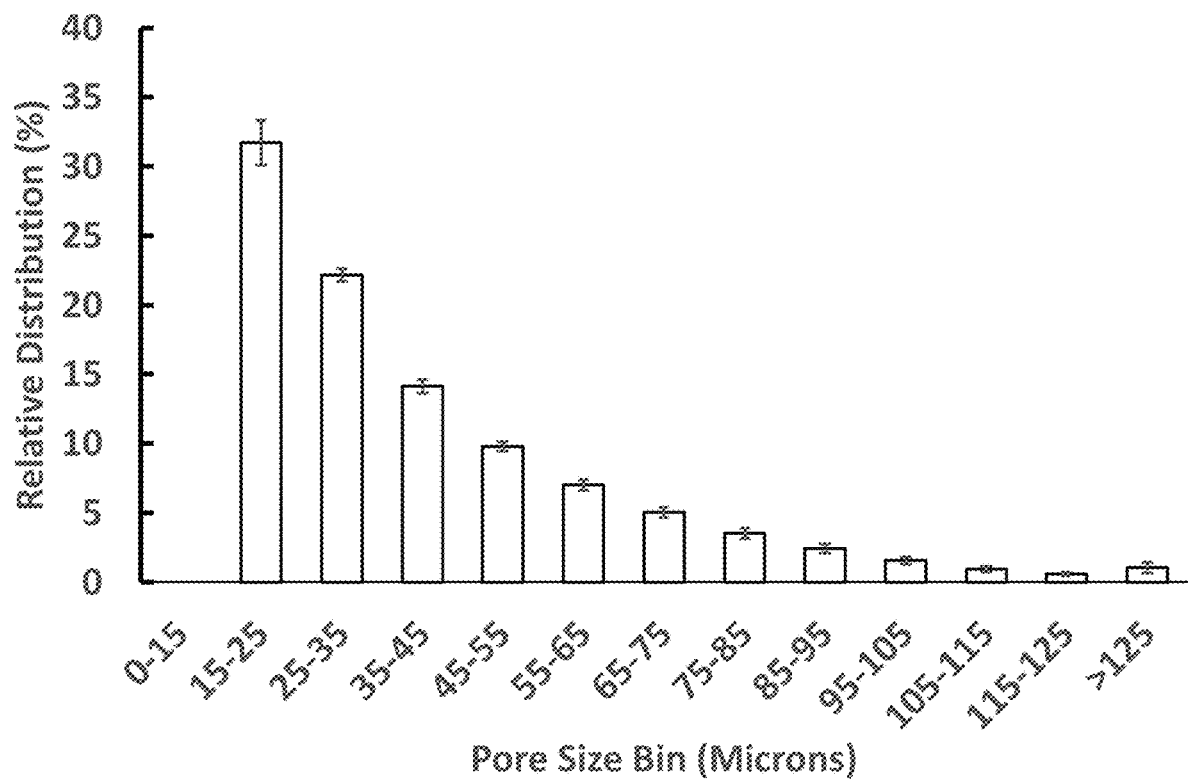
FIGS. 50A-50B show a pore size distribution (FIG. 50A) of silk fibroin particles according to one set of embodiments described herein, as determined by scanning electron microscopy and image analysis, with a representative image of the cross-section of a silk fibroin particle (FIG. 50B). The "pore size" in the graph refers to circle equivalent diameter.
Figure 50B:
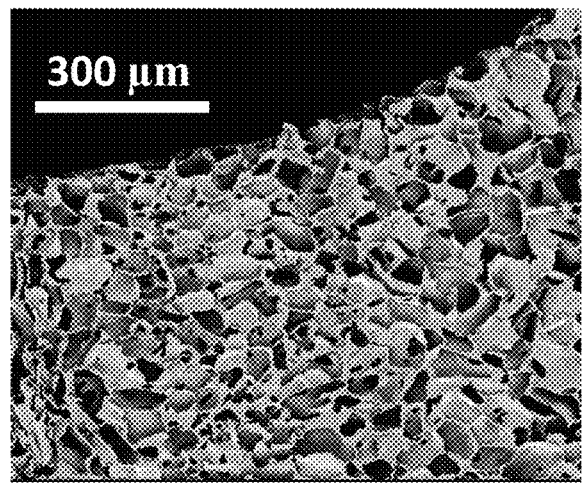

FIG. 50A shows experimental data showing pore size distribution of pores present in a freeze-dried silk fibroin material produced by one set of embodiments of the methods described herein. FIG. 50B shows a representative SEM image of a cross-section of the silk fibroin sponges. As shown in FIG. 50A, the average circle equivalent diameter of pores within a silk fibroin sponge according to one set of the embodiments described herein is about 41.1 µm (ranging between about 31 µm and about 51 µm). In some embodiments, at least about 35% of pores have a circle equivalent diameter of below 25 µm. In some embodiments, at least about 50% of pores have a circle equivalent diameter of below 35 µm. In some embodiments, at least about 70% of pores have a circle equivalent diameter of below 55 µm. In some embodiments, at least about 85% of pores have a circle equivalent diameter of below 75 µm. In some embodiments, at least about 35% of pores have a circle equivalent diameter of below 100 µm.

Figure 12A:
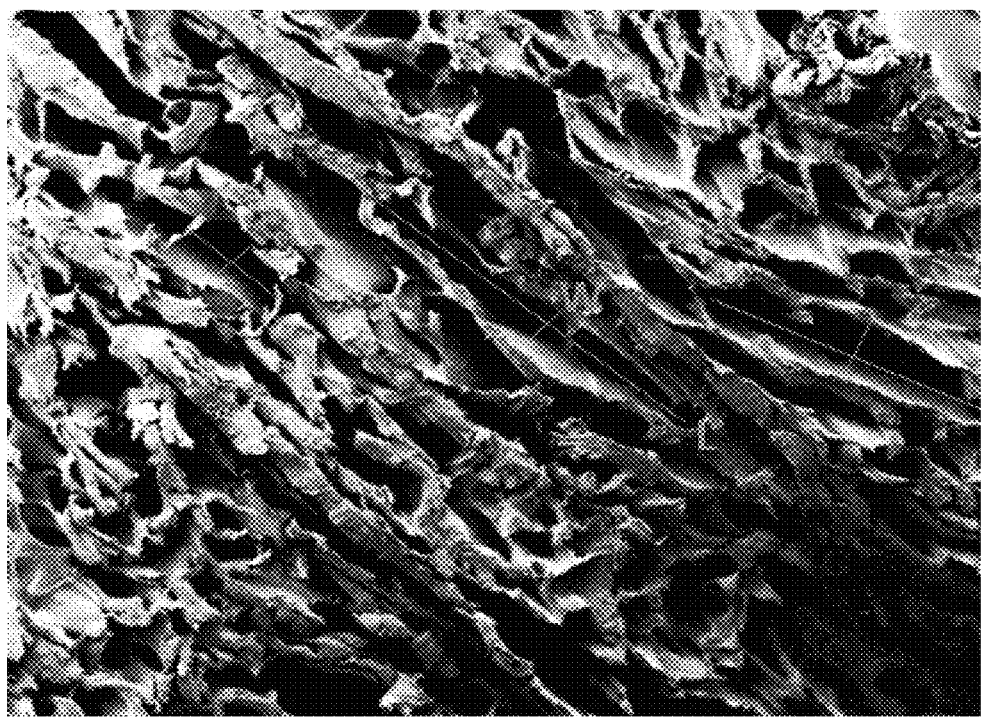
FIG. 12A shows SEM analysis of a cross-section of a silk fibroin sponge, depicting lamellar pore formation and the length and width of the pores. SEM analysis of silk fibroin sponge cross-sections after post-treatment and air-hood drying was performed. Contrast was manipulated such that silk fibroin are presented as white pixels and pores are presented as black pixels. The aspect ratio (AR) of pores (AR=length (L)/width (W)) was determined using image analysis software. An AR value of 1 indicates a perfect circular cross-section. In some embodiments, the silk fibroin sponges have AR values near 1.
Figure 12B:
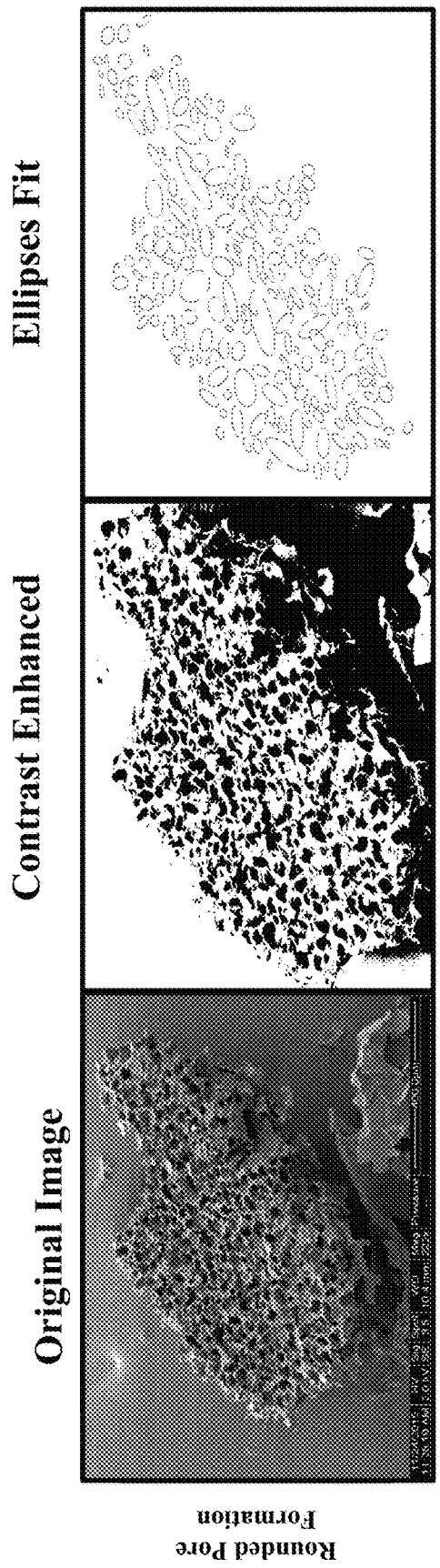
FIGS. 12B-12C show the original image (left), contrast-enhanced image (middle), and ellipses fit image (right) of desirable rounded pore formation (FIG. 12B) and undesirable lamellar pore formation (FIG. 12C).
Figure 12C:
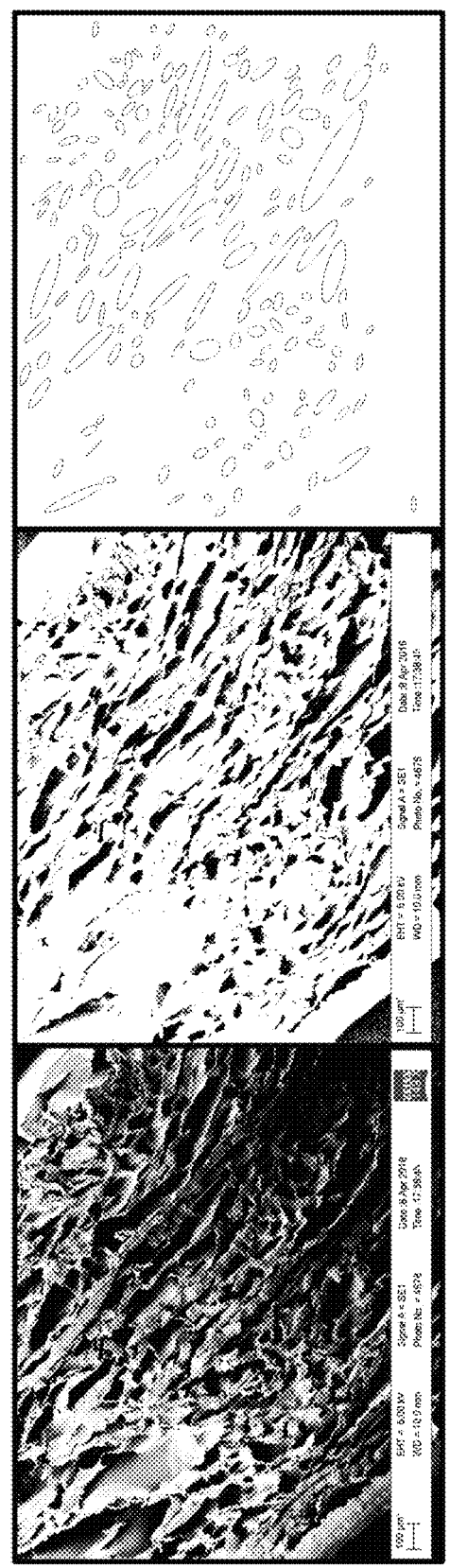
Figure 12D:
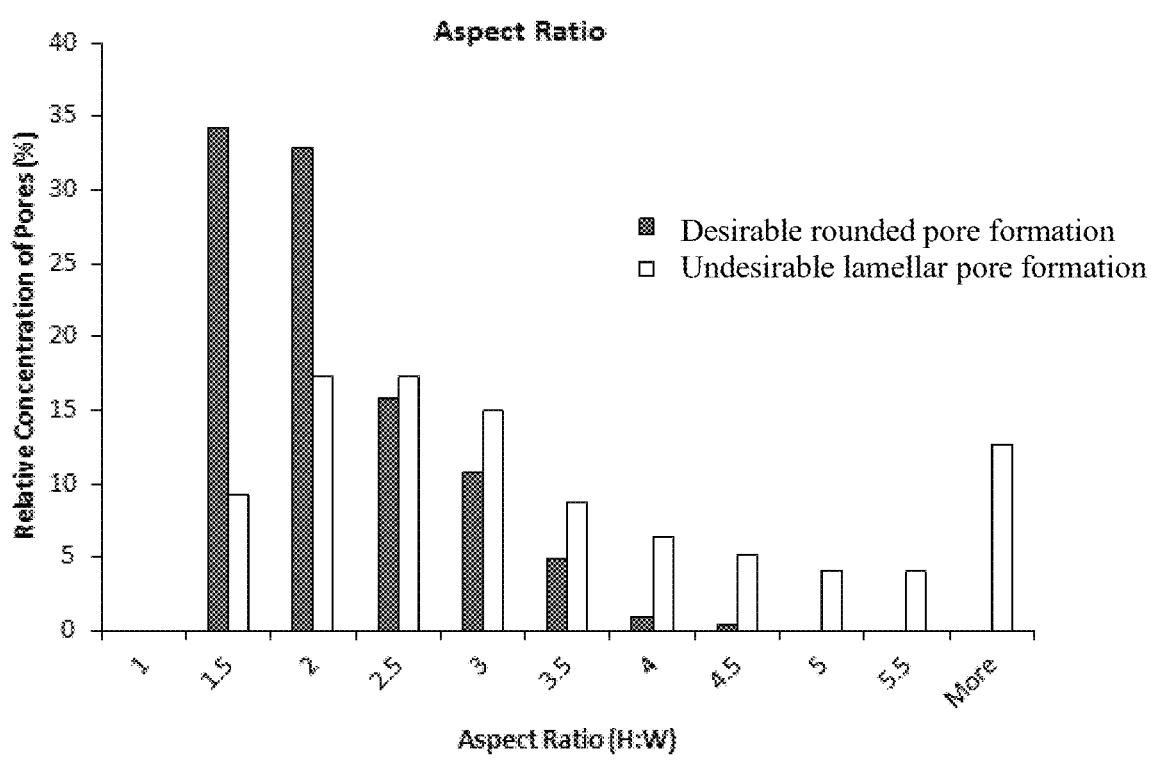
FIG. 12D is a graph showing the aspect ratio distribution of pores based on the cross-section of the silk fibroin sponge with pores of rounded morphology (desirable) or lamellar morphology (undesirable).

The pore shape can be characterized, for example, using an aspect ratio of pores and/or a circularity value for pores. The aspect ratio (AR) of pores (AR=length (L)/width (W)), as shown in FIG. 12A, was determined using image analysis software. An AR value of 1 indicates a perfect circular cross-section. In some embodiments, the silk fibroin sponges have AR values near 1. FIGS. 12B-12C show the original image (left), contrast-enhanced image (middle), and ellipses fit image (right) of desirable rounded pore formation (FIG. 12B) and undesirable lamellar pore formation (FIG. 12C). FIG. 12D is a graph showing the aspect ratio distribution of pores based on the cross-section of the silk fibroin sponge with pores of rounded morphology (desirable) or lamellar morphology (undesirable). Silk fibroin sponges with desirable pore formation have pore aspect ratios where: approximately 20% or more of the pores have AR≤1.5; approximately 40% or more have AR≤2.0, and approximately 10% or less have AR≥4.0. With respect to the aspect ratio, rounded pores can have values near 1.5, while lamellar pores may have values in excess of 5.0.

Figure 13D:
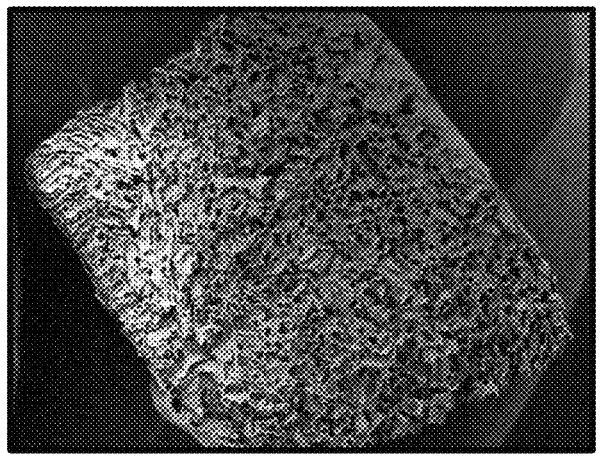
Figure 13E:
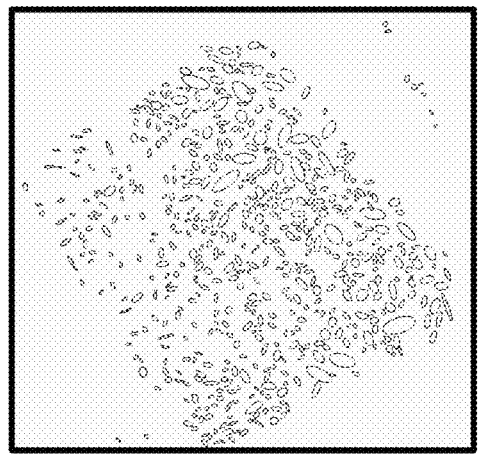
Figure 13F:
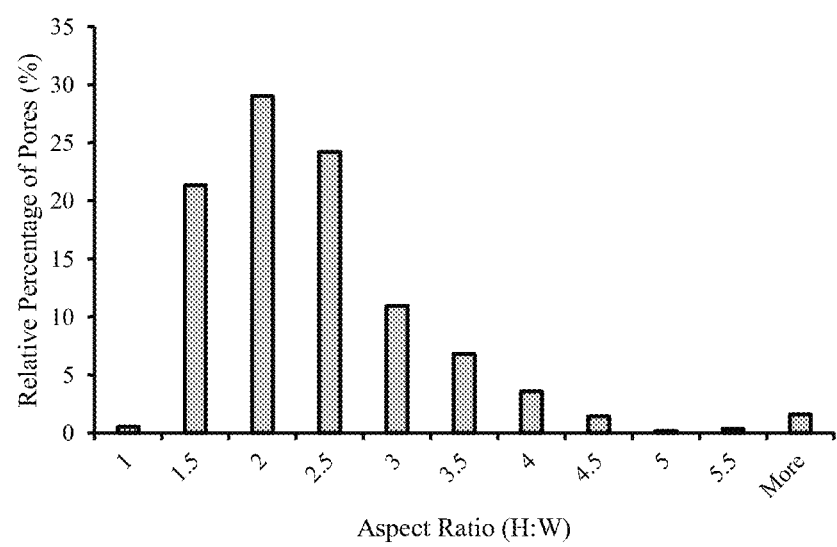

FIGS. 13A-13F show additional experimental data showing aspect ratios of pores present in the silk fibroin sponge produced by the method described in the International Patent Publication No. WO 2016/145281. The aspect ratios were determined from SEM images of cross sections of silk fibroin sponges as described above. FIGS. 13A and 13D are SEM images of cross-sections of the silk fibroin sponges. FIGS. 13B and 13E show the outline of the pores by ellipses fit. FIGS. 13C and 13F are distribution graphs showing aspect ratios of the pores.

Figure 14A:
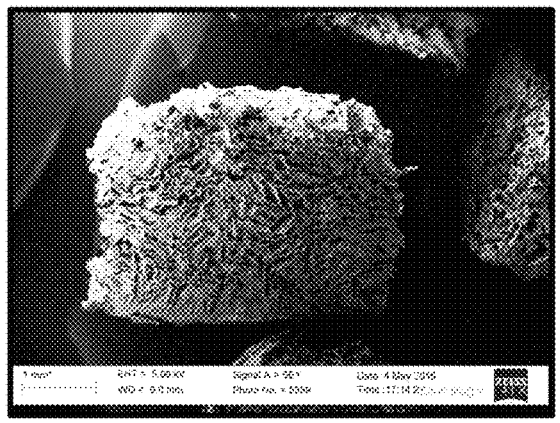
FIGS. 14A-14F show additional experimental data showing aspect ratios of pores present in the silk fibroin material produced by the method described in the International Patent Publication No. WO 2013/071123. The aspect ratios were determined from SEM images of cross sections of silk fibroin materials.
Figure 14B:
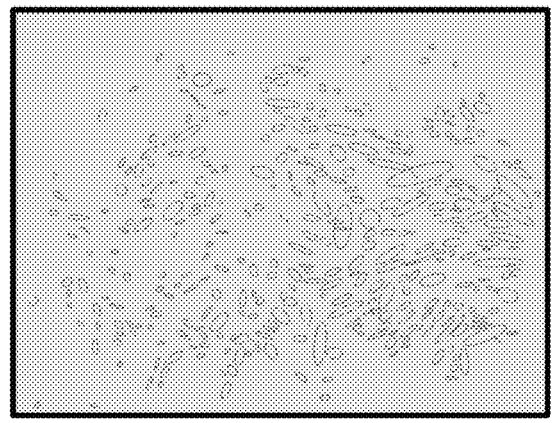
Figure 14C:
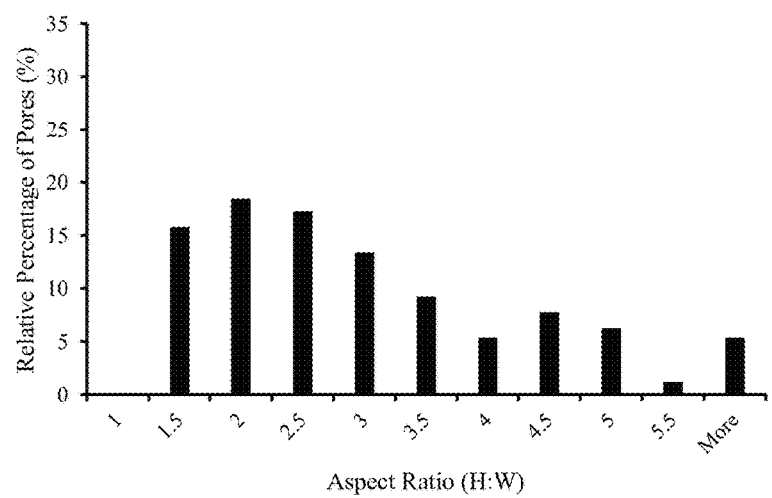
Figure 14D:
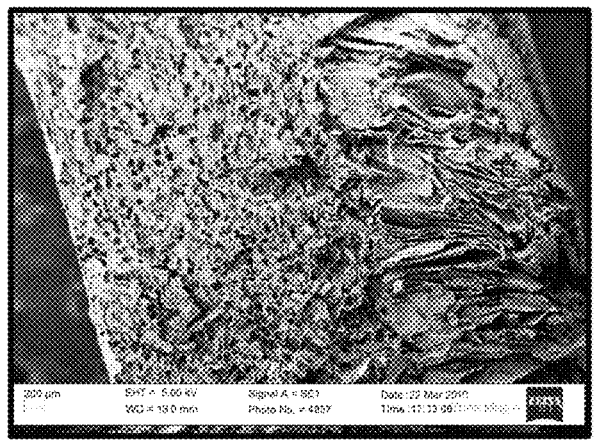
Figure 14E:
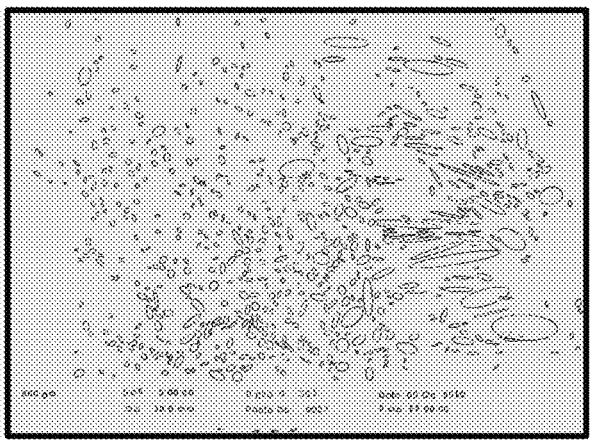
Figure 14F:
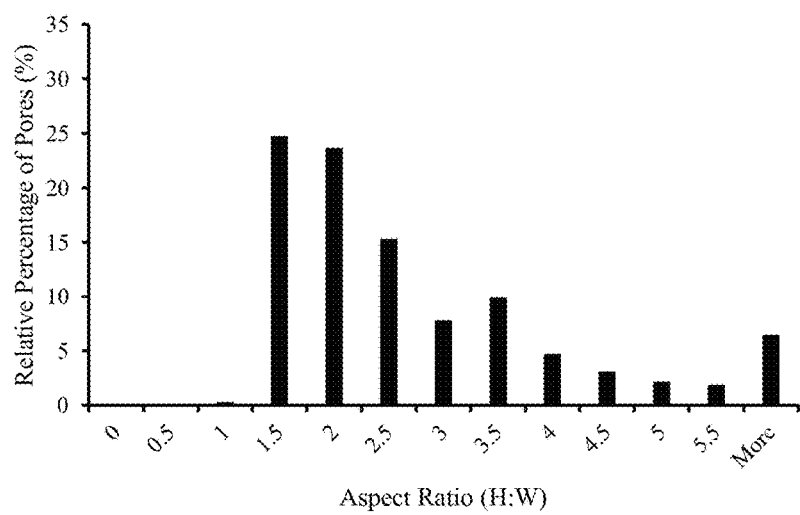

FIGS. 14A-14F show additional experimental data showing aspect ratios of pores present in the silk fibroin material produced by the method described in the International Patent Publication No. WO 2013/071123. The aspect ratios were determined from SEM images of cross sections of silk fibroin materials as described above. FIGS. 14A and 14D are SEM images of cross-sections of the silk fibroin sponges. FIGS. 14B and 14E show the outline of the pores by ellipses fit. FIGS. 14C and 14F are distribution graphs showing aspect ratios of the pores.

Figure 52:
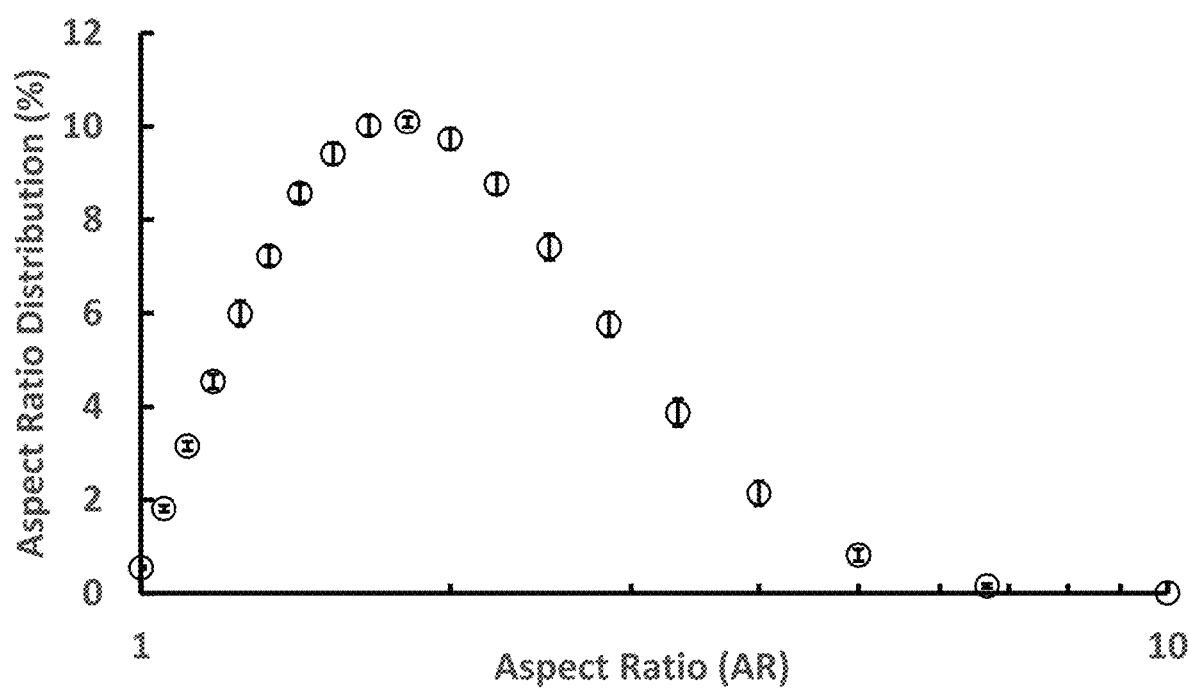
FIG. 52 is the pore aspect ratio distribution of silk fibroin particles according to one set of embodiments described herein, as determined by scanning electron microscopy and image analysis. The pore shape is characterized by an aspect ratio, which is a ratio of pore major axis to pore minor axis.

FIG. 52 shows experimental data showing aspect ratio distribution of pores present in a freeze-dried silk fibroin material produced by one set of embodiments of the methods described herein. The aspect ratios were determined from SEM images of cross sections of silk fibroin materials as described above. FIG. 50B shows a representative SEM image of a cross-section of the silk fibroin sponges. As shown in FIG. 52, the average aspect ratio of pores within a silk fibroin sponge according to one set of the embodiments described herein is about 1.90±~0.08. In some embodiments, at least about 15% of pores have an aspect ratio between about 1 and about 1.33. In some embodiments, at least about 40% of pores have an aspect ratio between about 1.33 and about 2. In some embodiments, at least about 60% of pores have an aspect ratio between about 1 and about 2. In some embodiments, at least about 95% of pores have an aspect ratio between about 1 and about 4.

Figure 53:
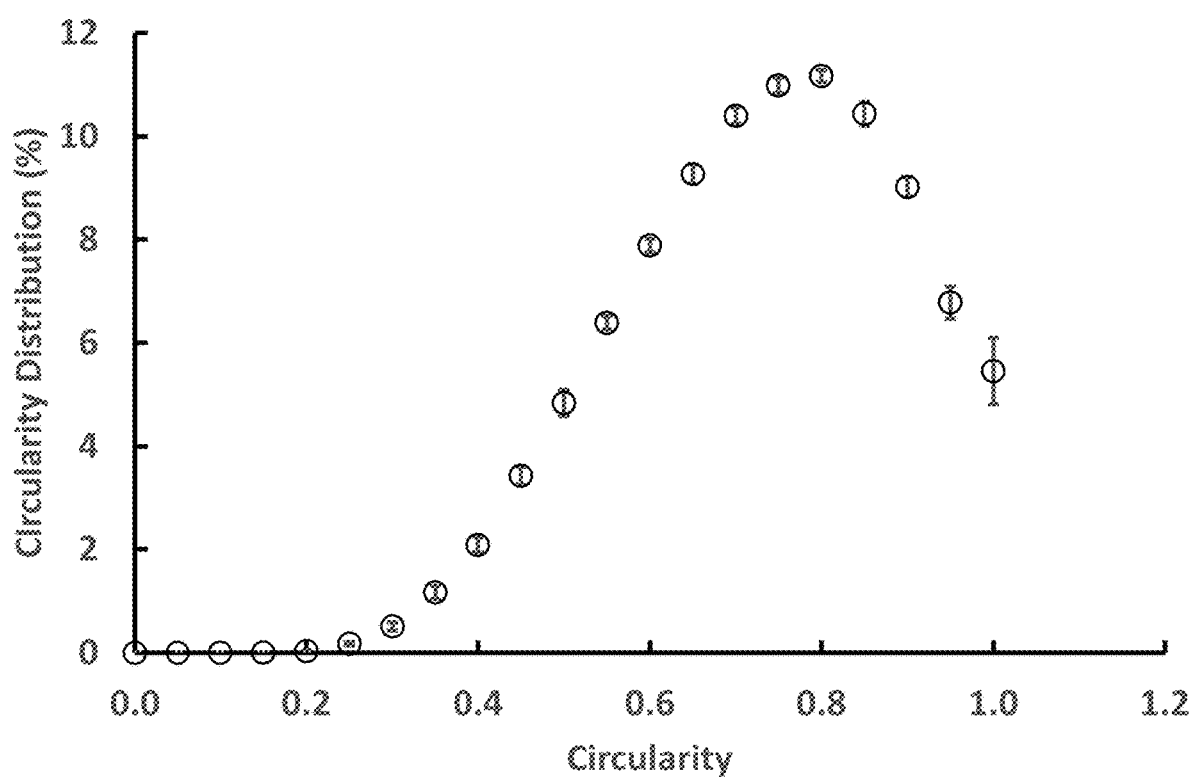
FIG. 53 is the pore circularity distribution of silk fibroin particles according to one set of embodiments described herein, as determined by scanning electron microscopy and image analysis. The pore shape is characterized by a circularity value, which is determined as: $(4\pi A_{pore}/P_{pore}^2)$, where $A_{pore}$ is the average cross-section area of the pores and $P_{pore}$ is the average perimeter forming the boundary of the cross-section area of the pores.

FIG. 53 shows experimental data showing circularity distribution of pores present in a freeze-dried silk fibroin material produced by one set of embodiments of the methods described herein. The circularity were determined from SEM images of cross sections of silk fibroin materials as described above, wherein the circularity is determined as: $(4\pi A_{pore}/P_{pore}^2)$, where $A_{pore}$ is the average cross-section area of the pores and $P_{pore}$ is the average perimeter forming the boundary of the cross-section area of pores. The circularity value has a scale of 0 to 1, where a value of 1 refers to a perfectly round circle, while a value toward 0 trends toward either increasing perimeter (e.g. circumference) or decreasing area. FIG. 50B shows a representative SEM image of a cross-section of the silk fibroin sponges. As shown in FIG. 53, the average circularity of pores within a silk fibroin sponge according to one set of the embodiments described herein is about 0.672±~0.026. In some embodiments, at least about 40% of pores have a circularity value between about 0.75 and about 1.00. In some embodiments, at least about 40% of pores have a circularity value between about 0.50 and about 0.75. In some embodiments, at least about 85% of pores have a circularity value between about 0.50 and about 1.00. In some embodiments, at least about 99% of pores have a circularity value between about 0.25 and about 1.00.

Figure 10:
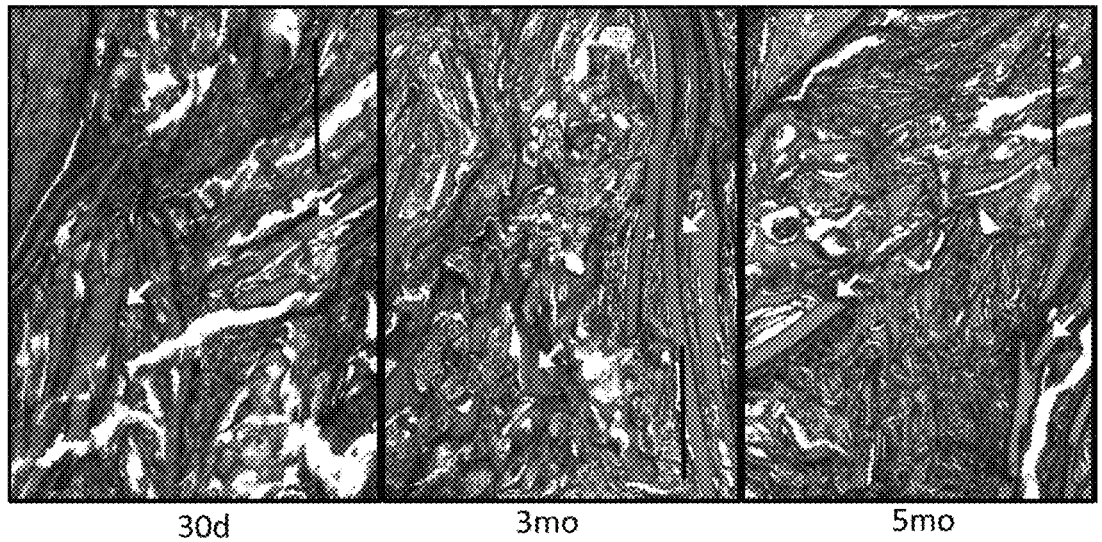
FIG. 10 shows histological analysis of silk fibroin particle implants after 12 month subcutaneous implantation in rats. Silk fibroin particles allowed infiltration of surrounding macrophages into the porous structure. Minimal immune response was detected throughout 12 months. Scale bar=250 μm. Arrows indicate silk fibroin particles.
Figure 10:
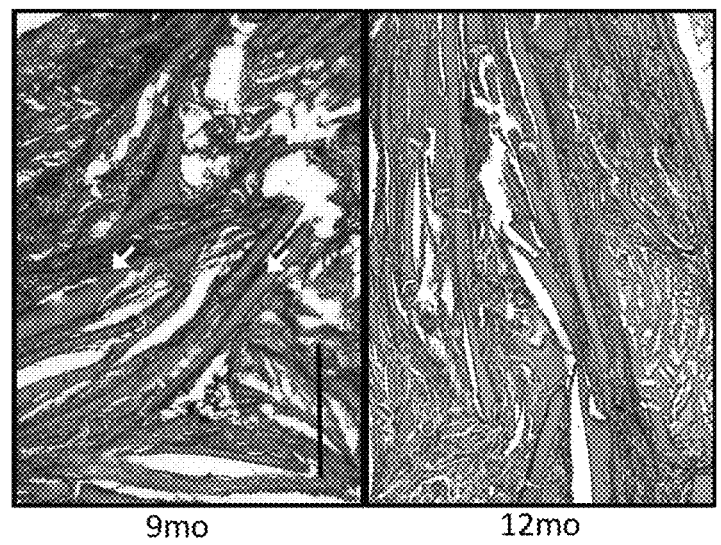
Figure 11:
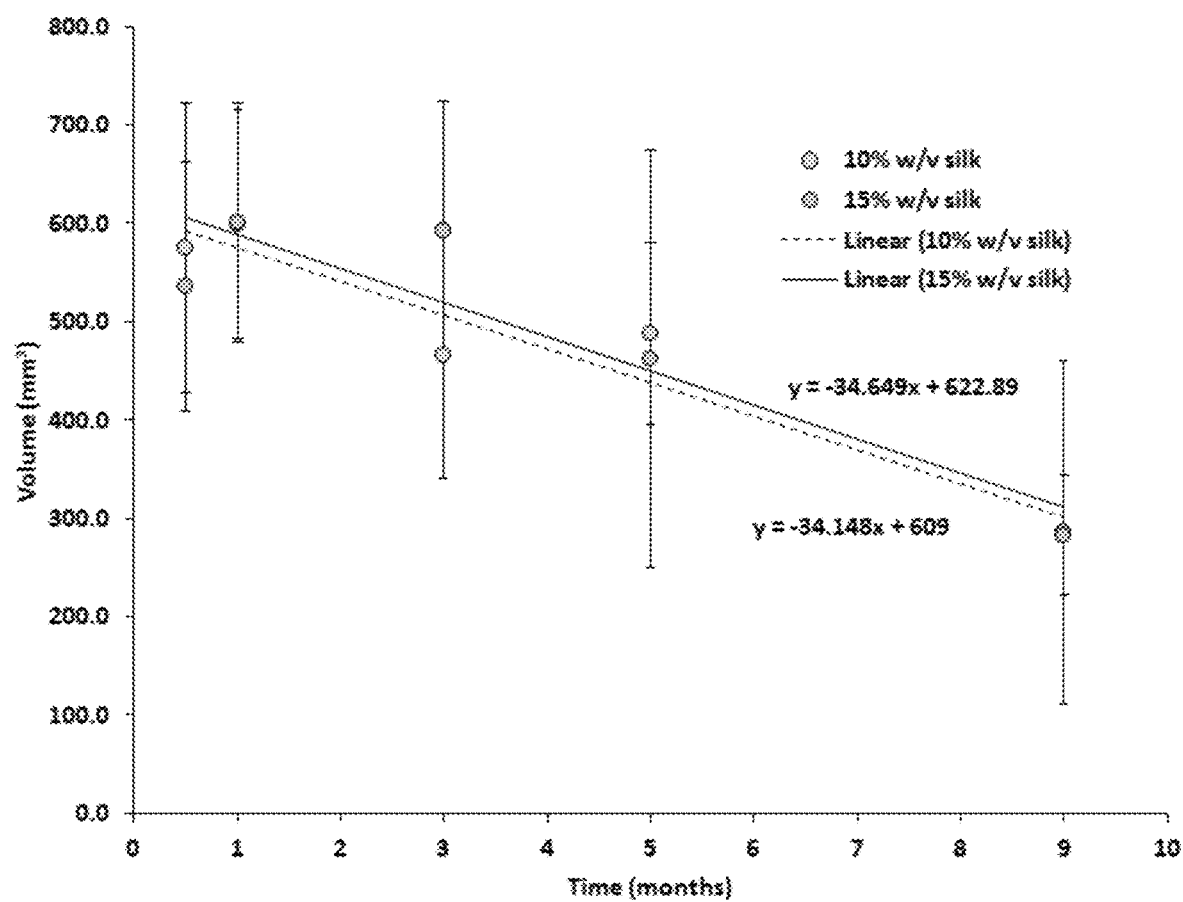
FIG. 11 is a graph showing in vivo degradation rate of silk fibroin particles alone according to some embodiments described herein upon implantation into animals as described in FIG. 10. The in vivo degradation rate was measured as a change in initial implant volume over time.

Example 9: Determination of In Vivo Immune Response and Degradation Rate of Compositions Comprising Silk Fibroin Particles According to Some Embodiments Described Herein Silk fibroin particles produced from 10% w/v or 15% w/v silk fibroin solution were implanted subcutaneously at an initial implant volume of 500 µL into rats for 12 months. Silk fibroin particles allow infiltration of surrounding macrophages into the porous structure. Minimal immune response (low immunogenicity), high cellular infiltration, and volume persistence for the silk particles alone were detected throughout 12 months as shown in FIG. 10. FIG. 11 is a graph showing in vivo degradation rate of silk fibroin particles alone upon implantation into animals. The in vivo degradation rate was measured as a change in initial implant volume over time. Approximately 50% of the implant volume remained 9 months after in vivo implantation. Extrapolation of the residence time by linear fit models was 18 months.

Example 10: Compressive Mechanical Analysis of Silk Fibroin Materials

Figure 15A:
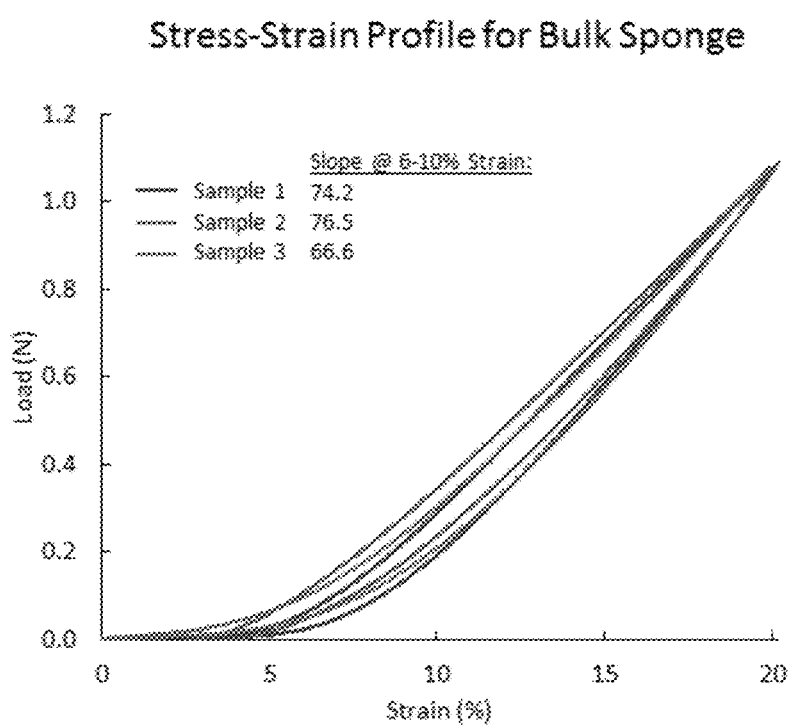
FIGS. 15A-15C show compressive mechanical analysis of silk fibroin materials according to some embodiments described herein. In some embodiments, silk fibroin particles are produced from silk fibroin sponges. The silk fibroin sponges were produced from the method described in the International Patent Publication No. WO 2016/145281.
Figure 15B:
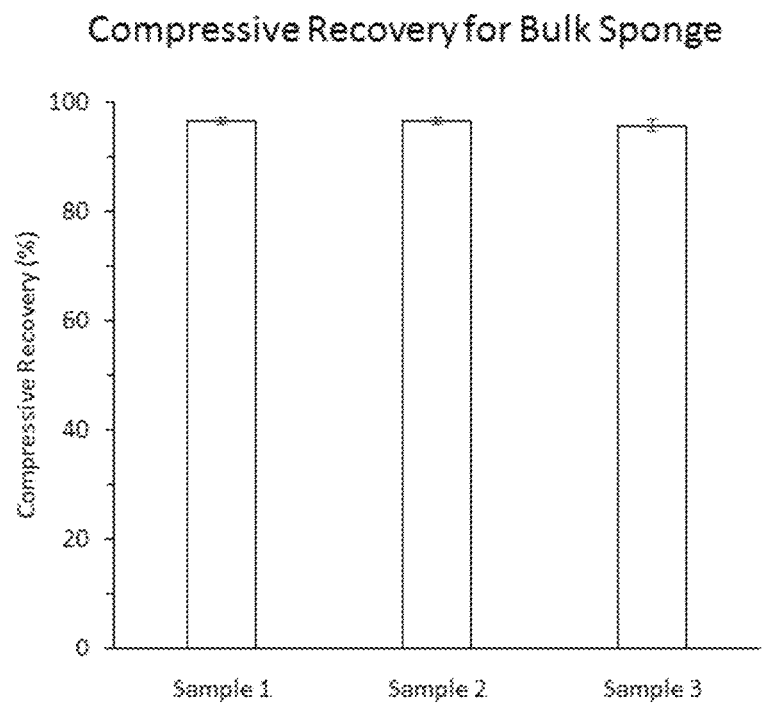

The silk fibroin sponges were produced from the method described in the International Patent Publication No. WO 2016/145281. FIG. 15A show stress-strain profile of the silk fibroin sponges in hydrated state. The elastic modulus (at 6-10% axial strain) of the silk fibroin sponges was found to be 72.4±5.2 kPa. FIG. 15B show compressive recovery for the silk fibroin sponges in hydrated state. The silk fibroin sponges have a high recovery from at least 20% compressive strain (e.g., >90% recovery to original shape/size after compression). Compressive recovery is, for example, determined by comparing the height (e.g., largest cross-sectional dimension) of the sponge samples after compression vs. the height of the sponge sample before compression. Since the sponges are highly elastic, they nearly recover to their original size after compression.

Figure 15C:
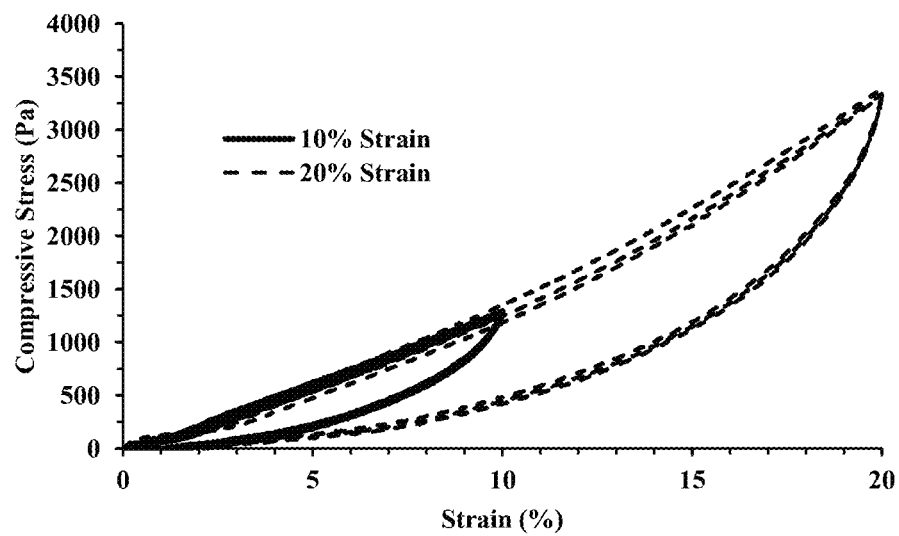

FIG. 15C shows cyclic uniaxial compression of a population of silk fibroin particles (approximately 0.1 mL) measured under confined compression conditions. The silk fibroin particles were loaded into a syringe, and the bottom of the syringe was submerged in 1×PBS so that the particles were hydrated during compression testing. The syringe plunger (with the rubber removed to reduced friction) was replaced, and the force transducer measured uniaxial force applied to the top of the plunger. Cyclic load/unload testing at 10% and 20% strains was performed at a rate of 1 mm/min. Compressed particle population recovered 91.2% of its original volume when compressed to 20% uniaxial strain (in other words, exhibited greater than 90% recovery from 20% compression) and had a tangent modulus (compressive modulus) of 12.2 kPa when measured at 6% uniaxial strain, which is close to the native modulus of typical soft tissues (which falls in the range of 1-10 kPa).

The compressive mechanics of the silk fibroin particles (FIG. 15C) appear to be softer when compared to the bulk sponges (FIGS. 15A-15B). The porous architecture of the bulk sponge may lend some mechanical integrity that might not be present once the bulk sponge was broken down into discrete units—silk fibroin particles.

Example 11: Air Extrusion Force of Exemplary Compositions Comprising Silk Fibroin Particles and Crosslinked Hyaluronic Acid (HA) as a Carrier Crosslinked HA was used in the HA/silk particle formulations in this Example. HA having a molecular weight of about 750 kDa to about 1000 kDa, with a weight average molecular weight of about 823 kDa, was diluted and subject to a crosslinking reaction as follows: First, 1.5 g Hyaluronic acid (Lifecore, 750-1000 kDa) was swelled in 0.25 M Sodium Hydroxide (10.725 mL, NaOH) for two hours. Next, 771 μL of a 220 mg/mL 1,4-butanediol diglycidyl ether (BDDE) solution (suspended in 0.25 M NaOH) was added to the hyaluronic acid and allowed to crosslink for two hours at 50° C. Afterwards, the HA was removed and 30 mL phosphate buffered saline was added to quench the reaction. The crosslinked HA prepared at a concentration of 3% w/v was then mixed with silk particles (e.g., having a volume mean diameter of 425-500 microns) in a volume ratio of 60% (HA):40% (silk fibroin particles).

Extrusion forces of the compositions were measured as described in Example 3. FIGS. 16A-16B is a set of graphs showing extrusion force data using a 1 mL syringe (21 gauge needle) for compositions comprising a crosslinked HA carrier, alone or in combination with silk fibroin particles, according to one set of embodiments described herein. The silk fibroin particles were sieved to select particles of about 355 to about 425 microns in diameter, and were about 40% v/v when mixed with 60% v/v crosslinked HA gel. The crosslinked HA gel was prepared with a crosslinking agent (CA), e.g., BDDE, and hyaluronic acid disaccharides (HAD) in a CA:HAD mole ratio of about 22%. Extrusions were performed at rate of 1 mL/10 seconds or 5.5 mm/s.

Figure 17A:
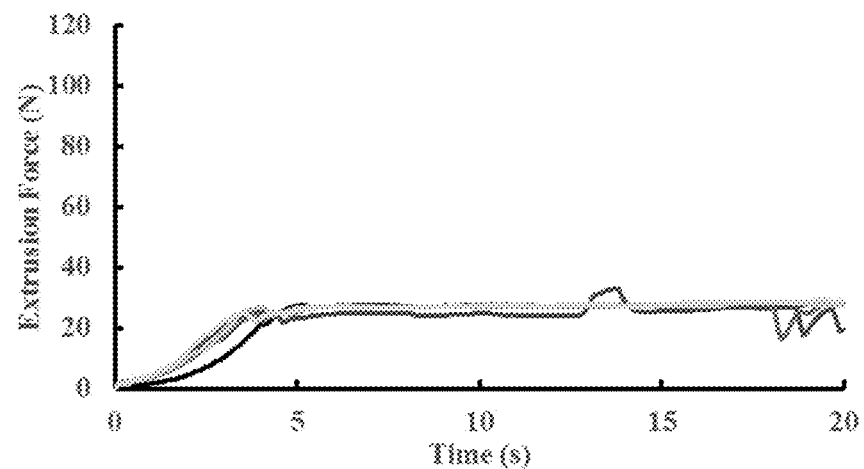
FIGS. 17A-17B is a set of graphs showing extrusion force data using a 3 mL syringe appended to a 18 gauge tulip cannula for compositions comprising a crosslinked HA carrier in combination with silk fibroin particles, according to some embodiments described herein. The silk fibroin particles were about 425 to about 500 microns in diameter, and were about 40% v/v when mixed with crosslinked HA gel.
Figure 17B:
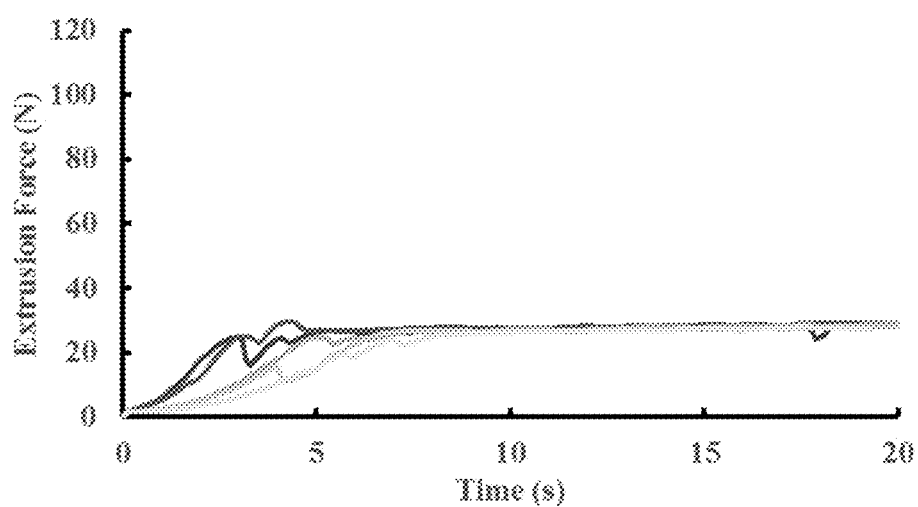

FIGS. 17A-17B is a set of graphs showing extrusion force data using a 3 mL syringe appended to a 18 gauge tulip cannula for compositions comprising a crosslinked HA carrier in combination with silk fibroin particles, according to some embodiments described herein. The silk fibroin particles were sieved to select particles of about 425 to about 500 microns in diameter, and were about 40% v/v when mixed with 60% v/v crosslinked HA gel (e.g., at about 2-3% w/v). The crosslinked HA was prepared with a crosslinking agent (CA), e.g., BDDE, and hyaluronic acid disaccharides (HAD) in a CA:HAD mole ratio of about 22% (FIG. 17A) or 30% (FIG. 17B).

Figure 18:
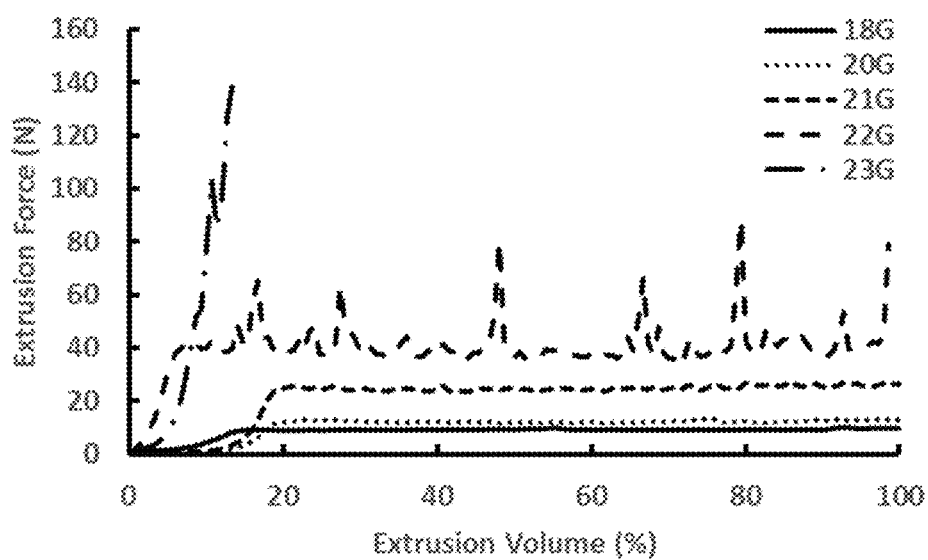
FIG. 18 is a graph showing extrusion force data using 1 mL syringe with different gauge needle sizes for compositions comprising a crosslinked HA and silk fibroin particles according to one set of embodiments described herein. The silk fibroin particles were about 355 to about 425 microns in diameter, and were about 40% v/v when mixed with crosslinked HA gel.

FIG. 18 shows the effect of needle gauge size on extrusion force of silk fibroin particle/crosslinked HA gel composition through 1 mL syringe. The composition comprises 40% v/v silk fibroin particles and 60% v/v crosslinked HA. The silk fibroin particles were sieved to select particles between 355-425 microns in diameter. The crosslinked HA (e.g., at about 2-3% w/v) was prepared with a crosslinking agent (CA), e.g., BDDE, and hyaluronic acid disaccharides (HAD) in a CA:HAD mole ratio of about 22%. Extrusions of the silk fibroin particle/crosslinked HA gel composition occurred at a rate of 1 mL/15 seconds or 3.6 mm/s. The silk fibroin particle/crosslinked HA gel composition extrudes smoothly up to 21G needle sizes. Extrusions are noisy using 22 gauge needles and the needle is clogged while attempting to extrude the silk fibroin particle/crosslinked HA gel through 23 gauge needles.

Figure 19:
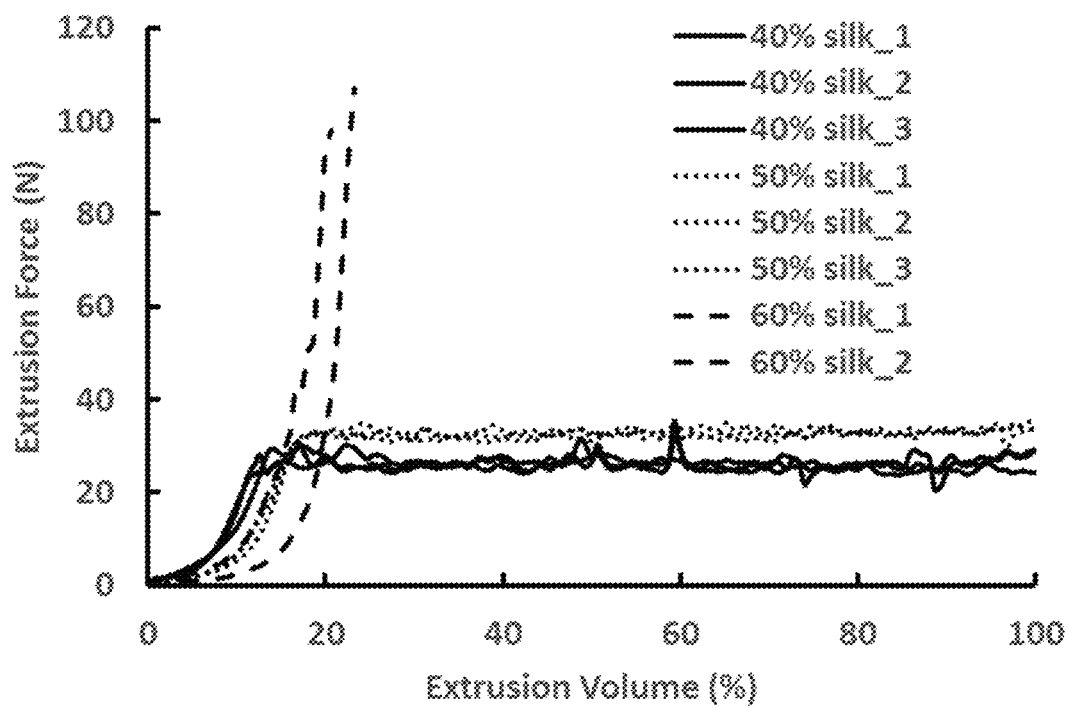
FIG. 19 is a graph showing extrusion force data using 1 mL syringe with a 21 gauge needle for compositions comprising a crosslinked HA and silk fibroin particles in varying amounts according to some embodiments described herein. The silk fibroin particles were about 355 to about 425 microns in diameter, and were mixed with crosslinked HA gel in varying amounts from about 40% v/v to about 60% v/v silk fibroin particles.

FIG. 19 shows the effect of varying volume ratios of silk fibroin particle and crosslinked HA in formulation on extrusions through 21 gauge needles. The silk fibroin particles were sieved to select particles between 355-425 microns in diameter. The crosslinked HA (e.g., at about 2-3% w/v) was prepared with a crosslinking agent (CA), e.g., BDDE, and hyaluronic acid disaccharides (HAD) in a CA:HAD mole ratio of about 22%. Extrusions of the silk fibroin particle/ crosslinked HA composition occurred at a rate of 1 mL/15 seconds or 3.6 mm/s. As shown in FIG. 19, extrusions of the compositions comprising 40% or 50% v/v silk fibroin particles are smooth but at higher silk fibroin particle concentrations, clogging sometimes occurs.

Example 12: Mechanical Analysis of Compositions Comprising Silk Fibroin Particles and Crosslinked HA According to One Set of Embodiments Described Herein FIGS. 20A-20D is a set of graphs showing rheometry data describing the shear properties for compositions comprising a crosslinked HA carrier in combination with silk fibroin particles according to one set of embodiments described herein. The silk fibroin particles were about 355 to about 425 microns in size, and 40% v/v silk fibroin particles were mixed with crosslinked HA gel. Dynamic rotational shear rheometry was used to assess the mechanical features of crosslinked HA carrier alone and silk fibroin particle/crosslinked HA compositions. The storage modulus (G'), loss modulus (G"), complex modulus (G*) and dynamic viscosity were measured as a function of oscillatory strain and frequency sweeps. Strain sweeps were performed from 0-200% at a frequency of 1Hz, and frequency sweeps were performed from 0.1-10 Hz at a shear strain of 1%. Testing was performed on a Discovery HR-3 (TA Instruments, New Castle, Del.) using a 40 mm diameter parallel plate attachment. For silk fibroin particle/crosslinked HA compositions, the nominal gap width used was 400 µm to accommodate the size of the particles with a sample volume of 500 µL.

Oscillatory frequency sweeps from 0.1-10 Hz of FIG. 20A show that both crosslinked HA alone and silk fibroin particle/crosslinked HA composition behave elastically over the tested range. Both crosslinked HA alone and silk fibroin particle/crosslinked HA composition respond to shear stress nearly independent of frequency, maintaining a predominantly elastic behavior with minimal change in tangent modulus.

Dynamic viscosity measurements of FIG. 20B reveal that both crosslinked HA alone and silk fibroin particle/crosslinked HA composition demonstrate shear thinning behavior with increasing frequency. This property is highly relevant for ease-of-injection, where shear thinning helps to reduce extrusion forces when injecting through small gauge needles.

Oscillatory strain ramps of FIG. 20C show how crosslinked HA alone is more strain independent (therefore, resistant to strain induced yielding) out to almost 100% strain, while silk fibroin particle/crosslinked HA composition, though generally stiffer than crosslinked HA alone, exhibit strain induced yielding as reflected by reduced stiffness observed at much lower strain (yielding begins at approximately 1% strain). This behavior may account for the smoother extrusion profiles observed for silk fibroin particle/crosslinked HA composition during injection, as compared to extrusion profiles for crosslinked HA alone. As shown in Example 20C, the stiffness (G') of the composition according to one set of embodiments described herein (a) is decreased by about 25%, as measured between about 0.1% strain and about 1% strain; (b) is decreased by about 35-40%, as measured between about 0.1% strain and about 10% strain; (c) is decreased by about 75-80% as measured between about 0.1% strain and about 100% strain; or (d) is decreased by about 30-35% as measured between about 10% strain and about 90% strain. By contrast, the stiffness (G') of a corresponding crosslinked carrier alone (e.g., crosslinked HA carrier alone) is substantially constant until about 40% strain. The stiffness (G') of the crosslinked carrier alone (e.g., crosslinked HA carrier alone) is decreased by only about 10-15%, as measured between about 0.1% strain and about 100% strain.

FIG. 20D compares the elasticity of the silk fibroin particle/crosslinked HA compositions and crosslinked HA alone. Elasticity is a measure of how well a material returns to its original shape after physical deformation and is calculated from the following equation at frequencies of 1 and 10 Hz: Elasticity=100×[G'/(G'+G")]. As shown in FIG. 20D, both crosslinked HA alone and silk fibroin particle/crosslinked HA composition offer favorable elasticity, with crosslinked HA alone (darker bars) slightly greater than silk fibroin particle/crosslinked HA composition (lighter bars).

Example 13: Determination of Final Crosslink Density in a Crosslinked HA Gel

Figure 21:
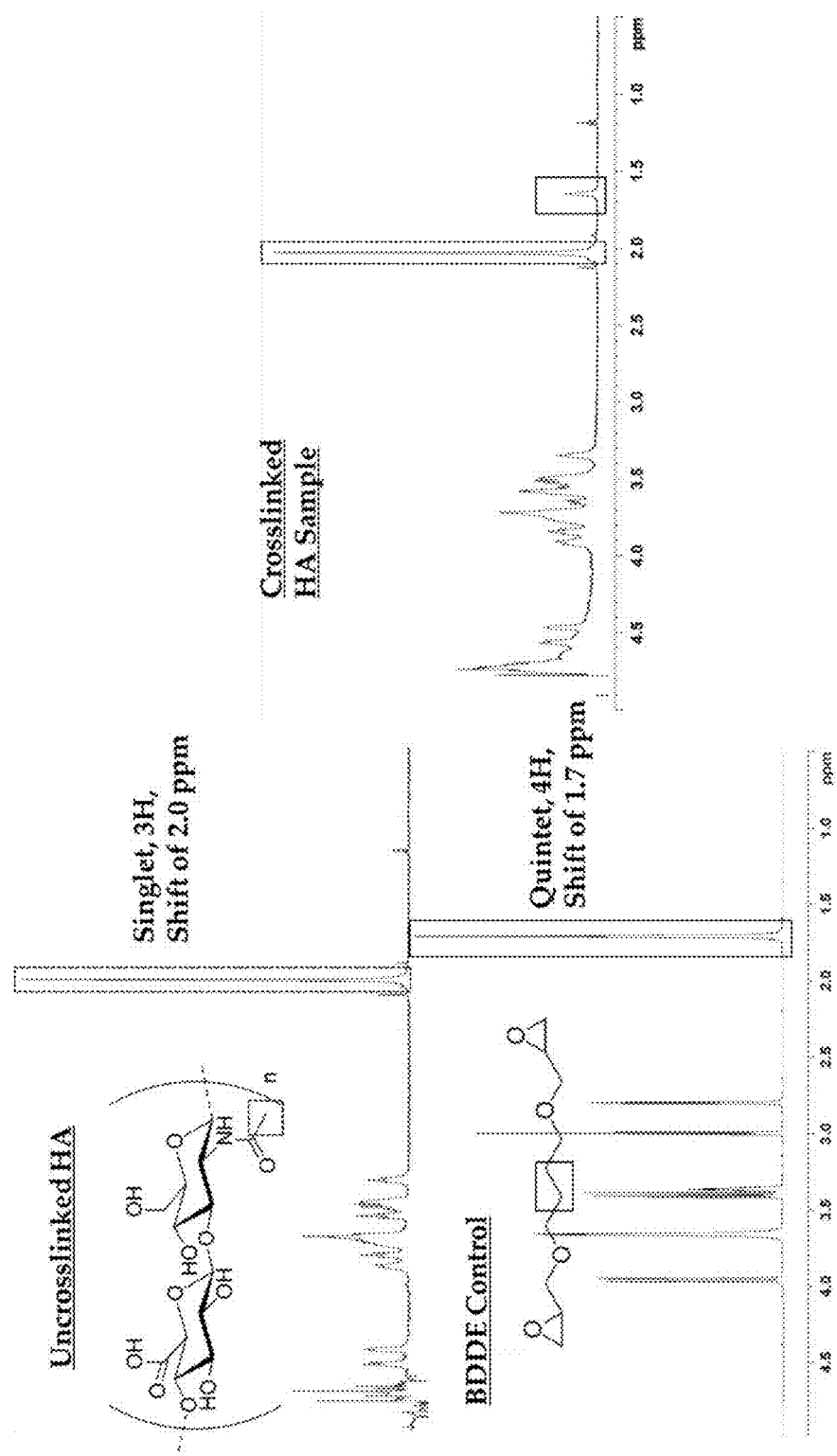
FIG. 21 is an illustration of an exemplary method to determine crosslink density in a crosslinked HA gel. Protocol adapted from: Kenne et al. Carbohydrate Polymers (2013) 91: 410-418.

FIG. 21 is an illustration of an exemplary method to determine crosslink density in a crosslinked HA gel. Protocol adapted from: Kenne et al. Carbohydrate Polymers (2013) 91: 410-418. The top left spectrum corresponds to uncrosslinked HA. The dotted line box corresponds to the three methyl protons on HA and possesses a peak at ~2.0 ppm. The bottom left spectrum corresponds to unreacted BDDE and possesses a unique peak at 1.7 ppm, which corresponds to the four methylene protons highlighted in the solid box. Crosslinked HA on the right of the figure possesses both peaks. When BDDE reacts with HA, it is reactive with the —OH groups on the HA, so the peaks at 2.0 ppm in HA is always present, whether BDDE reacts with HA or not.

An exemplary protocol is described as follows: Digested 1 mL crosslinked hyaluronic acid in 1 mL of a 1 mg/mL hyaluronidase solution suspended in PBS overnight at 37° C. Upon digestion, 100 µLs of the digested HA is added to 600 µLs of deuterium oxide (D2O). Proton nuclear magnetic resonance (1H NMR) experiments are performed to determine crosslink density of a crosslinked HA. The crosslink density of a crosslinked HA is calculated as a ratio of the BDDE peak (1H NMR) to HA peak (1H NMR) multiplied by ¾ (i.e.,)

$$\text{Crosslink density} = \frac{\text{integration } BDDE \text{ peak}}{\text{integration } HA \text{ peak}} \times \frac{3 \ HA \text{ protons}}{4 \ BDDE \text{ protons}}$$

The crosslink density is reflective of the number of BDDE molecules in the crosslinked HA divided by number of disaccharide repeats times 100%.

Using the protocol as described above, it was determined that the final crosslink density of a crosslinked HA (starting with 22% mol percent BDDE added for crosslinking reaction) is about 13%. The crosslinking reaction is typically about 50-75% efficient.

Example 14: Mechanical and Biological Evaluation of Injectable Silk Protein Microparticle-Based Fillers for Treatment of Glottic Insufficiency Ideal vocal fold injection augmentation materials should match native tissue viscoelasticity, afford low needle resistance during delivery, and slowly resorb over time to allow cellular in-growth without an immunogenic response. A novel injectable silk protein microparticle-based filler has been developed to meet these requirements and restore the native bulk to vocal fold tissues while also displaying durable in vivo longevity, promotion of cellular infiltration, and tissue regeneration.

The physical and mechanical properties of silk/hyaluronic acid (HA) materials were determined to characterize deformation resistance and recovery compared to commercially available Prolaryn Plus®. Porcine vocal fold tissue was used to simulate the mechanical outcomes of bulking procedures, while in vivo subcutaneous rodent implantation examined immune response and volume retention.

Data demonstrated that highly porous, elastomeric silk microparticles possess high recovery (at least 90% original volume) from compressive strain. When combined with a hyaluronic acid carrier, rotational shear modulus was in the range of soft tissues, 2-3 kPa, when measured from 0.1-10 Hz. Silk/HA only causes minimal stiffening during in situ injections into porcine vocal fold tissue, increasing complex modulus by 1.2× and 1.5× for 2-week and 7-week old animals, respectively, for injections of 300 µL. Silk particles implanted subcutaneously in a rat model support ingrowth of adjacent tissue, retain up to 30% volume after 12 months, and do not elicit a fibrotic response.

Accordingly, the physical properties of injectable silk/HA bulking materials demonstrate that such formulations can be used for vocal fold augmentation and treatment of glottic insufficiency.

Example 15: Mechanical Properties of Porcine Vocal Fold Tissue after Injection of Silk/HA Compositions This Example shows that silk/HA compositions described herein can advantageously stiffen vocal folds to only a small degree after injection therein.

Figure 42:
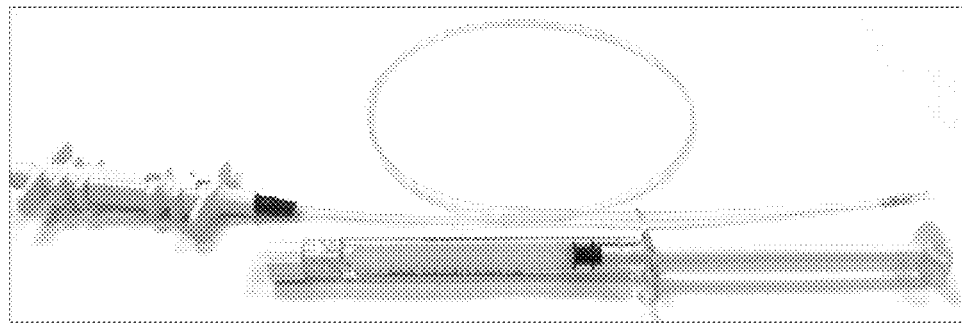
FIG. 42 is a photograph of a catheter, in accordance with certain embodiments.

250-300 µL of a silk/HA composition were directly injected into the vocal fold bulk of porcine tissues using the catheter shown in FIG. 42, which had a needle gauge of 23XX. The silk/HA composition had an average silk particle size of less than 500 microns and a concentration of particles in HA of about 20-60% v/v. The composition had an average extrusion force of <50 N through the needle of the catheter.

Vocal folds were excised and the mechanics of non-injected ("native") and injected ("bulked") tissues were assessed by dynamic rotational shear rheometry employing the following procedure. The storage modulus (G'), loss modulus (G"), complex modulus (G*) and dynamic viscosity were measured as a function of oscillatory frequency sweeps from 0.1-10 Hz at a shear strain of 1%. Testing was performed on a Discovery HR-3 rheometer (TA Instruments, New Castle, Del.) using a 40 mm diameter parallel plate attachment. For silk/HA compositions, the nominal gap width was 400 µm with a sample volume of 500 µL. Elasticity was calculated at frequencies of 1 and 10 Hz using the following equation:

$$\text{Elasticity} = 100 \cdot \frac{G'}{G' + G''}$$

Four hundred grit sand paper was used to reduce slippage. The gap distance was modulated to achieve an axial force of 40-50 grams.

Figure 36:
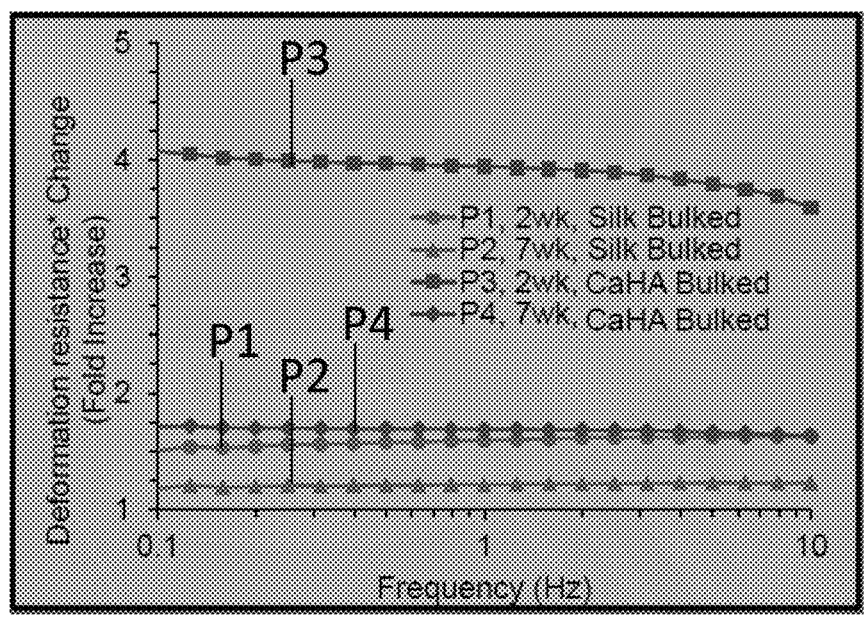
FIG. 36 is a chart showing rheology data for certain silk/HA compositions after ex vivo injection into porcine tissue.

FIG. 36 shows rheology data indicating that ex vivo injection of silk particles into 2 week old and 7 week old porcine (P) vocal fold tissue caused less stiffening of native tissue compared to calcium hydroxylapatite (CaHA)-based injectable fillers. The fold-change of bulked tissue was at most 1.5× for silk/HA and up to 4× for commercially available Prolaryn Plus®.

Figure 37:
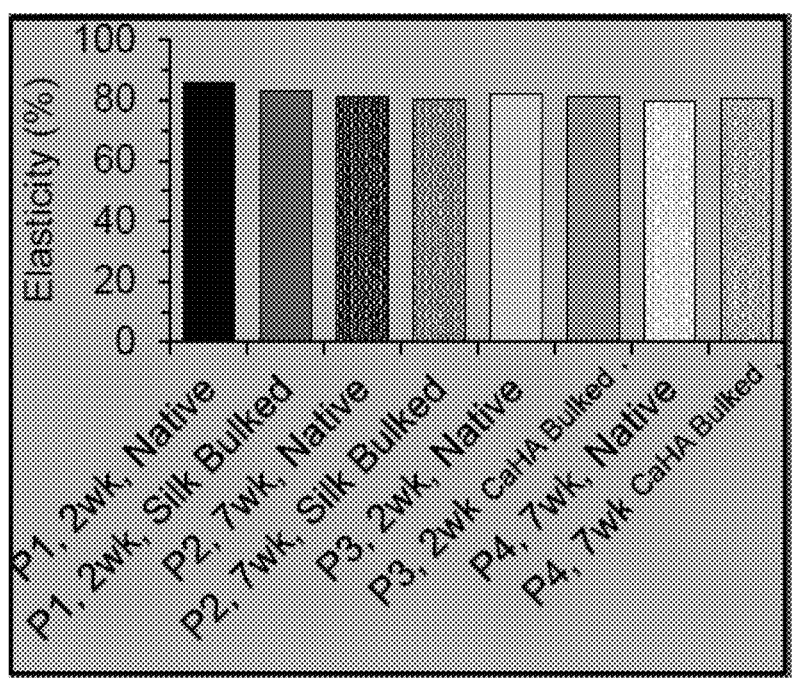
FIG. 37 is a chart showing the elasticity of certain silk/HA compositions after ex vivo injection into porcine tissue.

FIG. 37 shows elasticity data showing that the elasticity of all tissues were similar, approaching 80%, and that bulking did not greatly impact deformation recovery.

Example 16: Silk/HA Biocompatibility

This Example shows that silk/HA compositions described herein are biocompatible.

Biocompatibility of a silk/HA composition was assessed using protocols described in ISO 10993. The silk/HA composition had an average silk particle size of less than 500 microns, a concentration of particles in HA of about 20-60% v/v, and an average extrusion force of <50 N through a 23XX gauge needle of a catheter.

The genotoxicity was measured using the protocol described in ISO document 10993-5. This protocol is performed in vitro and includes the following three tests: (1) Gene mutation (AMES) assay; (2) Mouse lymphoma forward mutation; and (3) Rodent bone marrow micronucleus.

The acute systemic toxicity was measured using the protocol described in ISO document 10993-11. These studies were performed in mice to evaluate: general effects on organs and organ systems from absorption, distribution, and metabolites after single exposure; and acute effects, such as gross pathology, body weight, adverse clinical signs. A single model was chosen to evaluate all systemic toxicity. The observations were performed for 72 hours and one week.

The intracutaneous reactivity was measured using the protocol described in ISO document 10993-10. This is a test used to determine irritation using rabbit models. The composition was injected and then the appearance was noted at 24 hours, 48 hours, 72 hours, and 14 days post injection. At these time points, the edema was graded at each injection site.

Immunization/sensitization was measured using the protocol described in ISO document 10993-10. This is a guinea pig maximization test for determining the allergic/sensitizing capacity of the composition. There is a first intradermal induction phase, which is followed by 7 day and 14 day challenges with topical administration. Observations are made at 24 hours and 48 hours, at which point the redness and swelling are graded.

Table 2, below, summarizes the results from these tests.

TABLE 2

| Biocompatibility of Silk/HA compositions. | |
|---|---|
| Test/Study | Results |
| Genotoxicity | PASS-non-mutagenic |
| | PASS-no clastogenic effect |
| Acute Systemic Toxicity | PASS-no significant reaction vs. control |
| Intracutaneous Reactivity | PASS-no significant reaction vs. control |
| Acute Systemic Toxicity, Intramuscular Implant | PASS-non-reactive |
| Immunology/Sensitization | PASS-non-sensitizer |

Example 17: Silk/HA Biocompatibility Animal Studies

This Example shows that silk/HA compositions described herein are biocompatible.

Procedure: Animal procedures were carried out in full accordance with established standards set forth in the Guide for the Care and Use of Laboratory Animals, 8th edition (NIH Publication No. 85-23). Animals were sterilely housed and maintained pre- and post-operatively by the Department of Lab Animal Management (DLAM) and associated veterinarians at the Tufts University, Boston Campus. Two separate studies were conducted to evaluate a) biocompatibility of the silk/HA formulation (a formulation having an average silk particle size of less than 500 microns, a concentration of particles in HA of about 20-60% v/v, an average extrusion force of <50 N through a 23XX gauge needle) as compared to a marketed calcium hydroxylapatite—carboxymethylcellulose (CaHA/CMC) filler (Prolaryn Plus®, Merz Neurosciences, Raleigh, N.C.), and b) the degradation profile of silk particles. A subcutaneous model using rats (female, 8 weeks; Taconic Biosciences, Germantown, N.Y.) was used in both studies. Rats were anesthetized by isoflurane inhalation, 3% for inoculation and 2% for maintenance. For evaluation of biocompatibility, N=3 animals per time point received subcutaneous injections of 0.2 mL silk/HA or CaHA/CMC to each of the left and right sides in the lumbar region. 3- and 6-month time points were selected to assess the progressive host in-growth and immunological response of the injections. For evaluation of silk particle degradation, animals received four injections of 0.2 mL of the silk/HA formulation on the left and right side of the lumbar and scapular regions. A total of 15 animals received injections, with N=3 for time points of 1, 3, 5, 9, and 12 months. Animals were sacrificed by carbon dioxide asphyxiation and major organ removal as a secondary method. Samples were excised including the adjacent dermal tissue and dimensions (length, width, height) of the remaining implant were recorded. Explants were placed into tissue cassettes and immersed in 10% formalin for fixation. Tissues were taken through standard dehydration processing, and bisected prior to paraffin embedding. Tissue sections were stained using hemotoxylin and eosin (H&E) and imaged using an inverted light microscope (Axiovert CFL 40; Carl Zeiss, Germany) and Q-Capture software (Qlmaging; Surrey, BC).

Figure 38:
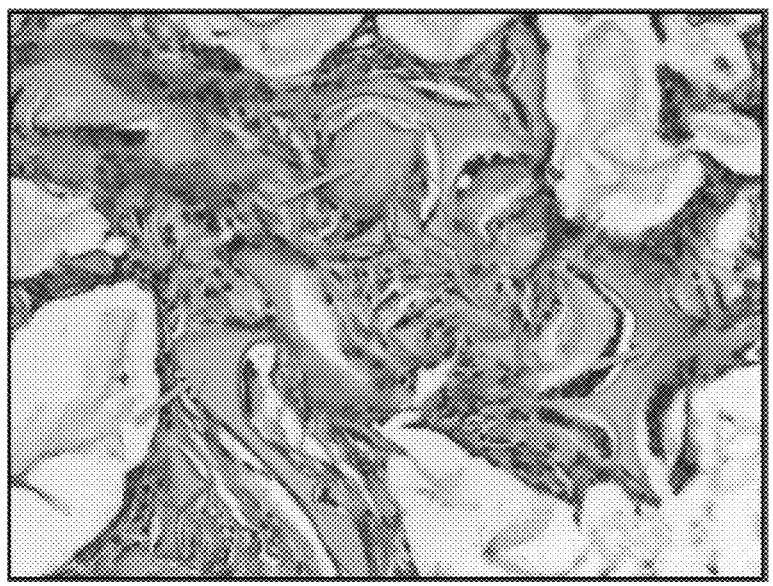
FIG. 38 is a micrograph showing a sample obtained 6 months after injection of a silk/HA material into a rat, in accordance with certain embodiments.

FIG. 38 is a micrograph showing a sample obtained at a 6 month time point for the silk/HA material. In this figure, the macrophage has infiltrated into the silk particle body. There is also giant cell formation, suggesting ongoing material breakdown. The silk has been stained; it is also pointed to by the arrows.

Figure 39:
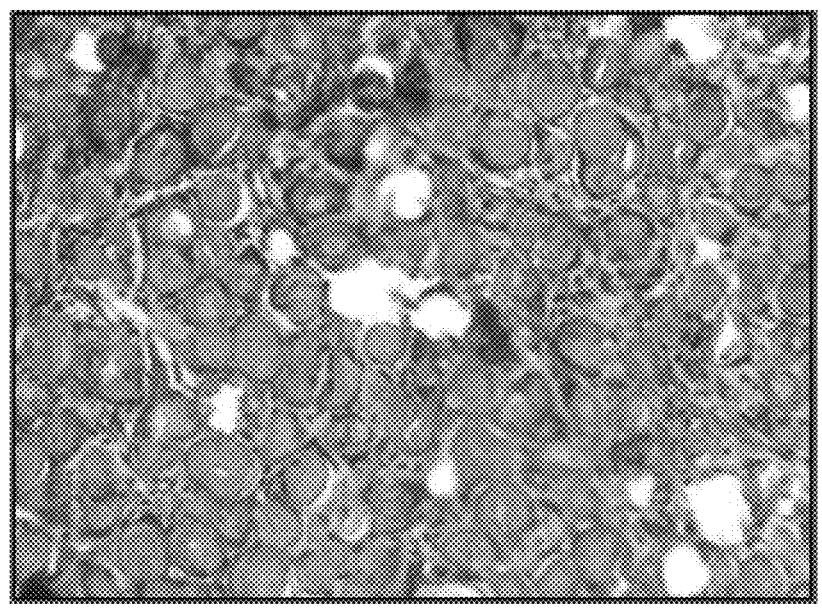
FIG. 39 is a micrograph showing a sample obtained 6 months after injection of a CaHA material into a rat, in accordance with certain embodiments.

FIG. 39 is a micrograph showing a sample obtained at a 6 month time point for the CaHA material. CaHA allowed cell migration around the particles but not throughout the particle bulk.

Figure 40A:
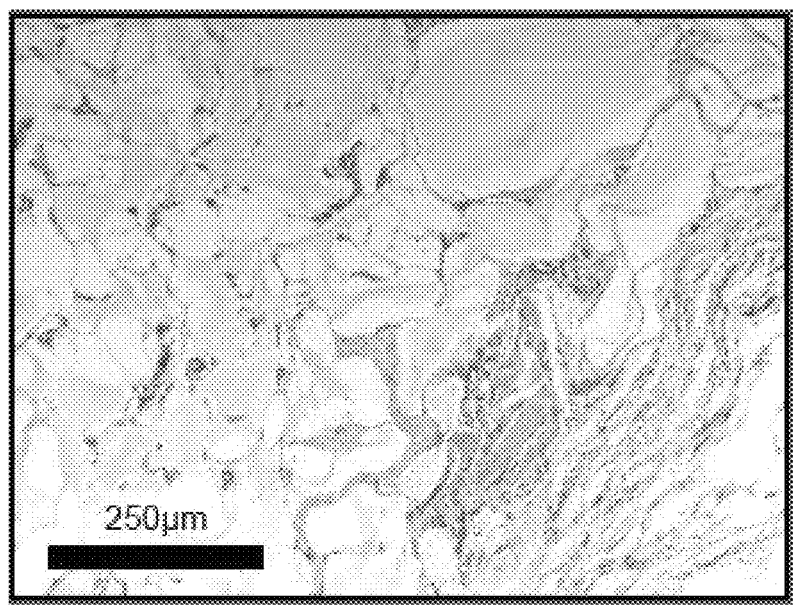
FIGS. 40A and 40B are micrographs showing samples obtained 12 months after injection of a silk/HA material into a rat, in accordance with certain embodiments.
Figure 40B:
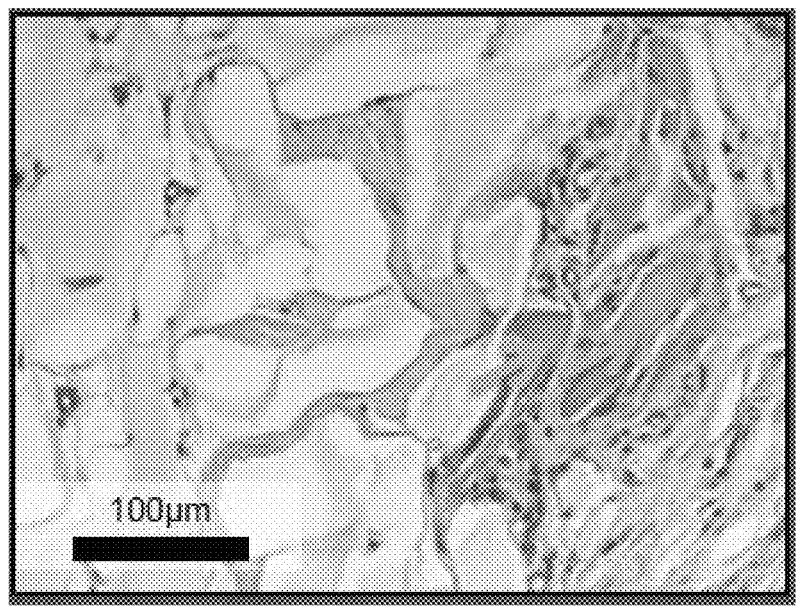

FIGS. 40A and 40B are micrographs showing samples obtained at a 12 month time point for the silk/HA material. Particles have been heavily degraded. Some volume persists. The silk has been stained; it is also pointed to by the arrows.

Figure 41A:
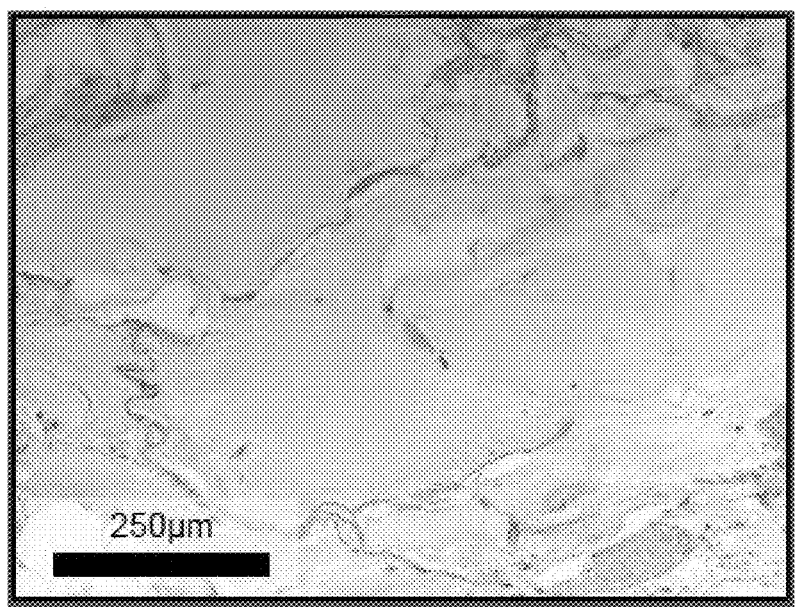
FIGS. 41A and 41B are micrographs showing samples obtained 12 months after injection of HA into a rat, in accordance with certain embodiments.
Figure 41B:
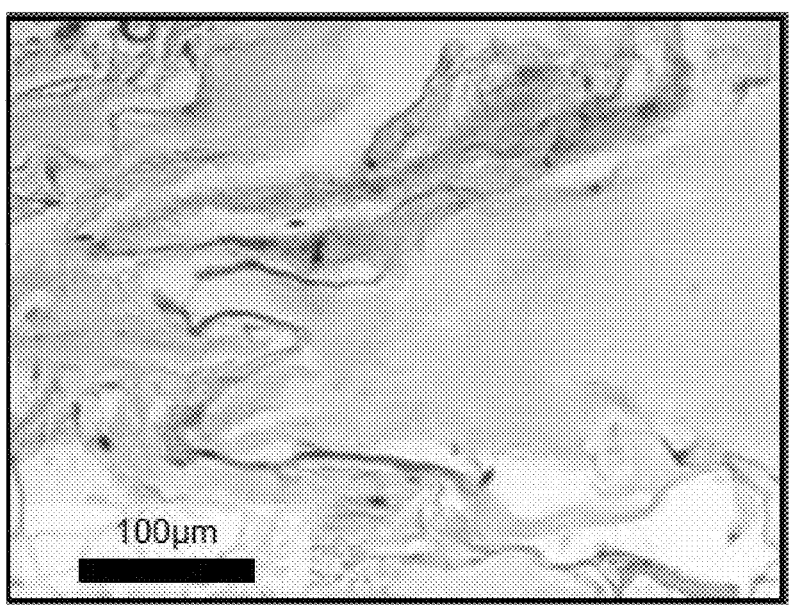

FIGS. 41A and 41B are micrographs showing samples obtained at a 12 month time point for HA alone. HA degrades outside and there is scant cellular infiltrate.

Example 18: Silk/HA Delivery System—Designed for One Surgeon, In-Office Delivery System This Example shows that silk/HA compositions described herein can be efficiently delivered by catheters with advantageous designs as described herein.

A silk/HA composition (a formulation with an average silk particle size of less than 500 microns, a concentration of particles in HA of about 20-60% v/v, an average extrusion force of <50 N through a 23XX gauge needle) was delivered to canines by a catheter as described herein. The catheter was 50 cm long and had a 1.8 mm diameter. A 23XX gauge angled needle was attached to the catheter and designed to interface with a flexible endoscope within a sheath. The sheath had an attached channel comprising a laryngoscope to give an optimal viewing point for delivery of silk injectable material into the vocal fold. The needle may be sheathed until it is voluntarily engaged. Augmentation can be viewed from above during delivery of the material. FIG. 42 is a photograph of the catheter.

Figure 43:
FIG. 43 is a photograph showing an injection of a silk/HA composition into a canine vocal fold, in accordance with certain embodiments.

Procedure: The needle begins in the unsheathed (proximal position) in the catheter. Next, the syringe is appended to the catheter handle and the catheter is primed with silk/HA material (or the CaHA material as described in Example 17 for the control experiment) to the opening of the needle. The catheter is next threaded through the cystoscope channel until the catheter tip protrudes out. The cystoscope/catheter device is next inserted into the mouth of the canine. The needle is then unsheathed from the catheter by changing the handle position. Afterwards, the vocal fold is punctured via the sheathed needle and 300 µL of silk/HA material (or the CaHA material as described in Example 17 for the control experiment) is injected into the right vocal fold of the canine (see FIG. 43, which shows silk/HA injection; note that the right vocal fold appears as the left vocal fold). Afterwards the needle is removed from the vocal fold and returned to the sheathed position via the handle. Finally, the catheter is retracted from the cystoscope and the canine is removed from the anesthetic.

Figure 44:
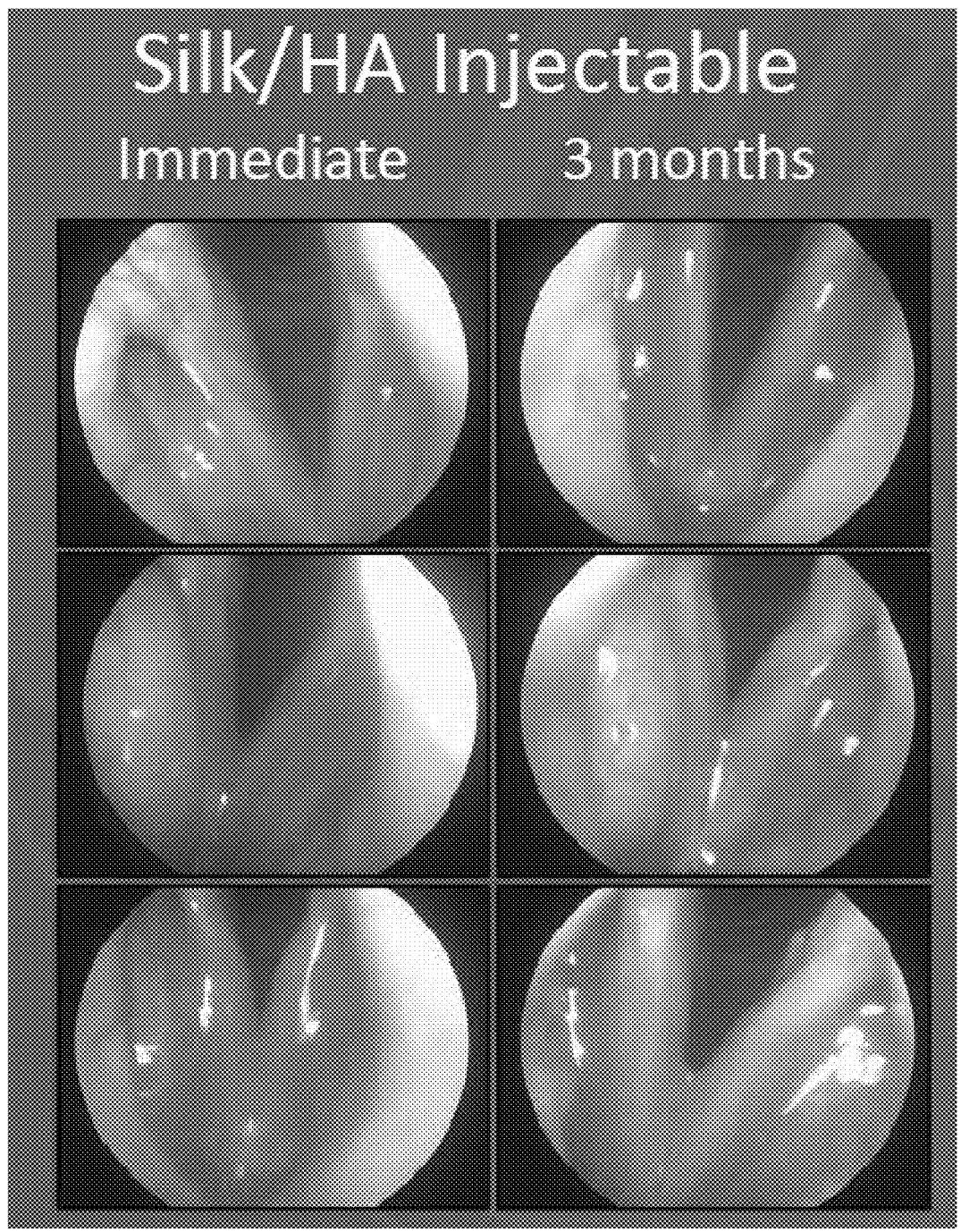
FIG. 44 shows micrographs of the immediate post injection appearance and the 3 months post injection appearance of augmentation in a canine model for a silk/HA composition, in accordance with certain embodiments.
Figure 45:
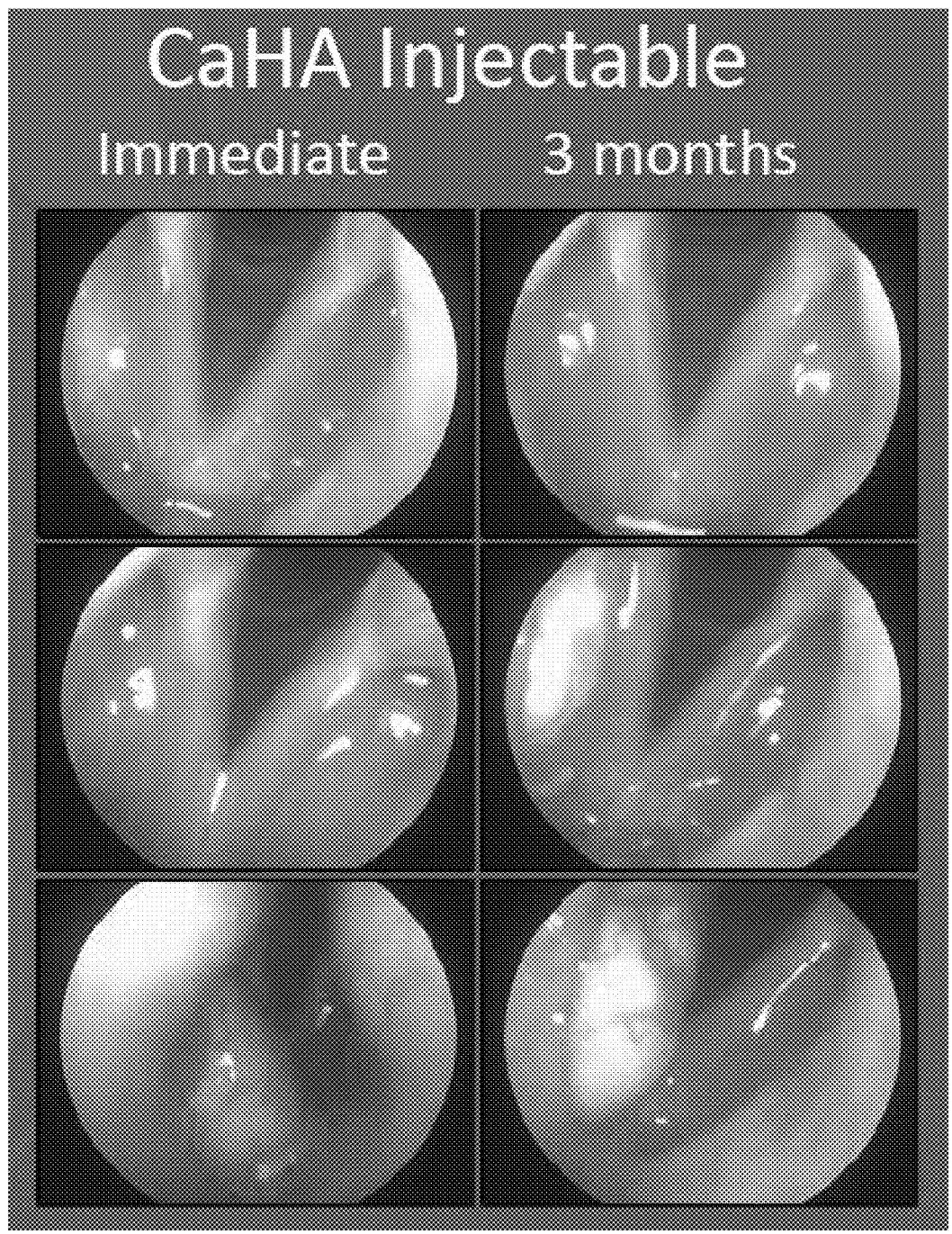
FIG. 45 shows micrographs of the immediate post injection appearance and the 3 months post injection appearance of augmentation in a canine model for a CaHA material, in accordance with certain embodiments.

FIG. 44 shows micrographs of the immediate post injection and 3 months post injection appearance of augmentation in a canine model for the silk/HA composition. FIG. 45 shows micrographs of the immediate post injection and 3 months post injection appearance of augmentation in a canine model for the CaHA material. The injections were performed into the right vocal folds of each dog; the left vocal fold was used as an additional control. Of note, there was no gross inflammation and both materials were still present and bulky at 3 months.

Example 19: Silk/HA Canine Studies

This Example shows that silk/HA compositions described herein can be delivered to canines, and have good properties for an extended period of time after delivery.

Figure 46:
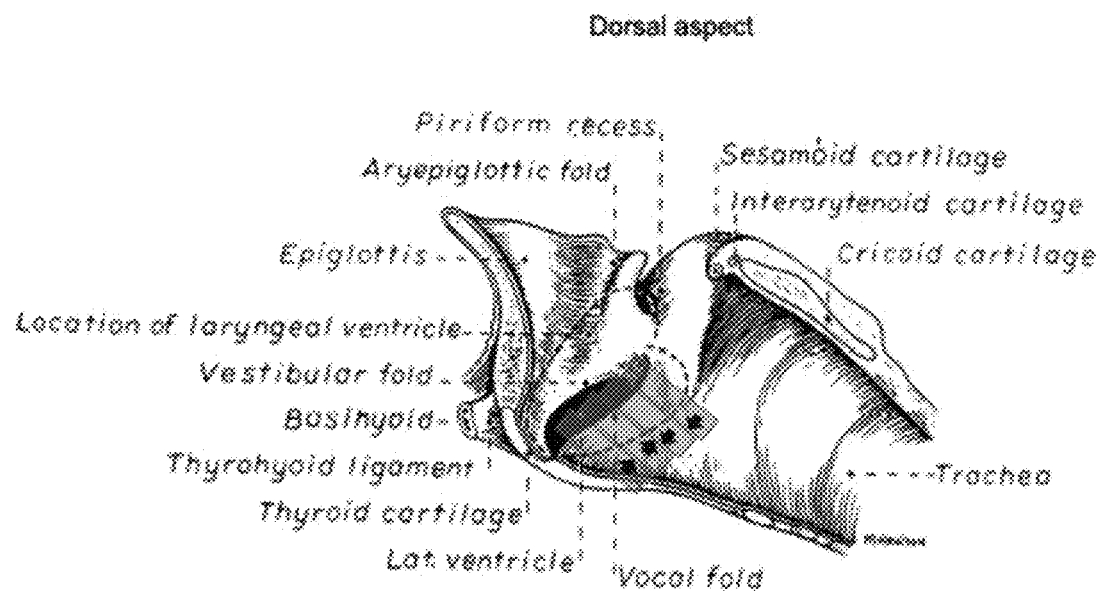
FIG. 46 is a schematic depicting a location at which a silk/HA composition may be delivered, in accordance with certain embodiments.
Figure 47:
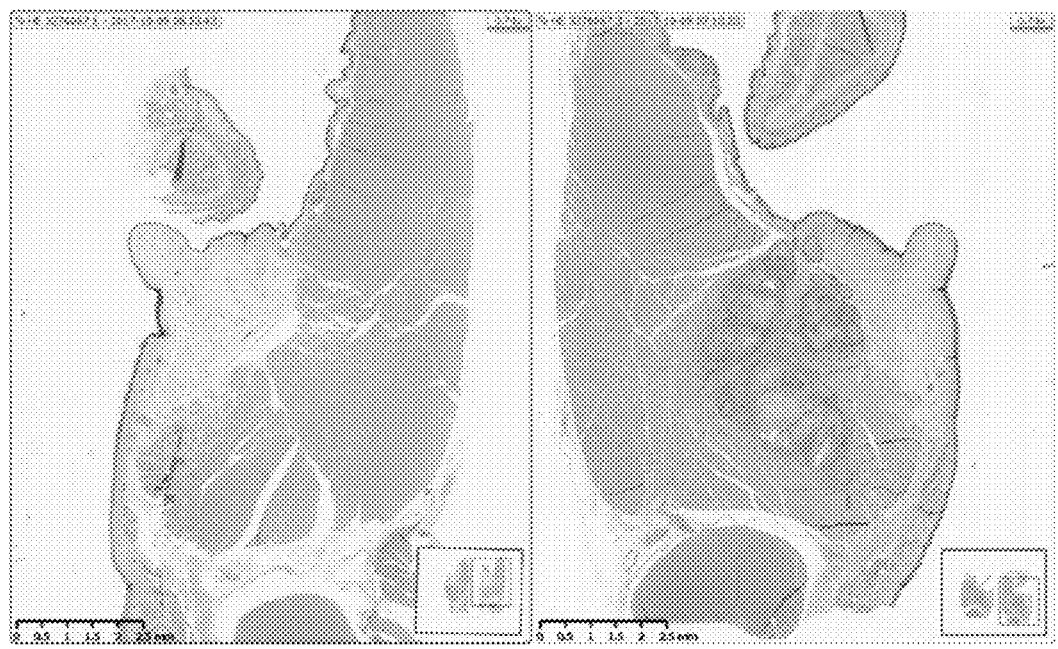
FIGS. 47-49 are micrographs showing canine vocal folds two months after injection of a silk/HA composition, and canine vocal folds into which a silk/HA composition has not been injected, in accordance with certain embodiments.
Figure 48:
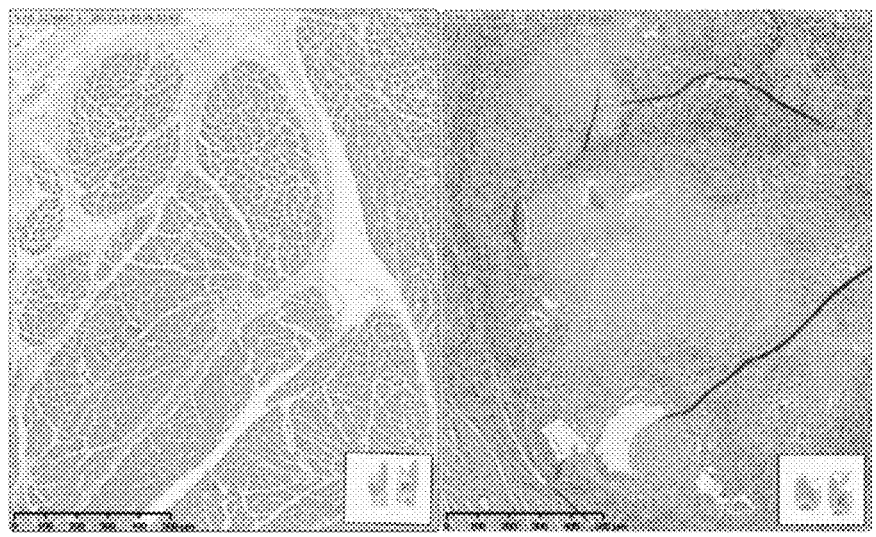
Figure 49:
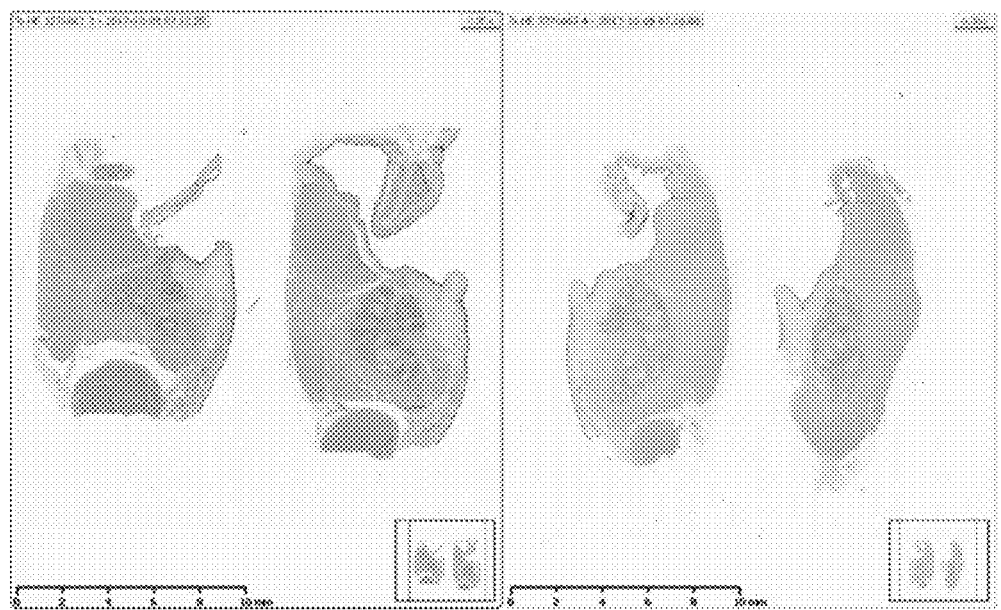

A silk/HA composition (a formulation with an average silk particle size of less than 500 microns, a concentration of particles in HA of about 20-60% v/v, an average extrusion force of <50 N through a 23XX gauge needle) was delivered to canine vocal folds using the catheter described in Example 18. FIG. 46 shows the position at which it was placed (rectangles designate approximate section location; arrows designate histologic face). FIGS. 47-49 are micrographs showing the excised vocal fold two months after injection. The left panel of each figure is a control (vocal fold lacking the silk/HA composition); the right panel of each figure is the vocal fold that has been injected with the silk/HA composition.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for injecting a composition into a vocal fold, comprising: injecting a composition into the vocal fold, wherein:
   the composition comprises crosslinked hyaluronic acid, particles comprising silk fibroin, and an anesthetic,
   a volume ratio of the crosslinked hyaluronic acid to the particles is greater than or equal to 50:50 and less than or equal to 75:25,
   the crosslinked hyaluronic acid has a concentration in the composition of greater than or equal to 1% (w/v) and less than or equal to 10% (w/v),
   the crosslinked hyaluronic acid has a crosslink density of greater than or equal to 8 mol % and less than or equal to 20 mol %,
   the particles have an average particle size of greater than or equal to 50 microns and less than or equal to 500 microns,
   the particles comprise interconnected pores,
   the particles have an average pore size of greater than or equal to 10 microns and less than or equal to 60 microns, and
   at least 50% of the interconnected pores have a circle equivalent diameter of between 5 microns and 75 microns.

2. A method as in claim 1, wherein the injection occurs with an average extrusion force of less than or equal to 50 N.

3. A method as in claim 1, wherein the particles comprise glycerol, and wherein the particles have a porosity of greater than or equal to 70% and less than or equal to 95%.

4. A method as in claim 3, wherein the particles have an average aspect ratio of greater than or equal to 1 and less than or equal to 3, wherein the composition further comprises non-crosslinked hyaluronic acid, and wherein the non-crosslinked hyaluronic acid has a molecular weight of greater than or equal to 200 kDa and less than or equal to 1 MDa.

5. A method as in claim 2, wherein the average extrusion force is the average of the extrusion forces measured when extruding the composition through a catheter, and wherein the composition has a complex shear modulus of greater than or equal to 1500 Pa and less than or equal to 4000 Pa.

6. A method as in claim 1, wherein no more than 10% of the interconnected pores have a diameter of 100 microns or greater.

7. A method as in claim 1, wherein no more than 15% of the interconnected pores have a circle equivalent diameter of 75 microns or greater.

* * * * *